United States Patent
Bell et al.

(10) Patent No.: US 8,592,629 B2
(45) Date of Patent: *Nov. 26, 2013

(54) SULFONAMIDE DERIVATIVES AS NAV 1.7 INHIBITORS

(75) Inventors: Andrew Simon Bell, Sandwich (GB); Alan Daniel Brown, Sandwich (GB); Marcel John De Groot, Sandwich (GB); Russell Andrew Lewthwaite, Sandwich (GB); Ian Roger Marsh, Sandwich (GB); David Simon Millan, Sandwich (GB); Manuel Perez Pacheco, Sandwich (GB); David James Rawson, Sandwich (GB); Nunzio Sciammetta, Sandwich (GB); Robert Ian Storer, Sandwich (GB); Nigel Alan Swain, Sandwich (GB); Steven Matthieu Gaulier, Sandwich (GB)

(73) Assignee: Pfizer Limited, Sandwich (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,587

(22) Filed: Jul. 11, 2011

(65) Prior Publication Data

US 2012/0010183 A1    Jan. 12, 2012

Related U.S. Application Data

(60) Provisional application No. 61/363,365, filed on Jul. 12, 2010, provisional application No. 61/477,897, filed on Apr. 21, 2011, provisional application No. 61/491,659, filed on May 31, 2011.

(51) Int. Cl.
C07C 303/00    (2006.01)
A61K 31/18    (2006.01)

(52) U.S. Cl.
USPC .......................................... 564/99; 514/605

(58) Field of Classification Search
None
See application file for complete search history.

(56) References Cited

U.S. PATENT DOCUMENTS

| | | | |
|---|---|---|---|
| 4,744,818 A | 5/1988 | Heiba et al. | |
| 5,084,085 A | 1/1992 | Theodoridis | |
| 5,851,745 A | 12/1998 | Takeuchi | |
| 6,251,827 B1 | 6/2001 | Ziemer et al. | |
| 6,348,474 B1 | 2/2002 | Kayakiri et al. | |
| 6,376,512 B1 | 4/2002 | Jayyosi et al. | |
| 7,772,285 B2 | 8/2010 | Chaki et al. | |
| 2002/0086887 A1 | 7/2002 | Augeri et al. | |
| 2003/0162818 A1 | 8/2003 | Ikawa et al. | |
| 2008/0188467 A1 | 8/2008 | Wong et al. | |
| 2010/0179137 A1 | 7/2010 | Kamikubo et al. | |
| 2011/0201616 A1 | 8/2011 | Kubota et al. | |
| 2012/0010182 A1 | 1/2012 | Brown et al. | |
| 2012/0010207 A1 * | 1/2012 | Bell et al. ......... | 514/247 |
| 2013/0109667 A1 | 5/2013 | Markworth et al. | |
| 2013/0109696 A1 | 5/2013 | Greener et al. | |
| 2013/0109701 A1 | 5/2013 | Brown et al. | |
| 2013/0109708 A1 | 5/2013 | Brown et al. | |
| 2013/0116285 A1 | 5/2013 | Bell et al. | |

FOREIGN PATENT DOCUMENTS

| | | |
|---|---|---|
| EP | 0003416 A1 | 8/1979 |
| EP | 0023100 A1 | 1/1981 |
| EP | 0029742 | 6/1981 |
| EP | 0194599 | 9/1986 |
| EP | 0281103 | 9/1988 |
| EP | 0325245 | 7/1989 |
| EP | 0399732 | 11/1990 |
| EP | 0412848 | 2/1991 |
| EP | 0453210 | 10/1991 |
| EP | 0570006 | 11/1993 |
| EP | 0585155 | 3/1994 |
| EP | 0620490 | 10/1994 |
| EP | 0684521 | 11/1995 |
| EP | 0753508 | 1/1997 |
| GB | 2266527 | 11/1993 |
| JP | 5289262 | 11/1993 |
| JP | 5307242 | 11/1993 |
| JP | 2001075213 | 3/2001 |
| WO | 8801133 | 2/1988 |
| WO | 8904303 | 5/1989 |
| WO | 8904304 | 5/1989 |
| WO | 8904305 | 5/1989 |
| WO | 8912628 | 12/1989 |
| WO | 9104964 A1 | 4/1991 |

(Continued)

OTHER PUBLICATIONS

Silverman, R. "The Organic Chemistry of Drug Design and Drug Action," 2004, Elsevier, pp. 29-32.*
Naganawa et al., "Further optimization of sulfonamide analogs as EP1 receptor antagonists: Synthesis and evaluation of bioisosteres for the carboxylic acid group", Bioorganic & Medicinal Chemistry, vol. 14(21), pp. 7121-7137 (2006).
Pinkerton et al., "Allosteric potentiators of the metabotropic glutamate receptor 2 (mGlu2). Part 3: Identification and biological activity of indanone containing mGlu2 receptor potentiators", Bioorganic & Medicinal Chemistry Letters, vol. 15(6), pp. 1565-1571 (2005).

(Continued)

Primary Examiner — Janet Andres
Assistant Examiner — Heidi Reese
(74) Attorney, Agent, or Firm — J. Michael Dixon

(57) ABSTRACT

This invention relates to sulfonamide derivative of formula (I), to their use in medicine, to compositions containing them, to processes for their preparation, and to intermediates used in such processes.

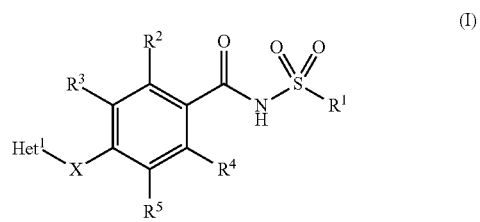

These compounds are inhibitors of Nav1.7.

25 Claims, No Drawings

(56) References Cited

FOREIGN PATENT DOCUMENTS

| | | |
|---|---|---|
| WO | 9300332 | 1/1993 |
| WO | 9413636 | 6/1994 |
| WO | 9421590 | 9/1994 |
| WO | 9604905 | 2/1996 |
| WO | 9609818 | 4/1996 |
| WO | 9900372 | 1/1999 |
| WO | 9916744 | 4/1999 |
| WO | 9920275 | 4/1999 |
| WO | 9947508 | 9/1999 |
| WO | 0039077 | 7/2000 |
| WO | 0064876 | 11/2000 |
| WO | 0066120 | 11/2000 |
| WO | 0136365 | 5/2001 |
| WO | 0166098 | 9/2001 |
| WO | 0224636 | 3/2002 |
| WO | 03042150 | 5/2003 |
| WO | 2004018386 | 3/2004 |
| WO | 2005080346 | 9/2005 |
| WO | 2005094810 | 10/2005 |
| WO | 2006015158 | 2/2006 |
| WO | 2006045514 | 5/2006 |
| WO | 2006121097 | 11/2006 |
| WO | 2007072782 | 6/2007 |
| WO | 2008025539 | 3/2008 |
| WO | 2008092231 | 8/2008 |
| WO | 2008149965 | 11/2008 |
| WO | 2009/012242 A2 | 1/2009 |
| WO | 2009/049181 A1 | 4/2009 |
| WO | 2009064250 | 5/2009 |
| WO | 2009064251 | 5/2009 |
| WO | 2009067541 | 5/2009 |
| WO | 2009067621 | 5/2009 |
| WO | 2009080835 | 7/2009 |
| WO | 2009157399 | 12/2009 |
| WO | 2010/079443 | 7/2010 |
| WO | WO 2012007883 A1 * | 1/2012 |

OTHER PUBLICATIONS

Ng et al., "Design, Synthesis, and Biological Activity of Novel Factor Xa Inhibitors: 4-Aryloxy Substituents of 2,6-Diphenoxypyridines", Bioorganic & Medicinal Chemistry, vol. 10(3), pp. 657-666 (2002).

Hamill et al., "Development of [11C]L-159,884: A Radiolabelled, Nonpeptide Angiotensin II Antagonist that is Useful for Angiotensin II, AT1 Receptor Imaging", Applied Radiation and Isotopes, vol. 47(2), pp. 211-218 (1996).

Matassa et al., "Synthesis and in Vitro LTD4 Antagonist Activity of Bicyclic and Monocyclic Cyclopentylurethane and Cyclopentylacetamide N-Arylsulfonyl Amides", Journal of Medicinal Chemistry, vol. 33(9), pp. 2621-2629 (1990).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", Journal of Medicinal Chemistry, vol. 33(1), pp. 240-245 (1990).

Brown et al., "Hydroxyacetophenone-Derived Antagonists of the Peptidoleukotriens", Journal of Medicinal Chemistry, vol. 32(4), pp. 807-826 (1989).

Dubois et al., "Dihydrochalcone Sweeteners. A Study of the Atypical Temporal Phenomena", Journal of Medicinal Chemistry, vol. 24(4), pp. 408-428 (1981).

Sobel et al., Journal of Chromatography Biomedical Applications, vol. 183(1), pp. 124-130 (1980).

Substituent effects on the toxicity for a series of herbicides, Roumanian Chemical Quarterly Reviews, 2000, pp. 127-137, 1999, 7(2).

International Search report for WO 2012/007868 published Jan. 19, 2012 corresponding to U.S. Appl No. 13/808,639.

International Search report for WO 2012/007869 published Jan. 19, 2012 corresponding to U.S. Appl. No. 13/808,653.

Silverman, Richard B. The Organic Chemistry of Drug Design and Drug Action. 2nd Ed., 2004, pp. 29-32, Elsevier, Burlington, MA.

* cited by examiner

SULFONAMIDE DERIVATIVES AS NAV 1.7 INHIBITORS

This application claims benefit of U.S. Provisional Application No. 61/363,365, filed Jul. 12, 2010; U.S. Provisional Application No. 61/477,897, filed Apr. 21, 2011; and U.S. Provisional Application No. 61/491,659, filed May 31, 2011; each application is hereby incorporated by reference in its entirety for any purpose.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_v$x.x. The VGSC family has been phylogenetically divided into two subfamilies $Na_v1$.x (all but SCN6A) and $Na_v2$.x (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir. (Wien)*, 144(8): 803-10 (2002)). Gain of function mutations of $Na_v1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.*; 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.*; 71(4): 311-9 (2007), Ahmad et al, *Hum Mol. Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v1.7$ inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

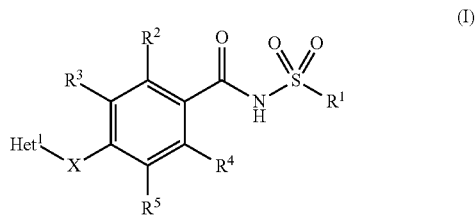

or a pharmaceutically acceptable salt thereof, wherein:
X is O, S, NH, or $CH_2$;
$Het^1$ is (i) a 9- or 10-membered heteroaryl comprising one to three nitrogen atoms; or (ii) a 6-, 9- or 10-membered heteroaryl comprising one to three nitrogen atoms which heteroaryl is independently substituted by one to three substituents selected from $Y^1$ and $Y^2$;

$Y^1$ and $Y^2$ are independently selected from F; Cl; CN; $NO_2$; $(C_1-C_8)$alkyl, optionally substituted by $(C_3-C_8)$cycloalkyl and/or, valency permitting, one to eight F; $(C_3-C_8)$cycloalkyl, optionally substituted, valency permitting, by one to eight F; $NR^7R^8$; $(C_1-C_8)$alkyloxy, optionally independently substituted by one to three $R^9$, or, valency permitting, one to eight F; $(C_3-C_8)$cycloalkyloxy; phenyl, optionally independently substituted by one to three $R^{10}$; phenoxy, optionally independently substituted by one to three $R^{10}$; $Het^2$; $Het^2$-oxy; and $Het^3$; wherein $(C_3-C_8)$cycloalkyloxy may be optionally fused to a phenyl ring or may be independently substituted, valency permitting, by one to eight F and/or by one to three $R^{10}$;

$R^1$ is $(C_1-C_6)$alkyl or $(C_3-C_8)$cycloalkyl, each of which is optionally substituted, valency permitting, by one to eight F;

$R^2$, $R^3$, $R^4$ are independently H, F, Cl or —$OCH_3$;

$R^5$ is H, CN, F, Cl or $R^6$;

$R^6$ is a group selected from $(C_1-C_6)$alkyl and $(C_1-C_6)$alkyloxy, wherein each group is optionally substituted, valency permitting, by one to eight F;

$R^7$ and $R^8$ are independently H; $(C_1-C_8)$alkyl, optionally independently substituted by one to three $R^{11}$; $(C_3-C_8)$cycloalkyl, optionally substituted, valency permitting, by one to eight F; 'C-linked' $Het^2$ or 'C-linked' $Het^3$; wherein $(C_3-C_8)$cycloalkyl may be optionally fused to a phenyl ring or may be independently substituted by one to three $R^{10}$; or $R^7$ and $R^8$, taken together with the nitrogen atom to which they are attached, form a saturated, bridged, 7 to 9-membered ring;

$R^9$ is $(C_1-C_6)$alkyloxy; $(C_3-C_8)$cycloalkyl, optionally substituted by one to three F or $(C_1-C_6)$alkyl; $Het^2$; or phenyl, optionally independently substituted by one to three $R^6$;

$R^{10}$ is Cl, CN or $R^6$;

$R^{11}$ is F; $(C_1-C_6)$alkyloxy; $(C_3-C_8)$cycloalkyl, optionally substituted by one to three F; 'C-linked' $Het^2$; or phenyl, optionally independently substituted by one to three $R^6$;

$Het^2$ is a 3- to 8-membered saturated monoheterocycloalkyl comprising one or two ring members selected from —$NR^{12}$— and —O—, said monoheterocycloalkyl being optionally substituted on a ring carbon atom by one to three substituents independently selected from F, $(C_1-C_6)$alkyl, $(C_1-C_4)$alkyloxy$(C_0-C_4)$alkylene and $(C_3-C_8)$cycloalkyl;

$Het^3$ is a 5- or 6-membered heteroaryl comprising one to three nitrogen atoms, said heteroaryl being optionally substituted by one to three substituents selected from F, Cl, CN and $R^6$; and $R^{12}$ is H, $(C_1-C_6)$alkyl or $(C_3-C_8)$cycloalkyl, wherein $(C_1-C_6)$alkyl and $(C_3-C_8)$cycloalkyl are optionally substituted by one to three F; or, when $Het^2$ is 'N-linked', is absent.

Described below are a number of embodiments (E) of this first aspect of the invention, where for convenience E1 is identical thereto.

E1 A compound of formula (I) as defined above or a pharmaceutically acceptable salt thereof.

E2 A compound according to E1 wherein $Het^1$ is a 6-membered heteroaryl comprising one or two nitrogen atoms which heteroaryl is independently substituted by one to three substituents selected from $Y^1$ and $Y^2$.

E3 A compound according to either E1 or E2 wherein $Het^1$ is a 6-membered heteroaryl comprising one or two nitrogen atoms which heteroaryl is independently substituted by one or two substituents selected from $Y^1$ and $Y^2$.

E4 A compound according to any of E1 to E3 wherein $Het^1$ is pyridyl or pyrimidinyl, each independently substituted by one or two substituents selected from $Y^1$ and $Y^2$.

E5 A compound according to any of E1 to E4 wherein $Het^1$ is pyridyl independently substituted by one or two substituents selected from $Y^1$ and $Y^2$.

E6 A compound according to any of E1 to E5 wherein $Het^1$ is pyridyl independently substituted by one or two substituents selected from $Y^1$ and $Y^2$ and wherein said pyridyl is orientated as below:

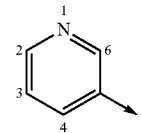

E7 A compound according to E6 wherein said pyridyl is 2-substituted by $Y^1$, 3-substituted by $Y^2$ or, where di-substituted, 2-substituted by $Y^1$ and 3-substituted by $Y^2$.

E8 A compound according to any of E1 to E7 wherein $Y^1$ is $(C_1-C_8)$alkyl, optionally substituted by $(C_3-C_8)$cycloalkyl and/or, valency permitting, by one to eight F; $(C_3-C_8)$cycloalkyl, optionally substituted, valency permitting, by one to eight F; $(C_1-C_6)$alkyloxy, optionally substituted, valency permitting, by one to eight F; $(C_3-C_8)$cycloalkyloxy; or $Het^2$.

E9 A compound according to any of E1 to E8 wherein $Y^1$ is $(C_1-C_6)$alkyl, optionally substituted by $(C_3-C_6)$cycloalkyl and/or, valency permitting, by one to eight F; $(C_3-C_6)$cycloalkyl, optionally substituted, valency permitting, by one to eight F; $(C_1-C_6)$alkyloxy, optionally substituted, valency permitting, by one to eight F; $(C_3-C_8)$cycloalkyloxy; or 4- to 6-membered $Het^2$.

E10 A compound according to any of E1 to E9 wherein $Y^2$ is F, Cl, CN, $(C_1-C_8)$alkyl, optionally substituted by $(C_3-C_8)$cycloalkyl and/or, valency permitting, by or one to eight F; $(C_3-C_8)$cycloalkyl, optionally substituted, valency permitting, by one to eight F; $(C_1-C_6)$alkyloxy, optionally substituted, valency permitting, by one to eight F; $(C_3-C_8)$cycloalkyloxy; or $Het^2$.

E11. A compound according to any of E1 to E10 wherein $Y^2$ is F, Cl, CN, $(C_1-C_4)$alkyl, optionally substituted by $(C_3-C_6)$cycloalkyl and/or, valency permitting, by one to eight F; $(C_3-C_6)$cycloalkyl, optionally substituted, valency permitting, by one to eight F; $(C_1-C_6)$alkyloxy, optionally substituted, valency permitting, by one to eight F; $(C_3-C_6)$cycloalkyloxy; or 4- to 6-membered $Het^2$.

E12 A compound according to any of E1 to E11 wherein $Y^2$ is F, Cl, CN, $(C_1-C_4)$alkyl, optionally substituted by $(C_3-C_6)$cycloalkyl and/or, valency permitting, by one to six F; $(C_3-C_6)$cycloalkyl, optionally substituted, valency permitting, by one to six F; $(C_1-C_6)$alkyloxy, optionally substituted, valency permitting, by one to six F; $(C_3-C_6)$cycloalkyloxy; or 4- to 6-membered $Het^2$.

E13 A compound according to any of E1 to E12 wherein $R^1$ is $(C_1-C_4)$alkyl or $(C_3-C_6)$cycloalkyl.

E14 A compound according to any of E1 to E13 wherein $R^1$ is $(C_1-C_3)$alkyl or $(C_3-C_4)$cycloalkyl.

E15 A compound according to any of E1 to E14 wherein $R^1$ is methyl or cyclopropyl.

E16 A compound according to any of E1 to E15 wherein $R^2$, $R^3$ and $R^4$ are independently H, F or Cl.

E17 A compound according to any of E1 to E16 wherein $R^2$, $R^3$ and $R^4$ are independently H or F.

E18 A compound according to any of E1 to E17 wherein $R^2$ is F; and $R^3$ and $R^4$ are independently H or F.

E19 A compound according to any of E1 to E18 wherein $R^5$ is H; CN; F; Cl; $(C_1-C_4)$alkyl, optionally substituted, valency permitting, by one to eight F; or $(C_1-C_4)$alkyloxy, optionally substituted, valency permitting, by one to eight F.

E20 A compound according to any of E1 to E19 wherein $R^5$ is H, CN, F, Cl, $CH_3$, $C_2H_5$, $CF_3$, $-OCH_3$, $-OC_2H_5$ or $-OCF_3$.

E21 A compound according to any of E1 to E20 wherein $R^5$ is F or Cl.

E22 A compound according to any of E1 to E21 wherein X is O.

E23 A compound according to E1 which is the compound of any one of:
Examples 1 to 14;
4-(5-chloro-6-methoxypyridin-3-yloxy)-N-(cyclopropylsulfonyl)-2,5-difluorobenzamide;
Examples 16 to 103;
5-chloro-4-(6-cyclopropyl-5-(1,1-difluoroethoxy)pyridin-3-yloxy)-2-fluoro-N-(methylsulfonyl)benzamide;
Examples 105 to 201; or
Examples L1 to L70;
or a pharmaceutically acceptable salt thereof.

Described below are a number of alternative embodiments (EM) of this first aspect of the invention.

EM1 A compound of formula (I)

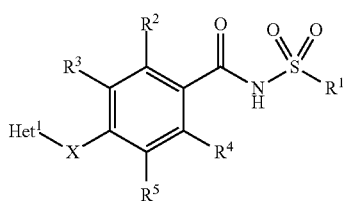

(I)

or a pharmaceutically acceptable salt thereof, wherein:
X is O;
$Het^1$ is (i) a 9- or 10-membered heteroaryl comprising one to three nitrogen atoms; or (ii) a 6-, 9- or 10-membered heteroaryl comprising one to three nitrogen atoms which heteroaryl is independently substituted by one to three substituents selected from $Y^1$ and $Y^2$;
$Y^1$ and $Y^2$ are independently selected from F; Cl; CN; $(C_1-C_8)$alkyl, optionally substituted by $(C_3-C_8)$cycloalkyl or one to three F; $(C_3-C_8)$cycloalkyl, optionally substituted by one to three F; $NR^7R^8$; $(C_1-C_8)$alkyloxy, optionally independently substituted by one to three $R^9$; $(C_3-C_8)$cycloalkyloxy; phenyl, optionally independently substituted by one to three $R^{10}$; $Het^2$ and $Het^3$; wherein $(C_3-C_8)$cycloalkyloxy may be optionally fused to a phenyl ring or may be independently substituted by one to three $R^{10}$;
$R^1$ is $(C_1-C_6)$alkyl or $(C_3-C_8)$cycloalkyl, each of which is optionally substituted by one to three F;
$R^2$, $R^3$, $R^4$ are independently H, F, Cl or $-OCH_3$;
$R^5$ is H, CN, F, Cl or $R^6$;
$R^6$ is a group selected from $(C_1-C_6)$alkyl and $(C_1-C_6)$alkyloxy, wherein each group is optionally substituted, valency permitting, by one to five F;
$R^7$ and $R^8$ are independently H; $(C_1-C_8)$alkyl, optionally independently substituted by one to three $R^{11}$; $(C_3-C_8)$cycloalkyl; or 'C-linked' $Het^2$; wherein $(C_3-C_8)$cycloalkyl may be optionally fused to a phenyl ring or may be independently substituted by one to three $R^{10}$; or
$R^7$ and $R^8$, taken together with the nitrogen atom to which they are attached, form a saturated, bridged, 7 to 9-membered ring;
$R^9$ is F; $(C_1-C_6)$alkyloxy; $(C_3-C_8)$cycloalkyl, optionally substituted by one to three F; $Het^2$; or phenyl, optionally independently substituted by one to three $R^6$;
$R^{10}$ is F, Cl $R^6$;
$R^{11}$ is F; $(C_1-C_6)$alkyloxy; $(C_3-C_8)$cycloalkyl, optionally substituted by one to three F; 'C-linked' $Het^2$; or phenyl, optionally independently substituted by one to three $R^6$;
$Het^2$ is a 3- to 8-membered saturated monoheterocycloalkyl comprising one or two ring members selected from $-NR^{12}-$ and $-O-$, said monoheterocycloalkyl being optionally substituted on a ring carbon atom by one to three substituents independently selected from F, $(C_1-C_6)$alkyl, $(C_1-C_4)$alkyloxy$(C_0-C_4)$alkylene and $(C_3-C_8)$cycloalkyl;
$Het^3$ is a 5- or 6-membered heteroaryl comprising one to three nitrogen atoms, said heteroaryl being optionally substituted by one to three substituents selected from F, Cl, CN and $R^6$; and
$R^{12}$ is H, $(C_1-C_6)$alkyl or $(C_3-C_8)$cycloalkyl, wherein $(C_1-C_6)$alkyl and $(C_3-C_8)$cycloalkyl are optionally substituted by one to three F; or, when $Het^2$ is 'N-linked', is absent.

EM2 A compound according to EM1 wherein $Het^1$ is a 6-membered heteroaryl comprising one or two nitrogen atoms which heteroaryl is independently substituted by one to three substituents selected from $Y^1$ and $Y^2$.

EM3 A compound according to either EM1 or EM2 wherein $Het^1$ is a 6-membered heteroaryl comprising one or two nitrogen atoms which heteroaryl is independently substituted by one or two substituents selected from $Y^1$ and $Y^2$.

EM4 A compound according to any of EM1 to EM3 wherein $Het^1$ is pyridyl or pyrimidinyl, each independently substituted by one or two substituents selected from $Y^1$ and $Y^2$.

EM5 A compound according to any of EM1 to EM4 wherein $Het^1$ is pyridyl independently substituted by one or two substituents selected from $Y^1$ and $Y^2$.

EM6 A compound according to any of EM1 to EM5 wherein $Het^1$ is pyridyl independently substituted by one or two substituents selected from $Y^1$ and $Y^2$ and wherein said pyridyl is orientated as below:

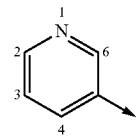

EM7 A compound according to EM6 wherein said pyridyl is 2-substituted by $Y^1$, 3-substituted by $Y^2$ or, where di-substituted, 2-substituted by $Y^1$ and 3-substituted by $Y^2$.

EM8 A compound according to any of EM1 to EM7 wherein $Y^1$ is $(C_1-C_8)$alkyl, optionally substituted by $(C_3-C_8)$cycloalkyl or one to three F; $(C_3-C_8)$cycloalkyl, optionally substituted by one to three F; $(C_1-C_6)$alkyloxy, optionally substituted by one to three F; $(C_3-C_8)$cycloalkyloxy; or Het$^2$.

EM9 A compound according to any of EM1 to EM8 wherein Y$^1$ is $(C_1-C_6)$alkyl, optionally substituted by $(C_3-C_6)$cycloalkyl or one to three F; $(C_3-C_6)$cycloalkyl, optionally substituted by one to three F; $(C_1-C_6)$alkyloxy, optionally substituted by one to three F; $(C_3-C_8)$cycloalkyloxy; or 4- to 6-membered Het$^2$.

EM10 A compound according to any of EM1 to EM9 wherein Y$^2$ is F, Cl, CN, $(C_1-C_8)$alkyl, optionally substituted by $(C_3-C_8)$cycloalkyl or one to three F; $(C_3-C_8)$cycloalkyl, optionally substituted by one to three F; $(C_1-C_6)$alkyloxy, optionally substituted by one to three F; $(C_3-C_8)$cycloalkyloxy; or Het$^2$.

EM11. A compound according to any of EM1 to EM10 wherein Y$^2$ is F, Cl, CN, $(C_1-C_4)$alkyl, optionally substituted by $(C_3-C_6)$cycloalkyl or one to three F; $(C_3-C_6)$cycloalkyl, optionally substituted by one to three F; $(C_1-C_6)$alkyloxy, optionally substituted by one to three F; $(C_3-C_6)$cycloalkyloxy; or 4- to 6-membered Het$^2$.

EM12 A compound according to any of EM1 to EM11 wherein R$^1$ is $(C_1-C_4)$alkyl or $(C_3-C_6)$cycloalkyl.

EM13 A compound according to any of EM1 to EM12 wherein R$^1$ is $(C_1-C_3)$alkyl or $(C_3-C_4)$cycloalkyl.

EM14 A compound according to any of EM1 to EM13 wherein R$^1$ is methyl or cyclopropyl.

EM15 A compound according to any of EM1 to EM14 wherein R$^2$, R$^3$ and R$^4$ are independently H, F or Cl.

EM16 A compound according to any of EM1 to EM15 wherein R$^2$, R$^3$ and R$^4$ are independently H or F.

EM17 A compound according to any of EM1 to EM16 wherein R$^2$ is F; and R$^3$ and R$^4$ are independently H or F.

EM18 A compound according to any of EM1 to EM17 wherein R$^5$ is H; CN; F; Cl; $(C_1-C_4)$alkyl, optionally substituted by one to three F; or $(C_1-C_4)$alkyloxy, optionally substituted by one to three F.

EM19 A compound according to any of EM1 to EM18 wherein R$^5$ is H, CN, F, Cl, CH$_3$, C$_2$H$_5$, CF$_3$, —OCH$_3$, —OC$_2$H$_5$ or —OCF$_3$.

EM20 A compound according to any of EM1 to EM19 wherein R$^5$ is F or Cl.

Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, thiazolyl, isothiazolyl, thiadiazolyl, pyridyl, pyridazinyl, pyrimidinyl and pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of 9- or 10-membered heteroaryl used in the definitions of formula (I) include indolyl, benzimidazolyl, indazolyl, benzotriazolyl, pyrrolo[2,3-b]pyridyl, pyrrolo[2,3-c]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-b]pyridyl, isoindolyl, indazolyl, purinyl, indolizinyl, imidazo[1,2-a]pyridyl, imidazo[1,5-a]pyridyl, pyrazolo[1,5-a]pyridyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-d]pyrazinyl and pyrido[3,4-b]pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of Het$^2$ include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or 1-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:

(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^-Na^+$, $—COO^-K^+$, or $—SO_3Na^+$) or non-ionic (such as $—N^-N^+(CH_3)_3$) polar head group. For more information, see *Crystals and the Polarizing Microscope* by N. H. Hartshorne and A. Stuart, $4^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

In one embodiment the isotopically-labelled compounds of formula (I) include one or more deuterium atoms. In another embodiment, when $Y^1$ and/or $Y^2$ are independently $(C_1-C_8)$alkyl or $(C_1-C_8)$alkyloxy, one or more hydrogen atoms may be replaced with deuterium atoms.

Certain isotopically-labelled compounds of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group)", incorporated herein by reference, which also describes methods for the removal of such groups.

In the following general methods, X, $R^1$, $R^2$, $R^3$, $R^4$, $R^5$ and $Het^1$ are as previously defined for a compound of the formula (I) unless otherwise stated. Pg is a suitable carboxylic acid protecting group, such as tert butyl, methyl, ethyl, or tolyl. Lg is a suitable leaving group, such as halo (e.g. Br) or sulphonate (e.g. mesylate, triflate or tosylate). E is an aldehyde or nitrile or Lg.

Where ratios of solvents are given, the ratios are by volume.

The skilled person may undertake the synthetic steps described below in any suitable order in order to arrive at the compounds of formula (I).

According to a first process, compounds of formula (I), wherein X is O, NH or S may be prepared by the process illustrated in Scheme 1.

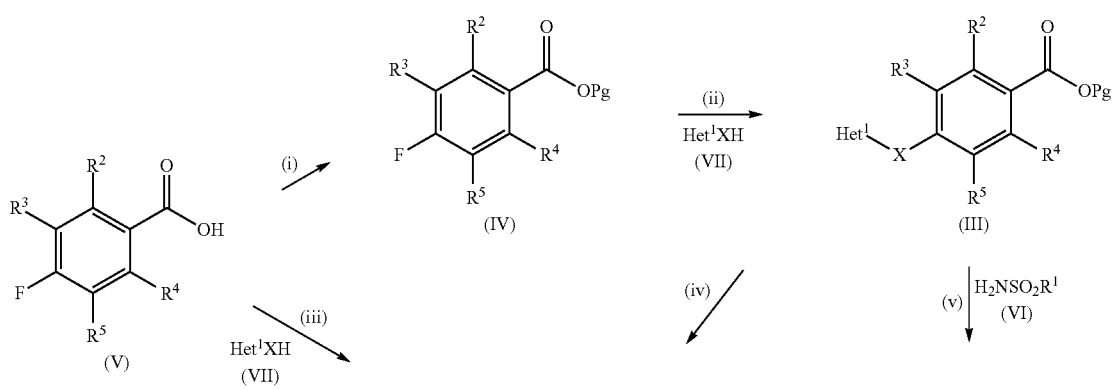

Scheme 1

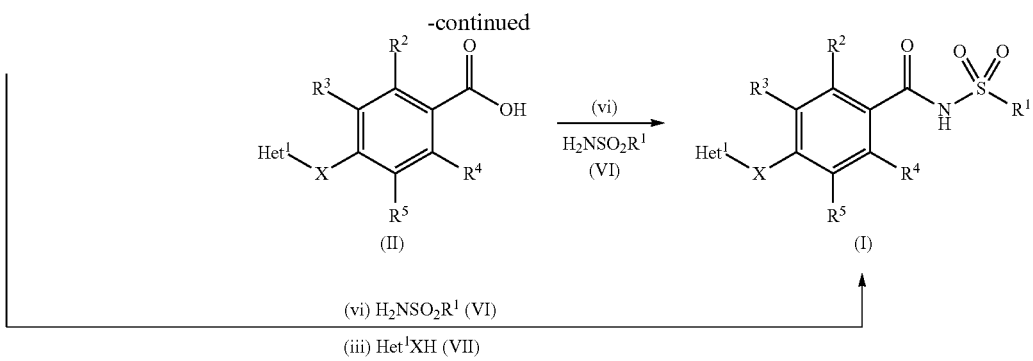

(vi) H₂NSO₂R¹ (VI)

(iii) Het¹XH (VII)

Compounds of formula (I) can be made from compounds of formula (III) according to process step (v) by displacement of the ester with compounds of formula (VI) and a suitable base. Suitable conditions include potassium tert-butoxide in THF at 60° C., NaH in THF at 65° C. and potassium carbonate and DBU in DMSO at 50° C. Preferred conditions comprise DBU in acetonitrile at 50° C.

Alternatively compounds of formula (I) can be made from compounds of formula (II) according to reaction step (vi) by activation of the acid group with reagents such as oxalyl chloride, carbonyl di-imidazole (CDI), a uronium based peptide coupling agent or a carbodiimide reagent followed by displacement with a sulfonamide of formula (VI) in the presence of a nucleophilic base, such as 4-dimethylaminopyridine. Preferred conditions comprise N,N-dimethylaminopropyl-N'-ethylcarbodiimide and 4-dimethylaminopyridine in DCM or N-[(dimethylamino)(3H-[1,2,3]triazolo[4,5-b]pyridin-3-yloxy)methylene]-N-methylmethanaminium hexafluorophosphate and N-ethyl-N-isopropylpropan-2-amine in DCM or 2,4,6-tripropyl-1,3,5,2,4,6-trioxatriphosphinane 2,4,6-trioxide and N-ethyl-N-isopropylpropan-2-amine in THF at 65° C.

Compounds of formula (I) can also be made from compounds of formula (V) by reversing process steps (iii) and (vi). Preferred conditions for process step (iii) are as described for process step (ii) below; for process step (vi), preferred conditions comprise potassium carbonate in DMSO at 90° C. or NaH in THF at 60° C.

Compounds of formula (III) can be made from compounds of formula (IV) according to process step (ii) by a nucleophilic aromatic substitution reaction (SNAr) using compounds of formula (VII) and base. Suitable conditions include potassium carbonate in DMF or DMSO, sodium hydride in NMP or DMF, and sodium hydroxide or potassium hydroxide in 1,4-dioxane and water or DMSO or potassium tert-butoxide in THF or cesium carbonate and copper powder in pyridine at 120° C. Preferred conditions comprise 2 equivalents of potassium carbonate in DMSO at room temperature.

Compounds of formula (IV) can be prepared from compounds of formula (V) according to process step (i) using protecting group methodology as referred to above in 'Greene's Protective Groups in Organic Synthesis'. When Pg is tolyl, preferred conditions comprise thionyl chloride at 50° C. using para-cresol. When Pg is tert-butyl, preferred conditions comprise di-tert-butyldicarbonate and 4-dimethylaminopyridine in tert-butanol.

Compounds of formula (II) can be made from compounds of formula (III) according to process step (iv) by hydrolysis of the ester under basic or acidic conditions. Preferred conditions are sodium hydroxide in a mixture of MeOH and THF or lithium hydroxide in a mixture of THF and water or TFA in DCM at room temperature.

Alternatively compounds of formula (II) can be made from compounds of formula (V) according to process step (iii) by a nucleophilic aromatic substitution reaction (SNAr) using compounds of formula (VII) and base as described for process step (ii) at elevated temperatures. Preferred conditions comprise potassium carbonate in DMSO at 90° C.

According to a second process, compounds of formula (I), wherein X is O, NH or S, may be prepared by the process illustrated in Scheme 2.

Scheme 2

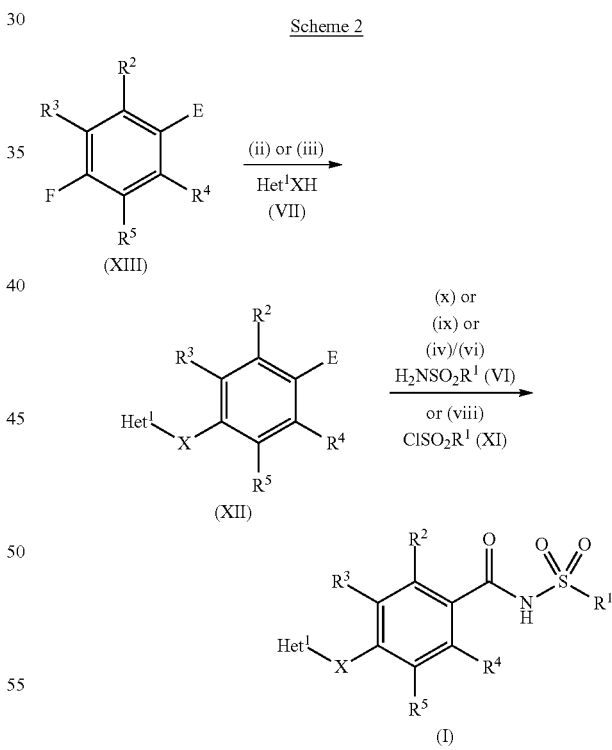

When E is nitrile, compounds of formula (I) can be prepared from compounds of formula (XII) according to reaction step (viii) by hydrolysis of the nitrile by either acidic or basic methods to the primary carboxamide followed by reaction with an appropriate sulfonyl chloride of formula (XI). Preferred conditions comprise hydrogen peroxide and potassium carbonate in DMSO followed by lithium hexamethyldisilazide in THF, at a temperature from room temperature to 60° C.

Alternatively when E is nitrile compounds of formula (I) can be prepared from compounds of formula (XII) according to reaction step (iv), by hydrolysis of the nitrile by either acidic or basic methods to the carboxylic acid, followed by displacement with a sulfonamide of formula (VI) according to process step (vi). Preferred conditions for both steps are described for the corresponding steps (iv) and (vi) in Scheme 1.

When E is aldehyde, compounds of formula (I) can be prepared from compounds of formula (XII) according to process step (ix), an oxidative rhodium insertion reaction with compounds of formula (VI). Preferred conditions comprise methane sulfonamide, bis(tert-butylcarbonyloxy)iodobenzene and bis[rhodium(alpha, alpha, alpha', alpha'-tetramethyl-1,3-benzenediproprionic acid)] in isopropyl acetate at 55° C.

When E is Lg, such as Br, I or triflate, compounds of formula (I) can be prepared from compounds of formulae (XII) and (VI) according to process step (x), a carbonylation reaction followed by carboamidation. Conveniently the reaction is effected using a carbonyl source such as molybdenumhexacarbonyl or carbon monoxide, a palladium catalyst such as trans-bis(acetato)bis[o-(di-o-tolylphosphino)benzyl]dipalladium(II) acetate, a phosphine ligand such as tri-tert-butylphosphonuim tetrafluoroborate, a base such as triethylamine and at 50-150° C. under pressure or under microwave irradiation for 10 minutes to 24 hours in a solvent such as THF, NMP or 1,4-dioxane. Preferred conditions comprise molybdenumhexacarbonyl, trans-bis(acetato)bis[o-(di-o-tolylphosphino)benzyl]dipalladium(II) acetate, tri-tert-butylphosphonuim tetrafluoroborate and 1,8-diazabicyclo [5.4.0]undec-7-ene in 1,4-dioxan under microwave irradiation at 140° C. for 15 minutes.

Compounds of formula (XII) can be made from compounds of formula (XIII) according to process step (ii) or (iii) by a nucleophilic aromatic substitution reaction (SNAr) with compounds of formula (VII) and base, using conditions described in Scheme 1 for the corresponding process step.

According to a third process, compounds of formula (I), wherein X is $CH_2$, may be prepared by the process illustrated in Scheme 3.

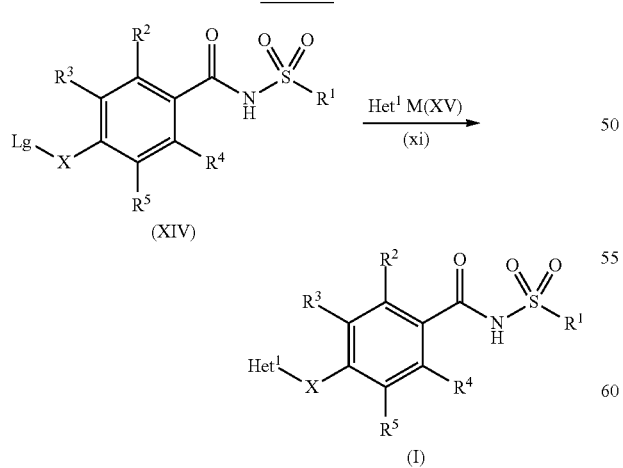

Scheme 3

Compounds of formula (I) can be made from compounds of formula (XIV) according to process step (xi) under Suzuki cross coupling reaction with compounds of formula (XV) and a suitable catalyst. Typical conditions comprise Palladium tetrakis triphenyl phosphine and potassium carbonate in water and THF at 65° C.

According to a fourth process, compounds of formula (I), wherein X is O, NH or S; $Y^1$ is selected from $R^7R^8N$; ($C_1$-$C_8$)alkyloxy, optionally independently substituted by one to three $R^9$; and ($C_3$-$C_8$)cycloalkyloxy and $R^7$, $R^8$ and $R^9$ are as defined above, may be prepared by interconversion from the corresponding compounds of formula (I) wherein $Y^1$ is F by the process illustrated in Scheme 4.

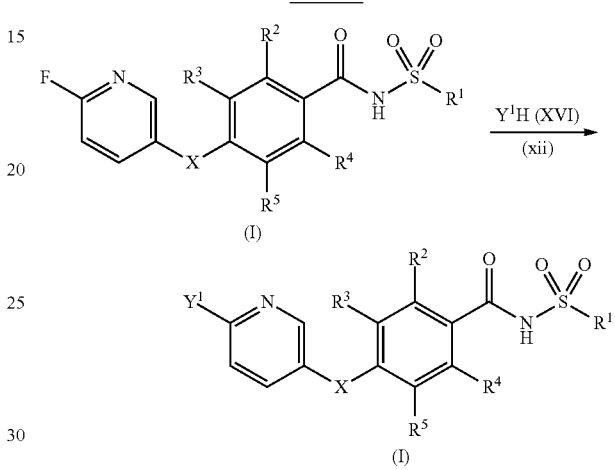

Scheme 4

Compounds of formula (I) wherein $Y^1$ is other than F may be prepared from corresponding compounds of formula (I) wherein $Y^1$ is F according to process step (xii) by displacement of the fluorine with compounds of formula (XVI) and a base. Suitable conditions for this interconversion of compounds of formula (I) comprise sodium hydride in THF at from room temperature to elevated temperatures, triethylamine in DMSO at elevated temperatures or cesium carbonate in DMSO at 100° C.

The skilled person will appreciate that the same process of interconversion may be effected on precursor compounds of formula (I) wherein the fluorinated pyridyl is also mono- or di-substituted by $Y^1$ other than F, so as to give the following compounds of formula (I) wherein $Y^1$ other than F:

Likewise, the skilled person will appreciate that the forgoing interconversion is equally applicable to the introduction of $Y^2$, wherein $Y^2$ is other than F.

According to a fifth process, compounds of formula (III), wherein X is S, may be prepared by the process illustrated in Scheme 5.

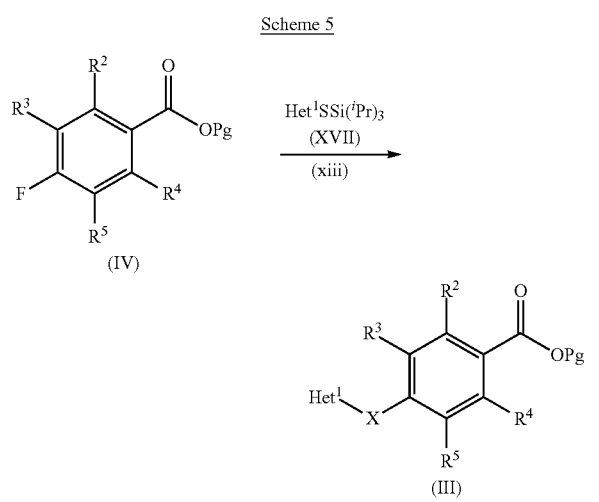

Compounds of formula (III) can also be prepared from compounds of formula (IV) according to process step (xiii) by nucleophilic aromatic substitution reaction with compounds of formula (XVII) and a base. Suitable conditions comprise potassium carbonate in DMSO at room temperature.

According to a sixth process, compounds of formula (III), wherein X is O, NH or S, may be prepared by the process illustrated in Scheme 6.

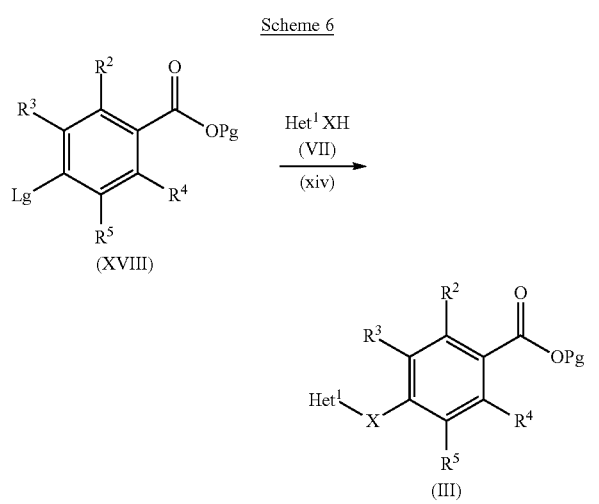

Compounds of formula (III) can also be prepared from compounds of formula (XVIII) according to process step (xiv) by displacement of a suitable leaving group with compounds of formula (VII) under Buchwald-Hartwig cross coupling conditions. Typical conditions comprise palladium acetate, BrettPhos and potassium carbonate in tert-butanol and water at 110° C.

According to a seventh process, compounds of formula (III), wherein X is O, NH or S, may be prepared by the process illustrated in Scheme 7.

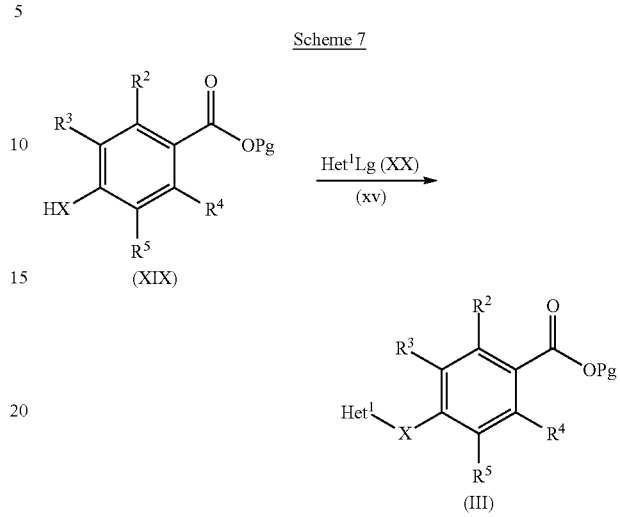

Compounds of formula (III) can also be prepared from compounds of formula (XIX) according to process step (xv) by displacement of a suitable leaving group with compounds of formula (XX) under Buchwald-Hartwig cross coupling conditions (for examples as described just above in connection with Scheme 6) or by a nucleophilic aromatic substitution reaction (SnAr). Typical conditions comprise potassium carbonate in DMSO at 60° C.

Compounds of formulae (V), (VI), (VII), (XI), (XIII), (XIV), (XVI), (XVII), (XVIII), (XIX), and (XX) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art.

Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 μg to 100 mg of the compound of formula (I). The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
an alternative Nav1.7 channel modulator, such as another compound of the present invention or a compound disclosed in WO 2009/012242;
an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;
a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene) piperidene-1-carboxamide);
an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
a barbiturate sedative, e.g. amobarbital, aprobarbital, butabarbital, butabital, mephobarbital, metharbital, methohexital, pentobarbital, phenobartital, secobarbital, talbutal, theamylal or thiopental;
a benzodiazepine having a sedative action, e.g. chlordiazepoxide, clorazepate, diazepam, flurazepam, lorazepam, oxazepam, temazepam or triazolam;
an $H_1$ antagonist having a sedative action, e.g. diphenhydramine, pyrilamine, promethazine, chlorpheniramine or chlorcyclizine;
a sedative such as glutethimide, meprobamate, methaqualone or dichloralphenazone;
a skeletal muscle relaxant, e.g. baclofen, carisoprodol, chlorzoxazone, cyclobenzaprine, methocarbamol or orphrenadine;
an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;
an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;
a tricyclic antidepressant, e.g. desipramine, imipramine, amitriptyline or nortriptyline;
an anticonvulsant, e.g. carbamazepine, lamotrigine, topiratmate or valproate;
a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro- 3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);
a muscarinic antagonist, e.g. oxybutynin, tolterodine, propiverine, tropsium chloride, darifenacin, solifenacin, temiverine and ipratropium;
a COX-2 selective inhibitor, e.g. celecoxib, rofecoxib, parecoxib, valdecoxib, deracoxib, etoricoxib, or lumiracoxib;
a coal-tar analgesic, in particular paracetamol;
a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;
a vanilloid receptor agonist (e.g. resinferatoxin) or antagonist (e.g. capsazepine);
a beta-adrenergic such as propranolol;
a local anaesthetic such as mexiletine;
a corticosteroid such as dexamethasone;
a 5-HT receptor agonist or antagonist, particularly a 5-HT$_{1B/1D}$ agonist such as eletriptan, sumatriptan, naratriptan, zolmitriptan or rizatriptan;
a 5-HT$_{2A}$ receptor antagonist such as R(+)-alpha-(2,3-dimethoxy-phenyl)-1-[2-(4-fluorophenylethyl)]-4-piperidinemethanol (MDL-100907);
a 5-HT$_3$ antagonist, such as ondansetron
a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
Tramadol®;
a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1:6,1]pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;
an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;
metabotropic glutamate subtype 1 receptor (mGluR1) antagonist;
a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;
a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;
an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;
an acetylcholinesterase inhibitor such as donepezil;
a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;
a microsomal prostaglandin E synthase type 1 (mPGES-1) inhibitor;
a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,
a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid,
$Cs_2CO_3$ is caesium carbonate;
$Cu(acac)_2$ is copper (II) acetylacetonate;
CuI is copper (I) iodide;
$Cu(OAc)_2$ is copper (II) acetate;
DAD is diode array detector;
DCM is dichloromethane; methylene chloride;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCI is 1-(3-dimethylaminopropyl)-3-ethylcarbodiimide hydrochloride;
EDTA is ethylenediaminetetraacetic acid;
ELSD is evaporative light scattering detection;
$Et_2O$ is diethyl ether;
EtOAc is ethyl acetate;
EtOH is ethanol;
HCl is hydrochloric acid;
IPA is isopropanol;
$Ir_2(OMe)_2COD_2$ is bis(1,5-cyclooctadiene)di-p-methoxy-diiridium (I);
$K_2CO_3$ is potassium carbonate;
$KHSO_4$ is potassium hydrogen sulfate;
KOAc is potassium acetate;
KOH is potassium hydroxide;
$K_3PO_4$ is potassium phosphate tribasic;
LCMS is liquid chromatography mass spectrometry ($R_t$=retention time)
LiOH is lithium hydroxide;
MeOH is methanol;
$MgSO_4$ is magnesium sulfate;
NaH is sodium hydride;
$NaHCO_3$ is sodium hydrogencarbonate;
$Na_2CO_3$ is sodium carbonate;
$NaHSO_3$ is sodium bisulfate;
$NaHSO_4$ is sodium hydrogensulfate;
NaOH is sodium hydroxide;
$Na_2SO_4$ is sodium sulfate;
$NH_4Cl$ is ammonium chloride;
NMP is N-Methyl-2-pyrrolidone;
Pd/C is palladium on carbon;
$Pd(PPh_3)_4$ is palladium tetrakis;
$Pd(dppf)_2Cl_2$ is [1,1'-bis(diphenylphosphino)ferrocene]dichloropalladium(II), complex with dichloromethane;
TBME is tert-butyl methy ether;
THF is tetrahydrofuran;
THP is tetrahydropyran;
TLC is thin layer chromatography; and
WSCDI is 1-(3-dimethylaminopropyl)-3-ethylcarbodiimide hydrochloride.

[1]H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; $d_6$-DMSO, deuterodimethylsulphoxide; and $CD_3OD$, deuteromethanol.

Mass spectra, MS (m/z), were recorded using either electrospray ionisation (ESI) or atmospheric pressure chemical ionisation (APCI). When relevant, and unless stated otherwise, the m/z data provided are for isotopes $^{19}F$, $^{35}Cl$ and $^{79}Br$.

Automated Preparative High Performance Liquid Chromatography (Auto-HPLC)

Certain compounds of the Examples and Preparations were purified using Automated Preparative High Performance Liquid Chromatography (HPLC). Reversed-phase HPLC conditions were either on FractionLynx systems or on a Trilution system.

In the case of the Fractionlynx system, Samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 μm). B-HPLC was carried out on an Xterra Prep MS C18 (19×100 mm, 5 μm), both from Waters. A flow rate of 18 mL/min was used with mobile phase A: water+

0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 30 v | Capillary: 3.20 kv |
| ES− Cone voltage: −30 v | Capillary: −3.00 kv |
| Desolvation gas: 600 L/hr | |
| Source Temp: 120° C. | |
| Scan range 150-900 Da | |

The fraction collection was triggered by both MS and ELSD.

Quality control (QC) analysis was performed using a LCMS method. Acidic runs were carried out on a Sunfire C18 (4.6×50 mm, 5 µm), basic runs were carried out on a Xterra C18 (4.6×50 mm, 5 µm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 25 v | Capillary: 3.30 kv |
| ES− Cone voltage: −30 v | Capillary: −2.50 kv |
| Desolvation gas: 800 L/hr | |
| Source Temp: 150° C. | |
| Scan range 160-900 Da | |

Where the reversed-phase Trilution system was used (T-HPLC) the conditions were as follows:
 Mobile phase A: 0.1% formic acid in water
 Mobile phase B: 0.1% formic acid in acetonitrile
 Column: Phenomenex C18 Luna 21.5 mm×15 cm with 5 micron particle size
 Gradient: 95-5% A over 15 min, 15 min hold, 15 mL/min flow rate
 UV: 200 nm-400 nm
 Temperature: Room temperature Liquid Chromatography Mass Spectrometry Unless carried out by Auto-HPLC (under conditions of A-HPLC or B_HPLC) as described just above, or as specifically set out in the Examples and Preparations that follow, LCMS conditions were run according to one of the conditions given below (where ratios of solvents are given, the ratios are by volume):

Acidic 2 Minute LCMS
 Mobile phase A: 0.1% formic acid in water
 Mobile phase B: 0.1% formic acid in 70% methanol:30% isopropanol
 Column: C18 phase Phenomenex 20×4.0 mm with 3 micron particle size
 Gradient: 98-10% A over 1.5 min, 0.3 min hold, 0.2 re-equiilbration, 2 mL/min flow rate
 UV: 210 nm-450 nm DAD
 Temperature: 75° C.
 Or
 Mobile phase A: 0.1% formic acid in water
 Mobile phase B: 0.1% formic acid in acetonitrile
 Column: C18 phase Phenomenex 20×4.0 mm with 3 micron particle size
 Gradient: 70-2% A over 1.5 min, 0.3 min hold, 0.2 re-equilibration, 1.8 mL/min flow rate
 UV: 210 nm-450 nm DAD
 Temperature: 75° C.

Acidic 4.5 Minute LCMS
 Mobile phase A: 0.05% formic acid in water
 Mobile phase B: acetonitrile
 Column: Phenomenex Gemini C18 45×45 mm with 5 micron particle size
 Gradient: 80-50% A over 0.5 min, 50-2% A over 3 min, 1 min hold, 0.2 min re-equilibration, 2.0 mL/min flow rate
 UV: 220 nm-254 nm DAD
 Temperature: 40° C.

Acidic 8 Minute LCMS
 Mobile phase A: 0.05% formic acid in water
 Mobile phase B: acetonitrile
 Column: Phenomenex Gemini C18 45×45 mm with 5 micron particle size
 Gradient: 80-50% A over 0.5 min, 50-2% A over 3 min, 4.5 min hold, 0.2 min re-equilibration, 2.0 mL/min flow rate
 UV: 220 nm-254 nm DAD
 Temperature: 40° C.

Acidic 6 Minute LCMS
 Mobile phase A: 0.1% formic acid in water
 Mobile phase B: 0.1% formic acid in acetonitrile
 Column: C18 phase Waters Sunfire 50×4.6 mm with 5 micron particle size
 Gradient: 95-5% A over 3 min, 1 min hold, 2 min re-equilibration, 1.5 mL/min flow rate
 UV: 210 nm-450 nm DAD
 Temperature: 50° C.

Basic 6 Minute LCMS
 Mobile phase A: 0.1% ammonium hydroxide in water
 Mobile phase B: 0.1% ammonium hydroxide in acetonitrile
 Column: C18 phase Fortis 50×4.6 mm with 5 micron particle size
 Gradient: 95-5% A over 3 min, 1 min hold, 2 min re-equilibration, 1 mL/min flow rate
 UV: 210 nm-450 nm DAD
 Temperature: 50° C.

Acidic 30 Minute LCMS
 Mobile phase A: 0.1% formic acid in water
 Mobile phase B: 0.1% formic acid in acetonitrile
 Column: Phenomenex C18 phase Gemini 150×4.6 mm with 5 micron particle size
 Gradient: 98-2% A over 18 min, 2 min hold, 1 mL/min flow rate
 UV: 210 nm-450 nm DAD
 Temperature: 50° C.

Basic 30 Minute LCMS
 Mobile phase A: 10 mM ammonium acetate in water
 Mobile phase B: 10 mM ammonium acetate in methanol
 Column: Phenomenex Phenyl Hexyl 150×4.6 mm with 5 micron particle size Gradient: 98-2% A over 18 min, 2 min hold, 1 mL/min flow rate UV: 210 nm-450 nm DAD Temperature: 50° C.

In the tabulated experimental details that follow, the Examples and Preparations were prepared according to the corresponding reference method (i.e. Method A, Method B, Preparation 15, and so on). The skilled person will appreciate that, in the synthesis of any specific Example or Preparation, it may be desirable to make minor variations to the reaction conditions of the reference method (e.g. with regard to solvent, temperature and so on).

EXAMPLE 1

4-[(5-Chloro-6-isobutoxypyridin-3-yl)oxy]-3-cyano-N-(methylsulfonyl)benzamide

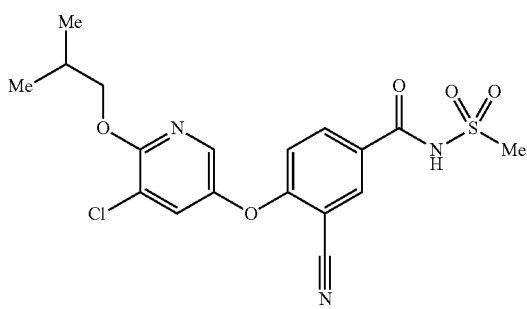 [SMILES: CC(C)COc1ncc(Oc2ccc(C(=O)NS(C)(=O)=O)cc2C#N)cc1Cl]

Method A

4-[(5-Chloro-6-isobutoxypyridin-3-yl)oxy]-3-cyanobenzoic acid (Preparation 1, 0.17 g, 0.49 mmol), methanesulfonamide (0.093 g, 0.98 mmol) and N-ethyl-N-isopropylpropan-2-amine (0.175 mL, 1.0 mmol) were suspended in dichloromethane (3.0 mL). N-[(dimethylamino) (3H-[1,2,3]triazolo[4,5-b]pyridin-3-yloxy)methylene]-N-methylmethanaminium hexafluorophosphate (0.195 g, 0.51 mmol) was then added and the mixture stirred at room temperature under nitrogen for 3 hours. The reaction mixture was concentrated in vacuo and the residue taken up in EtOAc (15.0 mL) and washed twice with an aqueous solution of hydrochloric acid (2.0M, 10.0 mL). The organic layer was then dried over sodium sulfate, filtered, and concentrated in vacuo. The crude residue was dissolved in EtOAc (1.0 mL) then heptane (10.0 mL) was added slowly until formation of a solid. The solid was collected by filtration and then further purified by silica gel column chromatography (ISCO®, gradient of 0-50% EtOAc in heptane, 12 g) to afford the title compound as a white solid (0.038 g, 18%):

$^1$H NMR (400 MHz, $d_6$-DMSO): δ 0.98 (s, 3H), 1.00 (s, 3H), 2.04-2.09 (m, 1H), 3.35 (s, 3H), 4.12 (d, 2H), 7.07 (d, 1H), 8.10-8.13 (m, 2H), 8.18 (d, 1H), 8.45 (d, 1H).

LCMS Rt=1.93 minutes MS m/z 424 [MH]$^+$

EXAMPLE 2

4-({5-Chloro-6-[(3,3-difluorocyclobutyl)methoxy]pyridin-3-yl}oxy)-2,5-difluoro-N-(methylsulfonyl)benzamide

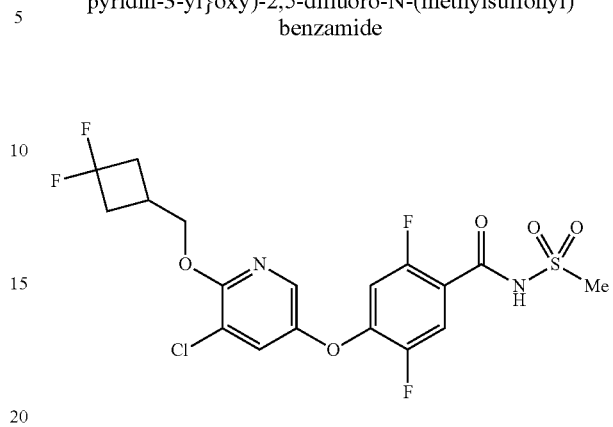

Method B 4-({5-Chloro-6-[(3,3-difluorocyclobutyl)methoxy]pyridin-3-yl}oxy)-2,5-difluorobenzoic acid (Preparation 8, 0.155 g, 0.38 mmol), N-[3-(dimethylamino)propyl]-N'-ethylcarbodiimide hydrochloride (0.110 g, 0.57 mmol), DMAP (0.070 g, 0.57 mmol) and N-ethyl-N-isopropylpropan-2-amine (0.243 mL, 1.4 mmol) were dissolved in dichloromethane (10.0 mL). Then methanesulfonamide (0.054 g, 0.57 mmol) was added and the mixture was stirred at room temperature under nitrogen for 16 hours. The solvent was removed in vacuo. The residue was purified by reverse phase preparative HPLC (Trilution method) to afford the title compound (0.073 g, 43%).

$^1$H NMR (400 MHz, $d_6$-DMSO): δ 2.40-2.60 (m, 2H), 2.60-2.80 (m, 3H), 3.30 (s, 3H), 4.40 (m, 2H), 7.15 (m, 1H), 7.75 (m, 1H), 8.00 (s, 1H), 8.10 (s, 1H)

LCMS Rt=4.36 minutes MS m/z 481 [M]$^-$

EXAMPLE 3

4-[(5-Chloro-6-isopropoxypyridin-3-yl)oxy]-2,5-difluoro-N-(methylsulfonyl)benzamide

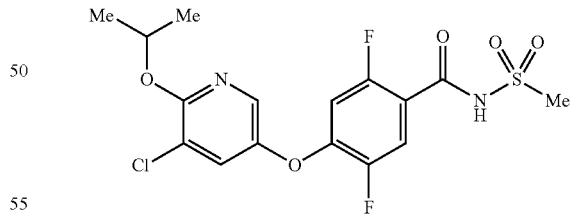

Method C

To a solution of methanesulfonamide (441 mg, 4.64 mmol) in anhydrous tetrahydrofuran (18 mL) was added sodium hydride (60% dispersion in oil, 186 mg, 4.64 mmol) and 4-methyl phenyl 4-[(5-chloro-6-isopropoxypyridin-3-yl)oxy]-2,5-difluorobenzoate (Preparation 9, 1.006 g, 2.32 mmol). The reaction mixture was heated to 65° C. and stirred for 16 hours. The reaction was cooled to 0° C. before the addition of 1M aqueous solution of hydrogen chloride (20 mL) and EtOAc (20 mL). The organics were separated, dried over sodium sulfate and concentrated in vacuo to a colourless solid. The crude material was dissolved in dichloromethane (10 mL), washed with water (2×5 mL) and dried over sodium sulfate. The organics were concentrated in vacuo to give a colourless solid which was slurried in 9:1 heptane/acetone (14 mL). The solid was filtered, washed with cold eluent (9:1 heptane/acetone, 10 mL) and dried to afford the title compound as a colourless solid (792 mg):

$^1$H NMR (400 MHz, CDCl$_3$): δ 1.42-1.43 (d, 6H), 3.44 (s, 3H), 5.30-3.39 (m, 1H), 6.63-6.68 (m, 1H), 7.48-7.49 (d, 1H), 7.92-7.97 (m, 2H), 8.70-8.73 (d, 1H).

LCMS Rt=1.58 minutes MS m/z 421 [MH]$^+$, 419 [M−H]$^−$

EXAMPLE 4

3-Chloro-N-(methylsulfonyl)-4-[(2-piperidin-1-ylpyrimidin-5-yl)oxy]benzamide

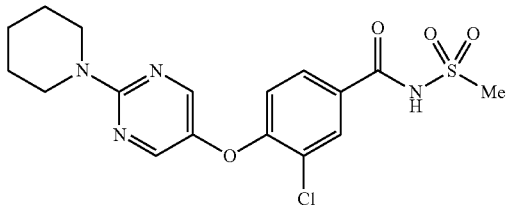 [SMILES: CS(=O)(=O)NC(=O)c1ccc(Oc2cnc(N3CCCCC3)nc2)c(Cl)c1]

To a solution of methyl 3-chloro-4-fluorobenzoate (23.6 mg, 0.125 mmol) and 2-piperidin-1-ylpyrimidin-5-ol (Preparation 10, 22.4 mg 0.125 mmol) in pyridine (0.5 mL) were added cesium carbonate (122 mg, 0.375 mmol) and copper powder (16 mg, 0.25 mmol) and the reaction mixture was shaken at 120° C. for 16 hours. The reaction mixture was filtered and evaporated in vacuo. Water (1 mL) was added and the mixture extracted with EtOAc (3×1 mL). The combined organic layers were dried over magnesium sulfate, filtered and evaporated in vacuo. The residue was dissolved in tetrahydrofuran (0.7 mL), aqueous lithium hydroxide solution (0.7 mL of a 1M solution, 0.7 mmol) was added and the reaction shaken at 30° C. for 16 hours. The reaction was evaporated in vacuo and a 1 M aqueous solution of hydrochloric acid (0.7 mL) was added. The mixture was extracted three times with EtOAc (3×1 mL), the combined organic layers were dried over magnesium sulfate, filtered and evaporated in vacuo. The resulting residue, methanesulfonamide (11.9 mg, 0.125 mmol), DMAP (45.8 mg, 0.375 mmol) and 1-(3-dimethylaminopropyl)-3-ethylcarbodiimide hydrochloride (55 mg, 0.28 mmol) were dissolved in dichloromethane (1 mL) and shaken at 30° C. for 16 hours before evaporation in vacuo. The residue purified on a HPLC column (YMC-pack ODS-AQ 150*30 mm*5 μm, acetonitrile-water (0.1% trifluoroacetic acid) gradient) to afford the title compound (5.23 mg, 12.7 μmol).

LCMS Rt=3.331 minutes MS m/z 411 [MH]$^+$

LCMS conditions

| Column | Welch XB-C18 2.1 × 50 mm 5 μm |
|---|---|
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 10% B |
| Time 0.00 mins | 10% B |
| Time 0.50 mins | 10% B |
| Time 4.00 mins | 100% B |
| Time 4.30 mins | 10% B |
| Time 4.70 mins | 10% B |
| Flow rate | 0.8 mL/min |
| Injection volume | 2 μl |
| Agilent | 1200 HPLC/1956 MSD/SEDEX 75 ELSD |
| Ionization Mode | API-ES |
| Polarity | Positive |

EXAMPLE 5

5-Chloro-2-fluoro-N-(methylsulfonyl)-4-(quinolin-3-yloxy)benzamide

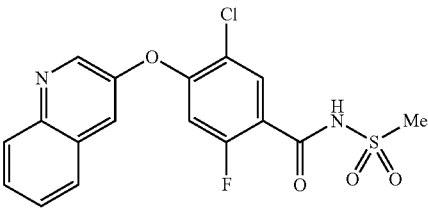 [SMILES: CS(=O)(=O)NC(=O)c1cc(Cl)c(Oc2cnc3ccccc3c2)cc1F]

To a solution of quinolin-3-ol (18.1 mg, 0.125 mmol) and methyl 5-chloro-2,4-difluorobenzoate (Preparation 11, 25.9 mg, 0.125 mmol) in pyridine (0.5 mL) were added cesium carbonate (82 mg, 0.25 mmol) and 16 mg (0.25 mmol) copper powder (16 mg, 0.25 mmol) and the resulting mixture was shaken at 120° C. for 16 hours. After cooling, the mixture was filtered and evaporated in vacuo. Water (1 mL) was added and the mixture extracted 3 times with EtOAc (3×1 mL), the combined organic layers were dried over anhydrous sodium sulfate, filtered and evaporated in vacuo.

To a solution of this residue in THF (0.7 mL) was added a 1M aqueous solution of lithium hydroxide (0.7 mL) and the mixture was shaken at 30° C. for 16 hours. The reaction mixture was evaporated in vacuo, 1M aqueous hydrochloric acid (0.7 mL) was added and extracted with EtOAc (3×1 mL). The combined organic layers were dried over anhydrous sodium sulfate, filtered and evaporated in vacuo.

To this residue were added methanesulfonamide (28.6 mg 0.300 mmol) and a solution of DMAP (24.4 mg, 0.200 mmol) and EDCI (38.3 mg, 0.200 mmol) in dichloromethane (1 mL). The solution was shaken at 30° C. for 16 hours and evaporated in vacuo. The resulting residue was purified on a HPLC column (Sepax BR-C18 100*21.2 mm*5 μm, acetonitrile-water (0.1% trifluoroacetic acid) gradient) to afford the title compound (3.81 mg, 7.50 μmol).

LCMS Rt=2.099 minutes MS m/z 393 [M−H]$^−$

LCMS method

| Column | Welch XB-C18 2.1 × 50 mm 5 μm |
|---|---|
| Temperature | 50° C. |
| Mobile Phase A | 0.05% NH4OH in water |
| Mobile Phase B | 100% acetonitrile |
| Gradient - Initial | 5% B |
| Time 0.00 min | 5% B |
| Time 0.50 min | 5% B |
| Time 3.40 min | 100% B |
| Time 4.20 min | 100% B |
| Time 4.21 min | 5% B |
| Time 4.70 min | 5% B |

| | |
|---|---|
| Flow rate | 0.8 mL/min |
| Injection volume | 2 μl |
| Agilent | 1200 HPLC/1956 MSD/SEDEX 75 ELSD |
| Ionization Mode | API-ES |
| Polarity | Negative |

EXAMPLE 6

2,5-Difluoro-N-(methylsulfonyl)-4-[(6-nitropyridin-3-yl)oxy]benzamide

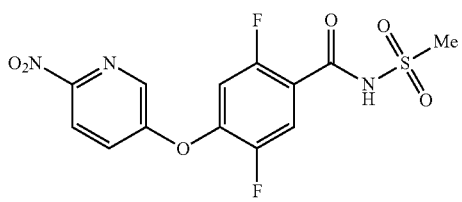 [SMILES: CS(=O)(=O)NC(=O)c1cc(F)c(Oc2ccc([N+](=O)[O-])nc2)cc1F]

Potassium carbonate (0.220 g, 1.59 mmol) was added to a stirred solution of 2,5-difluoro-4-hydroxy-N-(methylsulfonyl)benzamide (Preparation 34, 0.200 g, 0.796 mmol) and 5-bromo-2-nitropyridine (0.170 g, 0.836 mmol) in DMSO (2.5 mL) at room temperature. The mixture was stirred at room temperature for 2 hours and then at 60° C. for 24 hours. The reaction mixture was partitioned between EtOAc and 2M aqueous HCl ensuring the water layer was acidic. The organic layer was separated and washed further with citric acid, water and brine, then dried over magnesium sulfate, filtered, evaporated in vacuo and triturated in diethyl ether to yield the title compound (0.180 g, 60%):

$^1$H NMR (400 MHz, CDCl$_3$): δ 3.28 (s, 3H), 6.90-6.98 (m, 1H) 7.45 (d, 1H) 7.62-7.70 (m, 1H) 8.25 (d, 1H) 8.30 (s, 1H) MS m/z 372 [M–H]$^-$

EXAMPLE 7

5-Chloro-4-{[5-chloro-6-(1-fluoro-1-methylethyl)pyridin-3-yl]oxy}-2-fluoro-N-(methylsulfonyl)benzamide

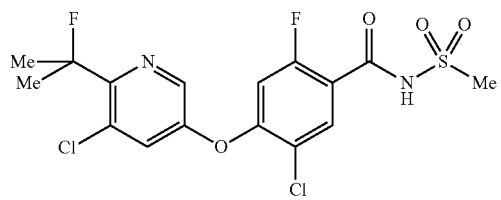 [SMILES: CC(C)(F)c1ncc(Oc2cc(F)c(C(=O)NS(C)(=O)=O)cc2Cl)cc1Cl]

Method E

Potassium tert-butoxide (6.4 mg, 0.057 mmol) was added to a suspension of methanesulfonamide (5.4 mg, 0.057 mmol) in THF (1.0 mL) and the mixture stirred at room temperature for 15 minutes. Then 4-methylphenyl 5-chloro-4-{[5-chloro-6-(1-fluoro-1-methylethyl)pyridin-3-yl]oxy}-2-fluorobenzoate (Preparation 36, 20.8 mg, 0.046 mmol) was added and the mixture stirred at 60° C. for 6 hours. Methanesulfonamide (2.7 mg, 0.029 mmol) and potassium tert-butoxide (3.2 mg, 0.029 mmol) were added and the mixture stirred for 2 hours more. The reaction was left stirring at room temperature for 16 hours, then concentrated in vacuo and the residue partitioned between DCM (15 mL) and 10% aqueous citric acid solution (15 mL). The organic layer was then washed with water (15 mL), dried over sodium sulfate, filtered and concentrated in vacuo to yield a crude oil. The oil was triturated in heptane (10 mL) to yield the title compound as a white solid (5.6 mg, 7%):

$^1$H NMR (400 MHz; CD$_3$OD): δ 1.78-1.83 (d, 6H), 3.36 (s, 3H), 7.08-7.11 (d, 1H), 7.61 (d, 1H), 7.93-7.95 (d, 1H), 8.26-8.27 (d, 1H)

LCMS Rt=1.70 minutes MS m/z 439 [MH]$^+$

EXAMPLE 8

5-Chloro-4-[(5-cyano-6-isopropoxypyridin-3-yl)oxy]-2-fluoro-N-(methylsulfonyl)benzamide

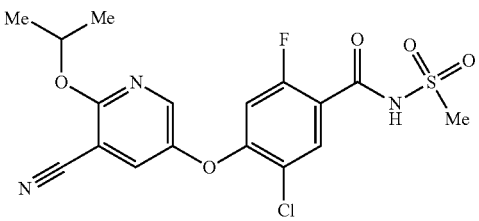 [SMILES: CC(C)Oc1ncc(Oc2cc(F)c(C(=O)NS(C)(=O)=O)cc2Cl)cc1C#N]

Method F

Potassium carbonate (232 mg, 1.68 mmol) was added to 5-hydroxy-2-isopropoxynicotinonitrile (Preparation 76, 100 mg, 0.56 mmol) and 5-chloro-2,4-difluoro-N-(methylsulfonyl)benzamide (Preparation 28, 150 mg, 0.56 mmol) in DMSO (7 mL) and the mixture was heated at 90° C. for 16 hours. The reaction was quenched by pouring it into saturated aqueous ammonium chloride (15 mL) and extracted with DCM (3×30 mL). The combined organics were washed with brine (2×30 mL), dried over sodium sulfate, filtered and concentrated in vacuo. The crude was purified by silica gel chromatography eluting with 0 to 5% MeOH in DCM to afford the title compound as a white solid (29 mg, 12%):

$^1$H NMR (400 MHz, d$_6$-DMSO): δ 1.37 (d, 6H), 5.34 (m, 1H), 7.14 (d, 1H), 7.93 (d, 1H), 8.31 (d, 1H), 8.43 (d, 1H), 12.30 (br, 1H). CH$_3$—SO$_2$ masked by the water at 3.33 ppm in d$_6$-DMSO.

LCMS Rt=2.64 minutes MS m/z 426 [M–H]

EXAMPLE 9

4-{[5-Chloro-6-(trifluoromethyl)pyridin-3-yl]oxy}-N-(methylsulfonyl)benzamide

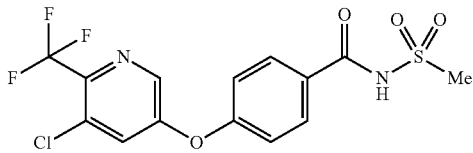 [SMILES: CS(=O)(=O)NC(=O)c1ccc(Oc2cnc(C(F)(F)F)c(Cl)c2)cc1]

Method G

Methanesulfonamide (8.4 mg, 0.088 mmol) and bis(tert-butylcarbonyloxy)iodobenzene (38.5 mg, 0.095 mmol) were dissolved in isopropylacetate (2.50 mL). 4-{[5-Chloro-6-(trifluoromethyl)pyridin-3-yl]oxy}benzaldehyde (Preparation 33, 26.5 mg, 0.088 mmol) was added and the mixture was stirred for 5 minutes. (Bis[rhodium(α,α,α',α'-tetramethyl-1,3-benzenedipropionic acid)]) (Rh$_2$(esp)$_2$) (4.5 mg, 0.006 mmol) was added and the mixture stirred at room temperature for 2 hours. The reaction mixture was concentrated in vacuo to yield the title compound, which was purified by A-HPLC:

LCMS Rt=2.29 minutes MS m/z 393 [M−H]$^-$, 395 [MH]$^+$

EXAMPLE 10

5-Chloro-4-{[5-chloro-6-(oxetan-3-yloxy)pyridin-3-yl]oxy}-2-fluoro-N-(methylsulfonyl)benzamide

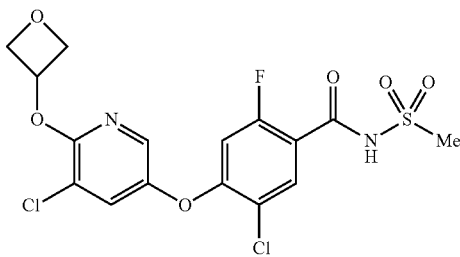 [SMILES: CS(=O)(=O)NC(=O)c1cc(Cl)c(Oc2cnc(OC3COC3)c(Cl)c2)cc1F]

Method H

5-Chloro-4-[(5-chloro-6-fluoropyridin-3-yl)oxy]-2-fluoro-N-(methylsulfonyl)benzamide (Example 19, 0.147 g, 0.37 mmol), oxetan-3-ol (0.082 g, 1.11 mmol) and Cs$_2$CO$_3$ (0.362 g, 1.11 mmol) were suspended in DMSO (1.0 mL) in a sealed vial and heated at 100° C. for 1 hour. The reaction was diluted with EtOAc (15 mL) and washed with 10%, aqueous citric solution (10 mL), and water (10 mL). The organic layer was dried over sodium sulfate, filtered and concentrated in vacuo to yield a solid (175 mg). The solid was triturated with heptane/acetone (9:1), then TBME, DCM and MeOH to yield the title compound as a white solid (19 mg, 11%). The filtrates were combined and concentrated in vacuo to yield a crude solid, which was purified by reverse phase chromatography (13 g C$_{18}$ Redisep©) eluting with 5 to 80% MeCN in water. The fractions were combined, diluted with EtOAc (300 mL), washed with 10%, aqueous citric solution (10 mL), water (2×10 mL). The organic layer was dried over sodium sulfate, filtered and concentrated in vacuo to yield a crude solid (100 mg), which was triturated in MeOH (3 mL) to yield the title compound as a white solid (45 mg, 27%). Overall yield is 64 mg (38%):

LCMS Rt=1.54 minutes. MS m/z 451 [MH]$^+$ $^1$H NMR (400 MHz, CD$_3$OD): δ 3.35 (s, 3H), 4.73-4.77 (m, 2H), 5.00-5.03 (m, 2H), 5.64-5.70 (m, 1H), 6.83-6.86 (d, 1H), 7.76-7.77 (d, 1H), 7.89-7.91 (m, 2H)

EXAMPLE 11

4-({5-Chloro-6-[isopropyl(methyl)amino]pyridin-3-yl}oxy)-2,5-difluoro-N-(methylsulfonyl)benzamide

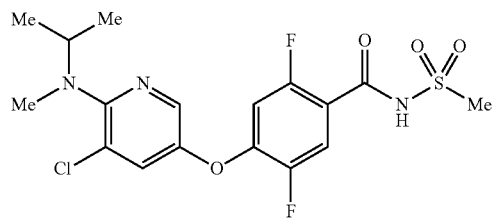 [SMILES: CC(C)N(C)c1ncc(Oc2cc(F)c(C(=O)NS(C)(=O)=O)cc2F)cc1Cl]

Method I

Triethylamine (35 μL, 0.25 mmol) and isopropylmethylamine (15 μL, 0.14 mmol) were added to a solution of 4-[(5-chloro-6-fluoropyridin-3-yl)oxy]-2,5-difluoro-N-(methylsulfonyl)benzamide (Preparation 30, 0.040 g, 0.105 mmol) in DMSO (1.00 mL) and the mixture was stirred at 60° C. for 16 hours in a sealed vial. Isopropylmethylamine (15 μL, 0.14 mmol) was added and the mixture stirred at 70° C. for 16 hours. Isopropylmethylamine (15 μL, 0.14 mmol) was further added and the mixture stirred at 70° C. for 16 hours. The reaction mixture was then partitioned between EtOAc (10 mL) and water (10 mL). The organic layer was washed with brine (20 mL), dried over sodium sulfate, filtered and concentrated in vacuo. It was purified by reverse phase chromatography (13 g C18 Redisep©) eluting with 5 to 70% MeCN in water to yield a white solid (250 mg) that was suspended in water, sonicated for 10 minutes and filtered to yield the title compound as a white solid (7.0 mg, 15%):

$^1$H NMR (400 MHz; d$^6$-DMSO): δ 1.12-1.14 (d, 6H), 2.71 (s, 3H), 3.34 (s, 3H), 3.98-4.05 (m, 1H), 7.10-7.15 (q, 1H), 7.72-7.77 (q, 1H), 7.79-7.80 (d, 1H), 8.13-8.14 (d, 1H), 12.22 (br, 1H).

LCMS Rt=1.60 minutes. MS m/z 434 [MH]$^+$

EXAMPLE 12

4-{[5-Chloro-6-(2,2,2-trifluoro-1-methylethoxy)pyridin-3-yl]oxy}-2,5-difluoro-N-(methylsulfonyl)benzamide

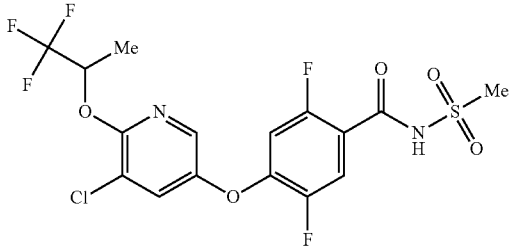 [SMILES: CC(Oc1ncc(Oc2cc(F)c(C(=O)NS(C)(=O)=O)cc2F)cc1Cl)C(F)(F)F]

Method J

NaH (0.023 g, 0.57 mmol) and 1,1,1-trifluoropropan-2-ol (0.03 mL, 0.29 mmol) were added to a solution of 4-[(5-chloro-6-fluoropyridin-3-yl)oxy]-2,5-difluoro-N-(methylsulfonyl)benzamide (Preparation 30, 0.055 g, 0.14 mmol) in THF and the mixture was stirred at room temperature for 18 hours. The reaction mixture was diluted in EtOAc (10 mL) and washed with water (2×5 mL). The organic layer was dried over sodium sulfate, filtered, and concentrated in vacuo. The resulting crude product was purified by preparative HPLC to afford the title compound:

LCMS Rt=3.36 minutes. MS m/z 473 [M–H]⁻

EXAMPLE 13

5-Chloro-4-{[5-chloro-6-(3,3,3-trifluoropropoxy)pyridin-3-yl]oxy}-2-fluoro-N-(methylsulfonyl)benzamide

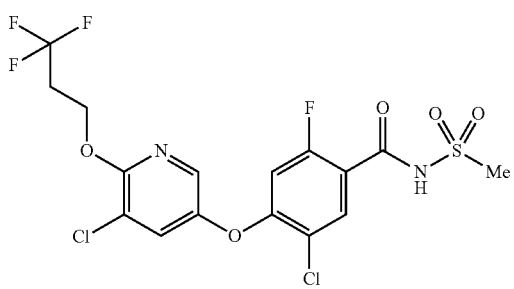 [SMILES: CS(=O)(=O)NC(=O)c1cc(Cl)c(Oc2cnc(OCCC(F)(F)F)c(Cl)c2)cc1F]

Method D

4-Methylphenyl 5-chloro-2,4-difluorobenzoate (Preparation 26, 150 mg, 0.53 mmol) was added to a DMSO (5 mL) solution of 5-chloro-6-(3,3,3-trifluoropropoxy)pyridin-3-ol (Preparation 95, 134 mg, 0.56 mmol) and K$_2$CO$_3$ (147 mg, 1.06 mmol). The reaction mixture was stirred at room temperature for 1.5 hours. Then, DBU (135 L, 0.90 mmol) and methanesulfonamide (56 mg, 0.58 mmol) were added to the reaction and heated for 2 hrs at 50° C. The reaction was quenched with water and extracted with EtOAc. Combined organics were dried and concentrated in vacuo. The resulting residue was purified by reverse phase chromatography to afford the title compound as a white solid (170 mg):

¹H NMR (400 MHz, d$_6$-DMSO): δ 2.80 (m, 2H), 3.40 (s, 3H), 4.60 (m, 2H), 7.10 (m, 1H), 7.95 (m, 1H), 8.00 (m, 1H), 8.15 (m, 1H).

LCMS Rt=3.13 minutes MS m/z 489 [M–H]⁻

EXAMPLE 14

4-[(5-Chloro-6-isobutoxypyridin-3-yl)oxy]-N-(methylsulfonyl)benzamide

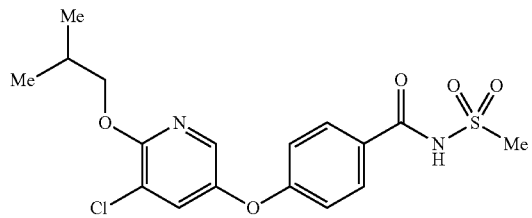 [SMILES: CC(C)COc1ncc(Oc2ccc(C(=O)NS(C)(=O)=O)cc2)cc1Cl]

Method L

A lithium bis(trimethylsilyl)amide solution in THF (0.66 mL, 0.66 mmol) was added to a solution of 4-[(5-chloro-6-isobutoxypyridin-3-yl)oxy]benzamide (Preparation 31, 0.090 g, 0.281 mmol) in THF (3 mL) at room temperature. After 30 minutes, methanesulphonyl chloride (0.052 mL, 0.672 mmol) was added and the mixture stirred for 16 hours at room temperature. The reaction mixture was concentrated in vacuo, dissolved in DMSO (1.5 mL) and purified by reverse phase chromatography (26 g C18 Redisep©) eluting with 5 to 95% MeCN (with 5% ammonia) in water. Fractions bearing product were combined and concentrated in vacuo. The residue was then partioned between EtOAc (15 mL) and aqueous HCl (2 M, 15 mL). The organic layer was dried over sodium sulfate, filtered and concentrated in vacuo to yield the title compound as a solid (18.5 mg, 17%):

¹H NMR (400 MHz; CD$_3$OD): δ 1.04 (s, 3H), 1.05 (s, 3H), 1.28 (t, 3H), 2.11 (m, 1H), 3.35 (s, 3H), 4.14 (d, 2H), 7.05 (m, 1H), 7.64 (d, 1H), 7.90-7.93 (m, 3H).

LCMS Rt=1.64 minutes. MS m/z 399 [MH]⁺

EXAMPLE 15

4-(5-Chloro-6-methoxypyridin-3-yloxy)-N-(cyclopropylsulfonyl)-2,5-difluorobenzamide diethylamine salt

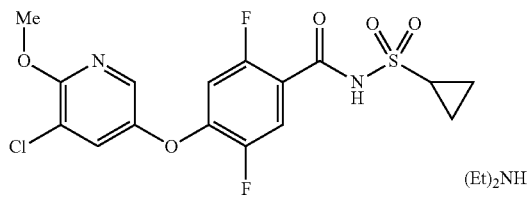 [SMILES: "(Et)2NH" ; COc1ncc(Oc2cc(F)c(C(=O)NS(=O)(=O)C3CC3)cc2F)cc1Cl]

Cyclopropane sulfonamide (282.2 mg, 2.33 mmol) was added to a mixture of the lithium salt of 4-(5-chloro-6-methoxypyridin-3-yloxy)-2,5-difluorobenzoic acid (Preparation 17, 59.2 mg, 0.176 mmol), N-[(dimethylamino)(3H-[1,2,3]triazolo[4,5-b]pyridin-3-yloxy)methylene]-N-methylmethanaminium hexafluorophosphate (0.174 g, 0.458 mmol), N,N-diisopropylethylamine (418 μL, 2.40 mmol) and 4-dimethylaminopyridine (6.1 mg, 0.499 mmol) in DCM (15 mL) and DMF (0.15 mL), after stirring at room temperature for 15 minutes. The reaction mixture was heated at 50° C. for 18 hours under a nitrogen atmosphere, cooled to room temperature and concentrated in vacuo. The crude residue was partitioned between aqueous HCl (0.5 M, 15 mL) and DCM (30 mL). The organic layer was washed with aqueous HCl (0.5 M, 2×15 mL), dried over sodium sulfate, filtered and concentrated in vacuo to afford a yellow solid (62 mg), which was purified by preparative B-HPLC to afford the title compound as the diethylamine salt.

LCMS Rt=3.28 minutes MS m/z 419 [MH]⁺

EXAMPLE 16

4-(5-Chloro-6-cyclobutoxypyridin-3-yloxy)-2,5-difluoro-N-(methylsulfonyl)benzamide

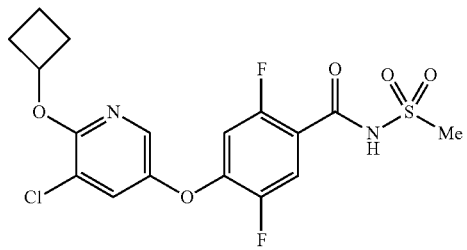 [SMILES: CS(=O)(=O)NC(=O)c1cc(F)c(Oc2cnc(OC3CCC3)c(Cl)c2)cc1F]

2,4,5-trifluoro-N-(methylsulfonyl)benzamide (Preparation 27, 0.317 g, 1.25 mmol), 5-chloro-6-cyclobutoxypyridin-3-ol (Preparation 19, 0.250 g, 1.25 mmol) and potassium carbonate (0.346 g, 2.50 mmol) were suspended in DMSO (16 mL) and heated at 90° C. for 48 hours. The reaction was diluted with water (50 mL) and extracted with EtOAc (3×20 mL). The combined organics were dried over magnesium sulfate, filtered and concentrated in vacuo. The crude residue was purified by silica gel chromatography eluting with 20% EtOAc (with 0.5% AcOH) in heptane to afford the title compound as a white solid (64 mg, 12%):

$^1$H NMR (400 MHz, CDCl$_3$): δ 1.71 (m, 1H), 1.89 (m, 1H), 2.24 (m, 2H), 2.50 (m, 2H), 3.43 (s, 3H), 5.23 (m, 1H), 6.65 (m, 1H), 7.47 (m, 1H), 7.90 (m, 1H), 7.93 (m, 1H), 8.70 (s, 1H).

LCMS Rt=3.56 minutes. MS m/z 433 [MH]$^+$

EXAMPLE 18

N-(sec-butylsulfonyl)-4-[(5-chloro-6-methoxypyridin-3-yl)oxy]-2,5-difluorobenzamide

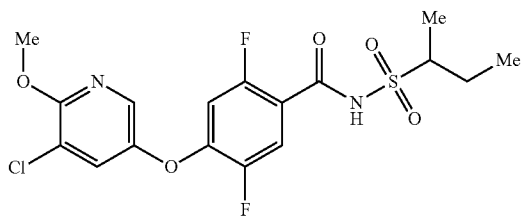 [SMILES: CCC(C)S(=O)(=O)NC(=O)c1cc(F)c(Oc2cnc(OC)c(Cl)c2)cc1F]

Potassium carbonate (0.140 g, 1.01 mmol) was added to a stirred solution of N-(sec-butylsulfonyl)-2,4,5-trifluorobenzamide (Preparation 68, 0.090 g, 0.30 mmol) in DMSO (1 mL). After 10 minutes a solution of 5-chloro-6-methoxypyridin-3-ol (Preparation 77, 0.088 g, 0.51 mmol) in DMSO (2 mL) was added at room temperature. The mixture was heated at 90° C. for 72 hours. The reaction mixture was diluted with water (25 mL) and extracted with EtOAc (3×25 mL). The combined organics were washed with water (25 mL), dried over magnesium sulfate, filtered, evaporated in vacuo. The resulting crude product was purified by silica gel chromatography eluting with 0 to 66% EtOAc in heptane to yield the title compound (0.068 g):

$^1$H NMR (400 MHz; in CDCl$_3$): δ 0.90 (m, 1H), 1.30 (m, 1H), 1.50 (m, 1H), 1.90 (m, 1H), 2.00 (m, 1H), 4.00 (s, 3H), 6.45 (m, 1H), 7.40 (s, 1H), 7.65 (m, 1H), 7.85 (s, 1H).

LCMS Rt=3.46 minutes. MS m/z 435 [MH]$^+$

EXAMPLE 19

5-Chloro-4-[(5-chloro-6-fluoropyridin-3-yl)oxy]-2-fluoro-N-(methylsulfonyl)benzamide

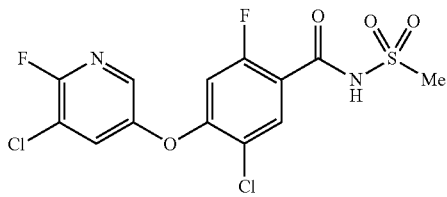 [SMILES: CS(=O)(=O)NC(=O)c1cc(Cl)c(Oc2cnc(F)c(Cl)c2)cc1F]

5-Chloro-4-(5-chloro-6-fluoropyridin-3-yloxy)-2-fluorobenzoic acid (Preparation 162, 6.100 g, 19.60 mmol), 4-dimethylaminopyridine (2.330 g, 19.06 mmol), N-[3-(dimethylamino)propyl]-N'-ethylcarbodiimide hydrochloride (5.480 g, 28.59 mmol) and methanesulfonamide (2.720 g, 28.59 mmol) were suspended in DCM (20 mL). The reaction mixture was stirred at room temperature for 18 hours, quenched with aqueous 1M HCl and extracted with EtOAc. Combined organics were concentrated in vacuo. The resulting residue was purified by reverse phase chromatography to afford the title compound as a white solid (4.50 g):

$^1$H NMR (400 MHz, d$_6$-DMSO): δ 3.40 (s, 3H), 3.10 (m, 1H), 7.95 (m, 1H), 8.20 (s, 1H), 8.30 (m, 1H).

LCMS Rt=2.93 minutes MS m/z 397 [MH]$^+$

EXAMPLE 20

5-Chloro-2-fluoro-4-[(1-isopropyl-1H-indazol-5-yl)oxy]-N-(methylsulfonyl)benzamide

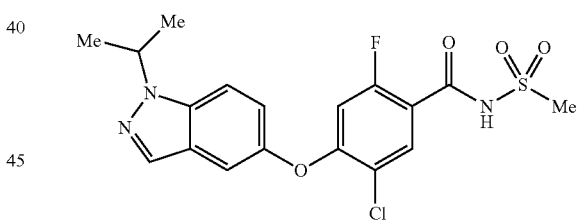

Sodium hydride (60% in mineral oil, 0.012 g, 0.306 mmol) was added to a solution of 1-isopropyl-1H-indazol-5-ol (Preparation 39, 0.045 g, 0.225 mmol) in THF (3.0 mL) while cooling the reaction in an ice bath and stirred for 40 minutes. 5-Chloro-2,4-difluoro-N(methylsulfonyl)benzamide (Preparation 28, 0.076 g, 0.28 mmol) was then added and the reaction was heated at 60° C. for 16 hours. The reaction mixture was concentrated in vacuo and the residue treated with EtOAc (25.0 mL) and washed with water (30.0 mL), followed by brine (30.0 mL). The organic layer was dried over sodium sulfate, filtered, concentrated in vacuo and the residue purified by silica gel chromatography eluting with 2% Methanol in DCM to yield the title compound as a white solid (8.3 mg):

$^1$H NMR (400 MHz, CDCl$_3$): δ 1.62 (s, 3H), 1.64 (s, 3H), 3.40 (s, 3H), 4.91-4.97 (m, 1H), 6.53 (d, 1H), 7.10 (d, 1H), 7.53 (s, 1H), 7.60 (d, 1H), 8.02 (s, 1H), 8.32 (d. 1H), 10.03 (s, 1H).

LCMS Rt=3.31 minutes. MS m/z 426 [MH]$^+$

EXAMPLE 21

5-chloro-4-[(5-chloro-6-cyclopropylpyridin-3-yl)oxy]-2-fluoro-N-(methanesulfonyl)benzamide

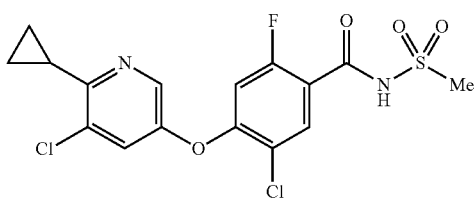

4-methyl phenyl 5-chloro-4-[(5-chloro-6-cyclopropylpyridin-3-yl)oxy]-2-fluorobenzoate (Preparation 70, 0.285 g, 0.659 mmol) and methanesulfonamide (0.069 g, 0.725 mmol) were suspended in acetonitrile (3.0 mL). 2,3,4,6,7,8,9,10-octahydropyrimido[1,2-a]azepine (0.110 mL, 0.737 mmol) was added and the mixture was stirred at 50° C. for 16 hours. The reaction mixture was concentrated in vacuo, diluted with DCM (15.0 mL), washed with water (15.0 mL), then with a 10% solution of aqueous citric acid (15.0 mL), followed by water (2×15.0 mL). The organic layer was dried over sodium sulfate, filtered and concentrated in vacuo to afford a solid, which was triturated in a heptane/acetone mixture (9:1, 10.0 mL) to yield the title compound as a white solid (0.208 g, 0.496 mmol, 75%):

LCMS Rt=1.29 minutes MS m/z 419 [MH]$^+$ $^1$H NMR (400 MHz, CDCl$_3$): δ 1.05-1.14 (m, 4H), 2.50-2.56 (m, 1H), 3.43 (s, 3H), 6.62 (d, 1H), 7.40 (d, 1H), 8.20 (d, 1H), 8.23 (d, 1H), 8.65-8.69 (br, 1H).

The compound of Example 21 was also prepared according to the following method. To a solution of 5-chloro-4-[(5-chloro-6-cyclopropylpyridin-3-yl)oxy]-2-fluorobenzoic acid (Preparation 265, 45.0 g, 131.52 mmol) in tetrahydrofuran (180 mL) at room temperature was added methansulphonamide (25.02 g, 263.04 mmol), N-ethyl-N-diisopropylpropan-2-amine (68.81 mL, 394.56 mmol) and 1-propanephosphonic acid cyclic anhydride (167.36 g, 263.04 mmol as a 50% solution in ethyl acetate) and the mixture stirred and heated at 70-75° C. for 16 hours. The reaction mixture was concentrated under reduced pressure at 45° C. and water added (450 mL), the resulting slurry was stirred for 30 minutes, filtered and dried. The crude product was dissolved in 2-propanol (1285 mL) at 85° C. and cooled slowly over 16 hours. The resulting slurry was filtered, washed with 2-propanol (2×40 mL) and dried to give the title compound as an off-white solid (46 g, 83%).

$^1$H NMR (400 MHz, CDCl$_3$): δ 1.05-1.17 (m, 4H), 2.54 (tt, 1H), 3.44 (s, 3H), 6.62 (d, 1H), 7.41 (d, 1H), 8.21 (d, 1H), 8.24 (d, 1H), 8.67 (br d, 1H)

HPLC Rt=6.14 minutes

EXAMPLE 22

5-chloro-4-{[5-chloro-6-(2,2,3,3-tetrafluoropropoxy)pyridin-3-yl]oxy}-2-fluoro-N-(methanesulfonyl)benzamide

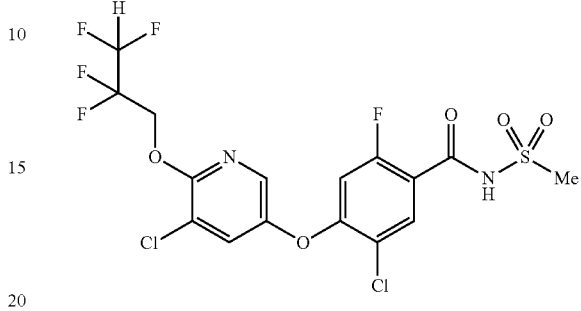

Methanesulfonamide (0.867 g, 9.12 mmol), N-ethyl-N-isopropylpropan-2-amine (2.40 mL, 13.8 mmol) and 2,4,6-tripropyl-1,3,5,2,4,6-trioxatriphosphinane 2,4,6-trioxide in EtOAc (8.15 mL, 13.7 mmol) was added to a solution of 5-chloro-4-{[5-chloro-6-(1,1,3,3-tetrafluoropropoxy)pyridin-3-yl]oxy}-2-fluorobenzoic acid (Preparation 72, 1.97 g, 4.56 mmol) in THF (40.0 mL) and the mixture stirred at reflux for 16 hours. The reaction mixture was concentrated in vacuo and then diluted with EtOAc (40.0 mL). The organics were washed with water (2×40.0 mL), dried over sodium sulfate, filtered, and concentrated in vacuo to yield a solid. The resulting solid was suspended in propan-2-ol (20.0 mL) and stirred at reflux until complete dissolution. The title compound was isolated by filtration after cooling as a pale yellow solid (1.62 g, 2.65 mmol, 58%):

LCMS Rt=2.56 minutes. MS m/z 509 [MH]$^+$ $^1$H NMR (400 MHz, CDCl$_3$) δ 3.42 (s, 3H), 4.76-4.83 (m, 2H), 5.93-6.22 (m, 1H), 6.60 (d, 1H), 7.55 (d, 1H), 7.93 (d, 1H), 8.23 (d, 1H), 8.65-8.69 (br, 1H).

The compound of Example 22 was also prepared according to the following method,
Method M:

5-chloro-4-{[5-chloro-6-(1,1,3,3-tetrafluoropropoxy)pyridin-3-yl]oxy}-2-fluorobenzoic acid (Preparation 72, 30.2 g, 0.699 mmol) and methanesulfonamide (13.5 g, 0.142 mol) were dissolved in tetrahydrofuran (150 mL). Then N-ethyl-N-diisopropylpropan-2-amine (37 mL, 0.212 mol) and 1-propanephosphonic acid cyclic anhydride in ethyl acetate (50% wt solution, 120 mL, 0.200 mol) were added and the mixture stirred at reflux for 18 hours. After cooling the reaction to room temperature, the solution was concentrated in vacuo and the residue suspended in water (150 mL), then extracted with ethyl acetate (150 mL). The organic layer was separated and washed with water (2×150 mL) The organic layer was collected, dried over sodium sulfate, filtered and concentrated in vacuo to give a beige solid. The solid was suspended in isopropanol (375 mL), heated to 100° C. and stirred until a complete solution was observed. The solution was cooled down to room temperature and the solid obtained was collected by filtration. The title compound was isolated as a pale yellow solid (30.98 g, 87%).

$^1$H NMR (400 MHz; CDCl$_3$): δ 3.45 (s, 3H), 4.82 (m, 2H), 5.96-6.25 (tt, 1H), 6.62 (d, 1H), 7.57 (d, 1H), 7.96 (d, 1H), 8.26 (d, 1H), 8.70 (br d, 1H)

HPLC Rt=6.489 minutes.

The following Examples were prepared by Method A, as described for Example 1 above, using the appropriate Preparations and conditions.

| Ex | Name | Data |
|---|---|---|
| 23 | 4-[(5-chloro-6-isobutoxypyridin-3-yl)oxy]-2,5-difluoro-N-(methylsulfonyl)benzamide | $^1$H NMR (400 MHz; d$_6$-DMSO): δ 0.97 (s, 3H), 0.99 (s, 3H), 2.05 (m, 1H), 3.35 (s, 3H), 4.10 (d, 2H), 7.11-7.16 (m, 1H), 7.72-7.77 (m, 1H), 8.00 (d, 1H), 8.09 (d, 1H), 12.21 (br, 1H) |
| 24 | 4-{[5-chloro-6-(tetrahydro-2H-pyran-4-yloxy)pyridin-3-yl]oxy}-2,5-difluoro-N-(methylsulfonyl)benzamide | $^1$H NMR (400 MHz, CDCl$_3$): δ 1.72-1.89 (m, 2H), 1.95-2.09 (m, 2H), 3.10 (s, 3H), 3.51-3.63 (m, 2H), 3.91-4.02 (m, 2H), 5.03 (m, 1H), 6.42-6.50 (m, 1H), 7.41 (s, 1H), 7.58-7.67 (m, 1H), 7.82 (s, 1H). |
| 25 | 4-[(5-chloro-6-methoxypyridin-3-yl)oxy]-2,5-difluoro-N-(methylsulfonyl)benzamide | $^1$H NMR (CD$_3$OD, 400 MHz): δ 3.20 (s, 3H), 3.89 (s, 3H), 6.66-6.77 (m, 1H), 7.56 (s, 1H), 7.62-7.67 (m, 1H), 8.02 (s, 1H). |
| 26 | 2,5-difluoro-N-(methylsulfonyl)-4-{[2-(trifluoromethyl)pyrimidin-5-yl]oxy}benzamide | LCMS Rt = 3.39 min. MS m/z 398 [MH]$^+$, 396 [M − H]$^-$ |
| 27 | 4-{[5-chloro-6-(2,2,2-trifluoroethoxy)pyridin-3-yl]oxy}-2,5-difluoro-N-(methylsulfonyl)benzamide | $^1$H NMR (400 MHz, d$_6$-DMSO): δ 3.4 (3H, s), 5.0 (2H, q), 7.2 (1H, m), 7.8 (1H, m), 8.1 (1H, s), 8.2 (1H, s). |
| 28 | 4-({5-chloro-6-[(1-methylcyclopropyl)methoxy]pyridin-3-yl}oxy)-2,5-difluoro-N-(methylsulfonyl)benzamide | $^1$H NMR (400 MHz, CD$_3$OD): δ 0.40 (m, 2H), 0.60 (m, 2H), 1.20 (s, 3H), 3.30 (s, 3H), 4.20 (s, 2H), 6.90 (s, 1H), 7.65 (m, 1H), 7.70 (s, 1H), 7.90 (s, 1H). |
| 29 | 4-[(5-chloro-6-isopropoxypyridin-3-yl)oxy]-2,3,6-trifluoro-N-(methylsulfonyl)benzamide | $^1$H NMR (400 MHz, CDCl$_3$): δ 1.36 (d, 6H), 3.07 (s, 3H), 5.24 (m, 1H), 6.30-6.37 (m, 1H), 7.39 (d, 1H), 7.80 (d, 1H). |
| 30 | 5-chloro-4-({5-chloro-6-[(1-methylpiperidin-4-yl)oxy]pyridin-3-yl}oxy)-2-fluoro-N-(methylsulfonyl)benzamide | $^1$H NMR (400 MHz, CDCl$_3$): δ 1.73-2.38 (m, 9H), 2.56-2.70 (m, 2H), 2.93 (s, 3H), 5.01-5.11 (m, 1H), 6.32 (d, 1H), 7.37 (s, 1H), 7.71-7.87 (m, 2H). |
| 31 | 4-[(5-chloro-6-isopropoxypyridin-3-yl)oxy]-2,6-difluoro-N-(methylsulfonyl)benzamide | $^1$H NMR (400 MHz, CDCl$_3$): δ 1.37 (d, 6H), 3.20 (s, 3H), 5.27 (m, 1H), 6.40 (d, 2H), 7.19 (s, 1H), 7.82 (s, 1H). |
| 32 | 4-[(5-chloro-6-isopropoxypyridin-3-yl)oxy]-3,5-difluoro-N-(methylsulfonyl)benzamide | $^1$H NMR (400 MHz, CD$_3$OD): δ 1.32 (d, 6H), 3.10 (s, 3H), 5.25 (m, 1H), 7.47 (s, 1H), 7.72-7.80 (m, 3H). LCMS Rt = 7.58 min. |

The following Examples were prepared by Method B, as described for Example 2 above, using the appropriate Preparations and conditions.

| Ex | Name | Data |
|---|---|---|
| 33 | 4-[(5-chloro-6-isopropoxypyridin-3-yl)oxy]-3-fluoro-N-(methylsulfonyl)benzamide | $^1$H NMR (400 MHz, d$_6$-DMSO): δ 1.3 (d, 6H), 3.3 (s, 3H), 5.2 (m, 1H), 7.1 (m, 1H), 7.8 (m, 1H), 7.9 (m, 2H), 8.05 (s, 1H). |
| 34 | 4-[(6-tert-butoxy-5-chloropyridin-3-yl)oxy]-2,5-difluoro-N-(methylsulfonyl)benzamide | $^1$H NMR (400 MHz, d$_6$-DMSO): δ 1.6 (s, 9H), 3.4 (s, 3H), 6.6 (m, 1H), 7.4 (s, 1H), 7.8 (s, 1H), 7.9 (m, 1H). |
| 35 | 4-{[5-chloro-6-(cyclopropylmethoxy)pyridin-3-yl]oxy}-2,5-difluoro-N-(methylsulfonyl)benzamide | LCMS Rt = 3.63 min. MS m/z 433 [MH]$^+$ |
| 36 | 4-[(5-chloro-6-isopropoxypyridin-3-yl)oxy]-2-fluoro-N-(methylsulfonyl)benzamide | $^1$H NMR (400 MHz, CDCl$_3$): δ 1.35 (d, 6H), 3.37 (s, 3H), 5.21-5.32 (m, 1H), 6.64 (d, 1H), 6.82 (d, 1H), 7.39 (s, 1H), 7.83 (s, 1H), 8.02 (t, 1H). |
| 37 | 5-chloro-4-{[5-chloro-6-(tetrahydro-2H-pyran-4-yloxy)pyridin-3-yl]oxy}-2-fluoro-N-(methylsulfonyl)benzamide | $^1$H NMR (400 MHz, CDCl$_3$): δ 1.80-1.97 (m, 2H), 2.07-2.18 (m, 2H), 3.41 (s, 3H), 3.60-3.72 (m, 2H), 3.98-4.07 (m, 2H), 5.26-5.33 (m, 1H), 6.58 (d, 1H), 7.55 (s, 1H), 7.92 (s, 1H), 8.20 (d, 1H). |

The following Examples were prepared by Method C, as described for Example 3 above, using the appropriate Preparations and conditions.

| Ex | Name | Data |
|----|------|------|
| 38 | 5-chloro-4-[(5-chloro-6-isobutoxypyridin-3-yl)oxy]-2-fluoro-N-(methylsulfonyl)benzamide | $^1$H NMR (400 MHz; d$^6$-DMSO): δ 0.97 (s, 3H), 0.99 (s, 3H), 2.06 (m, 1H), 2.48 (s, 3H), 4.10 (d, 2H), 7.06 (d, 1H), 7.91 (d, 1H), 7.99 (d, 1H), 8.07 (d, 1H) |
| 39 | 5-chloro-4-[(5-chloro-6-isopropoxypyridin-3-yl)oxy]-2-fluoro-N-(methylsulfonyl)benzamide | $^1$H NMR (400 MHz; CDCl$_3$): δ 1.37 (d, 6H), 3.07 (s, 3H), 5.23 (m, 1H), 6.36 (d, 1H), 7.39 (s, 1H), 7.81 (s, 1H), 7.89 (s, 1H). |
| 40 | -({5-chloro-6-[d7-propan-2-yloxy]pyridin-3-yl}oxy)-2,5-difluoro-N-(methylsulfonyl)benzamide | $^1$H NMR (400 MHz; CDCl$_3$): δ 3.44 (s, 3H), 6.64-6.68 (m, 1H), 7.48 (d, 1H), 7.92-7.97 (m, 2H), 8.69-8.73 (d, 1H). LCMS Rt = 1.61 min. MS m/z 428 [MH]$^+$ Contained up to 50% of the D8 analogue. Confirmed by: LCMS Rt = 1.61 mins. MS m/z 427 [M − H]$^−$ |
| 41 | 4-({5-chloro-6-[2-d1-propan-2-yloxy]pyridin-3-yl}oxy)-2,5-difluoro-N-(methylsulfonyl)benzamide | $^1$H NMR (400 MHz; CDCl$_3$): δ 1.42 (s, 6H), 3.44 (s, 3H), 6.64-6.68 (m, 1H), 7.48-7.49 (d, 1H), 7.92-7.97 (m, 2H), 8.71 (br, 1H). |
| 42 | 5-chloro-4-({5-chloro-6-[d7-propan-2-yloxy]pyridin-3-yl}oxy)-2-fluoro-N-(methylsulfonyl)benzamide | $^1$H NMR (400 MHz; CDCl$_3$): δ 3.44 (s, 3H), 6.57-6.60 (m, 1H), 7.48 (d, 1H), 7.92-7.93 (m, 1H), 8.22-8.24 (d, 1H), 8.66 (br, 1H). |

The following Example was prepared by Method D, as described for Example 13 above, using the appropriate Preparations and conditions.

| Ex | Name | Data |
|----|------|------|
| 43 | 5-chloro-4-{[5-chloro-6-(2,2,2-trifluoro-1-methylethoxy)pyridin-3-yl]oxy}-2-fluoro-N-(methylsulfonyl)benzamide | $^1$H NMR (400 MHz d$_6$-DMSO): δ 1.5 (d, 3H), 3.3 (s, 3H), 5.8 (m, 1H), 7.05 (m, 1H), 7.95 (m, 1H), 8.03 (s, 1H), 8.05 (s, 1H). |

The following Examples were prepared by Method E, as described for Example 7 above, using the appropriate Preparations and conditions.

| Ex | Name | Data |
|---|---|---|
| 44 | 5-chloro-4-{[5-chloro-6-(1,1-difluoroethyl)pyridin-3-yl]oxy}-2-fluoro-N-(methylsulfonyl)benzamide | ¹H NMR (400 MHz; CD₃OD): δ 2.01-2.10 (t, 3H), 3.37 (s, 3H), 7.20-7.23 (d, 1H), 7.68 (d, 1H), 7.95-7.96 (d, 1H), 8.30-8.31 (d, 1H) |
| 45 | 4-{[5-chloro-6-(2,2,3,3-tetrafluoropropoxy)pyridin-3-yl]oxy}-2,5-difluoro-N-(methylsulfonyl)benzamide | ¹H NMR (400 MHz, CDCl₃): δ 3.35 (s, 3H), 4.70 (t, 2H), 5.85-6.16 (m, 1H), 6.60-6.68 (m, 1H), 7.45 (s, 1H), 7.84-7.94 (m, 2H). |
| 46 | 5-chloro-4-({5-chloro-6-[2-d1-propan-2-yloxy]pyridin-3-yl}oxy)-2-fluoro-N-(methylsulfonyl)benzamide | ¹H NMR (400 MHz, CDCl₃): δ 1.40 (s, 6H), 3.42 (s, 3H), 6.58 (d, 1H), 7.47 (s, 1H), 7.92 (s, 1H), 8.22 (d, 1H), 8.55-8.70 (br, 1H). |

| Ex | Name | Data |
|---|---|---|
| 47 | 2,5-difluoro-4-[(6-isopropoxypyridin-3-yl)oxy]-N-(methylsulfonyl)benzamide | ¹H NMR (400 MHz; CD₃OD): δ 1.33-1.34 (d, 6H), 3.35 (s, 3H), 5.19-5.29 (m, 1H), 6.76-6.80 (q, 1H), 6.79-6.81 (d, 1H), 7.48-7.51 (m, 1H), 7.62-7.66 (q, 1H), 7.98-7.99 (d, 1H). |
| 48 | 5-chloro-4-{[5-chloro-6-(1-hydroxy-1-methylethyl)pyridin-3-yl]oxy}-2-fluoro-N-(methylsulfonyl)benzamide | LCMS Rt = 2.12 min. MS m/z 437[MH]⁺ |
| 49 | 4-[(5-chloro-6-isobutylpyridin-3-yl)oxy]-2,5-difluoro-N-(methylsulfonyl)benzamide | ¹H NMR (400 MHz, d₆-DMSO): δ 0.90-0.91 (d, 6H), 2.10-2.16 (m, 1H), 2.73-2.75 (d, 2H), 3.34 (s, 3H, under H₂O peak), 7.31-7.35 (m, 1H), 7.76-7.81 (m, 1H), 7.81-7.82 (d, 1H), 8.41 (d, 1H), 12.24 (br, 1H). |
| 50 | 4-[(5-chloro-6-cyclopropylpyridin-3-yl)oxy]-2,5-difluoro-N-(methylsulfonyl)benzamide | ¹H NMR (400 MHz; CD₃OD): δ 1.02-1.04 (m, 2H), 1.05 (m, 2H), 2.49-2.56 (m, 1H), 3.35 (s, 3H), 6.99-7.03 (m, 1H), 7.59-7.60 (d, 1H), 7.65-7.69 (m, 1H), 8.20 (d, 1H). |
| 51 | 4-[(6-tert-butyl-5-chloropyridin-3-yl)oxy]-2,5-difluoro-N-(methylsulfonyl)benzamide | ¹H NMR (400 MHz; CD₃OD): δ 1.50 (s, 9H), 3.35 (s, 3H), 7.05-7.09 (m, 1H), 7.56-7.57 (d, 1H), 7.66-7.71 (m, 1H), 8.26-8.27 (d, 1H). |
| 52 | 5-chloro-4-{[5-chloro-6-(2,2-difluoroethoxy)pyridin-3-yl]oxy}-2-fluoro-N-(methylsulfonyl)benzamide | ¹H NMR (400 MHz, CDCl₃): δ 3.40 (s, 3H), 4.60 (m, 2H), 6.20 (m, 1H), 6.60 (d, 1H), 7.55 (s, 1H), 7.95 (s, 1H), 8.20 (d, 1H). |
| 53 | 5-chloro-4-({5-chloro-6-[2-fluoro-1-(fluoromethyl)ethoxy]pyridin-3-yl}oxy)-2-fluoro-N-(methylsulfonyl)benzamide | ¹H NMR (400 MHz, d⁴-CD₃OD): δ 3.35 (s, 3H), 4.71 (s, 2H), 4.82 (m, 2H), 5.69 (m, 1H), 6.87 (d, 1H), 7.77 (d, 1H), 7.90 (d, 1H), 7.97 (d, 1H). |
| 54 | 5-chloro-4-{[5-chloro-6-(difluoromethoxy)pyridin-3-yl]oxy}-2-fluoro-N-(methylsulfonyl)benzamide | ¹H NMR (400 MHz, CDCl₃): δ 3.45 (s, 3H), 6.67 (d, 1H), 7.44 (t, 1H), 7.60 (d, 1H), 7.96 (d, 1H), 8.27 (d, 1H), 8.67 (d, 1H). |
| 55 | 5-chloro-4-{[5-chloro-6-(cyclopropyloxy)pyridin-3-yl]oxy}-2-fluoro-N-(methylsulfonyl)benzamide | ¹H NMR (400 MHz, CDCl₃): δ 0.87 (m, 4H), 3.44 (s, 3H), 4.37 (m, 1H), 6.60 (d, 1H), 7.49 (d, 1H), 8.01 (d, 1H), 8.24 (d, 1H), 8.66 (d, 1H). |
| 56 | 5-chloro-4-{[5-chloro-6-(2,2,3,3,3-pentafluoropropoxy)pyridin-3-yl]oxy}-2-fluoro-N-(methylsulfonyl)benzamide | ¹H NMR (400 MHz, CDCl₃): δ 3.43 (s, 3H), 4.90 (m, 2H), 6.60 (d, 1H), 7.55 (d, 1H), 7.93 (d, 1H), 8.24 (d, 1H), 8.66 (br, 1H) |
| 57 | 5-chloro-4-{[5-chloro-6-(2-fluoro-2-methylpropoxy)pyridin-3-yl]oxy}-2-fluoro-N-(methylsulfonyl)benzamide | ¹H NMR (400 MHz, CDCl₃): δ 1.53 (d, 6H), 3.43 (s, 3H), 4.40 (d, 2H), 6.57 (d, 1H), 7.51 (d, 1H), 7.92 (d, 1H), 8.23 (d, 1H.) |
| 58 | 5-chloro-4-{[5-chloro-6-(2,2,2-trifluoroethoxy)pyridin-3-yl]oxy}-2-fluoro-N-(methylsulfonyl)benzamide | ¹H NMR (400 MHz, d₆-DMSO): δ 2.06 (s, 3H), 5.04 (q, 2H), 7.11 (d, 1H), 7.93 (d, 1H), 8.10 (d, 1H), 8.15 (d, 1H). |

| Ex | Name | Data |
|---|---|---|
| 59 | 4-[(5-chloro-6-{[2-d3-methyl-d6-propan-2-yl]oxy}pyridin-3-yl)oxy]-2,5-difluoro-N-(methylsulfonyl)benzamide | $^1$H NMR (400 MHz, d$_6$-DMSO): δ 3.34 (s, 3H), 7.17 (m, 1H), 7.75 (m, 1H), 7.92 (d, 1H), 8.05 (d, 1H), 12.21 (br, 1H). |
| 60 | 5-chloro-4-{[5-chloro-6-(1,1-difluoro-2-methylpropyl)pyridin-3-yl]oxy}-2-fluoro-N-(methylsulfonyl)benzamide | $^1$H NMR (400 MHz; CD$_3$OD): δ 1.05-1.06 (d, 6H), 2.78-2.92 (m, 1H), 7.22-7.25 (d, 1H), 7.67-7.68 (d, 1H), 7.95-7.97 (d, 1H), 8.34 (d, 1H). |

The following Examples were prepared by Method F, as described for Example 8 above, using the appropriate Preparations and conditions.

| Ex | Name | Data |
|---|---|---|
| 61 | 5-chloro-2-fluoro-4-[(2-isopropoxypyrimidin-5-yl)oxy]-N-(methylsulfonyl)benzamide | LCMS Rt = 2.06 min. MS m/z 404 [MH]$^+$, 402 [M − H]$^−$ |
| 62 | 4-{[5-chloro-6-(3,3,3-trifluoropropoxy)pyridin-3-yl]oxy}-2,5-difluoro-N-(methylsulfonyl)benzamide | LCMS Rt = 3.60 min. MS m/z 473 [M − H]$^−$ |
| 63 | 4-{[5-chloro-6-(2-fluoro-2-methylpropoxy)pyridin-3-yl]oxy}-2,5-difluoro-N-(methylsulfonyl)benzamide | LCMS Rt = 3.51 min. MS m/z 453 [MH]$^+$ |
| 64 | 4-{[5-chloro-6-(2,2,3,3,3-pentafluoropropoxy)pyridin-3-yl]oxy}-2,5-difluoro-N-(methylsulfonyl)benzamide | $^1$H NMR (400 MHz, CDCl$_3$): δ 3.40 (s, 3H), 4.80 (t, 2H), 6.60 (m, 1H), 7.50 (s, 1H), 7.85 (s, 1H), 7.90 (m, 1H). |
| 65 | 4-({5-chloro-6-[(4,4-difluorocyclohexyl)oxy]pyridin-3-yl}oxy)-2,5-difluoro-N-(methylsulfonyl)benzamide | LCMS Rt = 3.80 min. MS m/z 495 [M − H]$^−$ |
| 66 | 4-{[5-chloro-6-(2,2-difluoroethoxy)pyridin-3-yl]oxy}-2,5-difluoro-N-(methylsulfonyl)benzamide | $^1$H NMR (400 MHz, CDCl$_3$): δ 3.40 (s, 3H), 4.60 (m, 2H), 6.20 (m, 1H), 6.60 (d, 1H), 7.55 (s, 1H), 7.95 (s, 1H), 8.20 (d, 1H). |
| 67 | 4-({5-chloro-6-[(1-methylpiperidin-4-yl)oxy]pyridin-3-yl}oxy)-2,5-difluoro-N-(methylsulfonyl)benzamide | $^1$H NMR (400 MHz, CDCl$_3$): δ 1.72-1.90 (m, 2H), 1.92-2.03 (m, 2H), 2.13-2.38 (m, 5H), 2.58-2.70 (m, 2H), 2.95 (s, 3H), 5.00-5.08 (m, 1H), 6.36-6.45 (m, 1H), 7.36 (d, 1H), 7.51-7.60 (m, 1H), 7.78 (d, 1H) |
| 68 | 4-{[5-chloro-6-(trifluoromethyl)pyridin-3-yl]oxy}-2,5-difluoro-N-(methylsulfonyl)benzamide | LCMS Rt = 2.18 min. MS m/z 431 [MH]$^+$ |

The following Examples were prepared by Method G, as described for Example 9 above, using the appropriate Preparations and conditions.

| Ex | Name | Data |
|---|---|---|
| 69 | 4-[(5-chloro-6-isopropoxypyridin-3-yl)oxy]-3-methoxy-N-(methylsulfonyl)benzamide | $^1$H NMR (400 MHz d$_6$-DMSO): δ 1.25 (d, 6H), 3.40 (s, 3H), 3.80 (s, 3H), 5.20 (m, 1H), 6.95 (d, 1H), 7.50 (d, 1H), 7.65 (m, 2H), 7.95 (m, 1H), 12.0 (br, 1H). |
| 70 | 4-[(5-chloro-6-isopropoxypyridin-3-yl)oxy]-5-fluoro-2-methoxy-N-(methylsulfonyl)benzamide | $^1$H NMR (400 MHz; d$_6$-DMSO): δ 1.29-1.31 (d, 6H), 3.22 (s, 3H), 3.81 (s, 3H), 5.19-5.25 (m, 1H), 6.88-6.89 (d, 1H), 7.55-7.57 (d, 1H), 7.67-7.68 (d, 1H), 7.90-7.91 (d, 1H), 11.89 (s, 1H). |
| 71 | 2,5-difluoro-4-[(5-fluoro-6-isopropoxypyridin-3-yl)oxy]-N-(methylsulfonyl)benzamide | $^1$H NMR (400 MHz; d$_6$-DMSO): δ 1.32-1.34 (d, 6H), 3.34 (s, 3H), 5.24-5.33 (m, 1H), 7.11-7.15 (q, 1H), 7.73-7.77 (q, 1H), 7.81-7.84 (m, 1H), 7.95 (d, 1H), 12.23 (br, 1H). |
| 72 | 4-[(5-chloro-6-isopropoxypyridin-3-yl)oxy]-3,6-difluoro-2-methoxy-N-(methylsulfonyl)benzamide | $^1$H NMR (400 MHz; CDCl$_3$): δ 1.40-1.42 (d, 6H), 3.41 (s, 3H), 4.15-4.16 (d, 3H), 5.30-5.36 (m, 1H), 6.36-6.41 (d, 1H), 7.45 (d, 1H), 7.90 (d, 1H), 8.96 (m, 1H). |
| 73 | 4-[(5-chloro-6-isopropoxypyridin-3-yl)oxy]-3-cyano-N-(methylsulfonyl)benzamide | $^1$H NMR (400 MHz; d$_6$-DMSO): δ 1.35-1.36 (d, 6H), 3.37 (s, 3H), 5.26-5.35 (m, 1H), 7.09-7.11 (d, 1H), 8.12-8.15 (d, 2H), 8.20-8.21 (d, 1H), 8.47-8.48 (d, 1H) |
| 74 | 4-[(5-chloro-6-isobutoxypyridin-3-yl)oxy]-2-fluoro-N-(methylsulfonyl)benzamide | $^1$H NMR (400 MHz, d$_6$-DMSO): δ 0.99 (d, 6H), 2.06 (m, 1H), 4.11 (d, 2H), 6.89 (m, 1H), 7.03 (m, 1H), 7.67 (t, 1H), 7.95 (d, 1H), 8.06 (d, 1H), 12.10 (br, 1H). |
| 75 | 4-[(5-chloro-6-isopropoxypyridin-3-yl)oxy]-2-fluoro-5-methyl-N-(methylsulfonyl)benzamide | $^1$H NMR (CDCl$_3$): δ 1.40 (6H, d), 2.35 (3H, s), 3.40 (3H, s), 5.35 (1H, m), 6.40 (1H, d), 7.40 (1H, d), 7.82 (1H, d), 7.95 (1H, d). |

The following Examples were prepared by Method H, as described for Example 10 above, using the appropriate Preparations and conditions.

| Ex | Name | Data |
|---|---|---|
| 76 | 5-chloro-4-{[5-chloro-6-(2,2,2-trifluoro-1,1-dimethylethoxy)pyridin-3-yl]oxy}-2-fluoro-N-(methylsulfonyl)benzamide | $^1$H NMR (400 MHz; CD$_3$OD): δ 1.82 (d, 6H), 3.34 (s, 3H), 6.89-6.91 (d, 1H), 7.74 (d, 1H), 7.90-7.91 (d, 1H), 7.96-7.97 (d, 1H). |
| 77 | 5-chloro-4-({5-chloro-6-[2,2,2-trifluoro-1-(trifluoromethyl)ethoxy]pyridin-3-yl}oxy)-2-fluoro-N-(methylsulfonyl)benzamide | $^1$H NMR (400 MHz; CDCl$_3$): δ 3.44 (s, 3H), 6.38-6.44 (m, 1H), 6.66-6.69 (d, 1H), 6.60 (d, 1H), 7.93 (d, 1H), 7.96-7.97 (d, 1H), 8.25-8.27 (d, 1H), 8.66-8.69 (d, 1H). |
| 78 | 4-{[5-chloro-6-(2,2,2-trifluoro-1,1-dimethylethoxy)pyridin-3-yl]oxy}-2,5-difluoro-N-(methylsulfonyl)benzamide | $^1$H NMR (400 MHz; CDCl$_3$): δ 3.44 (s, 3H), 6.38-6.44 (m, 1H), 6.66-6.69 (d, 1H), 6.60 (d, 1H), 7.93 (d, 1H), 7.96-7.97 (d, 1H), 8.25-8.27 (d, 1H), 8.66-8.69 (d, 1H). |

The following Example was prepared by Method I, as described for Example 11 above, using the appropriate Preparations and conditions.

| Ex | Name | Data |
|---|---|---|
| 79 | 4-{[5-chloro-6-(isopropylamino)pyridin-3-yl]oxy}-2,5-difluoro-N-(methylsulfonyl)benzamide | LCMS Rt = 2.29 min. MS m/z 420 [MH]$^+$ |

The following Examples were prepared by Method J as described for Example 12 above, using the appropriate Preparations and conditions.

| Ex | Name | Data |
|---|---|---|
| 80 | 4-({5-chloro-6-[2-fluoro-1-(fluoromethyl)ethoxy]pyridin-3-yl}oxy)-2,5-difluoro-N-(methylsulfonyl)benzamide | $^1$H NMR (400 MHz, CDCl$_3$): δ 3.40 (s, 3H), 4.80 (m, 4H), 5.60 (m, 1H), 6.65 (m, 1H), 7.55 (s, 1H), 7.90 (s, 1H), 7.95 (m, 1H). |
| 81 | 5-chloro-4-({5-chloro-6-[(1-methylazetidin-3-yl)oxy]pyridin-3-yl}oxy)-2-fluoro-N-(methylsulfonyl)benzamide | $^1$H NMR (400 MHz, d$_6$-DMSO): δ 1.95 (s, 3H), 2.92 (d, 3H), 4.08-4.19 (m, 2H), 4.40-4.50 (m, 2H), 5.31-5.40 (m, 1H), 6.82 (d, 1H), 7.83 (d, 1H), 8.00 (s, 2H). |

The following Examples were prepared by Method L, as described for Example 14 above, using the appropriate Preparations and conditions.

| Ex | Name | Data |
|----|------|------|
| 82 | 3-chloro-4-[(5-chloro-6-isopropoxypyridin-3-yl)oxy]-N-(methylsulfonyl)benzamide | LCMS Rt = 3.99 min. MS m/z 417 [MH]⁻ |
| 83 | 3-chloro-4-[(5-chloro-6-methoxypyridin-3-yl)oxy]-N-(methylsulfonyl)benzamide | LCMS Rt = 3.63 min. MS m/z 391 [MH]⁺ |
| 84 | 4-[(5-chloro-6-isopropoxypyridin-3-yl)oxy]-N-(methylsulfonyl)benzamide | LCMS Rt = 3.69 min. MS m/z 385 [MH]⁺ |
| 85 | 4-[(5-chloro-6-methoxypyridin-3-yl)oxy]-N-(methylsulfonyl)benzamide | LCMS Rt = 3.31 min. MS m/z 357 [MH]⁺ |
| 86 | 4-[(5-chloro-6-isopropoxypyridin-3-yl)oxy]-2-methoxy-N-(methylsulfonyl)benzamide | ¹H NMR (400 MHz, CDCl₃): δ 1.42 (d, 6H), 3.42 (s, 3H), 4.01 (s, 3H), 5.34 (m, 1H), 6.58 (d, 1H), 6.64 (d, 1H), 7.45 (d, 1H), 7.90 (d, 1H), 8.16 (d, 1H), 10.02 (s, 1H). |
| 87 | 4-[(5-chloroquinolin-8-yl)oxy]-2,5-difluoro-N-(methylsulfonyl)benzamide | ¹H NMR (400 MHz, CD₃OD): δ 2.99 (s, 3H), 6.55 (m, 1H), 7.15 (d, 1H), 7.51-7.56 (m, 3H), 8.52 (m, 1H), 8.71 (m, 1H). |
| 88 | 4-[(6-chloroquinolin-8-yl)oxy]-2,5-difluoro-N-(methylsulfonyl)benzamide | LCMS Rt = 2.18 min. MS m/s 413 [MH]⁺ |
| 89 | 2,5-difluoro-4-(4-methoxypyridin-3-yloxy)-N-(methylsulfonyl)benzamide | LCMS Rt = 2.06 min. MS m/z 359 [MH]⁺ |
| 90 | 2,5-difluoro-4-(imidazo[1,2-a]pyridin-8-yloxy)-N-(methylsulfonyl)benzamide | LCMS Rt = 2.10 min. MS m/z 368 [MH]⁺ |

EXAMPLE 91

2,5-Dichloro-4-(5-chloro-6-cyclopropylpyridin-3-yloxy)-N-(methylsulfonyl)benzamide

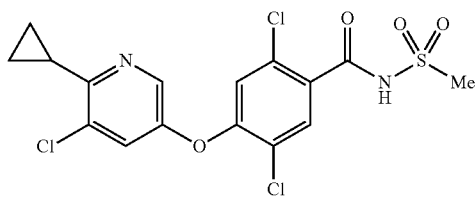 [SMILES: CS(=O)(=O)NC(=O)c1cc(Cl)c(Oc2cnc(C3CC3)c(Cl)c2)cc1Cl]

4-Dimethylaminopyridine (51 mg, 0.42 mmol) and N-(3-dimethylaminopropyl)-N'-ethylcarbodiimide hydrochloride (80 mg, 0.42 mmol) were added to a suspension of 2,5-dichloro-4-(5-chloro-6-cyclopropylpyridin-3-yloxy)benzoic acid (Preparation 220, 100 mg, 0.28 mmol) in dichloromethane (3 mL). The reaction mixture was stirred at room temperature for 20 minutes. Methylsulfonamide (40 mg, 0.42 mmol) was added and the reaction mixture was stirred at room temperature for 18 hours before concentrating in vacuo. The crude compound was purified by reverse phase column chromatography eluting with acetonitrile:water (from 5:95 to 95:5) followed by preparative HPLC to afford the title compound (15.1 mg, 12%).

LCMS Rt=3.72 minutes MS m/z 435 [MH]⁺

¹H NMR (400 MHz, CDCl₃): δ 1.05-1.12 (m, 4H), 2.48-2.55 (m, 1H), 3.41 (s, 3H), 6.87 (s, 1H), 7.35 (d, 1H), 8.02 (s, 1H), 8.16 (d, 1H)

EXAMPLE 92

5-chloro-4-(5-chloro-6-cyclopropylpyridin-3-yloxy)-N-(cyclopropylsulfonyl)-2-fluorobenzamide

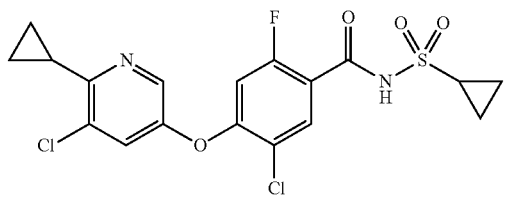 [SMILES: O=C(NS(=O)(=O)C1CC1)c1cc(Cl)c(Oc2cnc(C3CC3)c(Cl)c2)cc1F]

5-chloro-4-(5-chloro-6-cyclopropylpyridin-3-yloxy)-2-fluorobenzoic acid (Preparation 265, 15 mg, 0.44 mmol), 4-dimethylaminopyridine (81 mg, 0.66 mmol), and N-(3-dimethylaminopropyl)-N-ethylcarbodiimide hydrochloride (127 mg, 0.66 mmol) were suspended in dichloromethane (2.5 mL). The reaction mixture was stirred for 20 minutes then dimethyl formamide (4 mL) was added and the suspension was stirred for 10 minutes. Cyclopropanesulfonamide (107 mg, 0.88 mmol) and N,N-diisopropylethylamine (160 µL, 0.88 mmol) were added and the reaction mixture was stirred for 18 hours at room temperature. The crude reaction mixture was purified by semi-preparative reverse phase HPLC (Column phenomenex Luna C18 150×21.2 mm 110 A 5µ, 3 injections of 2 ml, detection at 254 nm, fractions of 5 ml each, Gradient Solvent A: 0.05% HCO₂H in acetonitrile, Solvent B: 0.05% HCO2H in water; 0 min 10% A, 2.5 min 10% A, 32.5 min 95% A, 37.5 min 95% A then return to initial conditions, flow rate 15 ml/min) to afford the title compound as a white solid (43 mg, 22%).

LCMS Rt=3.01 minutes MS m/z 445 [MH]⁺

¹H NMR (400 MHz, CD₃OD): δ 1.05 (m, 4H), 1.14 (m, 2H), 1.29 (m, 2H), 2.54 (m, 1H), 3.10 (m, 1H), 6.93 (m, 1H), 7.58 (m, 1H), 7.89 (m, 1H), 8.18 (m, 1H)

EXAMPLE 93

5-chloro-4-((5-chloro-6-cyclopropylpyridin-3-yl)methyl)-2-fluoro-N-(methylsulfonyl)benzamide

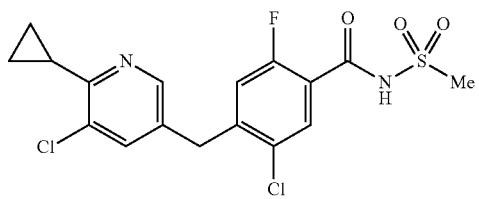 [SMILES: CS(=O)(=O)NC(=O)c1cc(Cl)c(Cc2cnc(C3CC3)c(Cl)c2)cc1F]

To a solution of tetrahydrofuran (10 mL) and water (2 mL) was added 3-chloro-2-cyclopropyl-5-(4,4,5,5-tetramethyl-1,3,2-dioxaborolan-2-yl)pyridine (Preparation 221, 32 mg, 0.11 mmol), 4-(bromomethyl)-5-chloro-2-fluoro-N-(methylsulfonyl)benzamide (Preparation 243, 43 mg, 0.13 mmol) and potassium carbonate (46 mg, 0.35 mmol). The flask was degassed with N₂ (×5), and tetrakistriphenylphosphinepalladium (13.2 mg, 0.01 mmol) was added. The flask was degassed with N₂ (×5), and heated to 65° C. for 18 hours. The reaction was allowed to cool to room temperature and washed with a saturated aqueous solution of ammonium chloride (100 mL). The reaction was extracted into ethyl acetate (3×50 mL). The combined organic layers were dried over MgSO₄, filtered and the solvent removed to leave a yellow oil. The material was purified by silica gel column chromatography eluting with 1:1 heptane:ethyl acetate to afford the title compound as a yellow oil that solidified to a pale yellow solid upon standing (23 mg, 48%).

LCMS Rt=2.82 minutes, MS m/z 417 [MH]⁺

¹HNMR (400 MHz, CDCl₃): δ 0.98-1.10 (m, 4H), 2.42-2.52 (m, 1H), 3.40 (s, 3H), 4.03 (s, 2H), 6.96 (d, 1H), 7.36 (s, 1H), 8.08 (d, 1H), 8.19 (s, 1H).

EXAMPLE 94

5-chloro-4-[(5-chloro-6-isopropoxypyridin-3-yl)thio]-2-fluoro-N-(methylsulfonyl)benzamide

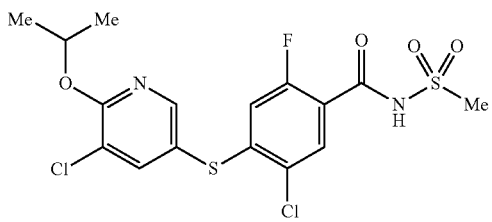

To a suspension of methanesulfonamide (93.4 mg, 0.98 mmol) in THF (2 mL) at room temperature was added potassium tert-butoxide (119 mg, 1.06 mmol) in one portion with stirring under nitrogen for 15 minutes. 4-Methylphenyl-5-chloro-4-[(5-chloro-6-isopropoxypyridin-3-yl)thio]-2-fluorobenzoate (Preparation 224, 352 mg, 0.75 mmol) was added as a solution in THF (2 mL). The mixture was then heated at 60° C. for 3 hours and then left at room temperature for 18 hours. The solvent was concentrated in vacuo and the residue was partitioned between EtOAc (10 mL) and water (5 mL). The organic layer was separated and then washed with 1M NaOH (5 mL), 2M HCl (5 mL), saturated aqueous brine (5 mL), dried over MgSO₄ filtered and evaporated. The residue was triturated with acetone/heptane (1:9) to afford a white solid which was filtered and washed with heptane to yield the title compound (45 mg, 13%) as a white solid.

LCMS Rt=2.97 minutes, MS m/z 451 [M−H]⁻

¹HNMR (400 MHz, d⁶-DMSO): δ 1.45 (d, 6H), 3.40 (s, 3H), 5.40-5.46 (m, 1H), 6.43 (d, 1H), 7.77 (s, 1H), 8.08 (d, 1H), 8.20 (s, 1H), 8.55-8.70 (br s, 1H).

EXAMPLE 95

5-chloro-4-(5-chloro-6-(3,3-difluoropyrrolidin-1-yl)pyridin-3-yloxy)-2-fluoro-N-(methylsulfonyl)benzamide

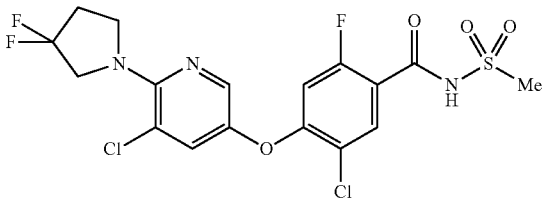 [SMILES: CS(=O)(=O)NC(=O)c1cc(Cl)c(Oc2cnc(N3CCC(F)(F)C3)c(Cl)c2)cc1F]

Triethylamine (0.21 mL, 1.51 mmol) was added to a mixture of 5-chloro-4-[5-chloro-6-fluoropyridin-3-yl)oxy]-2-fluoro-N-(methylsulfonyl)benzamide (Example 19, 150 mg, 0.38 mmol) and 3,3-difluoropyrrolidine hydrochloride salt (60 mg, 0.41 mmol), in DMSO (3.8 mL) and the reaction heated at 80° C. for 120 hours. The mixture was diluted to 5 mL by the addition of water and the mixture purified by preparative HPLC. The title compound was obtained as a beige solid (49 mg, 27%).

LCMS Rt=3.69 minutes, MS m/z 484 [MH]⁺

1HNMR (400 MHz, CDCl₃): δ 2.43 (m, 2H), 3.40 (d, 3H), 3.91 (t, 2H), 4.06 (t, 2H), 6.57 (d, 1H), 7.39 (d, 1H), 7.99 (d, 1H), 8.20 (m, 1H).

EXAMPLE 96

5-Chloro-4-(5-chloro-6-(3,3-difluoroazetidin-1-yl)pyridin-3-yloxy)-2-fluoro-N-(methylsulfonyl)benzamide

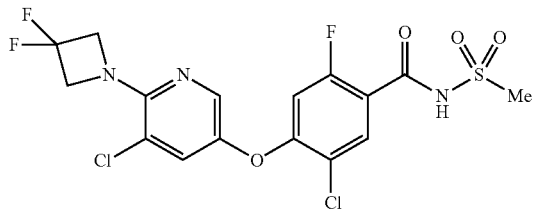 [SMILES: CS(=O)(=O)NC(=O)c1cc(Cl)c(Oc2cnc(N3CC(F)(F)C3)c(Cl)c2)cc1F]

3,3-Difluoroazetidine hydrochloride (98 mg, 0.76 mmol) was added to a suspension of 5-chloro-4-(5-chloro-6-fluoropyridin-3-yloxy)-2-fluoro-N-(methylsulfonyl)benzamide (Example 19, 150 mg, 0.38 mmol) and potassium carbonate (74 mg, 0.53 mmol) in dimethylsulfoxide (1 mL). The reaction mixture was stirred at 90° C. in the microwave for 15 hours. The reaction mixture was diluted with water (10 mL) and extracted with ethyl acetate (3×10 mL). The combined organic layers were dried (MgSO₄), filtered and concentrated in vacuo. The crude compound was purified by reverse phase preparative HPLC eluting with acetonitrile:water (from 5:95 to 95:5) to give the title compound as a colourless solid (44 mg, 25%).

LCMS Rt=3.61 minutes, MS m/z 470 [MH]⁺

¹H NMR (400 MHz, d⁶-DMSO): δ 3.27 (s, 3H), 4.53 (t, 4H), 6.91 (d, 1H), 7.83 (d, 1H), 7.89 (d, 1H), 8.11 (d, 1H).

EXAMPLE 97

4-[(6-tert-Butoxy-5-chloropyridin-3-yl)methyl]-2,5-difluoro-N-(methylsulfonyl)benzamide

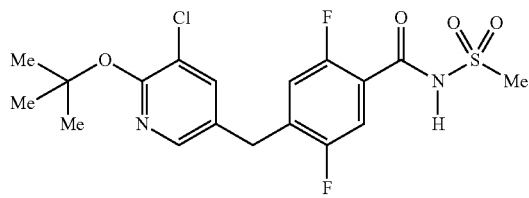 [SMILES: CC(C)(C)Oc1ncc(Cc2cc(F)c(C(=O)NS(C)(=O)=O)cc2F)cc1Cl]

4-(Bromomethyl)-2,5-difluoro-N-(methylsulfonyl)benzamide (Preparation 245, 70 mg, 0.21 mmol), 2-tert-butoxy-3-chloro-5-(4,4,5,5-tetramethyl-1,3,2-dioxaborolan-2-yl)pyridine (Preparation 118, 72.9 mg, 0.234 mmol), tetrakistriphenylphosphinepalladium (24.3 mg, 0.021 mmol), aqueous potassium carbonate solution (1.8 M, 0.35 mL, 0.639 mmol) and tetrahydrofuran (15 mL) were combined and stirred under nitrogen at reflux for 5 hours. After cooling, the mixture was filtered through Celite™ and the filtrate evaporated. The residue was dissolved in water (20 mL) and acidified with aqueous potassium hydrogen sulphate solution (0.5 M) to pH 2 and the mixture extracted with ethyl acetate (30 mL). The organic layer was separated and washed with brine (3×20 mL), dried over sodium sulphate, filtered and evaporated to give an oil. The oil was purified using silica gel column chromatography eluting with heptane to ethyl acetate:heptane 1:1 to give a solid. The solid was further purified by reverse phase HPLC to give the title compound (21 mg, 23%) as a white solid.

LCMS Rt=3.86 minutes. MS m/z 433 [MH]⁺.

EXAMPLE 98

5-chloro-4-({5-chloro-6-[(1S)-2,2,2-trifluoro-1-methylethoxy]pyridin-3-yl}oxy)-2-fluoro-N-(methylsulfonyl)benzamide

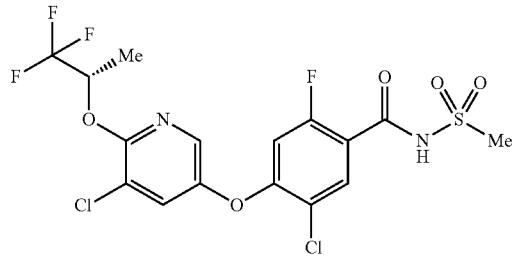 [SMILES: C[C@H](Oc1ncc(Oc2cc(F)c(C(=O)NS(C)(=O)=O)cc2Cl)cc1Cl)C(F)(F)F]

To a solution of methanesulfonamide (26 mg, 0.28 mmol) in THF (2 mL) was added potassium tert-butoxide (32 mg, 0.28 mmol) and the mixture was stirred for 10 minutes at room temperature. A solution of 4-methylphenyl 5-chloro-4-({5-chloro-6-[(1S)-2,2,2-trifluoro-1-methylethoxy]pyridin-3-yl}oxy)-2-fluorobenzoate (Preparation 230, 108 mg, 0.21 mmol) in THF (2 mL) was added and the mixture was stirred at 50° C. for 10 hours. The reaction mixture was allowed to cool to room temperature. The reaction was quenched with water and acidified with 1N aqueous citric acid solution. The mixture was extracted with DCM (3×5 mL) and filtered using a phase separation cartridge. The filtrate was concentrated in vacuo to give a crude product that was purified by silica gel chromatography eluting with 0-100% EtOAc in heptane to give a product mixture as a white solid. The solid was purified by reverse phase column chromatography eluting with 5-95% CH₃CN in water to give a white solid that was further purified using trituration with heptanes/acetone 9/1 to give the title compound (28 mg, 27%) as a white solid.

¹H NMR (400 MHz; d⁶-DMSO): δ 1.51 (d, 3H), 3.35 (s, 3H), 5.87 (m, 1H), 7.17 (d, 1H), 7.94 (d, 1H), 8.10 (d, 1H), 8.15 (d, 1H)

LCMS Rt=2.80 minutes MS m/z 491 [MH]⁺, 489 [M−H]⁻

The compound of Example 98 was also prepared as follows:

Diisopropylethyl amine (11.7 mL, 66.8 mmol) was added to a solution of (S)-5-chloro-4-((5-chloro-6-((1,1,1-trifluoropropan-2-yl)oxy)pyridin-3-yl)oxy)-2-fluorobenzoic acid (Preparation 299, 6.9 g, 16.7 mmol), (2-(7-Aza-1H-benzotriazole-1-yl)-1,1,3,3-tetramethyluronium hexafluorophosphate) (9.5 g, 25.1 mmol) and methylsulfonamide (2.4 g, 25.1 mmol) in dichloromethane (125 mL). The reaction mixture was stirred at room temperature for 20 hours, then quenched with an aqueous solution of hydrogen chloride (2M, 50 mL). Organics were removed in vacuo and the aqueous residue was extracted with ethyl acetate (3×100 mL). The combined organic layers were dried (MgSO₄), filtered and concentrated in vacuo. The crude compound was purified by silica gel chromatography, eluting with dichloromethane:methanol (from 100:0 to 96:4), followed by reverse phase chromatography, eluting with acetonitrile:water (from 5:95 to 95:5) to provide the title compound as a white solid (4.8 g, 56%).

LCMS Rt=4.13 minutes, m/z 491 [M+H]⁺

¹H NMR (400 MHz, CDCl₃): δ 1.49 (d, 3H), 3.34 (s, 3H), 5.84 (m, 1H), 7.15 (d, 1H), 7.92 (d, 1H), 8.08 (d, 1H), 8.13 (d, 1H).

¹⁹F NMR (400 MHz, CDCl₃): δ −77, −110.

EXAMPLE 99

5-chloro-4-({5-chloro-6-[(1R)-2,2,2-trifluoro-1-methylethoxy]pyridin-3-yl}oxy)-2-fluoro-N-(methylsulfonyl)benzamide

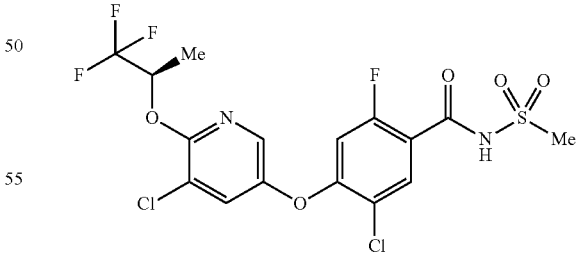

To a solution of methanesulfonamide (105 mg, 1.1 mmol) in THF (4 mL) was added potassium tert-butoxide (126 mg, 1.1 mmol) and the mixture was stirred for 10 minutes at room temperature. A solution of 4-methylphenyl 5-chloro-4-({5-chloro-6-[(1R)-2,2,2-trifluoro-1-methylethoxy]pyridin-3-yl}oxy)-2-fluorobenzoate (Preparation 234, 429 mg, 0.85 mmol) in THF (4 mL) was added and the resulting mixture was stirred at 50° C. for 3 hours. The reaction mixture was

EXAMPLE 100

5-chloro-4-[(5-chloro-6-phenoxypyridin-3-yl)oxy]-2-fluoro-N-(methylsulfonyl)benzamide

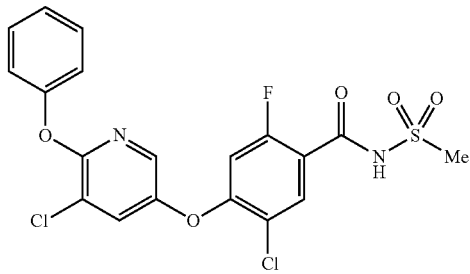 [SMILES: CS(=O)(=O)NC(=O)c1cc(Cl)c(Oc2cnc(Oc3ccccc3)c(Cl)c2)cc1F]

To a solution of 5-chloro-4-[(5-chloro-6-fluoropyridin-3-yl)oxy]-2-fluoro-N-(methylsulfonyl)benzamide (Example 19, 100 mg, 0.25 mmol) and phenol (71 mg, 0.76 mmol) in DMSO (1 mL) was added Cs$_2$CO$_3$ (246 mg, 0.76 mmol) at room temperature under N$_2$. The resulting mixture was stirred at 100° C. for 45 minutes. The reaction mixture was allowed to cool to room temperature. The reaction was quenched with water, and acidified with 1N aqueous citric acid solution. The mixture was extracted with DCM (3×3 mL) and filtered through a phase separation cartridge. The organic phase was washed with brine (3 mL), and filtered through a phase separation cartridge. The filtrate was dried by N$_2$ blowing to give a crude product that was purified by reverse phase column chromatography eluting with 5-95% CH$_3$CN in water to give a crude white solid. The solid was purified using trituration with heptane/acetone 9/1 to give the title compound (78 mg, 65%) as a white solid.

$^1$H NMR (400 MHz; d$^6$-DMSO): δ 3.36 (s, 3H), 7.20 (m, 3H), 7.25 (m, 1H), 7.44 (m, 2H), 7.95 (d, 1H), 8.07 (d, 1H), 8.16 (d, 1H).

LCMS Rt=2.71 minutes MS m/z 471 [MH]$^+$, 469 [MH]$^-$ allowed to cool to room temperature. The reaction was quenched with water and acidified with 1N aqueous citric acid solution. The mixture was partitioned between water and DCM (3×5 mL) and filtered through a phase separation cartridge. The filtrate was concentrated in vacuo to give a crude solid that was purified using trituration with heptanes/acetone 9/1 to give the title compound (199 mg, 48%) as a white solid.

$^1$H NMR (400 MHz; d$^6$-DMSO): δ 1.51 (d, 3H), 3.36 (s, 3H), 5.87 (m, 1H), 7.18 (d, 1H), 7.95 (d, 1H), 8.11 (d, 1H), 8.16 (d, 1H).

LCMS Rt=2.80 minutes MS m/z 491 [MH]$^+$, 489 [MH]$^-$

EXAMPLE 101

4-[(6-tert-butoxy-5-chloropyridin-3-yl)oxy]-5-chloro-2-fluoro-N-(methylsulfonyl)benzamide

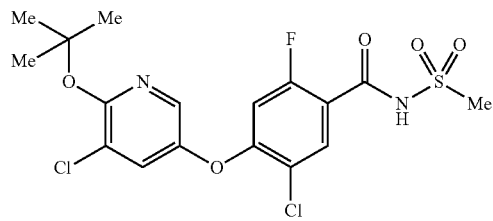 [SMILES: CC(C)(C)Oc1ncc(Oc2cc(F)c(C(=O)NS(C)(=O)=O)cc2Cl)cc1Cl]

To a solution of tert-butyl 3,3-difluorocyclobutanecarboxylate (Preparation 227, 126 mg, 0.66 mmol) in toluene (2 mL) was added a solution of sodium 1,1,1,3,3,3-hexamethyldisilazan-2-ide (1M solution in THF, 1.6 mL, 1.6 mmol) at 0° C. The resulting solution was stirred for 10 minutes at the same temperature, then 5-chloro-4-[(5-chloro-6-fluoropyridin-3-yl)oxy]-2-fluoro-N-(methylsulfonyl)benzamide (Example 19, 200 mg, 0.50 mmol) was added. The resulting mixture was warmed up to room temperature and stirred for 36 hours. The reaction was quenched with saturated aqueous NH$_4$Cl solution and extracted with EtOAc. The organic phase was washed with aqueous 1N citric acid solution, then brine, dried over Na$_2$SO$_4$, filtered, and concentrated in vacuo to give a crude product as a yellow oil. The crude product was purified by silica gel column chromatography eluting with 0-100% EtOAc in heptane to give a yellow foam. The foam was triturated with heptane to give the title compound (101 mg, 44%) as a white solid.

$^1$H NMR (400 MHz; d$^6$-DMSO): δ 1.58 (s, 9H), 3.35 (br s, 3H), 7.11 (d, 1H), 7.94 (m, 2H), 8.05 (d, 1H).

LCMS Rt=2.89 minutes MS m/z 451 [MH]$^+$, 449 [M−H]$^-$

No Example 102.

EXAMPLE 103

4-(5-chloro-6-(1,1,1,3,3,3-hexafluoropropan-2-yloxy)Pyridin-3-ylamino)-N-(methylsulfonyl)benzamide

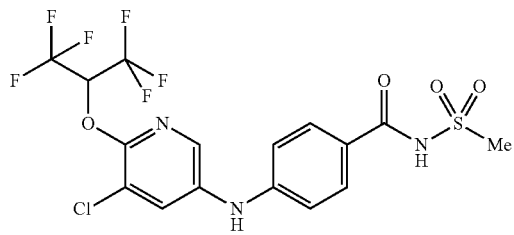 [SMILES: CS(=O)(=O)NC(=O)c1ccc(Nc2cnc(OC(C(F)(F)F)C(F)(F)F)c(Cl)c2)cc1]

To a solution of 4-(5-chloro-6-(1,1,1,3,3,3-hexafluoropropan-2-yloxy)pyridin-3-ylamino)benzoic acid (Preparation 259, 116 mg, 0.27 mmol) in dichloromethane (5 mL) was added 4-dimethylaminopyridine (50 mg, 0.41 mmol) and N-(3-dimethylaminopropyl)-N-ethylcarbodiimide hydrochloride (77 mg, 0.41 mmol). The solution was stirred for 25 minutes at room temperature and methanesulfonamide (39 mg, 0.41 mmol) was added. The reaction mixture was stirred for 18 hours at room temperature. The solution was concentrated in vacuo and the material was purified by reverse phase chromatography eluting with acetonitrile:water (from 5:95 to 95:5, 30 minutes gradient followed by 5 minutes isocratic) to afford the title compound as a white solid (98 mg, 74%).

LCMS rt=3.38 min, m/z 492 [MH]+

$^1$H NMR (400 MHz, CDCl$_3$): δ 3.30 (s, 3H), 7.00-7.15 (m, 3H), 7.85 (m, 2H), 7.90 (s, 1H), 8.05 (s, 1H), 8.90 (s, 1H).

EXAMPLE 104

5-chloro-4-(6-cyclopropyl-5-(1,1-difluoroethoxy)pyridin-3-yloxy)-2-fluoro-N-(methylsulfonyl)benzamide hydrochloride salt

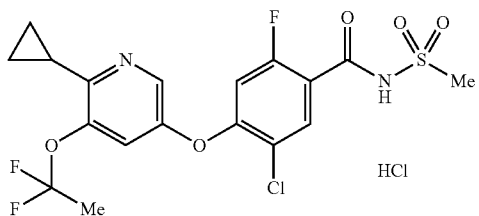 [SMILES: CC(F)(F)Oc1cc(Oc2cc(F)c(C(=O)NS(C)(=O)=O)cc2Cl)cnc1C1CC1 ; Cl]

To a dichloromethane (10 mL) solution of 5-chloro-4-(6-cyclopropyl-5-(1,1-difluoroethoxy)pyridin-3-yloxy)-2-fluorobenzoic acid (Preparation 271, 220 mg, 0.57 mmol) was added methanesulfonamide (64 mg, 0.68 mmol), HATU (259 mg, 0.68 mmol), and DIPEA (0.35 mL, 1.99 mmol). The reaction was left to stir at room temperature for 2 hours. The reaction was washed with a 2M aqueous solution of HCl (50 mL) and extracted into DCM (3×50 mL). The combined organics were dried over MgSO$_4$, filtered and the solvent removed to leave an off white solid. The solid was triturated in a minimum of methanol, filtered and dried in air, to leave the title compound as a white solid as the HCl salt. (131 mg, 50%).

LCMS Rt=2.64 minutes MS m/z 465 [MH]+

$^1$HNMR (400 MHz, CDCl$_3$): δ 0.91-1.02 (m, 4H), 2.02 (t, 3H), 2.30-2.39 (m, 1H), 3.35 (s, 3H), 7.12 (d, 1H), 7.41 (s, 1H), 7.93 (d, 1H), 8.26 (s, 1H).

EXAMPLE 105

5-Chloro-2-fluoro-N-(methylsulfonyl)-4-(6-(2,2,3,3-tetrafluoropropoxy)-5-(trifluoromethyl)pyridin-3-yloxy)benzamide

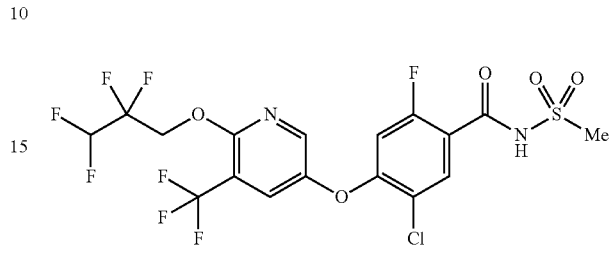

Methanesulphonamide (89.54 mg, 0.94 mmol) and 1,8-diazabicyclo[5.4.0]undec-7-ene (0.15 mL, 1.03 mmol) were added to 4-methylphenyl-5-chloro-4-(6-(2,2,3,3-tetrafluoropropoxy)-5-(trifluoromethyl)pyridin-3-yloxy)-2-fluorobenzoate (Preparation 263, 475 mg, 0.86 mmol) in acetonitrile (5 mL) and the reaction mixture was stirred for 18 hours at room temperature. The reaction was concentrated in vacuo and the residue was partitioned between ethyl acetate and water, the organic layer was separated, dried over anhydrous magnesium sulfate, filtered and the filtrate was concentrated in vacuo. The crude product was purified by reverse phase chromatography (acetonitrile/water both with 0.1% formic acid) to give the title compound as a white solid (303 mg, 55%).

LCMS Rt=2.97 minutes MS m/z 543 [MH]+

$^1$HNMR (400 MHz, CDCl$_3$): δ 3.43 (s, 3H), 4.85 (t, 2H), 6.16-5.87 (m, 1H), 6.61 (d, 1H), 7.73 (d, 1H), 8.19 (s, 1H), 8.27 (d, 1H), 8.65 (br s, 1H).

The following Examples were prepared by methods analogous to Methods M, B and E, as described for Example 22, 2 and 7 above, using methanesulfonamide. Unless otherwise noted, preparation details are as described for the method referred to.

| Ex | Name | Data |
|---|---|---|
| 106 | 5-chloro-4-(6-cyclopropyl-5-(difluoromethoxy)pyridin-3-yloxy)-2-fluoro-N-(methylsulfonyl)benzamide | LCMS Rt = 2.57 minutes MS m/z 449 [M−H]− |
| 107 | 5-chloro-4-(6-cyclopropyl-5-(trifluoromethyl)pyridin-3-yloxy)-2-fluoro-N-(methylsulfonyl)benzamide | LCMS Rt = 2.95 minutes MS m/z 453 [MH]+ $^1$H NMR (400 MHz, CDCl$_3$): δ 1.12 (m, 2H), 1.22 (m, 2H), 2.36 (m, 1H), 3.43 (s, 3H), 6.60 (m, 1H), 7.59 (m, 1H), 8.25 (m, 1H), 8.42 (m, 1H) |
| 108 | 5-chloro-4-[(5-chloro-6-phenylpyridin-3-yl)oxy]-2-fluoro-N-(methylsulfonyl)benzamide | $^1$H NMR (400 MHz; d$^6$-DMSO): δ 3.34 (s, 3H), 7.40 (d, 1H), 7.50 (m, 3H), 7.68 (m, 2H), 7.96 (d, 1H), 8.00 (d, 1H), 8.55 (d, 1H). LCMS Rt = 2.62 minutes MS m/z 455 [MH]+, 453 [M − H]− |
| 109 | 5-chloro-4-{[5-chloro-6-(3,3-difluorocyclobutyl)pyridin-3-yl]oxy}-2-fluoro-N-(methylsulfonyl)benzamide | $^1$H NMR (400 MHz; d$^6$-DMSO): δ 2.98 (m, 4H), 3.37 (s, 3H), 3.79 (m, 1H), 7.26 (d, 1H), 7.89 (d, 1H), 7.98 (d, 1H), 8.49 (d, 1H), 12.30 (br. s., 1H). LCMS Rt = 2.68 minutes MS m/z 469 [MH]+, 467 [MH]−. |
| 110 | 5-chloro-4-(6-cyclopropyl-5-(trifluoromethoxy)pyridin-3-yloxy)-2-fluoro-N-(methylsulfonyl)benzamide | LCMS Rt = 3.78 minutes MS m/z 469 [MH]+ $^1$H NMR (400 MHz, CDCl$_3$): δ 1.08 (m, 2H), 1.14 (m, 2H), 2.38 (m, 1H), 3.42 (s, 3H), 6.62 (m, 1H), 7.28 (m, 1H), 8.24 (m, 2H) |
| 111 | 5-Chloro-4-(5-chloro-6-isopropylpyridin-3-yloxy)-2- | LCMS Rt = 2.83 minutes, m/z 421 [MH]+. $^1$H NMR (400 MHz, d$^6$-DMSO): δ 1.21 (d, 6H), |

-continued

| Ex | Name | Data |
|---|---|---|
| | fluoro-N-(methylsulfonyl)benzamide | 3.33 (s, 3H), 3.46 (sept, 1H), 7.24 (d, 1H), 7.76 (d, 1H), 7.95 (d, 1H), 8.40 (d, 1H). |
| 112 | 5-chloro-4-(5-chloro-6-cyclobutylpyridin-3-yloxy)-2-fluoro-N-(methylsulfonyl)benzamide | LCMS Rt = 2.93 minutes, m/z 433 [MH]+ $^1$HNMR (400 MHz, CDCl$_3$): δ 1.85-1.96 (m, 1H), 2.02-2.17 (m, 1H), 2.31-2.50 (m, 4H), 3.42 (s, 3H), 4.00 (pent, 1H), 6.62 (d, 1H), 7.39 (s, 1H), 8.24 (d, 1H), 8.33 (s, 1H), 8.65 (br s, 1H). |
| 113 | 5-chloro-4-[(5,6-dicyclopropylpyridin-3-yl)oxy]-2-fluoro-N-(methylsulfonyl)benzamide | LCMS Rt = 2.48 minutes MS m/z 425 [MH]+ |

EXAMPLES 114-152

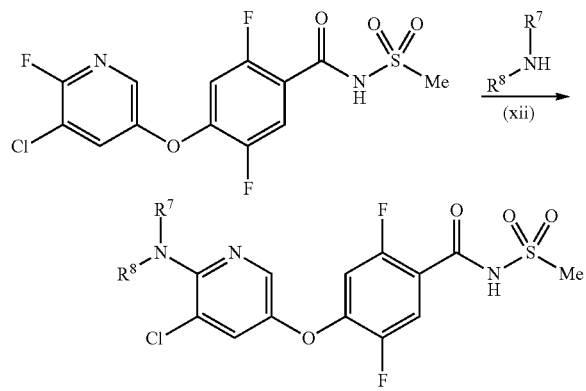

To amines of formula R$^7$R$^8$NH (wherein R$^7$ and R$^8$ are as previously defined for a compound of formula (I) unless otherwise stated) (0.105 mmol) was added a solution of 4-[(5-chloro-6-fluoropyridin-3-yl)oxy]-2,5-difluoro-N-(methylsulfonyl)benzamide (Preparation 30, 28.6 mg, 0.075 mmol) in DMSO (0.6 mL), cesium fluoride (23 mg, 0.15 mmol) and DIPEA (39 µL, 0.225 mmol). The reaction mixtures were shaken in a sealed vial at 80° C. for 16 hours. The reaction mixtures were purified by HPLC (column DIKMA Diamonsil(2) C18 200*20 mm*5 um or Boston Symmetrix ODS-H 150*30 mm*5 um, eluting with acetonitrile:water (containing 0.225% formic acid) gradient 10:90 to 85:15) to afford the title compounds.

| Ex | NAME | MS |
|---|---|---|
| 114 | 4-({5-chloro-6-[isopropyl(methyl)amino]pyridin-3-yl}oxy)-2,5-difluoro-N-(methylsulfonyl)benzamide | 434 [M + H]+ |
| 115 | 4-({5-chloro-6-[(cyclobutylmethyl)amino]pyridin-3-yl}oxy)-2,5-difluoro-N-(methylsulfonyl)benzamide | 446 [M + H]+ |
| 116 | 4-({5-chloro-6-[cyclopropyl(methyl)amino]pyridin-3-yl}oxy)-2,5-difluoro-N-(methylsulfonyl)benzamide | 432 [M + H]+ |
| 117 | 4-({5-chloro-6-[ethyl(methyl)amino]pyridin-3-yl}oxy)-2,5-difluoro-N-(methylsulfonyl)benzamide | 420 [M + H]+ |
| 118 | 4-{[5-chloro-6-(4-ethylpiperazin-1-yl)pyridin-3-yl]oxy}-2,5-difluoro-N-(methylsulfonyl)benzamide | 475 [M + H]+ |
| 119 | 4-({5-chloro-6-[(3R,4R)-3,4-difluoropyrrolidin-1-yl]pyridin-3-yl}oxy)-2,5-difluoro-N-(methylsulfonyl)benzamide | 468 [M + H]+ |
| 120 | 4-[(5-chloro-6-{[(1S,3S)-3-fluorocyclopentyl]amino}pyridin-3-yl)oxy]-2,5-difluoro-N-(methylsulfonyl)benzamide | 464 [M + H]+ |
| 121 | 4-({5-chloro-6-[2-(methoxymethyl)pyrrolidin-1-yl]pyridin-3-yl}oxy)-2,5-difluoro-N-(methylsulfonyl)benzamide | 476 [M + H]+ |
| 122 | 4-({5-chloro-6-[(2-methoxy-2-methylpropyl)amino]pyridin-3-yl}oxy)-2,5-difluoro-N-(methylsulfonyl)benzamide | 464 [M + H]+ |
| 123 | 4-{[5-chloro-6-(3,3-difluoropyrrolidin-1-yl)pyridin-3-yl]oxy}-2,5-difluoro-N-(methylsulfonyl)benzamide | 468 [M + H]+ |
| 124 | 4-{[5-chloro-6-(3-fluoropyrrolidin-1-yl)pyridin-3-yl]oxy}-2,5-difluoro-N-(methylsulfonyl)benzamide | 450 [M + H]+ |
| 125 | 4-{[5-chloro-6-(3-methoxy-3-methylazetidin-1-yl)pyridin-3-yl]oxy}-2,5-difluoro-N-(methylsulfonyl)benzamide | 462 [M + H]+ |
| 126 | 4-{[5-chloro-6-(4-methylpiperidin-1-yl)pyridin-3-yl]oxy}-2,5-difluoro-N-(methylsulfonyl)benzamide | 460 [M + H]+ |
| 127 | 4-({5-chloro-6-[(1-methylpiperidin-3-yl)amino]pyridin-3-yl}oxy)-2,5-difluoro-N-(methylsulfonyl)benzamide | 475 [M + H]+ |
| 128 | 4-({5-chloro-6-[(3R)-3-methoxypiperidin-1-yl]pyridin-3-yl}oxy)-2,5-difluoro-N-(methylsulfonyl)benzamide | 476 [M + H]+ |
| 129 | 4-[(5-chloro-6-{[1-(methoxymethyl)propyl]amino}pyridin-3-yl)oxy]-2,5-difluoro-N-(methylsulfonyl)benzamide | 464 [M + H]+ |

-continued

| Ex | NAME | MS |
|---|---|---|
| 130 | 4-{[5-chloro-6-(3,3-difluoroazetidin-1-yl)pyridin-3-yl]oxy}-2,5-difluoro-N-(methylsulfonyl)benzamide | 454 [M + H]+ |
| 131 | 4-({6-[(1R,4S)-2-azabicyclo[2.2.1]hept-2-yl]-5-chloropyridin-3-yl}oxy)-2,5-difluoro-N-(methylsulfonyl)benzamide | 458 [M + H]+ |
| 132 | 4-({5-chloro-6-[(2R)-2-methylpyrrolidin-1-yl]pyridin-3-yl}oxy)-2,5-difluoro-N-(methylsulfonyl)benzamide | 446 [M + H]+ |
| 133 | 4-({5-chloro-6-[cyclobutyl(methyl)amino]pyridin-3-yl}oxy)-2,5-difluoro-N-(methylsulfonyl)benzamide | 446 [M + H]+ |
| 134 | 4-{[5-chloro-6-(3-fluoroazetidin-1-yl)pyridin-3-yl]oxy}-2,5-difluoro-N-(methylsulfonyl)benzamide | 436 [M + H]+ |
| 135 | 4-({5-chloro-6-[isobutyl(methyl)amino]pyridin-3-yl}oxy)-2,5-difluoro-N-(methylsulfonyl)benzamide | 448 [M + H]+ |
| 136 | 4-[(5-chloro-6-{[(1S)-2-methoxy-1-methylethyl]amino}pyridin-3-yl)oxy]-2,5-difluoro-N-(methylsulfonyl)benzamide | 450 [M + H]+ |
| 137 | 4-{[5-chloro-6-(methylamino)pyridin-3-yl]oxy}-2,5-difluoro-N-(methylsulfonyl)benzamide | 392 [M + H]+ |
| 138 | 4-{[5-chloro-6-(cyclopentylamino)pyridin-3-yl]oxy}-2,5-difluoro-N-(methylsulfonyl)benzamide | 446 [M + H]+ |
| 139 | 4-({5-chloro-6-[methyl(tetrahydrofuran-3-yl)amino]pyridin-3-yl}oxy)-2,5-difluoro-N-(methylsulfonyl)benzamide | 462 [M + H]+ |
| 140 | 4-{[5-chloro-6-(cyclopropylamino)pyridin-3-yl]oxy}-2,5-difluoro-N-(methylsulfonyl)benzamide | 418 [M + H]+ |
| 141 | 4-({5-chloro-6-[(cyclopropylmethyl)(methyl)amino]pyridin-3-yl}oxy)-2,5-difluoro-N-(methylsulfonyl)benzamide | 446 [M + H]+ |
| 142 | 4-[(5-chloro-6-piperidin-1-ylpyridin-3-yl)oxy]-2,5-difluoro-N-(methylsulfonyl)benzamide | 446 [M + H]+ |
| 143 | 4-({5-chloro-6-[(2-methoxyethyl)amino]pyridin-3-yl}oxy)-2,5-difluoro-N-(methylsulfonyl)benzamide | 436 [M + H]+ |
| 144 | 4-[(5-chloro-6-{[(1R,2R)-2-fluorocyclopentyl]amino}pyridin-3-yl)oxy]-2,5-difluoro-N-(methylsulfonyl)benzamide | 464 [M + H]+ |
| 145 | 4-{[5-chloro-6-(tetrahydro-2H-pyran-3-ylamino)pyridin-3-yl]oxy}-2,5-difluoro-N-(methylsulfonyl)benzamide | 462 [M + H]+ |
| 146 | 4-[(5-chloro-6-pyrrolidin-1-ylpyridin-3-yl)oxy]-2,5-difluoro-N-(methylsulfonyl)benzamide | 432 [M + H]+ |
| 147 | 4-{[5-chloro-6-(ethylamino)pyridin-3-yl]oxy}-2,5-difluoro-N-(methylsulfonyl)benzamide | 406 [M + H]+ |
| 148 | 4-({5-chloro-6-[(1-methylpiperidin-4-yl)amino]pyridin-3-yl}oxy)-2,5-difluoro-N-(methylsulfonyl)benzamide | 475 [M + H]+ |
| 149 | 4-({5-chloro-6-[ethyl(2-methoxyethyl)amino]pyridin-3-yl}oxy)-2,5-difluoro-N-(methylsulfonyl)benzamide | 464 [M + H]+ |
| 150 | 4-{[5-chloro-6-(diethylamino)pyridin-3-yl]oxy}-2,5-difluoro-N-(methylsulfonyl)benzamide | 434 [M + H]+ |
| 151 | 4-{[5-chloro-6-(dimethylamino)pyridin-3-yl]oxy}-2,5-difluoro-N-(methylsulfonyl)benzamide | 406 [M + H]+ |
| 152 | 4-({5-chloro-6-[(cyclopropylmethyl)amino]pyridin-3-yl}oxy)-2,5-difluoro-N-(methylsulfonyl)benzamide | 432 [M + H]+ |

EXAMPLES 153-201

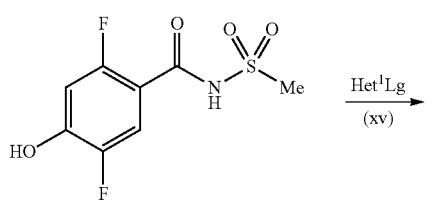

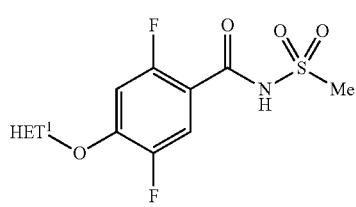

wherein $Het^1$ is as previously defined for a compound of formula (I) and Lg is as previously defined (e.g. halo).

To a solution of 2,5-difluoro-4-hydroxy-N-(methylsulfonyl)benzamide (Preparation 34, 0.10 mmol) in DMSO or NMP (1 mL) was added cesium or potassium carbonate (0.20 mmol) and a solution of $Het^1Lg$ ($Het^1Lg$, 0.13 mmol) in DMSO or NMP (1 mL) and the mixture heated in a sealed vial at 100-150° C. for 5-16 hrs. The reaction mixtures were purified by HPLC (column DIKMA Diamonsil(2) C18 200*20 mm*5 um or Boston Symmetrix ODS-H 150*30 mm*5 um or Agella Venusil ASB C18 150*21.2 mm*5 um or Kromasil Eternity-5-C18 150*30 mm*5 um, eluting with acetonitrile:water (containing 0.225% formic acid) or acetonitrile:aqueous $NH_4OH$ (pH10) gradient 0-76%) to afford the title compounds. Unless stated otherwise, the MS m/z data provided is for the [MH]+ ion.

| Ex | NAME | MS |
|---|---|---|
| 153 | 2,5-difluoro-4-[(4-methoxypyrimidin-2-yl)oxy]-N-(methylsulfonyl)benzamide | 360 |
| 154 | 2,5-difluoro-N-(methylsulfonyl)-4-(quinazolin-2-yloxy)benzamide | 380 |
| 155 | 2,5-difluoro-4-(isoquinolin-1-yloxy)-N-(methylsulfonyl)benzamide | 379 |
| 156 | 2,5-difluoro-N-(methylsulfonyl)-4-(pyrazolo[1,5-a]pyrimidin-7-yloxy)benzamide | 369 |
| 157 | 2,5-difluoro-N-(methylsulfonyl)-4-{5-(1H-pyrazol-1-yl)pyrimidin-2-yl]oxy}benzamide | 396 |
| 158 | 4-[(4,6-dimethylpyrimidin-2-yl)oxy]-2,5-difluoro-N-(methylsulfonyl)benzamide | 358 |
| 159 | 2,5-difluoro-N-(methylsulfonyl)-4-{[4-(trifluoromethyl)pyrimidin-2-yl]oxy}benzamide | 398 |
| 160 | 4-[(3-cyano-4-methylpyridin-2-yl)oxy]-2,5-difluoro-N-(methylsulfonyl)benzamide | 368 |
| 161 | 2,5-difluoro-N-(methylsulfonyl)-4-{[6-(trifluoromethyl)pyridin-2-yl]oxy}benzamide | 397 |
| 162 | 4-[(5-cyano-6-methylpyridin-2-yl)oxy]-2,5-difluoro-N-(methylsulfonyl)benzamide | 368 |
| 163 | 4-[(3-cyano-4-methoxypyridin-2-yl)oxy]-2,5-difluoro-N-(methylsulfonyl)benzamide | 384 |
| 164 | 2,5-difluoro-4-[(4-methylpyrimidin-2-yl)oxy]-N-(methylsulfonyl)benzamide | 344 |
| 165 | 4-[(4-cyanopyridin-2-yl)oxy]-2,5-difluoro-N-(methylsulfonyl)benzamide | 354 |
| 166 | 4-{[2-(dimethylamino)-6-methylpyrimidin-4-yl]oxy}-2,5-difluoro-N-(methylsulfonyl)benzamide | 387 |
| 167 | 4-[(3-cyano-6-methylpyridin-2-yl)oxy]-2,5-difluoro-N-(methylsulfonyl)benzamide | 368 |
| 168 | 4-[(5-cyclopropylpyrimidin-2-yl)oxy]-2,5-difluoro-N-(methylsulfonyl)benzamide | 370 |
| 169 | 4-[(3-cyanopyridin-2-yl)oxy]-2,5-difluoro-N-(methylsulfonyl)benzamide | 354 |
| 170 | 2,5-difluoro-4-[(8-methoxyquinolin-2-yl)oxy]-N-(methylsulfonyl)benzamide | 409 |
| 171 | 4-{[4-(dimethylamino)pyrimidin-2-yl]oxy}-2,5-difluoro-N-(methylsulfonyl)benzamide | 373 |
| 172 | 2,5-difluoro-4-[(5-methyl-7H-pyrrolo[2,3-d]pyrimidin-4-yl)oxy]-N-(methylsulfonyl)benzamide | 383 |
| 173 | 2,5-difluoro-N-(methylsulfonyl)-4-(5H-pyrrolo[3,2-d]pyrimidin-4-yloxy)benzamide | 369 |
| 174 | 4-[(5-cyanopyridin-2-yl)oxy]-2,5-difluoro-N-(methylsulfonyl)benzamide | 354 |
| 175 | 2,5-difluoro-N-(methylsulfonyl)-4-(pyrido[2,3-d]pyrimidin-2-yloxy)benzamide | 381 |
| 176 | 4-{[6-(dimethylamino)pyrimidin-4-yl]oxy}-2,5-difluoro-N-(methylsulfonyl)benzamide | 373 |
| 177 | 4-[(3-cyanopyrazin-2-yl)oxy]-2,5-difluoro-N-(methylsulfonyl)benzamide | 355 |
| 178 | 4-[(4-chloropyridin-2-yl)oxy]-2,5-difluoro-N-(methylsulfonyl)benzamide | 363 |
| 179 | 2,5-difluoro-N-(methylsulfonyl)-4-(quinoxalin-2-yloxy)benzamide | 380 |
| 180 | 4-[(2-ethylimidazo[1,2-b]pyridazin-6-yl)oxy]-2,5-difluoro-N-(methylsulfonyl)benzamide | 397 |
| 181 | 2,5-difluoro-4-[(6-methoxypyridin-2-yl)oxy]-N-(methylsulfonyl)benzamide | 359 |
| 182 | 2,5-difluoro-N-(methylsulfonyl)-4-{[3-(trifluoromethyl)pyridin-2-yl]oxy}benzamide | 397 |
| 183 | 4-[(2,6-dimethylpyrimidin-4-yl)oxy]-2,5-difluoro-N-(methylsulfonyl)benzamide | 358 |
| 184 | 4-[(5-chloropyridin-2-yl)oxy]-2,5-difluoro-N-(methylsulfonyl)benzamide | 363 |
| 185 | 4-[(6-cyano-4-methylpyridin-2-yl)oxy]-2,5-difluoro-N-(methylsulfonyl)benzamide | 368 |
| 186 | 4-{[4-(dimethylamino)-6-methylpyrimidin-2-yl]oxy}-2,5-difluoro-N-(methylsulfonyl)benzamide | 387 |
| 187 | 2,5-difluoro-4-[(3-methylquinoxalin-2-yl)oxy]-N-(methylsulfonyl)benzamide | 394 |
| 188 | 2,5-difluoro-4-[(4-methylpyridin-2-yl)oxy]-N-(methylsulfonyl)benzamide | 343 |
| 189 | 2,5-difluoro-4-[(3-methylpyrazin-2-yl)oxy]-N-(methylsulfonyl)benzamide | 344 |
| 190 | 2,5-difluoro-4-[(6-methoxyquinolin-2-yl)oxy]-N-(methylsulfonyl)benzamide | 409 |
| 191 | 2,5-difluoro-4-[(6-methylpyridin-2-yl)oxy]-N-(methylsulfonyl)benzamide | 343 |
| 192 | 4-[(3-chloropyridin-2-yl)oxy]-2,5-difluoro-N-(methylsulfonyl)benzamide | 363 |
| 193 | 2,5-difluoro-4-[(3-isopropylpyrazin-2-yl)oxy]-N-(methylsulfonyl)benzamide | 372 |
| 194 | 2,5-difluoro-N-(methylsulfonyl)-4-{[5-(trifluoromethyl)pyridin-2-yl]oxy}benzamide | 397 |
| 195 | 2,5-difluoro-N-(methylsulfonyl)-4-(phthalazin-1-yloxy)benzamide | 380 |
| 196 | 2,5-difluoro-4-[(3-methylquinolin-2-yl)oxy]-N-(methylsulfonyl)benzamide | 393 |
| 197 | 2,5-difluoro-4-[(5-fluoro-2-propylpyrimidin-4-yl)oxy]-N-(methylsulfonyl)benzamide | 390 |

| Ex | NAME | MS |
|---|---|---|
| 198 | 4-[(5-chloropyrimidin-2-yl)oxy]-2,5-difluoro-N-(methylsulfonyl)benzamide | 364 |
| 199 | 2,5-difluoro-4-[(6-methylpyrimidin-4-yl)oxy]-N-(methylsulfonyl)benzamide | 344 |
| 200 | 2,5-difluoro-4-[(6-methoxypyrimidin-4-yl)oxy]-N-(methylsulfonyl)benzamide | 360 |
| 201 | 4-[(2-cyanopyridin-3-yl)oxy]-2,5-difluoro-N-(methylsulfonyl)benzamide | 354 |

The compounds of formula (I) that follow were prepared by procedures described in the aforementioned Schemes, foregoing Examples and the corresponding Preparations, using the appropriate reagents and conditions, or by processes similar to either. Unless stated otherwise, the MS m/z data provide is for the [MH]⁺ ion.

| Ex | Name | MS |
|---|---|---|
| L1 | 2,5-difluoro-4-[(6-isobutoxypyridin-3-yl)oxy]-N-(methylsulfonyl)benzamide | 401 |
| L2 | 2,5-difluoro-4-[(6-methoxypyridin-3-yl)oxy]-N-(methylsulfonyl)benzamide | 359 |
| L3 | 2,5-difluoro-4-[(6-methylquinolin-8-yl)oxy]-N-(methylsulfonyl)benzamide | 393 |
| L4 | 4-({2-[ethyl(methyl)amino]-4-methylpyrimidin-5-yl}oxy)-2,5-difluoro-N-(methylsulfonyl)benzamide | 401 |
| L5 | 4-[(6-ethylpyridin-3-yl)oxy]-2,5-difluoro-N-(methylsulfonyl)benzamide | 357 |
| L6 | 2,5-difluoro-4-[(7-fluoroquinolin-8-yl)oxy]-N-(methylsulfonyl)benzamide | 397 |
| L7 | 2,5-difluoro-4-[(2-methylquinolin-6-yl)oxy]-N-(methylsulfonyl)benzamide | 393 |
| L8 | 2,5-difluoro-4-[(5-methylquinolin-8-yl)oxy]-N-(methylsulfonyl)benzamide | 393 |
| L9 | 2,5-difluoro-N-(methylsulfonyl)-4-{[6-(trifluoromethyl)pyridin-3-yl]oxy}benzamide | 397 |
| L10 | 2,5-difluoro-N-(methylsulfonyl)-4-(quinolin-6-yloxy)benzamide | 379 |
| L11 | 2,5-difluoro-4-[(5-methylpyridin-3-yl)oxy]-N-(methylsulfonyl)benzamide | 343 |
| L12 | 2,5-difluoro-4-[(6-fluoroquinolin-8-yl)oxy]-N-(methylsulfonyl)benzamide | 397 |
| L13 | 2,5-difluoro-4-[(2-methylquinolin-8-yl)oxy]-N-(methylsulfonyl)benzamide | 393 |
| L14 | 2,5-difluoro-N-(methylsulfonyl)-4-(quinolin-7-yloxy)benzamide | 379 |
| L15 | 2,5-difluoro-4-(isoquinolin-7-yloxy)-N-(methylsulfonyl)benzamide | 379 |
| L16 | 2,5-difluoro-4-[(8-methylquinolin-5-yl)oxy]-N-(methylsulfonyl)benzamide | 393 |
| L17 | 2,5-difluoro-4-[(4-methyl-2-pyrrolidin-1-ylpyrimidin-5-yl)oxy]-N-(methylsulfonyl)benzamide | 413 |
| L18 | 4-[(1,2-dimethyl-1H-benzimidazol-5-yl)oxy]-2,5-difluoro-N-(methylsulfonyl)benzamide | 396 |
| L19 | 2,5-difluoro-4-[(4-methyl-2-piperidin-1-ylpyrimidin-5-yl)oxy]-N-(methylsulfonyl)benzamide | 427 |
| L20 | 2,5-difluoro-4-[(6-methylpyridin-3-yl)oxy]-N-(methylsulfonyl)benzamide | 343 |
| L21 | 2,5-difluoro-N-(methylsulfonyl)-4-(quinolin-5-yloxy)benzamide | 379 |
| L22 | 2,5-difluoro-4-(isoquinolin-5-yloxy)-N-(methylsulfonyl)benzamide | 379 |
| L23 | 2,5-difluoro-N-(methylsulfonyl)-4-(quinolin-4-yloxy)benzamide | 379 |
| L24 | 4-{[2-(dimethylamino)-4-methylpyrimidin-5-yl]oxy}-2,5-difluoro-N-(methylsulfonyl)benzamide | 387 |
| L25 | 4-{[2-(dimethylamino)-4,6-dimethylpyrimidin-5-yl]oxy}-2,5-difluoro-N-(methylsulfonyl)benzamide | 401 |
| L26 | 2,5-difluoro-4-[(7-fluoroquinolin-4-yl)oxy]-N-(methylsulfonyl)benzamide | 397 |
| L27 | 2,5-difluoro-4-[(5-methylpyridin-2-yl)oxy]-N-(methylsulfonyl)benzamide | 343 |
| L28 | 2,5-difluoro-N-(methylsulfonyl)-4-[(6-propylpyridin-3-yl)oxy]benzamide | 371 |
| L29 | 2,5-difluoro-N-(methylsulfonyl)-4-[(2-piperidin-1-ylpyrimidin-5-yl)oxy]benzamide | 413 |
| L30 | 4-[(2-ethyl-4,6-dimethylpyrimidin-5-yl)oxy]-2,5-difluoro-N-(methylsulfonyl)benzamide | 386 |
| L31 | 3-chloro-4-[(1-methyl-1H-benzimidazol-7-yl)oxy]-N-(methylsulfonyl)benzamide | 380 |
| L32 | 3-cyano-N-(methylsulfonyl)-4-[(4-phenylpyridin-2-yl)oxy]benzamide | 392 |
| L33 | 3-cyano-N-(methylsulfonyl)-4-[(6-phenylpyridin-2-yl)oxy]benzamide | 392 |
| L34 | 3-cyano-N-(methylsulfonyl)-4-(quinolin-2-yloxy)benzamide | 366 |
| L35 | 3-cyano-N-(methylsulfonyl)-4-(quinolin-3-yloxy)benzamide | 366 |
| L36 | 3-chloro-4-(isoquinolin-1-yloxy)-N-(methylsulfonyl)benzamide | 375 |
| L37 | 3-cyano-4-(isoquinolin-4-yloxy)-N-(methylsulfonyl)benzamide | 366 |
| L38 | 5-chloro-2-fluoro-4-(isoquinolin-1-yloxy)-N-(methylsulfonyl)benzamide | 393 |
| L39 | 5-chloro-2-fluoro-N-(methylsulfonyl)-4-(quinolin-2-yloxy)benzamide | 393 |
| L40 | 5-chloro-2-fluoro-4-(isoquinolin-3-yloxy)-N-(methylsulfonyl)benzamide | 393 |
| L41 | 5-chloro-2-fluoro-N-(methylsulfonyl)-4-(quinolin-3-yloxy)benzamide | 393 |
| L42 | 4-[(1-methyl-1H-benzimidazol-7-yl)oxy]-N-(methylsulfonyl)benzamide | 344 |
| L43 | 3-cyano-4-(isoquinolin-3-yloxy)-N-(methylsulfonyl)benzamide | 366 |
| L44 | 5-chloro-2-fluoro-4-[(1-methyl-1H-benzimidazol-7-yl)oxy]-N-(methylsulfonyl)benzamide | 396 |
| L45 | 3-fluoro-4-[(6-methoxypyridin-3-yl)oxy]-N-(methylsulfonyl)benzamide | 341 |
| L46 | 3-chloro-4-[(6-methoxypyridin-3-yl)oxy]-N-(methylsulfonyl)benzamide | 357 |
| L47 | 3-fluoro-4-{[6-(4-fluorophenoxy)pyridin-3-yl]oxy}-2-methoxy-N-(methylsulfonyl)benzamide | 451 |

-continued

| Ex | Name | MS |
|---|---|---|
| L48 | 3-fluoro-N-(methylsulfonyl)-4-[(6-propylpyridin-3-yl)oxy]benzamide | 353 |
| L49 | 3-chloro-4-[(6-methylpyridin-3-yl)oxy]-N-(methylsulfonyl)benzamide | 341 |
| L50 | 3-chloro-4-[(6-ethylpyridin-3-yl)oxy]-N-(methylsulfonyl)benzamide | 355 |
| L51 | 3-fluoro-4-[(6-methylpyridin-3-yl)oxy]-N-(methylsulfonyl)benzamide | 325 |
| L52 | 4-[(6-ethylpyridin-3-yl)oxy]-3-fluoro-N-(methylsulfonyl)benzamide | 339 |
| L53 | 3-fluoro-4-[(6-isobutoxypyridin-3-yl)oxy]-2-methoxy-N-(methylsulfonyl)benzamide | 413 |
| L54 | 4-[(6-isobutoxypyridin-3-yl)oxy]-N-(methylsulfonyl)benzamide | 365 |
| L55 | 4-[(6-ethylpyridin-3-yl)oxy]-2-methyl-N-(methylsulfonyl)benzamide | — |
| L56 | 3-chloro-N-(methylsulfonyl)-4-[(6-propylpyridin-3-yl)oxy]benzamide | 369 |
| L57 | 4-[(6-methoxypyridin-3-yl)oxy]-N-(methylsulfonyl)benzamide | 323 |
| L58 | 3-chloro-4-[(2-methylpyrimidin-5-yl)oxy]-N-(methylsulfonyl)benzamide | 342 |
| L59 | 3-methyl-N-(methylsulfonyl)-4-[(2-piperidin-1-ylpyrimidin-5-yl)oxy]benzamide | 391 |
| L60 | 3-chloro-N-(methylsulfonyl)-4-[(2-piperidin-1-ylpyrimidin-5-yl)oxy]benzamide | 411 |
| L61 | 4-[(2-methylpyrimidin-5-yl)oxy]-N-(methylsulfonyl)-3-(trifluoromethyl)benzamide | 376 |
| L62 | 3-fluoro-2-methoxy-N-(methylsulfonyl)-4-[(2-piperidin-1-ylpyrimidin-5-yl)oxy]benzamide | 425 |
| L63 | 4-[(6-methoxypyridin-3-yl)oxy]-N-(methylsulfonyl)-3-(trifluoromethyl)benzamide | 391 |
| L64 | 3-chloro-N-(methylsulfonyl)-4-(pyrimidin-5-yloxy)benzamide | 328 |
| L65 | 4-[(5-chloro-6-methoxypyridin-3-yl)oxy]-N-(cyclopropylsulfonyl)-2,5-difluorobenzamide | 419 |
| L66 | 2,5-difluoro-4-[(2-methoxypyridin-3-yl)oxy]-N-(methylsulfonyl)benzamide | 359 |
| L67 | 4-[(6-chloro-5-isopropoxypyridin-3-yl)oxy]-2,5-difluoro-N-(methylsulfonyl)benzamide | 421 |
| L68 | 2,5-difluoro-4-[(4-methoxypyridin-3-yl)oxy]-N-(methylsulfonyl)benzamide | 359 |
| L69 | 4-[(5-chloropyridin-3-yl)oxy]-2,5-difluoro-N-(methylsulfonyl)benzamide | 327[1] |
| L70 | 3-chloro-4-[(5-chloropyridin-3-yl)oxy]-N-(methylsulfonyl)benzamide | 359[2] |

[1]'Crude observed'
[2][M – H]–

Preparation 1

4-[(5-Chloro-6-isobutoxypyridin-3-yl)oxy]-3-cyanobenzoic acid

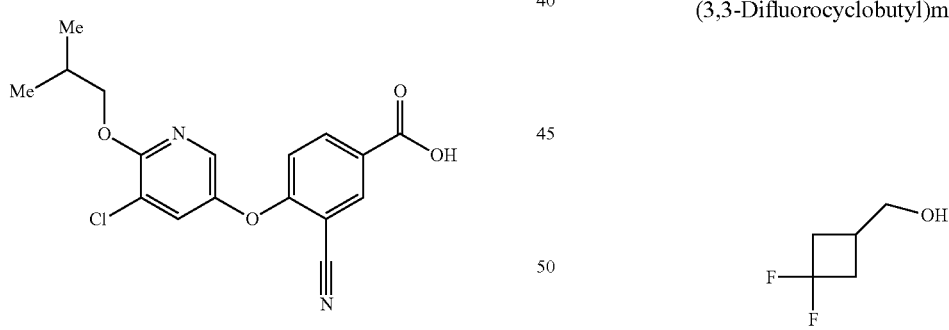

5-Chloro-6-isobutoxypyridin-3-ol (Preparation 16, 0.124 g, 0.62 mmol) and potassium carbonate (0.28 g, 2.03 mmol) were suspended in DMSO (3.0 mL). Then 3-cyano-4-fluorobenzoic acid (0.0835 g, 0.51 mmol) was added portionwise. The reaction was then stirred at 90° C. under nitrogen for 16 hours, diluted in EtOAc (15 mL) and washed twice with an aqueous solution of HCl (2.0 M, 10 mL). The organic layer was then dried over sodium sulfate, filtered, and concentrated in vacuo. The residue was purified by reverse phase column chromatography (ISCO®, gradient of 5-95% acetonitrile in water, 13 g C18 column) to afford the title compound as an orange oil (0.21 g, 120%):

$^1$H NMR (400 MHz, $d_6$-DMSO): δ 0.98-0.99 (d, 6H), 2.04-2.09 (m, 1H), 4.12 (d, 2H), 7.03 (d, 1H), 8.09-8.13 (m, 2H), 8.17 (d, 1H), 8.32 (d, 1H).

LCMS Rt=1.61 minutes MS m/z 347 [MH]$^+$

Preparation 2

(3,3-Difluorocyclobutyl)methanol 3,3-Difluorocyclobutanecarboxylic acid (5.0 g, 36.7 mmol) was dissolved in THF (50.0 mL) and the reaction was cooled to 0° C. under nitrogen with an ice bath. Then thiodimethane—borane (1:1) (5.23 mL, 61.4 mmol) was added drop wise and the mixture stirred at 0° C. for 4 hours. An aqueous solution of HCl (1.0 M, 75 mL) and EtOAc (100 mL) were added and the organic layer was then collected and further washed with water (30 mL). The organic layer was then dried over sodium sulfate, filtered, and concentrated in vacuo to afford title compound (3.25 g, 73%):

¹H NMR (400 MHz, d₆-DMSO): δ 2.15-2.40 (m, 3H), 2.40-2.60 (m, 2H), 3.40 (m, 2H), 4.75 (m, 1H).

Preparation 3

3-Chloro-2-[(3,3-difluorocyclobutyl)methoxy]pyridine

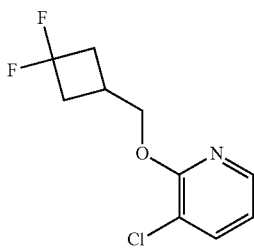 [SMILES: FC1(F)CC(COc2ncccc2Cl)C1]

Sodium hydride (60% dispersion in mineral oil, 1.017 g, 70.6 mmol) was suspended in THF (30.0 mL) and the reaction was cooled to 0° C. under nitrogen with an ice bath. (3,3-Difluorocyclobutyl)methanol (Preparation 2, 2.95 g, 24.2 mmol) in THF (30 mL) was added dropwise to the mixture maintaining the temperature at 0° C. After stirring for 30 minutes, 2,3-dichloropyridine (3.25 g, 22.0 mmol) was added and the suspension was heated to reflux for 16 hours. An aqueous solution of HCl (1.0M, 20 mL) was added and the reaction was extracted with EtOAc (2×100 mL). The combined organics were then dried over sodium sulfate, filtered, and concentrated in vacuo. The residue was purified by silica gel chromatography (Biotage®, gradient of 0-50% EtOAc in heptane,) to afford the title compound (4.82 g, 85%):

¹H NMR (400 MHz, d₆-DMSO): δ 2.40-2.50 (m, 2H), 2.60-2.80 (m, 3H), 4.40 (m, 2H), 7.00 (m, 1H), 7.90 (m, 1H), 8.10 (m, 1H).

LCMS Rt=3.11 minutes MS m/z 234 [MH]⁺

Preparation 4

3-Chloro-2-[(3,3-difluorocyclobutyl)methoxy]-5-(4,4,5,5-tetramethyl-1,3,2-dioxaborolan-2-yl)pyridine

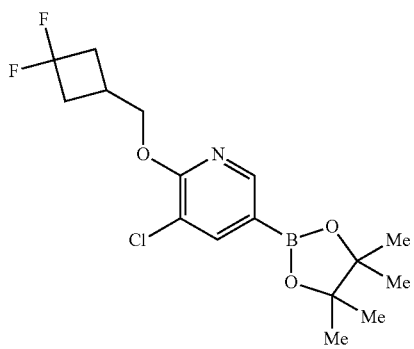 [SMILES: CC1(C)OB(c2cnc(OCC3CC(F)(F)C3)c(Cl)c2)OC1(C)C]

3-Chloro-2-[(3,3-difluorocyclobutyl)methoxy]pyridine (Preparation 3, 4.82 g, 20.6 mmol) was dissolved in 1,4-dioxane (50 mL) and 4,4,4',4',5,5,5',5'-octamethyl-2,2'-bi-1,3,2-dioxaborolane (10.48 g, 41.2 mmol) was added. The reaction mixture was degassed and di-methanolatodiiridium(Ir—Ir)-cycloocta-1,5-diene (1:2) (0.41 g, 0.62 mmol) and 4,4'-di-tert-butyl-2,2'-bipyridine (0.33 g, 1.23 mmol) were also added. The reaction mixture was then stirred at room temperature under nitrogen for 60 hours. Methanol (20 mL) was added and bubbling was observed. When the bubbling stopped, the mixture was concentrated in vacuo and the residue purified by silica gel chromatography (Biotage®, gradient of 0-40% EtOAc in heptane) to afford the title compound (6.4 g, 86%):

¹H NMR (400 MHz, d₆-DMSO): δ 1.30 (s, 12H), 2.50 (m, 2H), 2.60-2.80 (m, 3H), 4.40 (m, 2H), 7.90 (s, 1H), 8.30 (s, 1H).

LCMS Rt=5.24 minutes

Preparation 5

5-Chloro-6-[(3,3-difluorocyclobutyl)methoxy]pyridin-3-ol

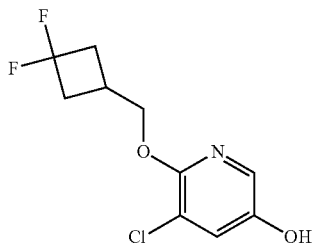 [SMILES: Oc1cnc(OCC2CC(F)(F)C2)c(Cl)c1]

3-Chloro-2-[(3,3-difluorocyclobutyl)methoxy]-5-(4,4,5,5-tetramethyl-1,3,2-dioxaborolan-2-yl)pyridine (Preparation 4, 4.5 g, 12.5 mmol) was suspended in methanol (30 mL). Hydrogen peroxide (1.6 mL, 21.3 mmol) was added and the mixture stirred at room temperature under nitrogen for 16 hours. An aqueous solution of thiosulfite (10%, 10 mL) was added and the mixture was extracted with EtOAc (2×200 mL). The combined organics were dried over sodium sulfate, filtered, and concentrated in vacuo. The residue was purified by silica gel chromatography (Biotage®, gradient of 0-50% EtOAc in heptane) to afford the title compound (2.53 g, 81%):

¹H NMR (400 MHz, d₆-DMSO): δ 2.50 (m, 2H), 2.60-2.80 (m, 3H), 4.25 (m, 2H), 7.35 (s, 1H), 7.60 (s, 1H), 9.75 (s, 1H).

LCMS Rt=2.50 minutes MS m/z 248 [M−H]⁻

Preparation 6 tert-Butyl 2,4,5-trifluorobenzoate

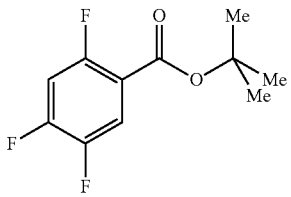 [SMILES: CC(C)(C)OC(=O)c1cc(F)c(F)cc1F]

2,4,5-Trifluorobenzoic acid (10.0 g, 56.8 mmol) was dissolved in tert-butanol (280 mL). Di-tert-butyl dicarbonate (24.8 g, 114 mmol) was added portionwise followed by DMAP (0.694 g, 5.68 mmol) and the mixture stirred at 30° C. under nitrogen for 16 hours. EtOAc (400 mL) was added and the mixture washed with an aqueous solution of HCl (1.0 M, 2×50 mL), then with a saturated aqueous solution of sodium hydrogen carbonate (2×50 mL), and finally with brine (2×50 mL). The organic layer was dried over sodium sulfate, filtered, and concentrated in vacuo to afford the title compound as a colourless oil (12.31 g, 93%):

¹H NMR (400 MHz, CDCl₃): δ 1.58 (s, 9H), 6.93-6.99 (m, 1H), 6.68-6.74 (m, 1H).

Preparation 7 tert-Butyl 4-({5-chloro-6-[(3,3-difluorocyclobutyl)methoxy]pyridin-3-yl}oxy)-2,5-difluorobenzoate

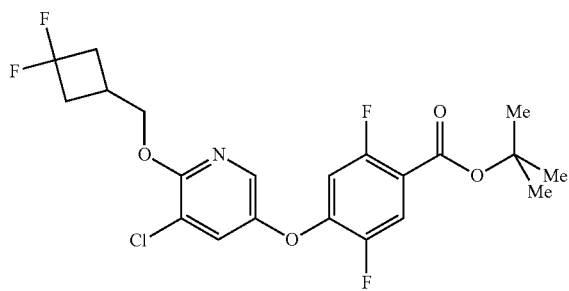 [SMILES: CC(C)(C)OC(=O)c1cc(F)c(Oc2cnc(OCC3CC(F)(F)C3)c(Cl)c2)cc1F]

tert-Butyl 2,4,5-trifluorobenzoate (Preparation 6, 0.200 g, 0.86 mmol), 5-chloro-6-[(3,3-difluorocyclobutyl)methoxy]pyridin-3-ol (Preparation 5, 0.258 g, 1.03 mmol) and potassium carbonate (0.178 g, 1.29 mmol) were suspended in DMSO (5.0 mL). The mixture was stirred at room temperature under nitrogen for 16 hours. EtOAc (50 mL) was added and the mixture was washed with water (3×150 mL). The organic layer was dried over sodium sulfate, filtered, and concentrated in vacuo to afford the title compound (0.400 g, 101%):

¹H NMR (400 MHz, d₆-DMSO): δ 1.50 (s, 9H), 2.50 (m, 2H), 2.60-2.80 (m, 3H), 4.40 (m, 2H), 7.10 (m, 1H), 7.75 (m, 1H), 8.00 (s, 1H), 8.10 (s, 1H).

LCMS Rt=4.75 minutes MS m/z 462 [MH]⁺

Preparation 8

4-({5-Chloro-6-[(3,3-difluorocyclobutyl)methoxy]pyridin-3-yl}oxy)-2,5-difluorobenzoic acid

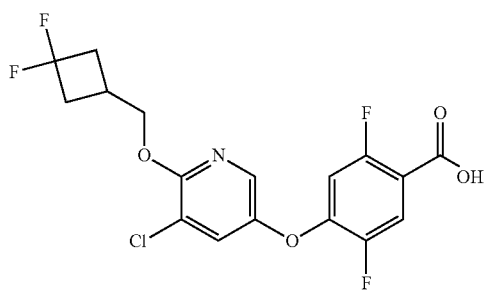 [SMILES: O=C(O)c1cc(F)c(Oc2cnc(OCC3CC(F)(F)C3)c(Cl)c2)cc1F]

tert-Butyl 4-({5-chloro-6-[(3,3-difluorocyclobutyl)methoxy]pyridin-3-yl}oxy)-2,5-difluorobenzoate (Preparation 7, 0.400 g, 0.87 mmol) was dissolved in THF (5.0 mL) and methanol (5.0 mL). Then an aqueous solution of sodium hydroxide was added (3.0 M, 5.0 mL) and the mixture was stirred at room temperature under nitrogen for 3 hours. Aqueous solution of HCl (1.0 M, 75.0 mL) was added and the mixture was extracted with EtOAc (100 mL). The organic layer was dried over sodium sulfate, filtered, and concentrated in vacuo. The residue was purified by reverse phase preparative HPLC (trilution method) to afford the title compound (0.31 g, 88%):

¹H NMR (400 MHz, d₆-DMSO): δ 2.50 (m, 2H), 2.60-2.80 (m, 3H), 4.40 (m, 2H), 7.10 (m, 1H), 7.80 (m, 1H), 8.00 (s, 1H), 8.10 (s, 1H).

LCMS Rt=3.53 minutes MS m/z 404 [M−H]⁻

Preparation 9

4-Methylphenyl 4-[(5-chloro-6-isopropoxypyridin-3-yl)oxy]-2,5-difluorobenzoate

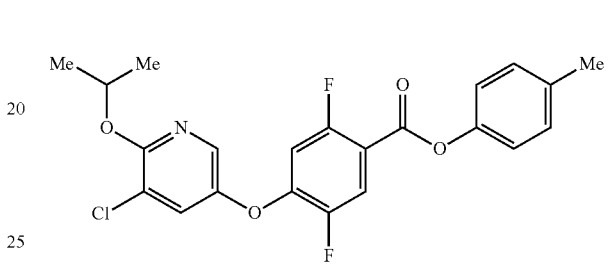

4-Methylphenyl 2,4,5-trifluorobenzoate (Preparation 12, 1.00 g, 3.54 mmol) and potassium carbonate (1.66 g, 12.04 mmol) were suspended in DMSO (24 mL). 5-chloro-6-isopropoxypyridin-3-ol (Preparation 15, 651 mg, 3.47 mmol) was added portionwise over 5 minutes. The mixture was stirred at room temperature for 60 minutes, then partitioned between water (100 mL) and EtOAc (2×75 mL). The combined organics were dried over sodium sulfate, filtered and concentrated in vacuo to afford a green oil (2.5 g) which crystallised on standing. The solid was triturated with heptane to afford the title compound as a colourless solid (1.01 g, 65%):

¹H NMR (400 MHz, CDCl₃): δ 1.42-1.43 (d, 6H), 2.38 (s, 3H), 5.30-5.40 (m, 1H), 6.67-6.71 (m, 1H), 7.08-7.11 (m, 2H), 7.21-7.25 (m, 2H), 7.48-7.49 (d, 1H), 7.91-7.95 (m, 2H).

LCMS Rt=1.81 minutes MS m/z 434 [MH]⁺

Preparation 10

2-Piperidin-1-ylpyrimidin-5-ol

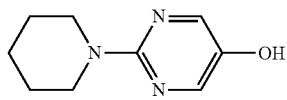 [SMILES: Oc1cnc(N2CCCCC2)nc1]

A solution of 5-bromo-2-piperidin-1-ylpyrimidine (1.00 g, 4.15 mmol) in freshly distilled THF (5.2 mL), was purged with argon and cooled to −78° C. To the cooled reaction mixture was added drop-wise a solution of n-butyllithium in hexane (2.5 M, 1.99 mL, 4.98 mmol). The reaction mixture was stirred at −78° C. for 10 minutes and then added dropwise over 10 minutes to a solution of trimethyl borate (0.559 mL, 4.98 mmol) in THF (5.2 mL), which had been purged with argon and cooled to 0° C. The resulting reaction mixture was stirred at 0° C. for a further 20 minutes, followed by addition of acetic acid (0.356 mL, 6.22 mmol). After a further 5 minutes of stirring, a 30% aqueous solution of hydrogen peroxide (0.517 mL, 4.57 mmol) was added dropwise and stirring continued at 0° C. for 5 minutes. A saturated aqueous solution of sodium bisulfite (50 mL) was added and the mixture extracted with EtOAc. The organic extract was washed with a saturated aqueous brine solution, dried over anhydrous sodium sulfate, filtered over Celite™ and concentrated in vacuo. The crude material was purified using silica gel chromatography eluting with 25% EtOAC in hexane to afford the title compound (728 mg, 98%):

$^1$H NMR (400 MHz, CDCl$_3$): δ 1.40-1.70 (br, 6H), 3.55-3.75 (br, 4H), 8.05 (d, 2H). MS m/z 180 [MH]$^+$, 178 [M−H]$^−$

CHN Theory—C, 60.32%, H, 7.31%, N, 23.45%
CHN Found—C, 60.32%; H, 7.43%; N, 23.10%.

Preparation 11

Methyl 5-chloro-2,4-difluorobenzoate

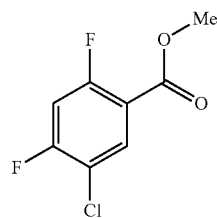 [SMILES: COC(=O)c1cc(Cl)c(F)cc1F]

A solution of 5-chloro-2,4-difluorobenzoic acid (2.8 g, 15 mmol) in a solution of HCl in methanol (4 M, 10 mL) was stirred at 60° C. for 4 hours. The reaction was cooled down and the solvent was evaporated to afford the title compound, which was used for the next step without further purification.

Preparation 12

4-Methylphenyl 2,4,5-trifluorobenzoate

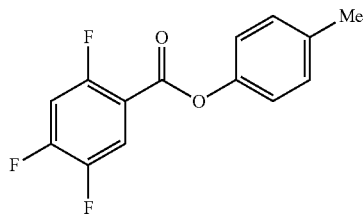

Thionyl chloride (50 mL, 680 mmol) was added to 2,4,5-trifluorobenzoic acid (10 g, 57 mmol) and the mixture stirred at 55° C. for 18 hours. After cooling, the excess thionyl chloride was removed in vacuo. The resulting crude oil was azeotroped twice with DCM (30 mL) and toluene (20 mL) and the residue redissolved in DCM (50 mL), then cooled to 0° C. with an ice bath. A mixture of 4-methylphenol (6.4 g, 59 mmol) and triethylamine (10 mL, 71 mmol) in DCM (20 mL) was added over 30 minutes. The reaction was allowed to warm up to room temperature over 1 hour. The crude reaction mixture was partitioned between EtOAc (200 mL) and saturated sodium bicarbonate solution (70 mL). The aqueous layer was further extracted with EtOAc (100 mL). The combined organic extracts were combined, washed with saturated sodium bicarbonate solution (70 mL) and water (100 mL). The organic layer was dried over magnesium sulfate and concentrated to provide a crude solid, which was purified by silica gel chromatography eluting with 5% EtOAc in heptane to provide the title compound (10.08 g, 66%) as a white solid.

The title compound can also be prepared according to the following method: 4-methylphenol (80.0 g, 739.8 mmol) was added to a suspension of 2,4,5-trifluorobenzoic acid (136.8 g, 776.8 mmol) and 1,1-carbonyldiimidazole (83-85% wt, 163.6 g, 849.7 mmol) in EtOAc (1.20 L) at 40° C. The reaction mixture was stirred at 40° C. for 2 hours, then cooled to 20° C. and washed with water (480 mL), a 0.5 M aqueous solution of sodium hydroxide (2×400 mL) and water (400 mL). The organics were concentrated in vacuo and azeotroped with heptane to give a yellow oil. Heptane (640 mL) was added and the reaction was stirred at room temperature for 16 hours. A seed was used to facilitate the formation of a suspension. The resulting suspension was cooled to 10° C. and filtered. The residue was washed with cold heptane (80 mL) and dried to afford the title compound as an off white solid (147.5 g, 75%):

$^1$H NMR (400 MHz, CDCl$_3$): δ 2.40 (s, 3H), 7.10 (m, 3H), 7.24 (m, 2H), 7.95 (m, 1H).

LCMS Rt=3.53 minutes

Preparation 13

3-Chloro-2-isopropoxypyridine

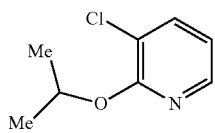

iso-Propanol (128 mL; 1.07 mol) was added dropwise over 50 minutes to a suspension of sodium hydride (64.10 g; 1.07 mol) in THF (1.65 L) at 5° C. The reaction mixture was then warmed to room temperature and stirred for 1 hour. 2,3-Dichloropyridine (154.6 g; 1.11 mol) was added and the reaction mixture was heated to a gentle reflux and left to stir for 18 hours. The reaction mixture was cooled to 5-10° C. and carefully quenched with a brine:water mixture (50:50; 100 mL) followed by water (300 mL). The aqueous layer was extracted with EtOAc (3×600 mL). The combined organics were washed with brine, dried over anhydrous magnesium sulfate, filtered and evaporated to afford the title compound as a dark red oil (164.1 g, 89%):

$^1$H NMR (400 MHz, CDCl$_3$): δ 1.40 (d, 6H), 5.36 (m, 1H), 6.80 (m, 1H), 7.6 (m, 1H), 8.05 (m, 1H).

LCMS Rt=3.09 minutes

Preparation 14

3-Chloro-2-isopropoxy-5-(4,4,5,5-tetramethyl-1-1,3,2-dioxaborolan-2-yl)pyridine

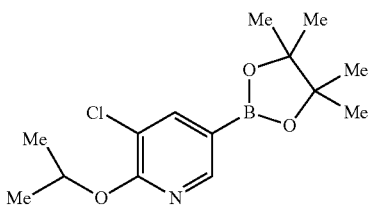 [SMILES: CC(C)Oc1ncc(B2OC(C)(C)C(C)(C)O2)cc1Cl]

3-Chloro-2-isopropoxypyridine (Preparation 13, 154.1 g, 897.9 mmol), bis(pinacolato)diboron (273.6 g, 1077.4 mmol), 4,4-di-tert-butyl-2,2-dipyridyl (2.459 g, 8.979 mmol) were added to heptane (400 mL), followed by di-methanolatodiiridium(Ir—Ir)-cycloocta-1,5-diene (1:2) (0.193 g, 0.2914 mmol). The reaction was stirred at room temperature for 18 hours, quenched with MeOH and concentrated to dryness to afford the title compound as red-brown oil (479 g). The product was carried through to the next step without further purification.

$^1$H NMR (400 MHz, CDCl$_3$): δ 1.32 (s, 12H), 1.38 (d, 6H), 5.41 (m, 1H), 6.75 (m, 1H), 7.94 (d, 1H), 8.37 (d, 1H).

LCMS Rt=5.10 minutes m/z 256 [MH]$^+$

Preparation 15

5-Chloro-6-isopropoxypyridin-3-ol

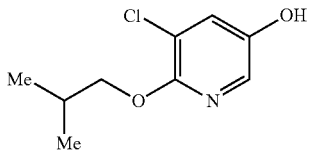

Peracetic acid (191 mL, 1077 mmol) was added to a solution of 3-chloro-2-isopropoxy-5-(4,4,5,5-tetramethyl-1,3,2-dioxaborolan-2-yl)pyridine (Preparation 14, 479 g of crude material, 897.9 mmol if 100% yield in previous Preparation 14) in aqueous acetic acid at 5-10° C. The reaction was warmed slowly to room temperature over 4 hours, concentrated to 10% volume and extracted with EtOAc. The resulting crude material was purified by silica gel chromatography eluting with 50% EtOAc in heptane to afford the title compound as a white solid (110 g, 65%, over two steps).

$^1$H NMR (400 MHz, CDCl$_3$): δ 1.35 (d, 6H), 5.19 (m, 1H), 7.26 (d, 1H), 7.68 (d, 1H).

LCMS Rt=2.10 minutes m/z 186 [MH]$^+$

Preparation 16

5-Chloro-6-isobutoxypyridin-3-ol

To a suspension of 5-chloro-6-isobutoxypyridin-3-ylboronic acid (3.02 g, 13.1 mmol) in acetic acid/water (1:1, 20 mL) cooled to 0° C. was slowly added peracetic acid (3.9 mL, 20.0 mmol) and the reaction mixture was maintained at 0° C. for 1.5 hours and then at room temperature for 1 hour. Additional peracetic acid (3.9 mL, 20.0 mmol) was added and the reaction stirred at room temperature for 40 minutes after which time the suspension dissolved. The reaction mixture was quenched with sodium thiosulphate solution (15 mL) and stirred for 5 minutes. The mixture was extracted with EtOAc (2×30 mL) and the combined organic extracts washed with brine (30 mL), dried over magnesium sulfate and filtered. The solvent was removed under reduced pressure to afford a yellow oil (3.66 g). The oil was purified by silica gel chromatography (Biotage™ 50 g) eluting with 80 to 100% methanol in DCM to afford the title compound as a white solid (1.94 g, 73%):

$^1$H NMR (400 MHz, CDCl$_3$): δ 1.02 (d, 6H), 2.11 (m, 1H), 4.05 (d, 2H), 6.03 (br, 1H), 7.31 (d, 1H), 7.65 (d, 1H).

LCMS Rt=2.51 minutes MS m/z 200 [M–H]$^-$

Preparation 17

4-(5-Chloro-6-methoxypyridin-3-yloxy)-2,5-difluorobenzoic acid lithium salt

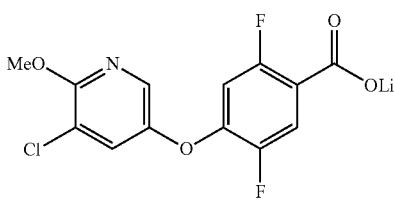

Aqueous lithium hydroxide solution (1 M, 0.88 mL, 0.88 mmol) was added to a solution of tert-butyl 4-(5-chloro-6-methoxypyridin-3-yloxy)-2,5-difluorobenzoate (Preparation 18, 65 mg, 0.176 mmol) in THF (2 mL) and stirred overnight at room temperature under a nitrogen atmosphere. The reaction was then concentrated in vacuo to afford the title compound as the lithium salt (59 mg, 107%):

$^1$H NMR (400 MHz, CDCl$_3$): δ 3.95 (s, 3H), 6.57 (m, 1H), 7.38 (d, 1H), 7.83 (m, 1H), 8.04 (d, 1H).

LCMS Rt=3.12 minutes. MS m/z 316 [MH]$^+$

Preparation 18 tert-Butyl 4-(5-chloro-6-methoxypyridin-3-yloxy)-2,5-difluorobenzoate

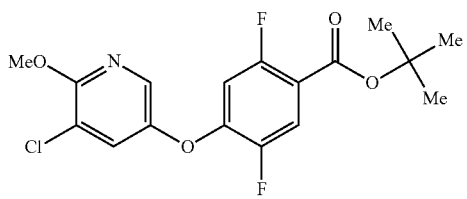 [SMILES: COc1ncc(Oc2cc(F)c(C(=O)OC(C)(C)C)cc2F)cc1Cl]

A mixture of 5-chloro-6-methoxypyridin-3-ol (Preparation 77, 100 mg, 0.627 mmol), tert-butyl 2,4,5-trifluorobenzoate (Preparation 6, 147 mg, 0.633 mmol), and potassium carbonate (260 mg, 1.88 mmol) in DMSO (5 ml) was stirred overnight at 25° C. under a nitrogen atmosphere. The reaction was diluted with water (50 mL) and extracted with EtOAc (3×30 mL). The combined organics were washed with aqueous sodium hydroxide solution (1.0 M, 30 mL), brine (2×40 mL), dried over sodium sulfate, filtered and concentrated in vacuo. The crude was purified by silica gel chromatography eluting with 5% EtOAc in heptane to afford the title compound as a white solid (65 mg, 28%):

$^1$H NMR (400 MHz, CDCl$_3$): δ 1.59 (s, 9H), 3.95 (s, 3H), 6.57 (m, 1H), 7.29 (s, 1H), 7.70 (m, 1H), 8.00 (s, 1H).

LCMS Rt=3.98 minutes. MS m/z 372 [MH]$^+$

Preparation 19

5-Chloro-6-cyclobutoxypyridin-3-ol

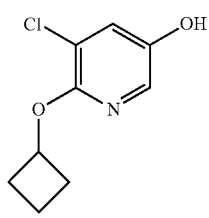 [SMILES: Oc1cnc(OC2CCC2)c(Cl)c1]

Acetic acid solution of peracetic acid (35%, 4.2 mL, 21.3 mmol) was added to a solution of 3-chloro-2-cyclobutoxy-5-(4,4,5,5-tetramethyl-1,3,2-dioxaborolan-2-yl)pyridine (Preparation 20, 4.4 g, 14.2 mmol) in glacial acetic acid (26 mL) and water (13 mL) at 0° C. The reaction mixture was stirred at 0° C. for 1 hour. Aqueous solution of sodium thiosulfate (0.5 M, 80 mL) was added and the mixture was stirred for 30 minutes at room temperature. The aqueous layer was extracted with EtOAc (3×40 mL). The combined organics were dried over magnesium sulfate, filtered and concentrated in vacuo. The crude residue was purified by silica gel chromatography eluting with 10% EtOAc in heptane to afford the title compound as a clear oil (2.05 g, 72%):

$^1$H NMR (400 MHz, CDCl$_3$): δ 1.67 (m, 1H), 1.83 (m, 1H), 2.17 (m, 2H), 2.45 (m, 2H), 5.13 (m, 1H), 5.60 (s, 1H), 7.27 (m, 1H), 7.65 (m, 1H)

LCMS Rt=2.44 minutes. MS m/z 202 [MH]$^+$.

Preparation 20

3-Chloro-2-cyclobutoxy-5-(4,4,5,5-tetramethyl-1,3,2-dioxaborolan-2-yl)pyridine

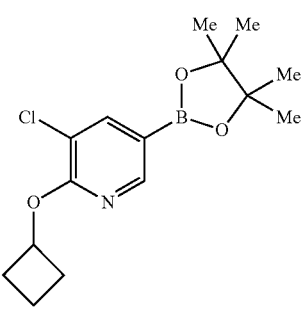 [SMILES: CC1(C)OB(c2cnc(OC3CCC3)c(Cl)c2)OC1(C)C]

3-Chloro-2-cyclobutoxypyridine (Preparation 21, 3.7 g, 20.1 mmol) and bis(pinacolato)diboron (5.6 g, 22.1 mmol) were suspended in heptane (35 mL) and degassed with nitrogen. 4,4'-di-tert-butyl-2,2'-dipyridyl (54 mg, 0.20 mmol) and (1,5-cyclooctadiene) (methoxy)iridium (I) dimer (67 mg, 0.10 mmol) were added and the resulting suspension degassed with nitrogen and stirred at room temperature under nitrogen for 16 hours. Methanol (10 mL) was added dropwise, then the reaction mixture was concentrated in vacuo and the residue purified by silica gel chromatography eluting with 20% of EtOAc in heptane to afford the title compound as a clear oil (4.4 g, 71%):

$^1$H NMR (400 MHz, CDCl$_3$): δ 1.32 (s, 12H), 1.68 (m, 1H), 1.84 (m, 1H), 2.19 (m, 2H), 2.48 (m, 2H), 5.29 (m, 1H), 7.94 (m, 1H), 8.35 (m, 1H).

LCMS Rt=4.42 minutes. MS m/z 310 [MH]$^+$

Preparation 21

3-Chloro-2-cyclobutoxypyridine

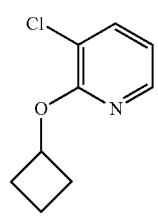 [SMILES: Clc1cccnc1OC1CCC1]

Sodium hydride dispersion (60%, 1.22 g, 30.5 mmol) was suspended in anhydrous THF (40 mL) under a nitrogen atmosphere. A solution of cyclobutanol (2.0 g, 27.7 mmol) in THF (10 mL) was added dropwise at room temperature then the reaction was stirred 1 hour at room temperature. 2,3-dichloropyridine (5.0 g, 33.8 mmol) was added and the reaction mixture was stirred at 60° C. under nitrogen for 16 hours. Water (50 mL) was added and the reaction mixture was concentrated in vacuo. The aqueous layer was extracted with EtOAc (3×30 mL). The combined organics were dried over magnesium sulfate, filtered and concentrated in vacuo. The crude material was purified by silica gel chromatography eluting with 3% EtOAc in heptane to afford the title compound as a clear oil (3.7 g, 72%):

¹H NMR (400 MHz, CDCl₃): δ 1.70 (m, 1H), 1.87 (m, 1H), 2.22 (m, 2H), 2.50 (m, 2H), 5.25 (m, 1H), 6.83 (m, 1H), 7.61 (m, 1H), 8.05 (m, 1H).

LCMS Rt=2.99 minutes. Molecular ion not observed.

Preparation 22

4-{[5-Chloro-6-(tetrahydro-2H-pyran-4-yloxy)pyridin-3-yl]oxy}-2,5-difluorobenzoic acid

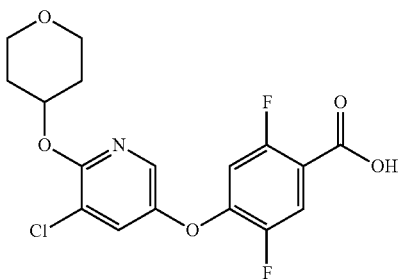 [SMILES: O=C(O)c1cc(F)c(Oc2cnc(OC3CCOCC3)c(Cl)c2)cc1F]

Trifluoroacetic acid (5 mL) was added to a solution of tert-butyl 4-{[5-chloro-6-(tetrahydro-2H-pyran-4-yloxy)pyridin-3-yl]oxy}-2,5-difluorobenzoate (Preparation 23, 0.28 g, 0.64 mmol) in DCM (10 mL) and stirred at room temperature for 16 hours. The reaction mixture was diluted with water (50 mL), and extracted with DCM (3×50 mL). The combined organics were dried over magnesium sulfate, filtered, and concentrated in vacuo to yield a yellow oil, which was purified by silica gel chromatography eluting with EtOAc to afford an off white solid. The solid was triturated with 4:1, heptane: EtOAc to afford the title compound as a white solid (0.24 g):

¹H NMR (400 MHz, CD₃OD): δ 1.72-1.85 (m, 2H), 2.03-2.12 (m, 2H), 3.57-3.67 (m, 2H), 3.91-3.99 (m, 2H), 5.32 (m, 1H), 6.80-6.86 (m, 1H), 7.74-7.81 (m, 1H), 7.96 (s, 1H).

LCMS Rt=2.70 minutes. MS m/z 385 [MH]⁺

Preparation 23 tert-Butyl 4-{[5-chloro-6-(tetrahydro-2H-pyran-4-yloxy)pyridin-3-yl]oxy}-2,5-difluorobenzoate

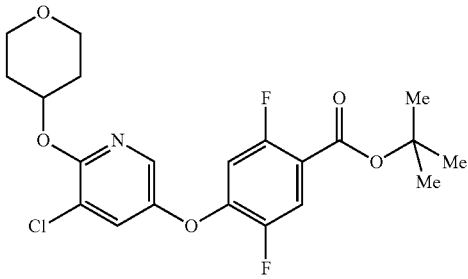 [SMILES: CC(C)(C)OC(=O)c1cc(F)c(Oc2cnc(OC3CCOCC3)c(Cl)c2)cc1F]

Potassium carbonate (0.14 g, 1.63 mmol) was added to a solution of 5-chloro-6-(tetrahydro-2H-pyran-4-yloxy)pyridin-3-ol (Preparation 24, 0.23 g, 0.65 mmol) in DMSO (10 mL). After 1 minute, 2,4,5-trifluoro-tert-butylester (Preparation 6, 0.24 g, 0.69 mmol) was added in one portion, and the reaction was stirred at room temperature for 18 hours. The reaction was diluted with aqueous sodium hydroxide solution (1 M, 100 mL), and extracted with EtOAc (3×50 mL). The combined organics were then dried over magnesium sulfate, filtered, and concentrated in vacuo to afford the title compound as a yellow oil, which was taken onto the next step without further purification (0.28 g, 98%):

¹H NMR (400 MHz, CDCl₃): δ 1.61 (s, 9H), 1.80-1.91 (m, 2H), 2.03-2.11 (m, 2H), 3.57-3.67 (m, 2H), 3.95-4.04 (m, 2H), 5.22-5.31 (m, 1H), 6.56-6.64 (m, 1H), 7.23 (s, 1H), 7.69-7.74 (m, 1H), 7.86 (s, 1H).

LCMS Rt=4.76 minutes. MS m/z 442 [MH]⁺

Preparation 24

5-Chloro-6-(tetrahydro-2H-pyran-4-yloxy)pyridin-3-ol

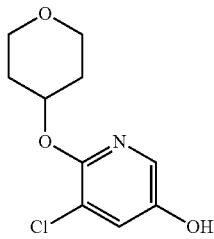 [SMILES: Oc1cnc(OC2CCOCC2)c(Cl)c1]

3-Chloro-2-(tetrahydro-2H-pyran-4-yloxy)pyridine (Preparation 25, 1.40 g, 6.55 mmol) and bis(pinacolato)diboron (6.65 g, 13.11 mmol) were dissolved in heptane (30 mL) and degassed five times with nitrogen. Di-tert-butyldipyridyl (0.017 mg, 0.066 mmol) was added, followed by (1,5-cyclooctadiene)(methoxy)Iridium(I) dimer (0.022 mg, 0.033 mmol). The mixture was again degassed five times with nitrogen and stirred at room temperature for 18 hours. The reaction was quenched by slow addition of methanol (50 mL) and concentrated in vacuo to afford a red/orange oil, which was purified by silica gel chromatography eluting with 66% EtOAc in heptane to afford an impure product. The obtained crude product was dissolved in and a 1:1 mixture of acetic acid:water (30 mL) was added and cooled to 5° C. (ice bath). Peracetic acid was slowly added over 2 minutes. The reaction was stirred at 5° C. for 30 minutes, then a 1 M aqueous solution of sodium thiosulfate was added. The reaction was allowed to slowly warm to room temperature over 30 minutes, diluted with water (50 mL) and extracted with EtOAc (3×50 mL). The combined organics were then dried over magnesium sulfate, filtered, and concentrated in vacuo to afford a yellow oil, which was purified by silica gel chromatography eluting with EtOAc to afford an off-white solid. The solid was triturated in heptane to afford the title compound as a white solid (0.483 g, 43%):

¹H NMR (400 MHz, CDCl₃): δ 1.79-1.90 (m, 2H), 2.01-2.12 (m, 2H), 3.58-3.68 (m, 2H), 3.95-4.08 (m, 2H), 5.18 (m, 1H), 7.27 (s, 1H), 7.63 (s, 1H).

LCMS Rt=1.72 minutes MS m/z 230 [MH]⁺

Preparation 25

3-Chloro-2-(tetrahydro-2H-pyran-4-yloxy)pyridine

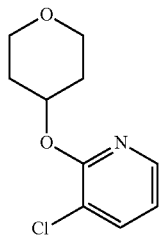 [SMILES: Clc1cccnc1OC1CCOCC1]

Tetrahydro-2H-pyran-4-ol (1.03 g, 10.1 mmol) was added slowly over 1 min to a suspension of NaH (60% in mineral oil) (0.41 g, 10.16 mmol) in anhydrous THF (20 mL) at 5° C. (ice bath). The suspension was then warmed to room temperature. After 30 mins, 2,3-dichloropyridine (1.00 g, 6.76 mmol) was added, and the reaction heated at 70° C. for 18 hours. The reaction was cooled to room temperature and quenched with water (50 mL). The mixture was extracted with EtOAc (3×50 mL). The combined organics were then dried over magnesium sulfate, filtered, and concentrated in vacuo to afford the title compound as a yellow oil, which was taken onto the next step without further purification (1.40 g, 98%):

$^1$H NMR (400 MHz, CDCl$_3$): δ 1.60-2.10 (m, 4H), 3.58-3.67 (m, 2H), 3.95-4.04 (m, 2H), 5.32 (m, 1H), 6.81 (m, 1H), 7.62 (d, 1H), 8.00 (d, 1H).

LCMS Rt=2.53 minutes. Molecular ion not observed.

Preparation 26

4-Methylphenyl 5-chloro-2,4-difluorobenzoate

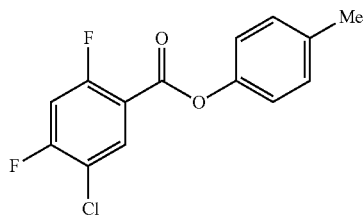 [SMILES: Cc1ccc(OC(=O)c2cc(Cl)c(F)cc2F)cc1]

5-Chloro-2,4-difluorobenzoic acid (1.17 g, 6.08 mmol) was dissolved in thionyl chloride (5.0 mL) and heated at 60° C. under a nitrogen atmosphere for 5 hours. The reaction mixture was concentrated in vacuo and azeotroped with DCM (2×10 mL) and toluene (10 mL). Then the crude was dissolved in DCM (15 mL) and cooled to 0° C. 4-Methylphenol (0.665 g, 6.15 mmol) and triethylamine (1.05 mL, 7.53 mmol) in DCM (10 mL) were added dropwise and the reaction mixture was stirred at room temperature under a nitrogen atmosphere for 18 hours. The reaction mixture was concentrated in vacuo and the residue dissolved in EtOAc (10 mL), then washed with saturated aqueous solution of sodium hydrogencarbonate (2×10 mL). The organic layer was dried over sodium sulfate and concentrated in vacuo to yield the crude solid. The solid was triturated in the minimum amount of heptanes to afford the title compound as a white solid (1.20 g, 69%):

$^1$H NMR (400 MHz; d$_6$-DMSO): δ 7.15-7.20 (d, 2H), 7.25-7.30 (d, 2H), 7.80 (t, 1H), 8.28 (t, 1H).

LCMS Rt=1.89 minutes. MS m/z 283 [MH]$^+$

Preparation 27

2,4,5-Trifluoro-N-(methylsulfonyl)benzamide

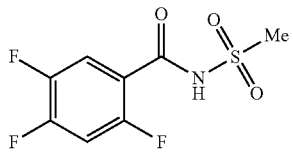 [SMILES: CS(=O)(=O)NC(=O)c1cc(F)c(F)cc1F]

2,4,5-Trifluorobenzoic acid (3.00 g, 17.0 mmol), N-ethyl-N-isopropylpropan-2-amine (8.9 mL, 6.6 g, 51.1 mmol), 2,4,6-Tripropyl-1,3,5,2,4,6-trioxatriphosphorinane-2,4,6-trioxide 50% solution in EtOAc/DMF (12.7 mL, 13.6 g, 42.6 mmol) and methanesulfonamide (3.24 g, 34.1 mmol) were suspended in THF (40 mL) and stirred under a nitrogen atmosphere at reflux for 18 hours. The reaction mixture was cooled, concentrated in vacuo and the residue suspended in water (pH=4). The mixture was acidified to pH=2 with an aqueous solution of potassium hydrogen sulfate (0.5 M). The mixture was extracted with EtOAc (1×100 mL). The organic layer was washed with brine (2×50 mL), dried over sodium sulfate, filtered and evaporated to yield the crude solid. The crude solid was triturated with hexane to yield the title compound as an off-white crystalline solid (3.08 g, 72%):

$^1$H NMR (400 MHz, CDCl$_3$): δ 3.45 (s, 3H), 7.10-7.13 (m, 1H), 7.97-8.02 (m, 1H), 8.74 (br, 1H).

$^{19}$F NMR (400 MHz, CDCl$_3$): δ −112.4, −121.9, −138.5.

Preparation 28

5-Chloro-2,4-difluoro-N-(methylsulfonyl)benzamide

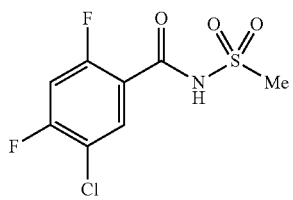 [SMILES: CS(=O)(=O)NC(=O)c1cc(Cl)c(F)cc1F]

5-Chloro-2,4-dilfluorobenzoic acid (0.291 g, 1.511 mmol), N-Ethyl-N'-(3-dimethylaminopropyl)carbodiimide hydrochloride (0.438 g, 2.285 mmol) and 4-dimethylaminopyridine (0.420 g, 3.438 mmol) were suspended in DCM (5 mL). methanesulfonamide (0.222 g, 2.334 mmol) was added and the mixture was stirred at room temperature for 18 hours. The reaction mixture was diluted with DCM (10 mL) and washed with aqueous HCl solution (2 M, 2×15 mL). The organic layer was dried with a phase separating cartridge and concentrated in vacuo to yield the title compound as a white solid (0.388 g, 95%):

$^1$H NMR (400 MHz; d$_6$-DMSO): δ 3.38 (s, 3H), 7.65 (t, 1H), 7.95 (t, 1H)

LCMS Rt=1.43 minutes. MS m/z 268 [M−H]$^−$

Preparation 29

Butane-2-sulfonamide

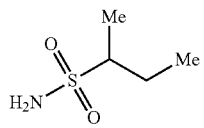

Butane-2-sulfonyl chloride (0.800 g, 5.10 mmol) was added carefully to a cooled solution of ammonium hydroxide solution (~35%, 5.00 mL) and the reaction mixture was stirred vigorously for 4 hours. The solvent was evaporated in vacuo. The resulting residue was triturated with acetone. The filtrate was evaporated in vacuo and the residue triturated with EtOAc/heptane (1:1) to yield the title compound as a clear oil (0.487 g, 70%):

$^1$H NMR (400 MHz; in CDCl$_3$): δ 0.95 (t, 3H), 1.20 (t, 3H), 1.35 (m, 1H), 1.90 (m, 1H), 2.75 (m, 1H), 6.60 (br, 2H).

Preparation 30

4-[(5-Chloro-6-fluoropyridin-3-yl)oxy]-2,5-difluoro-N-(methylsulfonyl)benzamide

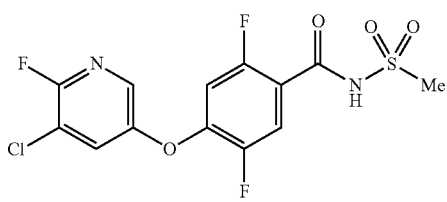 [SMILES: CS(=O)(=O)NC(=O)c1cc(F)c(Oc2cnc(F)c(Cl)c2)cc1F]

Methanesulfonamide (52.0 mg, 0.547 mmol) was suspended in MeCN (3 mL) in a sealed vial. 2,3,4,6,7,8,9,10-Octahydropyrimidol[1,2-a]azepine (0.085 mL, 0.57 mmol) was added followed by 4-methylphenyl 4-[(5-chloro-6-fluoropyridin-3-yl)oxy]-2,5-difluorobenzoate (Preparation 67, 215.0 mg, 0.546 mmol). The mixture was heated at 45° C. for 2 hours. The reaction mixture was diluted in EtOAc (15 mL), then washed with 10% aqueous citric acid solution (2×15 mL). The organic layer was dried over sodium sulfate, filtered, and concentrated in vacuo. The resulting solid was partitioned between DCM (10 mL) and water (10 mL). The organic layer was further washed water (2×10 mL) and concentrated in vacuo to yield the title compound as a white solid (75 mg). EtOAc (15 mL) was added to the combined aqueous. The organic layer was then washed with water (3×10 mL), dried over sodium sulfate, filtered and concentrated in vacuo to yield a second batch of the title compound as a white solid (75.0 mg, 35%):

$^1$H NMR (400 MHz, CDCl$_3$): δ 3.44 (s, 3H), 6.79-6.84 (q, 1H), 7.59-7.62 (m, 1H), 7.95-7.96 (m, 1H), 7.96-8.01 (q, 1H), 8.71-8.75 (br, 1H).

LCMS Rt=1.29 minutes. MS m/z 381 [MH]$^+$ $^{19}$F NMR (400 MHz, CDCl$_3$): −73.88, −112.29, −132.68

Preparation 31

4-[(5-Chloro-6-isobutoxypyridin-3-yl)oxy]benzamide

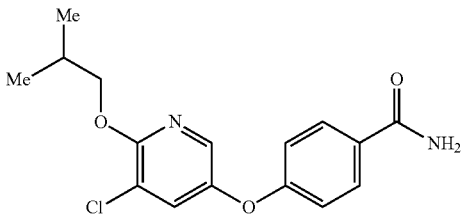 [SMILES: CC(C)COc1ncc(Oc2ccc(C(N)=O)cc2)cc1Cl]

4-[(5-chloro-6-isobutoxypyridin-3-yl)oxy]benzonitrile (Preparation 32, 162 mg, 0.535 mmol) and potassium carbonate (150 mg, 1.085 mmol) were suspended in DMSO (3 mL). Hydrogen peroxide aqueous solution (0.250 mL, 8.08 mmol) was added dropwise (exothermic reaction) and the mixture was stirred at room temperature for 18 hours. The reaction mixture was diluted with EtOAc (15 mL) and washed with water (2×15 mL). The organic layer was dried over sodium sulfate, filtered and concentrated in vacuo to yield a white solid which was triturated in DCM to yield the title compound. The filtrate was concentrated in vacuo and residue treated again triturated with DCM to yield a second crop of the title compound as a white solid (2 crops combined 85.0 mg, 49%):

$^1$H NMR (400 MHz; d$_6$-DMSO): δ 0.97 (s, 3H), 0.98 (s, 3H), 2.05 (m, 1H), 4.10 (d, 2H), 7.01 (d, 2H), 7.29 (br, 1H), 7.85-7.88 (m, 3H), 7.91 (br, 1H), 8.01 (d, 1H).

LCMS Rt=1.64 minutes. MS m/z 321 [MH]$^+$

Preparation 32

4-[(5-Chloro-6-isobutoxypyridin-3-yl)oxy]benzonitrile

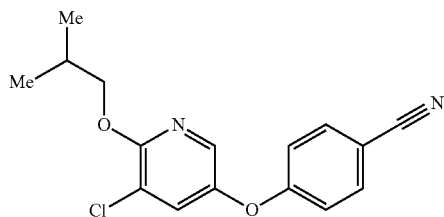 [SMILES: CC(C)COc1ncc(Oc2ccc(C#N)cc2)cc1Cl]

5-Chloro-6-isobutoxypyridin-3-ol (Preparation 16, 145 mg, 0.719 mmol) and potassium carbonate (400 mg, 2.561 mmol) were dissolved in DMSO (3.00 mL). Then 4-fluorobenzonitrile (200 mg, 1.651 mmol) was added and mixture was heated at 110° C. for 18 hours. The reaction mixture was diluted with EtOAc (15 mL) and washed with water (15 mL). The organic layer was dried over sodium sulfate, filtered and concentrated in vacuo. The crude material was purified by silica gel chromatography eluting with 0 to 20% EtOAc in heptane to yield the title compound as a clear oil (162 mg, 74%):

$^1$H NMR (400 MHz; d$_6$-DMSO): δ 0.97 (s, 3H), 0.98 (s, 3H), 2.05 (m, 1H), 4.10 (d, 2H), 7.13 (d, 2H), 7.82 (d, 2H), 7.97 (d, 1H), 8.05 (d, 1H).

LCMS Rt=1.64 minutes. MS m/z 303 [MH]$^+$

Preparation 33

4-{[5-Chloro-6-(trifluoromethyl)pyridin-3-yl]oxy}benzaldehyde

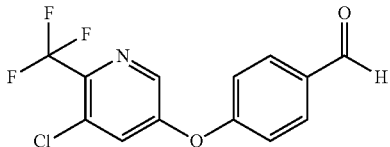 [SMILES: O=Cc1ccc(Oc2cnc(C(F)(F)F)c(Cl)c2)cc1]

5-Chloro-6-(trifluoromethyl)pyridin-3-ol (Preparation 83, 250 mg, 1.266 mmol) was added to a solution of 4-fluorobenzaldehyde (150 mg, 1.209 mmol) and potassium carbonate (260 mg, 1.881 mmol) in DMSO (5 mL). The mixture was stirred at 85° C. for 18 hours, then at 125° C. for 72 hours. The mixture was diluted with EtOAc (15 mL) and washed with water (2×10 mL). The organic layer was dried over sodium sulfate, filtrated and concentration in vacuo. The crude oil was purified by silica gel chromatography eluting with 0 to 20% EtOAc in heptane to yield the title compound as a yellow oil (26.5 mg, 70%):

$^1$H NMR (400 MHz; CDCl$_3$): δ 7.20-7.24 (m, 2H), 7.47-7.48 (d, 1H), 7.96-8.00 (m, 2H), 8.37-8.38 (d, 1H), 10.01 (s, 1H).

LCMS Rt=1.65 minutes. Molecular ion not observed.

Preparation 34

2,5-Difluoro-4-hydroxy-N-(methylsulfonyl)benzamide

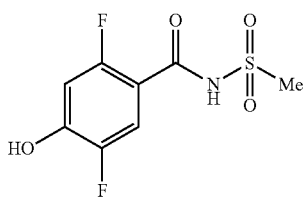 [SMILES: CS(=O)(=O)NC(=O)c1cc(F)c(O)cc1F]

Hydrochloric acid solution in dioxane (4 M, 30 mL) was added to the 4-tert-butoxy-2,5-difluoro-N-(methylsulfonyl)benzamide (Preparation 35, 1.76 g, 5.73 mmol) and the resulting solution stirred at room temperature. After 3 hours the reaction mixture was concentrated in vacuo and the residue azeotroped repeatedly with DCM to yield the title compound as a white solid (1.49 g, 100%):

$^1$H NMR (400 MHz; CDCl$_3$): δ 3.25 (s, 3H), 6.60-6.68 (m, 1H), 7.45-7.55 (m, 1H), 9.80-9.95 (br, 1H), 10.50-10.65 (br, 1H)

LCMS Rt=0.72 minutes. MS m/z 250 [M−H]$^−$, 252 [MH]$^+$

Preparation 35

4-tert-butoxy-2,5-difluoro-N-(methylsulfonyl)benzamide

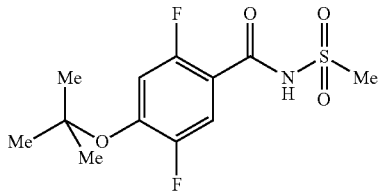 [SMILES: CC(C)(C)Oc1cc(F)c(C(=O)NS(C)(=O)=O)cc1F]

Potassium tert-butoxide (1.46 g, 13.0 mmol) was added to a solution of 2,4,5-trifluoro-N-(methylsulfonyl)benzamide (Preparation 27, 1.5 g, 5.924 mmol) in DMSO (10 mL) and stirred at room temperature. After 3 hours, potassium tert-butoxide (140 mg, 1.3 mmol) was further added and stirred for 18 hours more. The reaction mixture was diluted with EtOAc and 10% aqueous citric acid solution. The pH of the water layer was acidic. The organic layer was washed with more 10% aqueous citric acid and brine, then dried over magnesium sulfate, filtered and concentrated in vacuo to yield the title compound as a cream solid (1.76 g, 100%):

$^1$H NMR (400 MHz; CDCl$_3$): δ 1.45 (s, 9H), 3.42 (s, 3H), 6.88-6.93 (m, 1H), 7.80-7.87 (m, 1H), 8.70-8.85 (br, 1H).

Preparation 36

4-Methyl phenyl 5-chloro-4-{[5-chloro-6-(1-fluoro-1-methylethyl)pyridin-3-yl]oxy}-2-fluorobenzoate

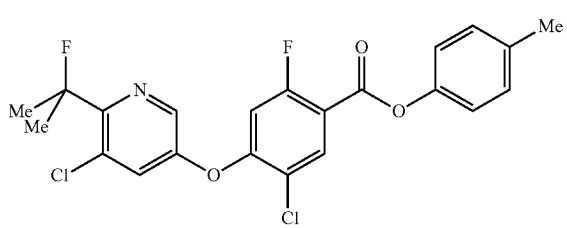 [SMILES: Cc1ccc(OC(=O)c2cc(Cl)c(Oc3cnc(C(C)(C)F)c(Cl)c3)cc2F)cc1]

4-Methylphenyl 5-chloro-2,4-difluorobenzoate (Preparation 26, 141 mg, 0.199 mmol) was added to a suspension of 5-chloro-6-(1,1-difluoroethyl)pyridin-3-ol (Preparation 90, 120 mg, 0.51 mmol) and potassium carbonate (115 mg, 0.832 mmol) in DMSO (3 mL) and the resulting mixture was stirred at room temperature for 2 hours. The reaction mixture was diluted with EtOAc (15 mL) and washed with water (3×20 mL). The organic layer was dried over sodium sulfate, filtered and concentrated in vacuo. The crude material was then purified by silica gel chromatography eluting with 0 to 15% EtOAc in heptanes to yield the title compound (20.8 mg, 23%):

$^1$H NMR (400 MHz; CDCl$_3$): δ 1.83-1.88 (d, 6H), 2.38 (s, 3H), 2.33 (s, 3H), 6.78-6.81 (d, 1H), 7.08-7.11 (m, 2H), 7.22-7.24 (m, 2H), 7.43 (m, 1H), 8.25-8.26 (d, 1H), 8.28-8.29 (m, 1H)

LCMS Rt=1.87 minutes. MS m/z 452 [MH]$^+$.

Preparation 37

4-[(5-Chloro-6-isobutoxypyridin-3-yl)oxy]-2,5-difluorobenzoic acid

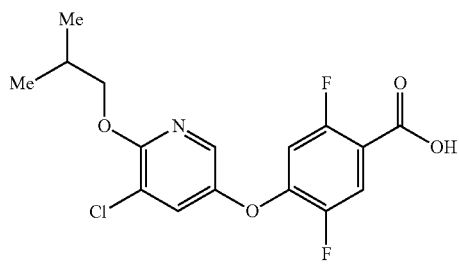 [SMILES: CC(C)COc1ncc(Oc2cc(F)c(C(=O)O)cc2F)cc1Cl]

Ethyl 4-[(5-chloro-6-isobutoxypyridin-3-yl)oxy]-2,5-difluorobenzoate (Preparation 38, 150 mg, 0.389 mmol) and lithium hydroxide (250 mg, 10.44 mmol) were dissolved in water (2.5 mL) and THF (2.5 mL) and stirred at room temperature for 72 hours. The reaction mixture was concentrated in vacuo. The residue was dissolved in EtOAc (10 mL), washed with water (10 mL) and aqueous HCl (2 M, 10 mL), then was dried over sodium sulfate, filtered and concentrated in vacuo to yield the title compound as a white solid (140 mg, 100%):

$^1$H NMR (400 MHz; $d_6$-DMSO): δ 0.97 (s, 3H), 0.99 (s, 3H), 2.05 (m, 1H), 4.10 (d, 2H), 7.04-7.08 (q, 1H), 7.76-7.80 (q, 1H), 8.01 (d, 1H), 8.10 (d, 1H).

LCMS Rt=1.72 minutes. MS m/z 358 [MH]$^+$

Preparation 38

Ethyl 4-[(5-chloro-6-isobutoxypyridin-3-yl)oxy]-2,5-difluorobenzoate

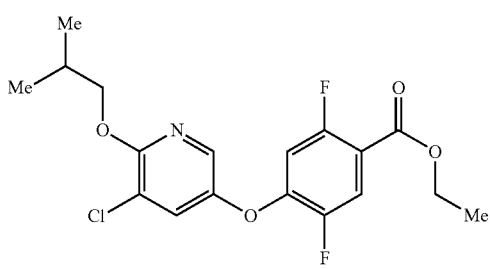 [SMILES: CCOC(=O)c1cc(F)c(Oc2cnc(OCC(C)C)c(Cl)c2)cc1F]

Ethyl 2,4,5-trifluorobenzoate (135 mg, 0.661 mmol) and potassium carbonate (156 mg, 1.129 mmol) were dissolved in DMSO (3.0 mL). 5-Chloro-6-isobutoxypyridin-3-ol (Preparation 16, 127.5 mg, 0.632 mmol) was added portion wise and the mixture was stirred at room temperature for 2 hours. The reaction was diluted in EtOAc (10.0 mL) and washed with brine (3×10 mL). The organic layer was dried over sodium sulfate, filtered and concentrated in vacuo. The residue was purified by silica gel chromatography eluting with 0 to 10% EtOAc in heptane to yield the title compound as a clear oil that solidified upon standing (155 mg, 35%):

$^1$H NMR (400 MHz; $d_6$-DMSO): δ 0.97 (s, 3H), 0.99 (s, 3H), 1.28 (t, 3H), 2.05 (m, 1H), 4.10 (d, 2H), 4.29 (q, 2H), 7.10 (q, 1H), 7.82 (q, 1H), 8.02 (d, 1H), 8.10 (d, 1H).

LCMS Rt=1.77 minutes. MS m/z 386 [MH]$^+$

Preparation 39

1-Isopropyl-1H-indazol-5-ol

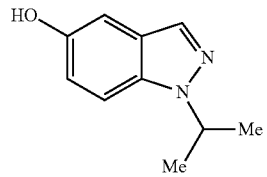 [SMILES: CC(C)n1ncc2cc(O)ccc21]

5-{[tert-Butyl(dimethyl)silyl]oxy}-1-isopropyl-1H-indazole (Preparation 40, 238 mg, 0.819 mmol), triethylamine trishydrofluoride (132 mg, 0.819 mmol) and methanol were combined and stirred at room temperature for 18 hours under a nitrogen atmosphere. The reaction mixture was concentrated in vacuo and the residue redissolved with methanolic ammonia and again concentrated in vacuo. The procedure was repeated once more and the residue purified by silica gel chromatography eluting with 0 to 30% EtOAc in heptane to yield the title compound (123 mg, 86%):

$^1$H NMR (400 MHz, CDCl$_3$): δ 1.60 (d, 6H), 4.82 (m, 1H), 7.11 (m, 1H), 7.14 (m, 1H), 7.34 (m, 1H), 7.90 (br, 1H).

Ms m/z 177 [MH]$^+$

Preparation 40

5-{[tert-Butyl(dimethyl)silyl]oxy}-1-isopropyl-1H-indazole

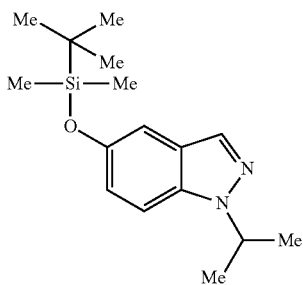 [SMILES: CC(C)n1ncc2cc(O[Si](C)(C)C(C)(C)C)ccc21]

Sodium hydride (60% oil dispersion, 211 mg, 5.28 mmol) was added to a solution of 5-{[tert-butyl(dimethyl)silyl]oxy}-1H-indazole (Preparation 41, 1.09 g, 4.40 mmol) in THF (10 mL) and stirred at room temperature for 15 minutes. The solution was then heated at 50° C. for 18 hours, then at reflux for 8 hours. The reaction mixture was diluted with EtOAc and washed with water, 0.5 N aqueous citric acid solution and brine, then dried over magnesium sulfate, filtered and concentrated in vacuo. The resulting residue was purified by silica gel chromatography eluting with 0 to 10% EtOAc in heptane to yield the title compound as a clear oil (261 mg, 20%):

$^1$H NMR (400 MHz, CDCl$_3$): δ 0.20 (s, 6H), 1.00 (s, 9H), 1.59 (d, 6H), 4.82 (m, 1H), 6.97 (d, 1H), 7.08 (s, 1H), 7.30 (d, 1H) and 7.89 (s, 1H).

MS m/z 291 [MH]$^+$

Preparation 41

5-{[tert-butyl(dimethyl)silyl]oxy}-1H-indazole

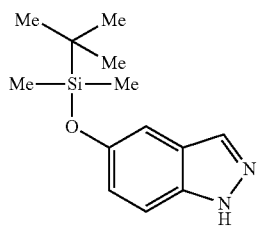 [SMILES: CC(C)(C)[Si](C)(C)Oc1ccc2[nH]ncc2c1]

5-Hydroxyindazole (3.00 g, 22.37 mmol), tert-butyldimethylsilyl chloride (4.05 g, 26.8 mmol) and imidazole (2.28 g, 33.5 mmol) were mixed in DCM (50 mL) and stirred at room temperature for 18 hours. The reaction mixture was poured into 0.5 N aqueous citric acid solution and extracted with DCM (3×25 mL). The combined organics were dried over magnesium sulfate, filtered and evaporated to dryness. The residue was purified by silica gel chromatography eluting with 0 to 50% EtOAc in hexane to yield the title compound as an orange solid (5.09 g, 90%):

$^1$H NMR (400 MHz, CDCl$_3$): δ 0.21 (s, 6H), 1.00 (s, 9H), 7.11 (d, 1H), 7.13 (s, 1H) 7.52 (d, 1H) and 8.06 (s, 1H), NH not observed.

MS m/z 249 [MH]$^+$, 247 [M–H]$^−$

Preparation 42

6-Chloroquinolin-8-ol

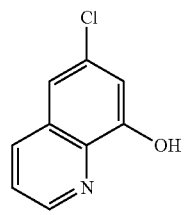

6-Chloro-8-methoxyquinoline (Preparation 43, 10 g, 51.6 mmol) was added to pyridine hydrochloride (43 g, 375 mmol) and the mixture heated at 150° C. 1 hour. The reaction mixture was diluted with water (200 mL), basified to pH=8 with saturated aqueous sodium bicarbonate solution, filtered and concentrated in vacuo. The resulting crude product was purified with silica gel chromatography eluting with 5 to 10% EtOAc in petroleum ether to yield the title compound as a pale yellow solid (5.6 g, 70%):

$^1$H NMR (300 MHz, CDCl$_3$): δ 4.76 (br, 1H), 7.16 (m, 1H), 7.33 (m, 1H), 7.46 (m, 1H), 8.06 (m, 1H), 8.76 (m, 1H).

Preparation 43

6-Chloro-8-methoxyquinoline

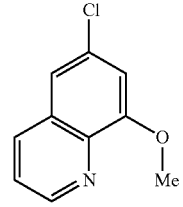

Concentrated sulphuric acid (40 mL) was added to a mixture of 4-chloro-2-anisidine hydrochloride (20 g, 127 mmol), m-nitrobenzene sulfonic acid sodium salt (42.4 g, 190 mmol), boric acid (10 g, 161.8 mmol), ferrous sulfate (6.0 g, 21.5 mmol) and glycerol (400 mL) at room temperature. The mixture was heated at 140° C. for 30 minutes. The reaction mixture was diluted with water (500 mL) and the pH adjusted to 10 with 10% aqueous sodium hydroxide solution. DCM (1 L) was added, stirred for 30 minutes, filtered through celite and the layers separated. The aqueous layer was extracted with DCM (2×500 mL) and the combined organic layers were washed with brine (500 mL), dried over anhydrous sodium sulfate and concentrated in vacuo. The resulting crude product was purified with silica gel chromatography eluting with 20% EtOAc in petroleum ether to yield the title compound as a liquid (14.2 g, 58%):

$^1$H NMR (300 MHz, CDCl$_3$): δ 4.09 (s, 3H), 7.01 (m, 1H), 7.38 (m, 1H), 7.46 (m, 1H), 8.03 (m, 1H), 8.90 (m, 1H).

Preparation 44

2-Isopropoxypyrimidin-5-ol

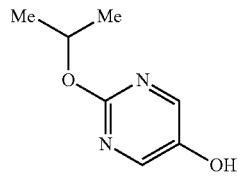 [SMILES: CC(C)Oc1ncc(O)cn1]

An aqueous solution (5 mL) of potassium peroxymonosulfate (1.40 g, 2.27 mmol) was added dropwise to a solution of 2-isopropoxy-5-(4,4,5,5-tetramethyl-1,3,2-dioxaborolan-2-yl)pyrimidine (Preparation 45, 500 mg, 1.89 mmol) in acetone (5 ml) under a nitrogen atmosphere at 0° C. The mixture was stirred at room temperature for 2 hours, then filtered, the filtrate diluted with water (30 mL) and extracted with EtOAc (1×20 mL). The organic layer was washed with brine (2×20 mL), dried over sodium sulfate, filtered and evaporated in vacuo. The resulting oil was dissolved in DCM and purified by silica gel chromatography eluting with 0 to 5% MeOH (with 10% aqueous ammonia) in DCM to yield a solid. The solid was suspended in diethyl ether and evaporated to yield the title compound as a white solid (100 mg, 34%):

$^1$H NMR (400 MHz; CDCl$_3$): δ 1.37 (d, 6H), 1.97 (br, 1H), 5.14-5.31 (m, 1H), 8.20 (s, 2H).
LCMS Rt=10 minutes. Ms m/z 153 [M−H]$^-$ Preparation 45

2-Isopropoxy-5-(4,4,5,5-tetramethyl-1,3,2-dioxaborolan-2-yl)pyrimidine

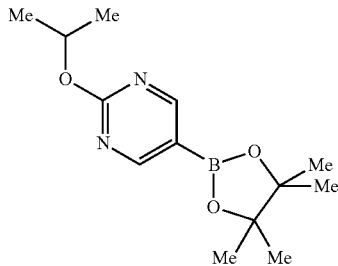 [SMILES: CC(C)Oc1ncc(B2OC(C)(C)C(C)(C)O2)cn1]

5-Bromo-2-isoproxypyrimidine (171.0 g, 787.8 mmol), bis(pinacolato)diboron (290.0 g, 1142.0 mmol), potassium acetate (237.0 g, 2360 mmol) and 1,1'-bis(diphenylphosphino)ferrocene palladium dichloride (9.10 g, 12.44 mmol) were mixed under nitrogen at room temperature in dioxane (1.0 L). The mixture was heated at 95° C. for 30 minutes, then at 105° C. until reaction was complete. The solution was diluted with water (1000 mL) and DCM (2 L), then filtered through celite. The layers were separated and the organic layer was washed with water (1 L), dried over sodium sulfate, filtered and evaporated to give an oil. The oil was purified by silica gel chromatography eluting with 0 to 5% EtOAc in hexane to yield the title compound as a white solid (162 g, 54%):
$^1$H NMR (400 MHz, d$_6$-DMSO): δ 1.30-1.32 (m, 10H), 5.22-5.28 (m, 1H), 8.70 (s, 2H). Molecular ion not observed.

Preparation 46

6-Isopropoxypyridin-3-ol

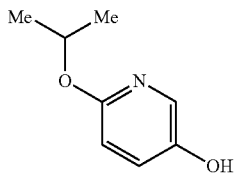 [SMILES: CC(C)Oc1ccc(O)cn1]

5-Chloro-6-isopropoxypyridin-3-ol (0.288 g, 1.54 mmol) was dissolved in absolute ethanol (5 mL) and heated to reflux. Then 10% palladium on Carbon (0.085 g, 0.799 mmol) and ammonium formate (1.35 g, 0.0214 mol) were added and the mixture was stirred at reflux under nitrogen for one hour. The reaction mixture was filtered on a pad of Arbocel® under a nitrogen stream and washed with MeOH (15 mL). The filtrate was concentrated in vacuo. The resulting crude was then diluted in EtOAc (20 mL) and washed with water (30 mL). The organic layer was then dried over sodium sulfate, filtered, and concentrated in vacuo to give title compound as a white solid (0.23 g, 97%):
$^1$H NMR (400 MHz, d$_6$-DMSO): δ 1.20-1.22 (d, 6H), 5.00-5.09 (m, 1H), 6.54-6.56 (d, 1H), 7.10-7.13 (m, 1H), 7.63-7.64 (d, 1H), 9.18 (s, 1H)
LCMS Rt=0.72 minutes MS m/z 154 [MH]$^+$ Preparation 47

3-Chloro-2-iodopyridine

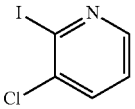

2-Bromo-3-chloropyridine (6.25 g, 0.033 mol) and sodium iodide (14.5 g, 0.10 mol) were dissolved in propionitrile (26 mL). Chloro(trimethyl)silane (4.1 mL, 32 mmol) was then added dropwise to the mixture. After the bubbling stopped, the reaction mixture was brought to reflux under nitrogen for two hours. The mixture was diluted in EtOAc (75 mL) and washed three times with water (50 mL). The organic layer was then dried over sodium sulfate, filtered, and concentrated in vacuo to give title compound as pale yellow solid (6.69 g, 86%):
$^1$H NMR (400 MHz, d$_6$-DMSO): δ 7.42-7.45 (q, 1H), 7.94-7.97 (m, 1H), 8.30-8.32 (m, 1H)
LCMS Rt=1.38 minutes MS m/z 240 [MH]$^+$ Preparation 48

3-Chloro-2-cyclopropylpyridine

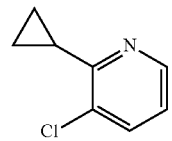

3-Chloro-2-bromopyridine (5.0 g, 26 mmol) and potassium phosphate tribasic (19.3 g, 90.9 mol) were suspended in toluene (40.0 mL) and water (2.0 mL). The mixture was sonicated for 10 minutes, then cyclopropylboronic acid (1.12 g, 13.0 mmol), palladium diacetate (0.093 g, 0.414 mol) and tricyclohexylphosphine (0.243 g, 0.867 mol) were added to the reaction mixture, which was heated into a pre heated DrySyn® at 100° C., under a nitrogen atmosphere for 2 hours. Then cyclopropylboronic acid (1.12 g, 13.0 mmol), palladium diacetate (0.093 g, 0.41 mol) and tricyclohexylphosphine (0.243 g, 0.87 mol) were added to the reaction mixture and the mixture was stirred for 2 hours. Then cyclopropylboronic acid (1.12 g, 13.0 mmol), palladium diacetate (0.093 g, 0.41 mol) and tricyclohexylphosphine (0.243 g, 0.87 mol) were added to the reaction mixture and the mixture was stirred for 2 hours more. The reaction mixture was then left to stir at room temperature for 16 hours. The reaction mixture was diluted with EtOAc (40.0 mL) and water (40.0 mL) and was filtered on a pad of Arbocel® under a stream of nitrogen. The organic layer was separated and washed with a 10% solution of aqueous citric acid (3×25.0 mL), followed by an aqueous hydrochloric acid solution (1.0 M, 3×20.0 mL). The organic layer was discarded and the aqueous layer basified again with careful addition of a saturated aqueous solution of sodium hydrogen carbonate (100.0 mL). The product was extracted with tert-butyl methyl ether (3×20.0 mL). The combined organics were washed once more with a 10% solution of aqueous citric acid (25.0 mL). The organic layer was then dried over sodium sulfate, filtered, and concentrated in vacuo to yield the title compound as a pale brown oil (2.45 g, 62%).

¹H NMR (400 MHz, d₆-DMSO): δ 0.94-1.01 (m, 4H), 2.40-2.48 (m, 1H), 7.13-7.16 (m, 1H), 7.78-7.81 (m, 1H), 8.33-8.34 (m, 1H).

LCMS Rt=2.27 minutes MS m/z 154 [MH]⁺

Preparation 49

3-Chloro-2-isobutylpyridine

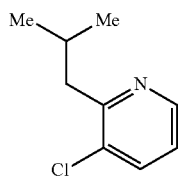 [SMILES: CC(C)Cc1ncccc1Cl]

3-Chloro-2-iodopyridine (1.552 g, 6.482 mmol), isobutylboronic acid (0.725 g, 7.112 mmol), potassium carbonate (2.7 g, 0.0195 mol) and silver oxide (3.8 g, 0.0164 mol) were suspended in THF (25 mL). The mixture was degassed three times and 1,1-Bis(diphenylphosphino)ferrocene-palladium (11)dichloride dichloromethane (1:1) (0.520 g, 0.637 mmol) was added. The reaction mixture was heated at 75° C. under nitrogen for seven hours. The mixture was diluted EtOAc (15 mL) and washed with an aqueous solution of hydrochloric acid (2.0 M, 2×15 mL). The organic layer was discarded and the aqueous layer basified with careful addition of a saturated aqueous solution of sodium hydrogen carbonate (50 mL). The product was extracted with EtOAc (2×15 mL). The organics were combined, dried over sodium sulfate, filtered, and concentrated in vacuo. The resulting crude was purified by silica gel chromatography eluting with 0 to 5% EtOAc in heptane to yield the title compound as a colourless oil (0.582 g, 53% yield).

¹H NMR (400 MHz, d₆-DMSO): δ 0.87-0.89 (d, 6H), 2.09-2.17 (m, 1H), 2.72-2.74 (d, 2H), 7.24-7.27 (m, 1H), 7.83-7.86 (m, 1H), 8.44-8.45 (m, 1H).

LCMS Rt=1.30 minutes MS m/z 170 [MH]⁺

Preparation 50

2-tert-Butyl-3-chloropyridine

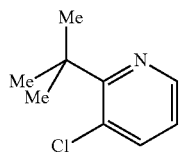 [SMILES: CC(C)(C)c1ncccc1Cl]

2,3-Dichloropyridine (1.0 g, 0.0068 mol) and copper iodide (0.065 g, 0.341 mmol) were dissolved in THF (6 mL). The mixture was degassed three times then cooled to 0° C. with an ice bath. Then tert-butyl(chloro)magnesium in diethylether (5.10 mL, 0.0102 mol) was added drop wise to the reaction mixture under nitrogen keeping the temperature at 0° C. with an ice bath. When the addition was complete, it was left to warm up to room temperature for 16 hours. A saturated aqueous solution of sodium chloride was slowly added to the reaction mixture (20 mL). The product was then extracted with tert-butyl methyl ether (20 mL). The organic layer was then dried over sodium sulfate, filtered, and concentrated in vacuo. The resulting crude was purified by silica gel chromatography eluting with 0 to 5% EtOAc in heptanes to yield the title compound as a yellow oil (0.108 g, 9% yield).

¹H NMR (400 MHz, CDCl₃): δ 1.51 (s, 3H), 7.07-7.10 (m, 1H), 7.61-7.63 (m, 1H), 8.42-8.44 (m, 1H).

LCMS Rt=1.55 minutes MS m/z 170 [MH]⁺

Preparation 51

5-Chloro-6-(1-hydroxy-1-methylethyl)pyridin-3-ol

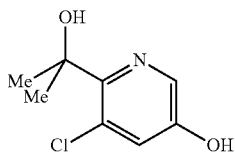 [SMILES: CC(C)(O)c1ncc(O)cc1Cl]

1-(3-Chloro-5-hydroxypyridin-2-yl)ethanone (0.075 g, 0.0068 mol) was dissolved in THF (2 mL). The mixture was degassed three times then cooled to 0° C. with an ice bath. Then bromo(methyl)magnesium in diethylether (0.3 mL, 0.0009 mol) was added dropwise to the reaction mixture under nitrogen keeping the temperature at 0° C. with an ice bath. When the addition was complete, it was left to warm up to room temperature for 16 hours. Then bromo(methyl)magnesium in diethylether (0.3 mL, 0.0009 mol) was added dropwise to the reaction mixture and was stirred at room temperature for further 3 hours. A saturated aqueous solution of sodium chloride was slowly added to the reaction mixture (10 mL) and then it was extracted with EtOAc (2×10 mL). The organic layers were combined, dried over sodium sulfate, filtered, and concentrated in vacuo to obtain the title compound as a translucent solid (0.049 g, 4% yield):

¹H NMR (400 MHz, CDCl₃): δ 1.50 (s, 6H), 2.31 (s, 3H), 5.30 (s, 1H), 7.24-7.25 (d, 1H), 8.00-8.01 (d, 1H).

LCMS Rt=0.81 minutes MS m/z 188 [MH]⁺

Preparation 52

3,4,6-Trifluoro-2-methoxybenzaldehyde

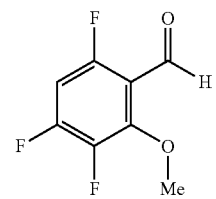

Paraformaldehyde (0.960 g, 0.01066 mol) and magnesium dichloride (0.505 g, 0.005304 mol) were suspended in THF (10.0 mL). Triethylamine (0.75 mL, 0.0054 mol) was added and the mixture was stirred under nitrogen for 10 minutes. Then 2,3,5-trifluorophenol (0.524 g, 0.00027 mol) was added and the reaction mixture was stirred at refluxed for 16 hours. The reaction mixture was subjected to filtration and the filtrate was diluted with an aqueous solution of hydrochloric acid (2.0 M, 15 mL). The product was then extracted with tert-butyl methyl ether (20 mL). The organic layer was dried over sodium sulfate, filtered, and concentrated in vacuo. The crude was dissolved in DMF (5.0 mL). Then potassium carbonate (0.55 g, 0.003979 mol) and methyl iodide (0.175 mL, 0.00072 mol) were added to the mixture, which was stirred at 50° C. under nitrogen for 3 hours, then left to stir at room temperature for 72 hours. The reaction was diluted in an aqueous solution of saturated brine (15 mL) and extracted with tert-butyl methyl ether (20 mL). The organics were combined, dried over sodium sulfate, filtered, and concentrated in vacuo. The resulting crude was purified by silica gel chromatography eluting with 0 to 10% EtOAc in heptane to yield the title compound as a colourless oil (0.080 g, 0.432 mmol).

$^1$H NMR (400 MHz, CDCl$_3$): δ 4.14-4.15 (d, 3H), 6.68-6.74 (m, 1H), 10.27 (m, 1H).

LCMS Rt=1.07 minutes

Preparation 53

3-Chloro-2-(1,1-difluoro-2-methylpropyl)pyridine

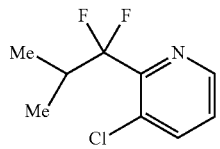

N-Ethyl-N-(trifluoro-lambda~4~-sulfanyl)ethanamine (5.29 mL, 0.040 mol) was added dropwise to a solution of 1-(3-chloropyridin-2-yl)-2-methylpropan-1-one (0.74 g, 4.4 mmol) in DCM (20 mL) under a nitrogen atmosphere. The reaction mixture was stirred at room temperature for 240 hours. DCM was added to the reaction mixture (10 mL), followed by an aqueous solution of saturated brine (3 mL) and water (5 mL). The aqueous layer was further extracted with DCM (2×15 mL). The organics were combined, dried over sodium sulfate, filtered, and concentrated in vacuo. The resulting crude was purified by silica gel chromatography eluting with 0 to 10% EtOAc in heptane to yield the title compound as a brown oil (0.803 g, 44% yield).

$^1$H NMR (400 MHz, CDCl$_3$): δ 1.06-1.07 (d, 6H), 2.74-2.90 (m, 1H), 7.32-7.35 (m, 1H), 7.77-7.80 (m, 1H), 8.50-8.53 (m, 1H).

Preparation 54

1-(3-Chloropyridin-2-yl)-2-methylpropan-1-one

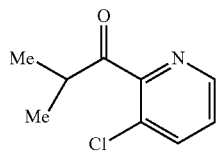 [SMILES: CC(C)C(=O)c1ncccc1Cl]

Chloro(isopropyl)magnesium in THF (35.0 mL, 0.070 mol) was added dropwise to a solution of chloro-2-pyridinecarbonitrile (5.01 g, 0.036 mol) in THF (100 mL) under nitrogen atmosphere at 0° C. It was kept at 0° C. for 2 hours after the addition was complete. The reaction mixture was poured into ice (100 g) and then acidified to pH=3 with an aqueous solution of hydrochloric acid (2.0 M, 100 mL). The product was then extracted with EtOAc (3×100 mL). The organics were combined, dried over sodium sulfate, filtered, and concentrated in vacuo. The resulting crude was purified by silica gel chromatography eluting with 3 to 10% EtOAc in heptane to yield the title compound as a yellow oil (1.98 g, 15% yield):

$^1$H NMR (400 MHz, CDCl$_3$): δ 1.18 (d, 6H), 3.70 (m, 1H), 7.34 (m, 1H), 7.78 (m, 1H), 8.52 (m, 1H).

LCMS Rt=2.89 minutes MS m/z 184 [MH]$^+$

Preparation 55

3-Chloro-2-(1,1-difluoroethyl)pyridine

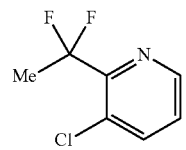 [SMILES: CC(F)(F)c1ncccc1Cl]

Prepared according to Preparation 53 using 1-(3-chloropyridin-2-yl)ethanone:

$^1$H NMR (400 MHz, CDCl$_3$): δ 2.04-2.13 (t, 3H), 7.32-7.34 (m, 1H), 7.78-7.81 (m, 1H), 8.49-8.51 (m, 1H).

LCMS Rt=1.24 minutes MS m/z 178 [MH]$^+$

Preparation 56

Cyclopropanol

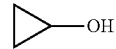

A solution of aqueous H$_2$O$_2$ (30%, 20 mL, 200 mmol) was added dropwise with continuous stirring at 0° C. to a suspension of cyclopropyl boronic acid (0.62 g, 7.2 mmol) in 10% aqueous NaOH (5 mL). The resulting mixture was stirred for 1 hour at 0° C. The reaction mixture was quenched with saturated aqueous Na$_2$S$_2$O$_3$ and extracted with Et$_2$O. The combined organics were dried over sodium sulfate, filtered, and concentrated in vacuo at 0° C. The material was dissolved in Et$_2$O (15 ml), 4 Å Molecular sieves were added and it was left overnight at room temperature to yield the title compound as pale yellow oil (140 mg, 33%):

$^1$H NMR (400 MHz, CDCl$_3$): δ 0.43 (m, 4H), 3.36 (m, 1H).

Preparation 57

3-Chloro-2-(difluoromethoxy)pyridine

2-Hydroxy pyridine (1.0 g, 7.7 mmol) was added slowly to a suspension of NaH (0.34 g, 8.5 mmol) in dry acetonitrile under a nitrogen atmosphere at room temperature and stirred for 10 minutes. Caesium fluoride (0.12 g, 0.77 mmol) was then added followed by slow addition of trimethylsilyl difluoro(fluorosulfonyl)acetate (1.7 ml, 2.1 g, 8.5 mmol). The reaction mixture was quenched with water and most of the solvent removed in vacuo. The residue was partitioned between water and EtOAc. The combined organics were washed with brine, dried over sodium sulfate, filtered, and concentrated in vacuo to yield the title compound as a pale yellow oil (1.3 g, 94% yield):

$^1$H NMR (400 MHz, CDCl$_3$): δ 7.09 (d, 1H), 7.48 (t, 1H), 7.78 (d, 1H), 8.10 (d, 1H).

LCMS Rt=1.37 minutes MS m/z 180 [MH]$^+$

Preparation 58

6-d9-tert-butoxy-5-chloropyridin-3-ol

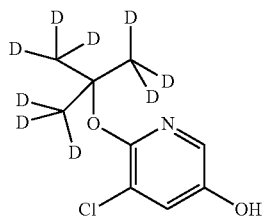 [SMILES: [2H]C([2H])([2H])C(Oc1ncc(O)cc1Cl)(C([2H])([2H])[2H])C([2H])([2H])[2H]]

Hydrogen peroxide solution (30%, 0.462 mL, 4.52 mmol) was added in five portions to a solution of 2-tert-butoxy-3-chloro-5-(4,4,5,5-tetramethyl-1,3,2-dioxaborolan-2-yl)pyridine-d__9_ (Preparation 112, 1.21 g, 3.773 mmol) in MeOH/H$_2$O (30 mL: 10 mL) at 0° C. The reaction mixture was stirred at room temperature for three and a half hours. An aqueous solution of sodium thiosulfate (0.1 M, 20 mL) was added, then stirred at room temperature for 5 minutes and extracted with 50 mL EtOAc. Organics were washed with brine (2×30 mL), dried over magnesium sulfate and evaporated in vacuo to afford the crude material as a yellow oil. The crude material was purified by silica gel chromatography eluting with 0 to 60% EtOAc in heptane to afford the title compound as a waxy white solid:

$^1$H NMR (400 MHz, CDCl$_3$): δ 4.73 (s, OH), 7.24 (d, 1H), 7.69 (d, 1H).

LCMS Rt=1.27 minutes MS m/z 209 [M−H]$^−$

Preparation 59 tert-Butyl 5-chloro-2,4-difluorobenzoate

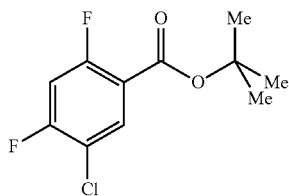 [SMILES: CC(C)(C)OC(=O)c1cc(Cl)c(F)cc1F]

Di-tert-butyl dicarbonate (22.7 g, 104 mmol) was added portionwise followed by N,N-dimethylpyridin-4-amine (0.635 g, 5.20 mmol) to a solution of 5-chloro-2,4-difluorobenzoic acid (10.0 g, 51.9 mmol) in tert-butanol (140.0 mL). The mixture stirred at 45° C. under nitrogen for 64 hours. The solvent was concentrated in vacuo and then EtOAc (50.0 mL) was added. The mixture was washed with an aqueous solution of hydrochloric acid (1.0 M, 50.0 mL), then with a saturated aqueous solution of sodium hydroxide (1.0 M, 50.0 mL), and finally with brine (50.0 mL). The organic layer was dried over sodium sulfate, filtered, and concentrated in vacuo. The resulting oil was filtered through a pad of silica eluting with a 30% solution of EtOAc in heptane to afford the title compound as a colourless oil (11.6 g, 90%):

$^1$H NMR (400 MHz, d$^6$-DMSO): δ 1.50 (s, 9H), 7.62-7.67 (m, 1H), 7.94-7.98 (m, 1H).

LCMS Rt=2.98 minutes

Preparation 60 tert-Butyl 2,4-difluorobenzoate

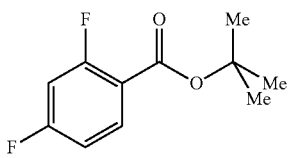

A solution of 2,4-difluorobenzoic acid (1 g, 6.32 mmol), di-tert-butyl carbonate (2.76 g, 12.65 mmol) and 4-dimethylaminopyridine (77 mg, 0.63 mmol) in tert-butanol (10 mL) was heated to 40° C. for 18 hours. The reaction was quenched with 2M aqueous HCl and extracted into EtOAc. Combined organics were washed with NaOH solution (1M) and evaporated to yield the title compound as a yellow oil (1.1 g, 81%):

$^1$H NMR (400 MHz, CD$_3$OD): δ 1.57 (s, 9H), 6.95-7.03 (m, 2H), 7.82-7.91 (m, 1H).

LCMS Rt=3.14 minutes Molecular ion not observed.

Preparation 61 tert-Butyl-3,4,5-trifluorobenzoate

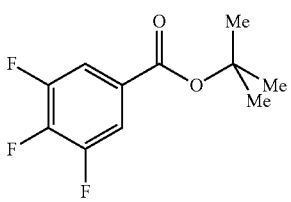 [SMILES: CC(C)(C)OC(=O)c1cc(F)c(F)c(F)c1]

To a solution of tBuOH (10 mL) was added 3,4,5-trifluorobenzoic acid (1.00 g, 5.67 mmol), 4-dimethylaminopyridine (70 mg, 0.57 mmol) and then di-tert-butyl carbonate (2.48 g, 11.35 mmol). The reaction mixture was heated at 40° C. for 18 hours, quenched with 1M aqueous HCl and extracted with EtOAc. Combined organics were dried and concentrated in vacuo to afford the title compound as a colourless oil (1.31 g, 100%):

$^1$H NMR (400 MHz, CDCl$_3$): δ 1.56 (s, 9H), 7.60 (t, 2H).

LCMS Rt=3.59 minutes Molecular ion not observed.

Preparation 62

4-[(5-Chloro-6-isopropoxypyridin-3-yl)oxy]-3,5-difluorobenzoic acid

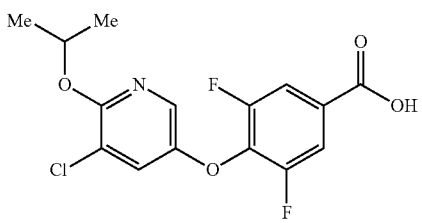 [SMILES: CC(C)Oc1ncc(Oc2c(F)cc(C(=O)O)cc2F)cc1Cl]

tert-Butyl 4-[(5-chloro-6-isopropoxypyridin-3-yl)oxy]-3,5-difluorobenzoate (Preparation 145, 426 mg, 1.06 mmol) and LiOH (100 mg) were added to a solution of THF:water (1:1) and heated at 50° C. for 3 hours. The reaction was then quenched with aqueous 1M HCl and extracted with EtOAc. The combined organics were dried and concentrated in vacuo to afford the title compound as a white solid (342 mg, 94% yield):

$^1$H NMR (400 MHz, CD$_3$OD): δ 1.33 (d, 6H), 5.25 (m, 1H), 7.52 (s, 1H), 7.76 (d, 2H), 7.81 (s, 1H).

LCMS Rt=3.59 minutes MS m/z 344 [MH]$^+$

Preparation 63 tert-Butyl 2,4,6-trifluorobenzoate

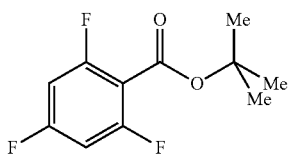 [SMILES: CC(C)(C)OC(=O)c1c(F)cc(F)cc1F]

Di-tert-butyl carbonate (4.95 g, 22.7 mmol) was added to a solution of 2,4,6-trifluorobenzoic acid (2.0 g, 11.3 mmol) and 4-dimethylaminopyridine (139 mg, 1.14 mmol) in tBuOH (30 mL) and the reaction mixture was heated at 40° C. for 18 hours. The reaction mixture was then quenched with aqueous 1M HCl and extracted into EtOAc. The combined organics were washed with aqueous 1M NaOH, followed by brine, dried and concentrated in vacuo to afford the title compound as a pale yellow oil (2.63 g, 52% yield):

$^1$H NMR (400 MHz, CDCl$_3$): δ 1.58 (s, 9H), 6.67 (t, 2H).

LCMS Rt=3.16 minutes Molecular ion not observed.

Preparation 64

2,3,4,6-Tetrafluorobenzoic acid

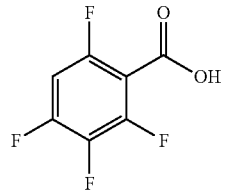

(2,3,4,6-Tetrafluorophenyl)methanol (1.50 g, 8.33 mmol), sodium periodate (8.91 g, 41.6 mmol) and ruthenium (III) chloride (345 mg, 1.67 mmol) was added to a mixture of MeCN (20 mL), water (10 mL) and carbon tetrachloride (20 mL). The reaction was stirred at room temperature for 6 hours, then filtered through arbocel (eluting with EtOAc) and the filtrate evaporated in vacuo. The resulting residue was purified by silica gel chromatography eluting with EtOAc to afford the title compound as a colourless oil (1.60 g, 99% yield):

$^1$H NMR (400 MHz, CD$_3$OD): δ 5.06 (m, 1H).

LCMS Rt=1.74 minutes Molecular ion not observed

Preparation 65 tert-butyl 2,3,4,6-tetrafluorobenzoate

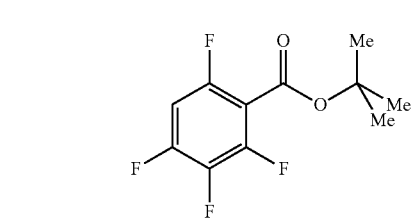 [SMILES: CC(C)(C)OC(=O)c1c(F)cc(F)c(F)c1F]

Di-tert-butyl carbonate (3.63 g, 16.7 mmol) was added to a mixture of 2,3,4,6-tetrafluorobenzoic acid (1.60 g, 8.88 mmol), 4-dimethylaminopyridine (102 mg, 0.83 mmol) in tBuOH (20 mL) and heated at 40° C. for 16 hours. The reaction mixture was quenched with aqueous 1M HCl and extracted with EtOAc. Combined organics were washed with aqueous 1M NaOH, then brine and evaporated in vacuo. The resulting crude was purified by silica gel chromatography eluting with 50% EtOAc in heptane to afford the title compound as a colourless oil (1.25 g, 59% yield):

$^1$H NMR (400 MHz, CDCl$_3$): δ 1.57 (s, 9H), 6.73-6.85 (m, 1H).

LCMS Rt=3.84 minutes Molecular ion not observed.

Preparation 66

3-chloro-2-d7-isopropoxypyridine

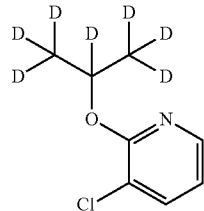 [SMILES: [2H]C([2H])([2H])C([2H])(Oc1ncccc1Cl)C([2H])([2H])[2H]]

A solution of d⁸-isopropyl alcohol (4.71 mL, 61.5 mmol) in anhydrous THF (10 mL) was added slowly over 1 min to a suspension of NaH (60% in mineral oil) (2.46 g, 61.5 mmol) in anhydrous THF (50 mL). After 10 mins a solution of 2-fluoro-3-chloropyridine (5.05 g, 38.4 mmol) in THF (10 mL) was added over 5 mins at 5° C. (ice bath). The reaction was then warmed to room temperature stirred for 18 hours. The reaction was diluted with THF (20 mL), cooled to 5° C. (ice bath) and quenched with water (50 mL). The mixture was extracted with EtOAc (50 mL). Brine was added to aid the separation. The organics were dried over magnesium sulfate, filtered, and concentrated in vacuo to afford a crude oil which was purified by silica gel chromatography eluting with 0 to 30% EtOAc in heptane to yield the title compound as a colourless oil (5.37 g, 53% yield):

$^1$H NMR (400 MHz, CDCl$_3$): δ 6.78-6.81 (m, 1H), 7.60-7.62 (m, 1H), 8.03-8.04 (m, 1H).

LCMS Rt=1.41 minutes. Molecular ion not observed.

Preparation 67 p-tolyl 4-(5-chloro-6-fluoropyridin-3-yloxy)-2,5-difluorobenzoate

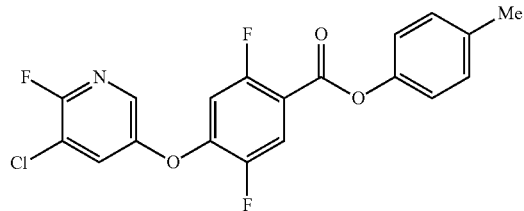 [SMILES: Cc1ccc(OC(=O)c2cc(F)c(Oc3cnc(F)c(Cl)c3)cc2F)cc1]

Potassium carbonate (1.40 g, 10.14 mmol) was added to a solution of 4-Methylphenyl 2,4,5-trifluorobenzoate (Preparation 12, 1.80 g, 6.76 mmol), 5-chloro-6-fluoropyridin-3-ol (1.05 g, 7.10 mmol) in DMSO and the mixture was stirred at room temperature for 18 hours. The reaction mixture was diluted in EtOAc (50 mL), washed with water (2×25 mL) and the organic layer dried over sodium sulfate, filtered, and concentrated in vacuo. The remaining crude was then purified by silica gel chromatography eluting with 10 to 50% EtOAc in heptane to afford the title compound (1.48 g, 56%):

$^1$H NMR (d$_6$-DMSO): δ 2.30 (m, 3H), 7.15 (m, 2H), 7.30 (m, 2H), 7.40 (m, 1H), 8.10 (m, 1H), 8.25 (m, 1H), 8.35 (m, 1H).

LCMS Rt=5.05 minutes. Molecular ion not observed

Preparation 68

N-(sec-butylsulfonyl)-2,4,5-trifluorobenzamide

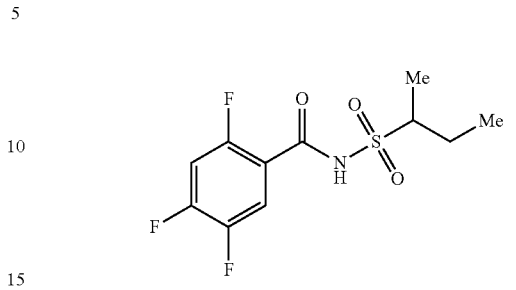

N-[3-(dimethylamino)propyl]-N'-ethylcarbodiimide hydrochloride (0.41 g, 2.1 mmol), 4-dimethylaminopyridine (0.26 g, 2.1 mmol) and N-ethyl-N-isopropylpropan-2-amine (0.9 mL, 4.2 mmol) were added to a solution of 2,4,5-trifluorobenzoic acid (0.25 g, 1.4 mmol) in DCM. After 10 minutes butane-2-sulfonamide (Preparation 29, 0.29 g, 2.1 mmol) was added and the reaction was left at room temperature for 18 hours. The reaction mixture was concentrated in vacuo and the residue purified by preparative HPLC to yield the title compound as a white solid (0.19 g, 31% yield):

$^1$H NMR (400 MHz; d$_6$-DMSO): δ 1.0 (m, 3H), 1.3 (s, 3H), 1.6 (m, 1H), 1.9 (m, 1H), 3.5 (m, 1H), 7.7 (m, 1H), 7.8 (m, 1H).

LCMS Rt=2.26 minutes. MS m/z 294 [M−H]$^−$

Preparation 69

5-Chloro-6-cyclopropylpyridin-3-ol

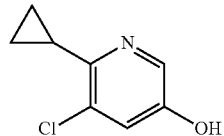

A round bottom flask was charged with 3-chloro-2-cyclopropylpyridine (Preparation 48, 0.475 g; 3.092 mmol), bis (pinacolato)diboron (0.980 g, 3.859 mol) and 4,4-di-tert-butyl-2,2-dipyridyl (0.025 g; 0.093 mmol) in heptane (1.55 L). The reaction mixture was cycled between vacuum and nitrogen 6 times over 15 minutes. Di-methanolatodiiridium(Ir—Ir)-cycloocta-1,5-diene (1:2) (0.063 g; 0.093 mmol) was then added and the reaction stirred for 18 hours under nitrogen atmosphere at room temperature. The reaction mixture was evaporated to dryness to afford a red viscous oil. The resulting oil was dissolved in acetone (10.0 mL) and cooled to 0° C. with an ice bath. Then potassium peroxymonosulfate (2.55 g, 4.15 mmol) in water (10.0 mL) was added dropwise to the mixture and stirred at this temperature for 1 hour. The reaction was then diluted in tert-butyl methyl ether (25.0 mL) and washed with brine (3×25.0 mL). The organic layer was then dried over sodium sulfate, filtered, and concentrated in vacuo. The resulting crude product was purified with silica gel chromatography eluting with 0 to 30% EtOAc in heptane to yield the title compound as a pale yellow solid (0.220 g, 1.28 mmol, 42%):

¹H NMR (400 MHz, d₆-DMSO): δ 0.81-0.85 (m, 2H), 0.86-0.91 (m, 2H), 2.26-2.32 (m, 1H), 7.19 (d, 1H), 7.94-7.95 (d, 1H), 10.05 (s, 1H).
LCMS Rt=1.85 minutes MS m/z 170 [MH]⁺

Preparation 70

4-methylphenyl 5-chloro-4-[(5-chloro-6-cyclopropylpyridin-3-yl)oxy]-2-fluorobenzoate

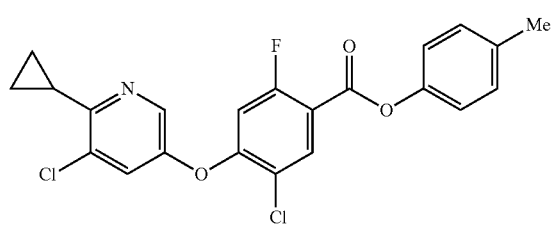 [SMILES: Cc1ccc(OC(=O)c2cc(Cl)c(Oc3cnc(C4CC4)c(Cl)c3)cc2F)cc1]

4-Methylphenyl 5-chloro-2,4-difluorobenzoate (Preparation 26, 0.330 g, 1.168 mmol) was added portionwise over 5 minutes to a suspension of 5-chloro-6-cyclopropylpyridin-3-ol (Preparation 69, 0.214 g, 1.262 mmol) and potassium carbonate (0.32 g, 2.315 mmol) in DMSO (5.0 mL). The mixture was stirred at room temperature for 3 hours, then partitioned between water (20.0 mL) and tert-butyl methyl ether (20.0 mL). The organic layer was further washed with water (2×20.0 mL). The organic layer was dried over sodium sulfate, filtered and concentrated in vacuo. The resulting crude product was purified with silica gel chromatography eluting with 0 to 5% EtOAc in heptane to yield the title compound as a white solid (0.289 g, 0.668 mmol, 57%):
¹H NMR (400 MHz, d₆-DMSO): δ 0.97-1.00 (m, 2H), 1.00-1.07 (m, 2H), 2.32 (s, 3H), 2.44-2.50 (m, 1H), 7.13-7.17 (m, 2H), 7.22-7.27 (m, 2H), 7.28-7.32 (m, 1H), 7.89 (d, 1H), 8.23 (d, 1H), 8.37 (d, 1H).
LCMS Rt=3.60 minutes MS m/z 432 [MH]⁺

Preparation 71 tert-Butyl 5-chloro-4-{[5-chloro-6-(2,2,3,3-tetrafluoropropoxy)pyridin-3-yl]oxy}-2-fluorobenzoate

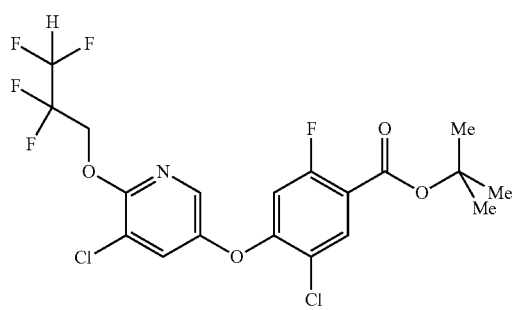 [SMILES: CC(C)(C)OC(=O)c1cc(Cl)c(Oc2cnc(OCC(F)(F)C(F)F)c(Cl)c2)cc1F]

Potassium carbonate (3.02 g, 21.85 mmol) was added portionwise to a suspension of tert-butyl 5-chloro-2,4-difluorobenzoate (Preparation 59, 2.26 g, 9.09 mmol), 5-chloro-6-(2,2,3,3-tetrafluoropropoxy)pyridin-3-ol (Preparation 73, 2.25 g, 8.67 mmol) in DMSO (13.5 mL). The mixture was stirred at room temperature under nitrogen for 3 hours. tert-butyl methyl ether (50.0 mL) was added and the mixture was washed with water (3×50.0 mL). The organic layer was dried over sodium sulfate, filtered, and concentrated in vacuo. The resulting oil was suspended with heptane (20.0 mL) and concentrated in vacuo. The resulting solid was suspended in heptane (20.0 mL) and heated to 90° C. until full dissolution. The mixture was cooled with stirring and the residual solid collected by filtration. The filtrate was concentrated in vacuo and the resulting solid was suspended in heptane (10.0 mL) and heated to 90° C. until dissolution. The mixture was again cooled with stirring and the residual solid collected by filtration. The two crops were combined to yield the title compound as a white solid (2.58 g, 5.29 mmol, 61%):
¹H NMR (400 MHz, d₆-DMSO): δ 1.52 (s, 9H), 4.93 (t, 2H), 6.50-6.78 (m, 1H), 7.08 (d, 1H), 7.95 (d, 1H), 8.08-8.14 (m, 2H).
LCMS Rt=3.41 minutes MS m/z 522 [MH]⁺

Preparation 72

5-Chloro-4-{[5-chloro-6-(1,1,3,3-tetrafluoropropoxy)pyridin-3-yl]oxy}-2-fluorobenzoic acid

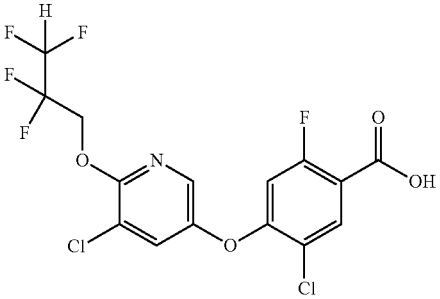 [SMILES: O=C(O)c1cc(Cl)c(Oc2cnc(OCC(F)(F)C(F)F)c(Cl)c2)cc1F]

Trifluoroacetic acid (5.0 mL) was added to a solution of tert-butyl 5-chloro-4-{[5-chloro-6-(2,2,3,3-tetrafluoropropoxy)pyridin-3-yl]oxy}-2-fluorobenzoate (Preparation 71, 2.56 g, 5.24 mmol) in DCM (5.0 mL) and stirred at room temperature for 16 hours. The reaction mixture was concentrated in vacuo and then diluted EtOAc (30.0 mL). The organic layer was washed with an aqueous solution of hydrochloric acid (2×15.0 mL). The organic layer was dried over sodium sulfate, filtered, and concentrated in vacuo to yield a yellow oil. This oil was taken in heptane (20.0 mL) and stirred at reflux for 2 hours, then it was left to cool to room temperature. The title compound was isolated by filtration as a white solid (1.98 g, 4.58 mmol, 87%):
¹H NMR (400 MHz, d₆-DMSO): δ 4.93 (t, 2H), 6.50-6.78 (m, 1H), 7.05 (d, 1H), 7.99 (d, 1H), 8.10-8.15 (m, 2H).
LCMS Rt=2.63 minutes. MS m/z 432 [MH]⁺

Preparation 73

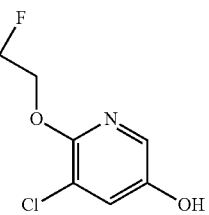

Hydrogen peroxide solution (30% aq solution, 30.2 mL, 0.26 mol) was added to a solution of 3-chloro-2-(2,2,3,3-tetrafluoropropoxy)-5-(4,4,5,5-tetramethyl-1,3,2-dioxaborolan-2-yl)pyridine (Preparation 74, 81.0 g, 0.22 mol) in methanol (500 mL) at 0° C. and the reaction was allowed to warm up to room temperature and stir for 4 hours. The reaction mixture was quenched with 10% sodium thiosulphate solution (100 mL) and the methanol removed unver vacuum. The resulting mixture was extracted with EtOAc (2×250 mL), the combined organics separated, dried over magnesium sulfate, filtered and evaporated to yield a yellow oil. This oil was purified by silica gel chromatogrpahy eluting with 10% EtOAc in heptane to afford the title compound as a viscopus colourless oil (46.7 g, 82%):

$^1$H NMR (400 MHz, CDCl$_3$): δ 4.60 (t, 2H), 5.60 (br, 1H), 5.95-6.20 (m, 1H), 7.36 (s, 1H), 7.70 (s, 1H).

LCMS Rt=2.43 minutes MS m/z 257 [MH]$^-$

Preparation 74

3-Chloro-2-(2,2,3,3-tetrafluoropropoxy)-5-(4,4,5,5-tetramethyl-1,3,2-dioxaborolan-2-yl)Pyridine

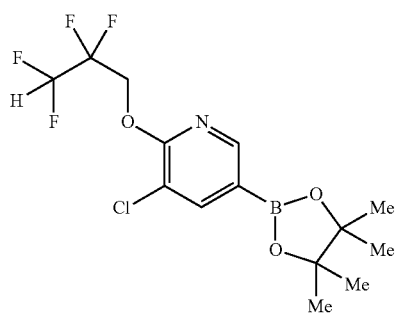 [SMILES: CC1(C)OB(c2cnc(OCC(F)(F)C(F)F)c(Cl)c2)OC1(C)C]

A 3-necked flask was charged with 3-chloro-2-(2,2,3,3-tetrafluoropropoxy)pyridine (Preparation 75, 71.0, 0.3 mol) and heptane (350 mL). The mixture was cycled three times between nitrogen and vacuum. Bispinacolatodiboron (74.0 g, 0.3 mol) and di-tert-butyl dipyridyl (4.70 g, 17.5 mmol) were then added and the mixture was degassed again and kept under a nitrogen atmosphere. Then di-methanolatodiiridium (Ir—Ir)-cycloocta-1,5-diene (1:2) (6.00 g, 9.05 mmol) was added and the resulting mixture stirred at room temperature for 16 hours. The reaction mixture was then cooled to 0° C. and MeOH (70 mL) was added dropwise, then concentrated in vacuo and the resulting mixture partitioned between EtOAc (500 mL) and water (300 mL). The organic layer was separated, dried over magnesium sulfate, filtered and evaporated to yield a brown oil. This oil was purified by silica gel chromatography eluting with 0 to 10% EtOAc in heptane to afford the title compound as a colourless oil (81 g, 75%):

$^1$H NMR (400 MHz, CDCl$_3$): δ 1.36 (s, 12H), 4.82 (t, 2H), 5.95-6.23 (m, 1H), 8.05 (s, 1H), 8.40 (s, 1H).

MS m/z 370 [M]$^+$

Preparation 75

3-Chloro-2-(2,2,3,3-tetrafluoropropoxy)pyridine

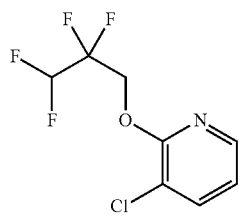 [SMILES: FC(F)C(F)(F)COc1ncccc1Cl]

2,2,3,3-Tetrafluoropropan-1-ol (60.0 g, 0.45 mol) was added to a slurry of NaH (60% dispersion in oil, 15.20 g, 0.63 mol) in anhydrous THF (450 mL) at 0° C. and the reaction mixture allowed to warm up to room temperature, then stirred for 1 hour. 2,3-dichloropyridine (45.0 g, 0.30 mol) was added and the reaction heated to a gentle reflux for 16 hours. The reaction mixture was cooled to room temperature and the solvent removed in vacuo. The residue was partitioned between EtOAc (300 mL) and brine (200 mL). The organic layer was dried over magnesium sulfate, filtered and evaporated to afford the title compound as a yellow oil (71 g, 96%):

$^1$H NMR (400 MHz, CDCl$_3$): δ 4.75 (t, 2H), 5.95-6.2 (m, 1H), 6.95 (m, 1H), 7.65 (m, 1H), 8.12 (m, 1H).

LCMS Rt=3.07 minutes Molecular ion not visible

The following Preparations were prepared by the method described for Preparation 15, using appropriate reagents and conditions.

| Prep | Name | Data |
|---|---|---|
| 76 | 5-hydroxy-2-isopropoxynicotinonitrile | $^1$H NMR (400 MHz, CDCl$_3$): δ 1.37 (d, 6H), 5.28 (m, 1H), 7.43 (d, 1H), 8.01 (d, 1H). |
| 77 | 5-chloro-6-methoxypyridin-3-ol | $^1$H NMR (400 MHz, CDCl$_3$): δ 3.96 (s, 3 H), 7.29 (d, 1 H), 7.70 (d, 1 H). LCMS: Rt = 1.00 |
| 78 | 5-chloro-6-(2,2,2-trifluoroethoxy)pyridin-3-ol | LCMS Rt = 2.61 min. MS m/z 228[MH]$^+$ |
| 79 | 5-chloro-6-((1-methylcyclopropyl)methoxy)pyridin-3-ol | $^1$H NMR (400 MHz, CDCl$_3$): δ 0.40 (m, 2H), 0.60 (m, 2H), 1.20 (s, 3H), 4.10 (s, 2H), 4.80 (br, 1H), 7.30 (s, 1H), 7.65 (s, 1H). |
| 80 | 5-chloro-6-[(1-methyl-piperidin-4-yl)oxy]pyridin-3-ol | $^1$H NMR (400 MHz, d$_6$-DMSO): δ 1.02 (br, 2H), 1.20 (br, 2H), 2.48 (s, 3H), 1.62 (br, 2H), 1.93 (br, 2H), 4.20 (br, 1H), 6.41 (s, 1H), 6.78 (s, 1H). |
| 81 | 5-chloro-6-(cyclopropylmethoxy)pyridin-3-ol | $^1$H NMR (400 MHz, CDCl$_3$): δ 0.30 (m, 2H), 0.55 (m, 2H), 1.25 (m, 1H), 4.10 (s, 2H), 4.85 (br, 1H), 7.30 (s, 1H), 7.60 (s, 1H). |
| 82 | 5-chloro-6-(2,2,3,3,3-pentafluoropropoxy)pyridin-3-ol | $^1$H NMR (400 MHz, CDCl$_3$): δ 4.80 (t, 2H), 5.20 (br, 1H), 7.30 (s, 1H), 7.65 (s, 1H). |

The following Preparations were prepared by methods analogous to the method described for Preparation 44.

| Prep | Name | Data |
|---|---|---|
| 83 | 5-chloro-6-(trifluoromethyl)pyridin-3-ol | $^1$H NMR (400 MHz, $d_6$-DMSO): δ 7.48-7.49 (d, 1H), 8.17-8.18 (d, 1H), 11.42 (s, 1H). |
| 84 | 5-chloro-6-isobutylpyridin-3-ol | $^1$H NMR (400 MHz, $d_6$-DMSO): δ 0.84-0.86 (d, 6H), 1.98-2.08 (m, 1H), 2.59-2.61 (d, 2H), 7.19-7.20 (d, 1H), 8.02 (d, 1H), 10.14 (s, 1H). |
| 85 | 5-chloro-6-(cyclopropyloxy)pyridin-3-ol | $^1$HNMR (400 MHz, CDCl$_3$): δ 0.82 (m, 4H), 4.25 (m, 1H), 7.31 (d, 1H), 7.78 (d, 1H). |
| 86 | 6-tert-butyl-5-chloropyridin-3-ol | $^1$H NMR (400 MHz; $d_6$-DMSO): δ 1.37 (s, 9H), (d, 1H), 7.99 (d, 1H), 10.13 (s, 1H). |
| 87 | 5-chloro-6-(1,1-difluoro-2-methylpropyl)pyridin-3-ol | $^1$H NMR (400 MHz; $d_6$-DMSO): δ 0.96-0.97 (d, 6H), 2.69-2.84 (m, 1H), 7.35 (d, 1H), 8.13 (d, 1H), 10.99 (s, 1H). |
| 88 | 5-fluoro-6-isopropoxypyridin-3-ol | $^1$H NMR (400 MHz; $d_6$-DMSO): δ 1.24-1.26 (d, 6H), 5.08-5.17 (m, 1H), 7.09-7.13 (m, 1H), 7.50 (d, 1H), 9.65 (br, 1H). |
| 89 | 1-(3-chloro-5-hydroxypyridin-2-yl)ethanone | $^1$H NMR (400 MHz; $d_6$-DMSO): δ 2.52 (s, 3H), 7.28-7.29 (d, 1H), 8.15-8.16 (d, 1H), 11.24 (s, 1H). |
| 90 | 5-chloro-6-(1,1-difluoroethyl)pyridin-3-ol | $^1$H NMR (400 MHz; $d_6$-DMSO): δ 1.95-2.04 (t, 3H), 7.37 (d, 1H), 8.09 (d, 1H), 10.96 (s, 1H). |
| 91 | 5-chloro-6-[2-fluoro-1-(fluoromethyl)ethoxy]pyridin-3-ol | $^1$H NMR (400 MHz, CDCl$_3$): δ 4.68 (d, 2 H), 4.80 (d, 2 H), 5.49 (m, 1 H), 7.31 (d, 1 H), 7.67 (d, 1 H). |
| 92 | 5-chloro-6-(difluoromethoxy)pyridin-3-ol | $^1$H NMR (400 MHz, CDCl$_3$): δ 7.32 (t, 1H), 7.38 (d, 1H), 7.73 (d, 1H). |
| 93 | 5-chloro-6-d1-isopropoxypyridin-3-ol | $^1$H NMR (400 MHz, CDCl$_3$): δ 1.36 (s, 6H), 7.28 (d, 1H), 7.69 (d, 1H). |

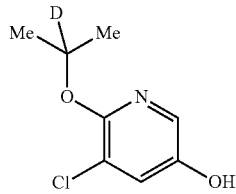 [SMILES: [2H]C(C)(C)Oc1ncc(O)cc1Cl]

| Prep | Name | Data |
|---|---|---|
| 94 | 5-chloro-6-d7-isopropoxypyridin-3-ol | $^1$H NMR (400 MHz, CDCl$_3$): δ 4.77 (s, 1H), 7.28 (d, 1 H), 7.68-7.69 (d, 1 H). |

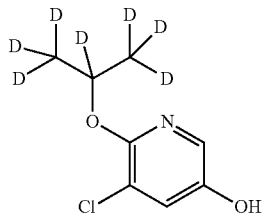 [SMILES: [2H]C([2H])([2H])C([2H])(Oc1ncc(O)cc1Cl)C([2H])([2H])[2H]]

The following Preparations were prepared by methods analogous to the method described for Preparation 58.

| Prep | Name | Data |
|---|---|---|
| 95 | 5-chloro-6-(3,3,3-trifluoropropoxy)pyridin-3-ol | $^1$H NMR (400 MHz, CDCl$_3$): δ 2.7 (m, 2H), 4.5 (t, 2H), 5.24 (br, 1H), 7.3 (s, 1H), 7.7 (s, 1H). |
| 96 | 6-tert-butoxy-5-chloropyridin-3-ol | $^1$H NMR (400 MHz, CDCl$_3$): δ 1.60 (s, 9H), 6.9 (br, 1H), 7.25 (s, 1H), 7.65 (s, 1H). |
| 97 | 5-chloro-6-(2-fluoro-2-methylpropoxy)pyridin-3-ol | $^1$H NMR (400 MHz, CDCl$_3$): δ 1.45 (s, 3H), 1.50 (s, 3H), 4.30 (d, 2H), 4.95 (br, 1H), 7.30 (s, 1H), 7.65 (s, 1H). |
| 98 | 5-chloro-6-(4,4-difluorocyclohexyloxy)pyridin-3-ol | $^1$H NMR (CDCl$_3$, 400 MHz): δ 2.1 (m, 8H), 3.8 (s, 1H), 5.2 (br, 1H), 7.3 (s, 1H), 7.7 (s, 1H). |
| 99 | 5-chloro-6-(2,2-difluoroethoxy)pyridin-3-ol | $^1$H NMR (400 MHz, CDCl$_3$): δ 4.50 (m, 2H), 5.75 (br, 1H), 6.07 (m, 1H), 7.26 (s, 1H), 7.82 (s, 1H). |
| 100 | 5-chloro-6-(1,1,1-trifluoropropan-2-yloxy)pyridin-3-ol | $^1$H NMR (400 MHz CDCl$_3$): δ 1.4 (d, 3H), 5.1 (br, 1H), 5.6 (m, 1H), 7.3 (s, 1H), 7.65 (s, 1H). |

The Preparations were prepared by the method described for Preparation 14, using appropriate reagents and conditions.

| Prep | Name | Data |
|---|---|---|
| 101 | 2-isopropoxy-5-(4,4,5,5-tetramethyl-1,3,2-dioxaborolan-2-yl)nicotinonitrile | $^1$H NMR (400 MHz, CDCl$_3$): δ 1.33 (s, 12H), 1.39 (d, 6H), 5.47 (m, 1H), 8.20 (d, 1H), 8.64 (d, 1H). |
| 102 | 3-chloro-5-(4,4,5,5-tetramethyl-1,3,2-dioxaborolan-2-yl)-2-(trifluoromethyl)pyridine | — |
| 103 | 3-chloro-2-isobutyl-5-(4,4,5,5-tetramethyl-1,3,2-dioxaborolan-2-yl)pyridine | $^1$H NMR (400 MHz; d$_6$-DMSO): δ 0.87-0.89 (d, 6H), 1.29 (s, 12H), 2.07-2.18 (m, 1H), 2.75-2.77 (d, 2H), 7.89-7.89 (d, 1H), 8.60 (d, 1H). |
| 104 | 2-tert-butyl-3-chloro-5-(4,4,5,5-tetramethyl-1,3,2-dioxaborolan-2-yl)pyridine | $^1$H NMR (400 MHz; d$_6$-DMSO): δ 1.29 (s, 12H), 1.43 (s, 9H), 7.85-7.86 (d, 1H), 8.58 (d, 1H). |
| 105 | 3-chloro-2-(1,1-difluoro-2-methylpropyl)-5-(4,4,5,5-tetramethyl-1,3,2-dioxaborolan-2-yl)pyridine | — |
| 106 | 3-fluoro-2-isopropoxy-5-(4,4,5,5-tetramethyl-1,3,2-dioxaborolan-2-yl)pyridine | $^1$H NMR (400 MHz; d$_6$-DMSO): δ 1.27-1.30 (m, 18H), 5.32-5.38 (m, 1H), 7.60-7.64 (m, 1H), 8.15 (m, 1H). |
| 107 | 1-[3-chloro-5-(4,4,5,5-tetramethyl-1,3,2-dioxaborolan-2-yl)pyridin-2-yl]ethanone | — |
| 108 | 3-chloro-2-(1,1-difluoroethyl)-5-(4,4,5,5-tetramethyl-1,3,2-dioxaborolan-2-yl)pyridine | — |
| 109 | 3-chloro-2-[2-fluoro-1-(fluoromethyl)ethoxy]-5-(4,4,5,5-tetramethyl-1,3,2-dioxaborolan-2-yl)pyridine | LCMS Rt = 1.89 min. MS m/z 334 [MH]$^+$ |
| 110 | 3-chloro-2-(difluoromethoxy)-5-(4,4,5,5-tetramethyl-1,3,2-dioxaborolan-2-yl)pyridine | LCMS Rt = 1.82 min. MS m/z 305 [M H]$^+$ |
| 111 | 3-chloro-2-(cyclopropyloxy)-5-(4,4,5,5-tetramethyl-1,3,2-dioxaborolan-2-yl)pyridine | LCMS Rt = 1.87 min. MS m/z 296[MH]$^+$ |
| 112 | 2-d9-tert-butoxy-3-chloro-5-(4,4,5,5-tetramethyl-1,3,2-dioxaborolan-2-yl)pyridine | $^1$H NMR (400 MHz, CDCl$_3$): δ 1.32 (s, 12H), 7.92 (d, 1H), 8.36 (d, 1H). |
| 113 | 3-chloro-5-(4,4,5,5-tetramethyl-1,3,2-dioxaborolan-2-yl)-2-(3,3,3-trifluoropropoxy)pyridine | $^1$H NMR (400 MHz, CDCl$_3$): 1.3 (s, 12H), 2.7 (m, 2H), 4.7 (m, 2H), 8.0 (s, 1H), 8.4 (s, 1H). |
| 114 | 3-chloro-2-(1-methylpiperidin-4-yloxy)-5-(4,4,5,5-tetramethyl-1,3,2-dioxaborolan-2-yl)pyridine | $^1$H NMR (400 MHz, CD$_3$OD): δ 1.19 (s, 12H), 1.83-1.97 (m, 2H), 2.02-2.17 (m, 2H), 2.41 (s, 3H), 2.48-2.62 (m, 2H), 2.80-2.87 (m, 2H), 2.19-5.30 (m, 1H), 7.93 (s, 1H), 8.28 (s, 1H). |

| Prep | Name | Data |
|---|---|---|
| 115 | 3-chloro-2-d7-isopropoxy-5-(4,4,5,5-tetramethyl-1,3,2-dioxaborolan-2-yl)pyridine | $^1$H NMR (400 MHz, CDCl$_3$): δ 1.34 (s, 12H), 7.95-7.96 (d, 1H), 8.38 (d, 1H). |
| 116 | 3-chloro-2-d1-isopropoxy-5-(4,4,5,5-tetramethyl-1,3,2-dioxaborolan-2-yl)pyridine | $^1$H NMR (400 MHz, CDCl$_3$): δ 1.34 (s, 12H), 1.39 (s, 6H), 7.95-7.96 (d, 1H), 8.38 (d, 1H). |
| 117 | 3-chloro-2-((1-methylcyclopropyl)methoxy)-5-(4,4,5,5-tetramethyl-1,3,2-dioxaborolan-2-yl)pyridine | $^1$H NMR (400 MHz, CDCl$_3$): δ 0.42 (m, 2H), 0.60 (m, 2H), 1.39-1.24 (m, 15H), 4.22 (s, 2H), 7.97 (d, 1H), 8.35 (d, 1H). |
| 118 | 2-tert-butoxy-3-chloro-5-(4,4,5,5-tetramethyl-1,3,2-dioxaborolan-2-yl)pyridine | $^1$H NMR (400 MHz, CDCl$_3$): δ 1.25 (s, 12H), 1.60 (s, 9H), 7.80 (s, 1H), 8.4 (s, 1H). |
| 119 | 3-chloro-2-(cyclopropylmethoxy)-5-(4,4,5,5-tetramethyl-1,3,2-dioxaborolan-2-yl)pyridine | $^1$H NMR (400 MHz, CDCl$_3$): δ 0.41-0.38 (m, 2H), 0.64-0.59 (m, 2H), 1.38-1.24 (m, 13H), 4.27 (d, 2H), 7.97 (d, 1H), 8.37 (d, 1H). |
| 120 | 3-chloro-2-(2,2,3,3,3-pentafluoropropoxy)-5-(4,4,5,5-tetramethyl-1,3,2-dioxaborolan-2-yl)pyridine | $^1$H NMR (400 MHz, CDCl$_3$): δ 1.30 (s, 12H), 4.85 (t, 2H), 8.00 (s, 1H), 8.30 (s, 1H). |
| 121 | 3-chloro-2-(2-fluoro-2-methylpropoxy)-5-(4,4,5,5-tetramethyl-1,3,2-dioxaborolan-2-yl)pyridine | $^1$H NMR (400 MHz, CDCl$_3$): δ 1.35 (s, 12H), 1.50 (s, 3H), 1.55 (s, 3H), 4.40 (d, 2H), 8.00 (s, 1H), 8.40 (s, 1H). |
| 122 | 3-chloro-2-(4,4-difluorocyclohexyloxy)-5-(4,4,5,5-tetramethyl-1,3,2-dioxaborolan-2-yl)pyridine | $^1$H NMR (400 MHz, CDCl$_3$): δ 1.4 (s, 12H), 2.1 (m, 8H), 5.4 (m, 1H), 8.0 (s, 1H), 8.4 (s, 1H). |
| 123 | 3-chloro-2-(2,2-difluoroethoxy)-5-(4,4,5,5-tetramethyl-1,3,2-dioxaborolan-2-yl)pyridine | $^1$H NMR (400 MHz, CDCl$_3$): δ 1.30 (br, 12H), 4.60 (m, 2H), 6.20 - 5.90 (m, 1H), 7.92 (s, 1H), 8.18 (s, 1H). |
| 124 | 3-chloro-5-(3,3,4,4-tetramethylborolan-1-yl)-2-(1,1,1-trifluoropropan-2-yloxy)pyridine | $^1$H NMR (400 MHz, CDCl$_3$): δ 1.4 (s, 12H), 1.5 (d, 3H), 5.8 (m, 1H), 8.0 (s, 1H), 8.4 (s, 1H). |
| 125 | 3-chloro-5-(4,4,5,5-tetramethyl-1,3,2-dioxaborolan-2-yl)-2-(2,2,2-trifluoroethoxy)pyridine | $^1$H NMR (400 MHz, CDCl$_3$): δ 1.35 (s, 12H), 4.86 (m, 2H), 8.05 (d, 1H), 8.38 (d, 1H). |

The following Preparations were prepared by the method described for Preparation 13 above, using appropriate reagents and conditions.

| Prep | Name | Data |
|---|---|---|
| 126 | 2-isopropoxynicotinonitrile | $^1$H NMR (400 MHz, CDCl$_3$): δ 1.40 (d, 6H), 5.41 (m, 1H), 6.91 (m, 1H), 7.85 (d, 1H), 8.32 (m, 1H). |
| 127 | 3-fluoro-2-isopropoxypyridine | $^1$H NMR (400 MHz; d$_6$-DMSO): δ 1.29-1.31 (d, 6H), 5.25-5.34 (m, 1H), 6.94-6.98 (m, 1H), 7.59-7.65 (m, 1H), 7.93-794 (m, 1H). |
| 128 | 3-chloro-2-[2-fluoro-1-(fluoromethyl)ethoxy]pyridine | $^1$H NMR (400 MHz, CDCl$_3$): δ 4.71 (d, 2H), 4.83 (d, 2H), 5.64 (m, 1H), 6.91 (d, 1H), 7.68 (d, 1H), 8.03 (d, 1H). |
| 129 | 3-chloro-2-(cyclopropyloxy) pyridine | $^1$H NMR (400 MHz, CDCl$_3$): δ 0.85 (m, 4 H), 0.35 (m, 1 H), 6.88 (d, 1 H), 7.63 (d, 1 H), 8.13 (d, 1 H). |
| 130 | 2-d9-tert-butoxy-3-chloropyridine | $^1$H NMR (400 MHz, CDCl$_3$): δ 6.72-6.80 (m, 1 H), 7.55-7.61 (m, 1 H), 8.00 (m, 1 H). |
| 131 | 3-chloro-2-(3,3,3-trifluoropropoxy)pyridine | $^1$H NMR (400 MHz, CDCl$_3$): δ 2.7 (m, 2H), 4.6 (t, 2H), 6.9 (m, 1H), 7.6 (d, 1H), 8.0 (s, 1H). |
| 132 | 3-chloro-2-[(1-methylpiperidin-4-yl)oxy]pyridine | $^1$H NMR (400 MHz, CDCl$_3$): δ 1.81-1.96 (m, 2H), 1.97-2.09 (m, 2H), 2.29 (s, 3H), 2.30-2.40 (m, 2H), 2.58-2.75 (m, 2H), 5.12-5.20 (m, 1H), 6.76-6.82 (m, 1H), 7.62 (d, 1H), 8.01 (d, 1H). |
| 133 | 3-chloro-2-d1-isopropoxypyridine | $^1$H NMR (400 MHz, CDCl$_3$): δ 1.39 (s, 6H), 6.78-6.81 (m, 1H), 7.60-7.62 (m, 1H), 8.02-8.04 (m, 1H). |
| 134 | 3-chloro-2-((1-methylcyclopropyl)methoxy) pyridine | $^1$H NMR (400 MHz, CDCl$_3$): δ 0.43 (m, 2H), 0.60 (m, 2H), 1.26 (s, 3H), 4.17 (s, 2H), 6.82 (m, 1H), 7.63 (m, 1H), 8.01 (m, 1H). |
| 135 | 3-chloro-2-(cyclopropylmethoxy)pyridine | $^1$H NMR (400 MHz, CDCl$_3$): δ 0.03-0.01 (m, 2H), 0.26-0.21 (m, 2H), 0.96 (m, 1H), 3.85 (d, 2H), 6.44 (m, 1H), 7.24 (m, 1H), 7.64 (m, 1H). |
| 136 | 2-tert-butoxy-3-chloropyridine | $^1$H NMR (400 MHz, CDCl$_3$): δ 1.6 (s, 9H), 6.80 (m, 1H), 7.60 (d, 1H), 8.0 (s, 1H). |
| 137 | 3-chloro-2-(2,2,3,3,3-pentafluoropropoxy)pyridine | $^1$H NMR (400 MHz, CDCl$_3$): δ 4.95 (t, 2H), 6.95 (m, 1H), 7.70 (s, 1H), 8.05 (d, 1H). |
| 138 | 3-chloro-2-(2-fluoro-2-methylpropoxy)pyridine | $^1$H NMR (400 MHz, CDCl$_3$): δ 1.50 (s, 3H), 1.55 (s, 3H), 4.40 (d, 2H), 6.85 (m, 1H), 7.65 (d, 1H), 8.00 (d, 1H). |
| 139 | 3-chloro-2-(4,4-difluorocyclohexyloxy)pyridine | $^1$H NMR (400 MHz, CDCl$_3$): δ 2.1 (8H, m), 5.3 (1H, m), 6.8 (1H, m), 7.6 (1H, d), 8.0 (1H, m). |
| 140 | 3-chloro-2-(2,2-difluoroethoxy)pyridine | $^1$H NMR (400 MHz, CDCl$_3$): δ 4.60 (2H, m), 6.08 (1H, m), 6.90 (1H, m), 7.63 (1H, d), 8.05 (1H, d). |
| 141 | 3-chloro-2-(1,1,1-trifluoropropan-2-yloxy)pyridine | $^1$H NMR (400 MHz, CDCl$_3$): δ 1.6 (d, 3H), 5.8 (m, 1H), 6.85 (m, 1H), 7.6 (m, 1H), 8.0 (m, 1H). |
| 142 | 3-chloro-2-(2,2,2-trifluoroethoxy)pyridine | $^1$H NMR (400 MHz, CDCl$_3$): δ 4.83 (m, 2H), 6.96 (m, 1H), 7.70 (m, 1H), 8.05 (m, 1H). |

The following Preparations were prepared by the method described for Preparation 7, using appropriate reagents and conditions.

| Prep | Name | Data |
|---|---|---|
| 143 | tert-butyl 5-chloro-4-{[5-chloro-6-(tetrahydro-2H-pyran-4-yloxy)pyridin-3-yl]oxy}-2-fluorobenzoate | $^1$H NMR (400 MHz, CDCl$_3$): δ 1.41 (s, 9H), 1.63-1.75 (m, 2H), 1.87-1.97 (m, 2H), 3.43-3.53 (m, 2H), 3.79-3.87 (m, 2H), 5.10-5.18 (m, 1H), 6.41 (d, 1H), 7.30 (s, 1H), 7.73 (s, 1H), 7.81 (d, 1H). |
| 144 | tert-butyl 4-[(5-chloro-6-isopropoxypyridin-3-yl)oxy]-2-fluorobenzoate | $^1$H NMR (400 MHz, CD$_3$OD): δ 1.30 (d, 6H), 1.51 (s, 9H), 5.18-5.24 (m, 1H), 6.54 (d, 1H), 6.63 (d, 1H), 6.72-6.83 (m, 1H), 7.74-7.82 (m, 2H). |
| 145 | tert-butyl 4-[(5-chloro-6-isopropoxypyridin-3-yl)oxy]-3,5-difluorobenzoate | $^1$H NMR (400 MHz, CDCl$_3$): δ 1.36 (d, 6H), 1.58 (s, 9H), 5.25 (m, 1H), 7.32 (s, 1H), 7.63 (d, 2H), 7.80 (s, 1H). |

-continued

| Prep | Name | Data |
|---|---|---|
| 146 | tert-butyl 4-[(5-chloro-6-isopropoxypyridin-3-yl)oxy]-2,6-difluorobenzoate | — |
| 147 | tert-butyl 5-chloro-4-(5-chloro-6-(1-methylpiperidin-4-yloxy)pyridin-3-yloxy)-2-fluorobenzoate | $^1$H NMR (400 MHz, CDCl$_3$): δ 1.58 (s, 9H), 1.82-1.94 (m, 2H), 1.97-2.09 (m, 2H), 2.17-2.39 (m, 5H), 2.61-2.72 (m, 2H), 5.06-5.17 (m, 1H), 6.50 (d, 1H), 7.40 (s, 1H), 7.82 (s, 1H), 7.92 (d, 1H). |
| 148 | tert-butyl 4-(5-chloro-6-isopropoxypyridin-3-yloxy)-2,3,6-trifluorobenzoate | $^1$H NMR (400 MHz, CDCl$_3$): δ 1.40 (d, 6H), 1.59 (s, 9H), 5.30 (m, 1H), 6.36-6.47 (m, 1H), 7.42 (s, 1H), 7.88 (s, 1H). |
| 149 | tert-butyl 5-chloro-4-(5-chloro-6-fluoropyridin-3-yloxy)-2-fluorobenzoate | $^1$H NMR (400 MHz, CDCl$_3$): δ 1.55 (s, 9H), 7.20 (m, 1H), 7.63 (m, 1H), 8.20 (m, 1H), 8.20 (m, 1H). |
| 150 | tert-butyl 4-(5-chloro-6-(2,2,2-trifluoroethoxy)pyridin-3-yloxy)-2,5-difluorobenzoate | $^1$H NMR (400 MHz, CDCl$_3$): δ 1.6 (9H, s), 4.8 (2H, q), 6.6 (1H, m), 7.5 (1H, s), 7.7 (1H, m), 7.8 (1H, s). |
| 151 | tert-butyl 4-(5-chloro-6-((1-methylcyclopropyl)methoxy)pyridin-3-yloxy)-2,5-difluorobenzoate | $^1$H NMR (400 MHz, CDCl$_3$): δ 0.40 (m, 2H), 0.60 (m, 2H), 1.25 (s, 3H), 1.55 (s, 9H), 4.20 (s, 2H), 6.60 (m, 1H), 7.45 (s, 1H), 7.70 (m, 1H), 7.85 (s, 1H). |
| 152 | tert-butyl 4-(5-chloro-6-(cyclopropylmethoxy)pyridin-3-yloxy)-2,5-difluorobenzoate | LCMS Rt = 1.80 min. Molecular ion not observed. |
| 153 | tert-butyl 4-(6-tert-butoxy-5-chloropyridin-3-yloxy)-2,5-difluorobenzoate | $^1$H NMR (400 MHz CDCl$_3$): δ 1.62 (s, 9H), 1.65 (s, 9H), 6.6 (m, 1H), 7.40 (s, 1H), 7.60 (m, 1H), 7.80 (s, 1H). |

The following Preparations were prepared by the method described for Preparation 8, using appropriate reagents and conditions.

| Prep | Name | Data |
|---|---|---|
| 154 | 4-(5-chloro-6-isopropoxypyridin-3-yloxy)-2,6-difluorobenzoic acid | $^1$H NMR (400 MHz, CD$_3$OD): δ 1.37 (d, 6H), 5.30 (m, 1H), 5.57 (d, 2H), 7.61 (d, 2H), 7.90 (s, 1H). |
| 155 | 4-(5-chloro-6-((1-methylcyclopropyl)methoxy)pyridin-3-yloxy)-2,5-difluorobenzoic acid | $^1$H NMR (400 MHz, CDCl$_3$): δ 0.40 (m, 2H), 0.60 (m, 2H), 1.20 (s, 3H), 4.20 (s, 2H), 6.60 (m, 1H), 7.50 (s, 1H), 7.80 (m, 1H), 7.90 (s, 1H). |
| 156 | 4-(5-chloro-6-(cyclopropylmethoxy)pyridin-3-yloxy)-2,5-difluorobenzoic acid | $^1$H NMR (400 MHz, CDCl$_3$): δ 0.30 (m, 2H), 0.60 (m, 2H), 1.25 (m, 1H), 4.15 (d, 2H), 6.55 (m, 1H), 7.40 (s, 1H), 7.65 (m, 1H), 7.85 (s, 1H). |
| 157 | 4-(6-tert-butoxy-5-chloropyridin-3-yloxy)-2,5-difluorobenzoic acid | $^1$H NMR (400 MHz, CDCl$_3$): δ 1.6 (s, 9H), 6.6 (m, 1H), 7.40 (s, 1H), 7.9 (m, 1H), 7.95 (s, 1H). |

The following Preparations were prepared by the method described for Preparation 22, using appropriate reagents and conditions.

| Prep | Name | Data |
|---|---|---|
| 158 | 5-chloro-4-{[5-chloro-6-(tetrahydro-2H-pyran-4-yloxy)pyridin-3-yl]oxy}-2-fluorobenzoic acid | $^1$H NMR (400 MHz, d$_6$-DMSO): δ 1.60-1.75 (m, 2H), 1.95-2.05 (m, 2H), 3.43-3.57 (m, 2H), 3.80-3.88 (m, 2H), 5.20-5.28 (m, 1H), 7.00 (d, 1H), 7.96 (d, 1H), 8.01 (s, 1H), 8.10 (s, 1H), 13.40 (br, 1H). |
| 159 | 4-(5-Chloro-6-isopropoxypyridin-3-yloxy)-2-fluorobenzoic acid | $^1$H NMR (400 MHz, CD$_3$OD): δ 1.37 (d, 6H), 5.27-5.39 (m, 1H), 6.72-6.81 (m, 2H), 7.64 (s, 1H), 7.91-7.98 (m, 2H). |
| 160 | 5-chloro-4-(5-chloro-6-(1-methylpiperidin-4-yloxy)pyridin-3-yloxy)-2-fluorobenzoic acid | $^1$H NMR (400 MHz, CD$_3$OD): δ 1.92-2.53 (m, 4H), 2.62 (s, 3H), 3.18-3.67 (m, 4H), 5.22-5.37 (m, 1H), 6.78 (d, 1H), 7.73-7.78 (m, 1H), 7.92-7.97 (m, 1H), 8.05 (d, 1H). |
| 161 | 4-(5-chloro-6-isopropoxypyridin-3-yloxy)-2,3,6-trifluorobenzoic acid | $^1$H NMR (400 MHz, CDCl$_3$): δ 1.37 (d, 6H), 5.26 (m, 1H), 6.27-6.35 (m, 1H), 7.39 (s, 1H), 7.82 (s, 1H). |
| 162 | 5-chloro-4-(5-chloro-6-fluoropyridin-3-yloxy)-2-fluorobenzoic acid | $^1$H NMR (400 MHz, d$_6$-DMSO): δ 7.20 (m, 1H), 8.00 (m, 1H), 8.20 (m, 1H), 8.30 (m, 1H). |
| 163 | 4-(5-chloro-6-(2,2,2-trifluoroethoxy)pyridin-3-yloxy)-2,5-difluorobenzoic acid | $^1$H NMR (CDCl$_3$, 400 MHz): δ 4.8 (2H, q), 6.7 (1H, m), 7.5 (1H, s), 7.8 (1H, m), 7.9 (1H, s). |

The following Preparations were prepared by the method described for Preparation 9, using appropriate reagents and conditions.

| Prep | Name | Data |
|---|---|---|
| 164 | 4-methylphenyl 2,5-difluoro-4-[(6-isopropoxypyridin-3-yl)oxy]benzoate | $^1$H NMR (400 MHz, d$_6$-DMSO): δ 1.29-1.30 (d, 6H), 2.31 (s, 3H), 5.18-5.24 (m, 1H), 6.83-6.85 (d, 1H), 6.99-7.04 (q, 1H), 7.12-7.14 (m, 2H), 7.24-7.26 (m, 2H), 7.64-7.67 (m, 1H), 8.01-8.05 (q, 1H), 8.12-8.13 (d, 1H). |
| 165 | 4-methylphenyl 4-[(5-chloro-6-isobutylpyridin-3-yl)oxy]-2,5-difluorobenzoate | $^1$H NMR (400 MHz, d$_6$-DMSO): δ 0.90-0.92 (d, 6H), 2.15-2.20 (m, 1H), 2.33 (s, 3H), 2.77-2.78 (d, 2H), 7.17-7.18 (d, 2H), 7.25-7.27 (d, 2H), 7.36-7.40 (q, 1H), 7.90 (d, 1H), 8.05-8.10 (q, 1H), 8.45 (d, 1H). |
| 166 | 4-methylphenyl 4-[(5-chloro-6-cyclopropylpyridin-3-yl)oxy]-2,5-difluorobenzoate | $^1$H NMR (400 MHz, d$_6$-DMSO): δ 0.95-1.00 (m, 2H), 1.00-1.06 (m, 2H), 2.31 (s, 3H), 2.43-2.50 (m, 1H), 7.12-7.16 (m, 2H), 7.24-7.26 (m, 2H), 7.28-7.32 (q, 1H), 7.90 (d, 1H), 8.04-8.08 (q, 1H), 8.38 (d, 1H). |
| 167 | 4-methylphenyl 4-[(6-tert-butyl-5-chloropyridin-3-yl)oxy]-2,5-difluorobenzoate | $^1$H NMR (400 MHz; d$_6$-DMSO): δ 1.45 (s, 9H), 2.31 (s, 3H), 7.13-7.15 (m, 2H), 7.24-7.26 (m, 2H), 7.35-7.39 (m, 1H), 7.82-7.83 (d, 1H), 8.05-8.09 (m, 1H), 8.43 (d, 1H). |

| Prep | Name | Data |
|---|---|---|
| 168 | 4-methylphenyl 4-[(6-d9-tert-butoxy-5-chloropyridin-3-yl)oxy]-2,5-difluorobenzoate | $^1$H NMR (400 MHz, CDCl$_3$): δ 2.37 (s, 3H), 6.66-6.74 (m, 1H), 7.09 (d, 2H), 7.21 (s, 2H), 7.45 (d, 1H), 7.91 (d, 2H). |

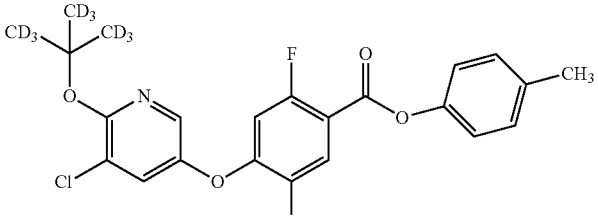

| | | |
|---|---|---|
| 169 | 4-methylphenyl 4-[(5-chloro-6-d7-isopropoxypyridin-3-yl)oxy]-2,5-difluorobenzoate | $^1$H NMR (400 MHz; CDCl$_3$): δ 2.38 (s, 3H), 6.66-6.71 (m, 1H), 7.08-7.10 (m, 2H), 7.22-7.24 (m, 2H), 7.48-7.49 (d, 1H), 7.91-7.95 (m, 2H). LCMS Rt = 1.86 mins MS m/z 442 [MH]$^+$ Contained up to 50% of a D8 analogue. Confirmed by LCMS: Rt = 1.86 mins. MS m/z 443 [MH]$^+$ |

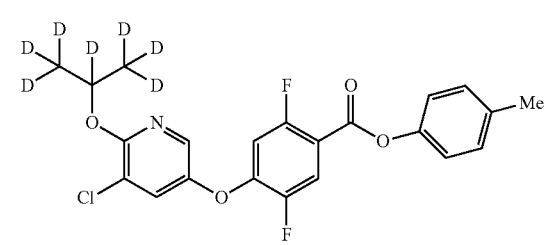 [SMILES: [2H]C([2H])([2H])C([2H])(Oc1ncc(Oc2cc(F)c(C(=O)Oc3ccc(C)cc3)cc2F)cc1Cl)C([2H])([2H])[2H]]

| | | |
|---|---|---|
| 170 | 4-methylphenyl 4-[(5-chloro-6-d1-isopropoxypyridin-3-yl)oxy]-2,5-difluorobenzoate | $^1$H NMR (400 MHz; CDCl$_3$): δ 1.42 (s, 6H), 2.38 (s, 3H), 6.66-6.71 (m, 1H), 7.08-7.11 (m, 2H), 7.22-7.24 (m, 2H), 7.48-7.49 (d, 1H), 7.91-7.95 (m, 2H). |

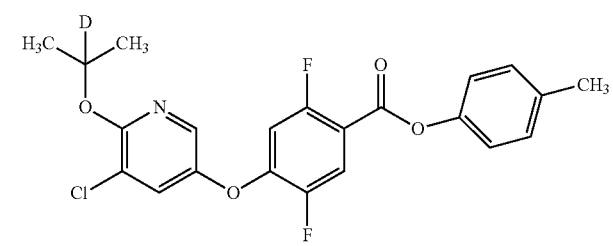 [SMILES: [2H]C(C)(C)Oc1ncc(Oc2cc(F)c(C(=O)Oc3ccc(C)cc3)cc2F)cc1Cl]

| | | |
|---|---|---|
| 171 | p-tolyl 4-(5-chloro-6-(2,2,3,3-tetrafluoropropoxy)pyridin-3-yloxy)-2,5-difluorobenzoate | $^1$H NMR (400 MHz, CDCl$_3$): δ 2.30 (s, 3H), 4.70 (s, 2H), 6.00 (m, 1H), 6.65 (m, 1H), 7.00 (d, 2H), 7.20 (d, 2H), 7.45 (s, 1H), 7.85 (m, 2H). |

The following Preparations were prepared by the method described for Preparation 36, using appropriate reagents and conditions.

| Prep | Name | Data |
|---|---|---|
| 172 | 4-methylphenyl 5-chloro-4-[(5-chloro-6-isobutoxypyridin-3-yl)oxy]-2-fluorobenzoate | $^1$H NMR (400 MHz, d$_6$-DMSO): δ 0.98 (s, 3H), 1.00 (s, 3H), 2.06 (m, 1H), 2.31 (s, 3H), 4.12 (d, 2H), 7.10-7.15 (m, 3H), 7.25 (d, 2H), 8.05 (d, 1H), 8.12 (d, 1H), 8.21 (d, 1H) |
| 173 | 4-methylphenyl 5-chloro-4-{[5-chloro-6-(1,1-difluoroethyl)pyridin-3-yl]oxy}-2-fluorobenzoate | $^1$H NMR (400 MHz, d$_6$-DMSO): δ 2.02-2.12 (t, 3H), 2.32 (s, 3H), 7.15-7.17 (m, 2H), 7.25-7.27 (m, 2H), 7.52.-755 (d, 1H), 8.05-8.06 (d, 1H), 8.27-8.29 (d, 1H), 8.54-8.55 (d, 1H). |
| 174 | 4-methylphenyl 5-chloro-4-{[5-chloro-6-(1-hydroxy-1-methylethyl)pyridin-3-yl]oxy}-2-fluorobenzoate | $^1$H NMR (400 MHz; d$_6$-DMSO): δ 1.58 (s, 6H), 2.32 (s, 3H), 5.32 (s, 1H), 7.15-7.17 (m, 2H), 7.27-7.27 (m, 2H), 7.31-7.33 (d, 1H), 7.85-7.86 (d, 1H), 8.25-8.27 (d, 1H), 8.2 (d, 1H). |

-continued

| Prep | Name | Data |
|---|---|---|
| 175 | 4-methylphenyl 5-chloro-4-{[5-chloro-6-(1,1-difluoro-2-methylpropyl)pyridin-3-yl]oxy}-2-fluorobenzoate | $^1$H NMR (400 MHz; d$_6$-DMSO): δ 1.00-1.02 (d, 6H), 2.33 (s, 3H), 2.76-2.87 (m, 1H), 7.15-7.18 (m, 2H), 7.26-7.28 (m, 2H), 7.55-7.58 (d, 1H), 8.04 (d, 1H), 8.27-8.29 (d, 1H), 8.58 (d, 1H). |
| 176 | 4-methylphenyl 5-chloro-4-({5-chloro-6-[2-fluoro-1-(fluoromethyl)ethoxy]pyridin-3-yl}oxy)-2-fluorobenzoate | LCMS Rt = 1.62 min. MS m/z 486[MH]$^+$ |
| 177 | 4-methylphenyl 5-chloro-4-{[5-chloro-6-(difluoromethoxy)pyridin-3-yl]oxy}-2-fluorobenzoate | LCMS Rt = 1.92 min. MS m/z 458[MH]$^+$ |
| 178 | 4-methylphenyl 5-chloro-4-{[5-chloro-6-(cyclopropyloxy)pyridin-3-yl]oxy}-2-fluorobenzoate | $^1$H NMR (400 MHz; CDCl$_3$): δ 0.87-0.91 (m, 4 H), 4.33-4.41 (m, 1 H), 6.63 (d, 1 H), 7.07-7.12 (m, 2 H), 7.23 (d, 2 H), 7.49 (d, 1 H), 8.02 (d, 1 H), 8.23 (d, 1 H). |
| 179 | 4-methylphenyl 5-chloro-4-{[5-chloro-6-(2,2,3,3,3-pentafluoropropoxy)pyridin-3-yl]oxy}-2-fluorobenzoate | $^1$H NMR (400 MHz, CDCl$_3$): δ 2.37 (s, 3H), 4.89 (m, 2H), 6.64 (d, 1H), 7.09 (d, 2H), 7.22 (d, 2H). 7.55 (d, 1H), 7.93 (d, 1H), 8.23 (d, 1H). |
| 180 | 4-methylphenyl 5-chloro-4-{[5-chloro-6-(2-fluoro-2-methylpropoxy)pyridin-3-yl]oxy}-2-fluorobenzoate | $^1$H NMR (400 MHz, CDCl$_3$): δ 1.46-1.54 (m, 6H), 2.37 (s, 3H), 4.40 (d, 2H), 6.60 (d, 1H), 7.08 (d, 2H), 7.22 (d, 2H), 7.51 (d, 1H), 7.92 (d, 1H), 8.22 (d, 1H). |
| 181 | p-tolyl 5-chloro-4-(5-chloro-6-isopropoxypyridin-3-yloxy)-2-fluorobenzoate | $^1$H NMR (400 MHz, CDCl$_3$): δ 1.40 (d, 6H), 2.37 (s, 3H), 5.35 (m, 1H), 6.60 (d, 1H), 7.06 (d, 2H), 7.21 (d, 2H), 7.46 (s, 1H), 7.91 (s, 1H), 8.20 (d, 1H). |
| 182 | p-tolyl 5-chloro-4-(5-chloro-6-(2,2-difluoroethoxy)pyridin-3-yloxy)-2-fluorobenzoate | $^1$H NMR (400 MHz, CDCl$_3$): δ 2.35 (s, 3H), 4.60 (m, 2H), 6.15 (m, 1H), 6.60 (s, 1H), 7.05 (d, 2H), 7.20 (d, 2H), 7.50 (s, 1H), 7.90 (s, 1H), 8.20 (s, 1H). |
| 184 | 4-methylphenyl 5-chloro-4-[(5-chloro-6-d7-isopropoxypyridin-3-yl)oxy]-2-fluorobenzoate 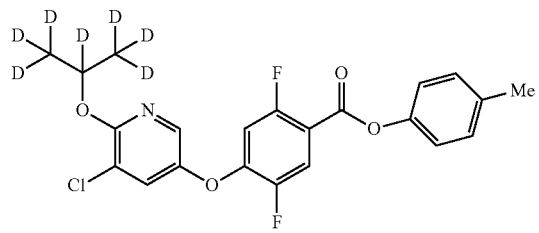 [SMILES: [2H]C([2H])([2H])C([2H])(Oc1ncc(Oc2cc(F)c(C(=O)Oc3ccc(C)cc3)cc2F)cc1Cl)C([2H])([2H])[2H]] | $^1$H NMR (400 MHz, CDCl$_3$): δ 2.38 (s, 3H), 6.60-6.62 (d, 1H), 7.08-7.11 (m, 2H), 7.21-7.25 (m, 2H), 7.48-7.49 (d, 1H), 7.93-7.94 (m, 1H), 8.22-8.23 (d, 1H) |
| 185 | 4-methylphenyl 5-chloro-4-[(5-chloro-6-d1-isopropoxypyridin-3-yl)oxy]-2-fluorobenzoate 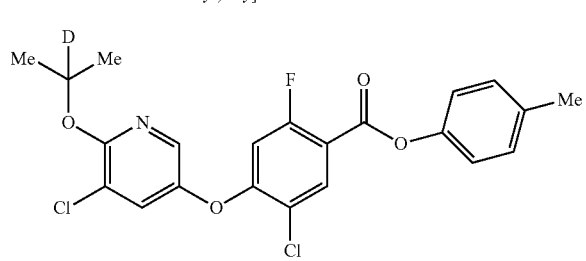 | $^1$H NMR (400 MHz; CDCl$_3$): δ 1.40 (s, 6H), 2.18 (s, 3H), 6.60 (d, 1H), 7.06-7.12 (m, 2H), 7.20-7.25 (m, 2H), 7.47 (s, 1H), 7.92 (s, 1H), 8.21 (d, 1H). |
| 186 | 4-methylphenyl 5-chloro-4-{[5-chloro-6-(2,2,2-trifluoroethoxy)pyridin-3-yl]oxy}-2-fluorobenzoate | $^1$H NMR (400 MHz; CDCl$_3$): δ 2.39 (s, 3H), 4.84 (q, 2H), 6.65 (d, 1H), 7.10 (d, 2H), 7.23 (d, 2H), 7.56 (s, 1H), 7.94 (s, 1H), 8.23 (d, 1H). |

The following Preparations were prepared by the method described for Preparation 31, using appropriate reagents and conditions.

| Prep | Name | Data |
|---|---|---|
| 187 | 4-[(5-chloro-6-isopropoxypyridin-3-yl)oxy]-2-methoxybenzamide | $^1$H NMR (400 MHz; CD$_3$OD): δ 1.37 (s, 3 H), 1.39 (s, 3 H), 3.94 (s, 3 H), 4.61 (br, 2H), 5.33 (t, 1 H), 6.56 (d, 1 H), 6.80 (d, 1 H), 7.63 (d, 1 H), 7.92 (d, 1 H), 7.98 (d, 1 H). |
| 188 | 4-[(5-chloro-6-methoxypyridin-3-yl)oxy]benzamide | $^1$H NMR (400 MHz, d$_6$-DMSO): δ 3.90 (s, 3H), 7.00 (m, 2H), 7.25 (m, 1H), 7.75 (m, 1H), 7.90 (m, 3H), 8.05 (m, 1H). |
| 189 | 4-[(5-chloro-6-isopropoxypyridin-3-yl)oxy]benzamide | $^1$H NMR (400 MHz, d$_6$-DMSO) δ: 1.35 (d, 6H), 3.25 (m, 1H), 7.00 (m, 2H), 7.25 (s, 1H), 7.95 (m, 4H), 8.00 (s, 1H). |
| 190 | 3-chloro-4-[(5-chloro-6-methoxypyridin-3-yl)oxy]benzamide | $^1$H NMR (400 MHz, d$_6$-DMSO): δ 3.80 (s, 3H), 6.99 (m, 1H), 7.40 (m, 1H), 7.80 (m, 1H), 8.05 (m, 2H). |
| 191 | 3-chloro-4-[(5-chloro-6-isopropoxypyridin-3-yl)oxy]benzamide | $^1$H NMR (400 MHz, d$_6$-DMSO): δ 1.38 (6H, d), 5.25 (1H, m), 7.05 (1H, d), 7.4 (2H, br), 7.80 (1H, m), 8.05 (1H, m), 8.15 (1H, m). |
| 192 | 4-(6-chloroquinolin-8-yloxy)-2,5-difluorobenzamide | $^1$H NMR (400 MHz, d$_6$-DMSO): δ 6.88 (m, 1H), 7.61 (d, 1H), 7.63-7.69 (m, 4H), 8.06 (d, 1H), 8.44 (m, 1H), 8.86 (m, 1H). |
| 193 | 4-(5-chloroquinolin-8-yloxy)-2,5-difluorobenzamide | $^1$H NMR (400 MHz, d$_6$-DMSO): δ 6.78 (m, 1H), 7.56 (m, 1H), 7.62-7.68 (m, 3H), 7.76 (m, 1H), 7.82 (d, 1H), 8.61 (m, 1H), 8.94 (m, 1H). |
| 194 | 2,5-difluoro-4-(4-methoxypyridin-3-yloxy)benzamide | $^1$H NMR (400 MHz, d$_6$-DMSO): δ 3.84 (s, 3H), 6.71 (m, 1H), 7.30 (d, 1H), 7.60-7.68 (m, 3H), 8.35 (br, 1H), 8.43 (m, 1H). |
| 195 | 2,5-difluoro-4-(imidazo[1,2-a]pyridin-8-yloxy)benzamide | $^1$H NMR (400 MHz, d$_6$-DMSO): δ 6.87 (t, 1H), 6.95 (d, 1H,), 7.02 (m, 1H,), 7.53 (s, 1H), 7.62-7.76 (m, 3H), 8.04 (m, 1H), 8.44 (m, 1H). |

The following Preparations were prepared by the method described for Preparation 32, using appropriate reagents and conditions.

| Prep | Name | Data |
|---|---|---|
| 196 | 4-[(5-chloro-6-isopropoxypyridin-3-yl)oxy]-2-methoxybenzonitrile | $^1$H NMR (400 MHz, CDCl$_3$): δ 1.41 (s, 3 H), 1.43 (s, 3 H), 3.90 (s, 3 H), 5.33 (t, 1 H), 6.47 (d, 1 H), 6.57 (d, 1 H), 7.44 (d, 1 H), 7.49 (d, 1 H), 7.89 (d, 1 H). |
| 197 | 4-[(5-chloro-6-methoxypyridin-3-yl)oxy]benzonitrile | — |
| 198 | 4-[(5-chloro-6-isopropoxypyridin-3-yl)oxy]benzonitrile | — |
| 199 | 3-chloro-4-[(5-chloro-6-methoxypyridin-3-yl)oxy]benzonitrile | LCMS Rt = 3.50 min. MS m/z 295 [MH]$^+$ |
| 200 | 3-chloro-4-[(5-chloro-6-isopropoxypyridin-3-yl)oxy]benzonitrile | LCMS Rt = 3.87 min. MS m/z 323 [MH]$^+$ |
| 201 | 4-(5-chloroquinolin-8-yloxy)-2,5-difluorobenzonitrile | $^1$H NMR (400 MHz, CDCl$_3$): δ 6.49 (m, 3H), 7.39 (d, 1H), 7.44 (m, 1H), 7.60 (m, 1H), 7.65 (d, 1H), 8.63 (m, 1H), 8.92 (m, 1H). |
| 202 | 4-(6-chloroquinolin-8-yloxy)-2,5-difluorobenzonitrile | $^1$H NMR (400 MHz, d$_6$-DMSO): δ 7.09 (m, 1H), 7.67 (m, 1H), 7.82 (d, 1H), 8.15 (d, 1H,) 8.18 (d, 1H), 8.47 (m, 1H), 8.85 (m, 1H). |
| 203 | 2,5-difluoro-4-(4-methoxypyridin-3-yloxy)benzonitrile | 1H NMR (400 MHz, d$_6$-DMSO): δ 7.09 (m, 1H), 7.67 (m, 1H), 7.82 (d, 1H), 8.15 (d, 1H,) 8.18 (d, 1H), 8.47 (m, 1H), 8.85 (m, 1H). |
| 204 | 2,5-difluoro-4-(imidazo[1,2-a]pyridin-8-yloxy)benzonitrile | 1H NMR (400 MHz, d$_6$-DMSO): δ 7.09 (m, 1H), 7.67 (m, 1H), 7.82 (d, 1H), 8.15 (d, 1H,) 8.18 (d, 1H), 8.47 (m, 1H), 8.85 (m, 1H). |

The following Preparations were prepared by the method described for Preparation 33, using appropriate reagents and conditions.

| Prep | Name | Data |
|---|---|---|
| 205 | 4-[(5-chloro-6-isopropoxypyridin-3-yl)oxy]-5-fluoro-2-methoxybenzaldehyde | $^1$H NMR (400 MHz, d$_6$-DMSO): δ 1.30-1.32 (d, 6H), 3.83 (s, 3H), 5.21-5.27 (m, 1H), 6.83-6.84(d, 1H), 7.56-7.59 (d, 1H), 7.86-7.87 (d, 1H), 8.03-8.04 (d, 1H), 10.15-10.16 (d, 1H). |
| 206 | 2,5-difluoro-4-[(5-fluoro-6-isopropoxypyridin-3-yl)oxy]benzaldehyde | $^1$H NMR (400 MHz, DMSO d$_6$): δ 1.32-1.34 (d, 6H), 5.28-5.37 (m, 1H), 7.13-7.18 (q, 1H), 7.76-7.80 (q, 1H), 7.86-7.89 (m, 1H), 7.99-8.00 (d, 1H), 10.07-10.08 (d, 1H). |
| 207 | 4-[(5-chloro-6-isopropoxypyridin-3-yl)oxy]-3,6-difluoro-2-methoxybenzaldehyde | $^1$H NMR (400 MHz, CDCl$_3$): δ 1.40-1.42 (d, 6H), 4.14-4.15 (d, 3H), 5.30-5.36 (m, 1H), 6.26-6.31 (q, 1H), 7.46-7.47 (d, 1H), 7.91 (d, 1H), 10.25 (m, 1H). |
| 208 | 4-[(5-chloro-6-isobutoxypyridin-3-yl)oxy]-2-fluorobenzaldehyde | — |
| 209 | 2-[(5-chloro-6-isopropoxypyridin-3-yl)oxy]-5-formylbenzonitrile | $^1$H NMR (400 MHz, CDCl$_3$): δ 1.42-1.44 (d, 6H), 5.31-5.41 (m, 1H), 6.94-6.96 (d, 1H), 7.52 (d, 1H), 7.96-7.97 (d, 1H), 8.00-8.03 (m, 1H), 8.21 (d, 1H), 9.95 (s, 1H). |
| 210 | 4-(5-chloro-6-isopropoxypyridin-3-yloxy)-2-fluoro-5-methyl benzaldehyde | $^1$H NMR (400 MHz, CDCl$_3$): δ 1.40 (6H, d), 2.35 (3H, s), 5.35 (1H, m), 6.40 (1H, d), 7.62 (1H, d), 7.75 (1H, d), 7.85 (1H, d), 10.10 (1H, s). |
| 211 | 4-(5-chloro-6-isopropoxypyridin-3-yloxy)-3-methoxy-benzaldehyde | $^1$H NMR (400 MHz, CDCl$_3$): δ 1.40 (d, 6H), 3.95 (s, 3H), 5.25 (m, 1H), 6.85 (d, 1H), 7.40 (d, 1H), 7.55 (s, 1H), 7.85 (d, 1H), 9.90 (s, 1H). |

The following Preparations were prepared by the method described for Preparation 38, using appropriate reagents and conditions.

| Prep | Name | Data |
|---|---|---|
| 212 | ethyl-2,5-difluoro-4-{[2-(trifluoromethyl)pyrimidin-5-yl]oxy}benzoate | $^1$H NMR (400 MHz, CDCl$_3$): δ 1.41 (t, 3H), 4.43 (q, 2H), 7.00-7.04 (m, 1H), 7.86-7.90 (m, 1H), 8.62 (s, 2H). |
| 213 | methyl 4-(5-chloro-6-isopropoxypyridin-3-yloxy)-3-fluorobenzoate | $^1$H NMR (400 MHz, CDCl$_3$): δ 1.4 (d, 6H), 3.9 (s, 3H), 5.3 (m, 1H), 6.9 (t, 1H), 7.4 (s, 1H), 8.0-7.7 (m, 3H). |

The following Preparations were prepared by the method described for Preparation 37, using appropriate reagents and conditions.

| Prep | Name | Data |
|---|---|---|
| 214 | 2,5-difluoro-4-{[2-(trifluoromethyl)pyrimidin-5-yl]oxy}benzoic acid | $^1$H NMR (400 MHz, CDCl$_3$): δ 7.31-7.35 (m, 1H), 7.87-7.92 (m, 1H), 8.80 (s, 2H). |
| 215 | 4-(5-chloro-6-isopropoxy-pyridin-3-yloxy)-3-fluorobenzoic acid | $^1$H NMR (400 MHz, d$_6$-DMSO): δ 0.6 (d, 6H), 4.5 (m, 1H), 6.2 (m, 1H), 6.8 (m, 1H), 7.0 (m, 2H), 7.1 (s, 1H). |

Preparation 216

3-Difluoromethoxy-2-cyclopropylpyridine

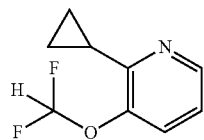 [SMILES: FC(F)Oc1cccnc1C1CC1]

Prepared according to Preparation 48 using 3-difluoromethoxy-2-bromopyridine (Preparation 217) and cyclopropylboronic acid. The reaction was heated to 95° C. for 18 hours before cooling to room temperature and filtering through arbocel. The filtrate was concentrated in vacuo and purified using silica gel column chromatography eluting with ethylacetate:heptane 1:5 to furnish the title compound as a colourless oil (273 mg, 58%).

$^1$H NMR (400 MHz; d$_6$-DMSO): δ 0.95 (m, 4H), 2.3 (m, 1H), 7.05-7.42 (t, 1H), 7.15 (m, 1H), 7.5 (m, 1H), 8.25 (m, 1H).

LCMS Rt=2.09 minutes MS m/z 186 [MH]$^+$

Preparation 217

3-Difluoromethoxy-2-bromopyridine

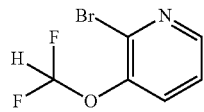 [SMILES: FC(F)Oc1cccnc1Br]

To a solution of 2-bromo-3-pyridinol (1.26 g, 7.23 mmol) in DMF (35 mL) and water (5 mL) was added sodium chlorodifluoroacetate (2.93 g, 18.1 mmol) followed by cesium carbonate (4.71 g, 14.5 mmol). The reaction was heated to 100° C. for 36 hours before partitioning between EtOAc and water. The organic layer was separated, dried over magnesium sulfate and concentrated in vacuo. The residue was purified using silica gel column chromatography eluting with EtOAc:Heptane 1:3 to afford the title compound as a colourless oil (570 mg, 35%).

$^1$H NMR (400 MHz; d$_6$-DMSO): δ 7.15-7.55 (t, 1H), 7.55 (m, 1H), 7.80 (m, 1H), 8.25 (m, 1H).

LCMS Rt=1.91 minutes MS m/z 226 [MH]$^+$

Preparation 218 tert-Butyl 2,5-dichloro-4-fluorobenzoate

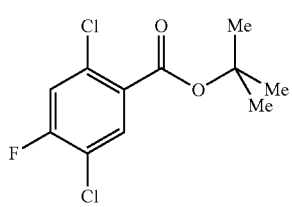 [SMILES: CC(C)(C)OC(=O)c1cc(Cl)c(F)cc1Cl]

Di-tert-butyl dicarbonate (940 mg, 4.31 mmol) was added to a solution of 2,5-dichloro-4-fluorobenzoic acid (J. Med. Chem., 1972, 15, p 79, 300 mg, 1.44 mmol) and dimethylaminopyridine (35 mg, 0.29 mmol) in tert-butyl alcohol (10 mL). The reaction mixture was stirred at 40° C. for 24 hours then diluted with water (10 mL) and extracted with ethyl acetate (3×20 mL). The combined organic layers were dried (MgSO$_4$), filtered and concentrated in vacuo. The crude compound was purified by silica gel column chromatography eluting with heptane:dichloromethane (from 95:5 to 60:40) to afford the title compound as a pale yellow oil (251 mg, 66%, mixture 5.5:1 of expected compound: starting material).

LCMS Rt=3.19 minutes, No mass ion.

$^1$H NMR (400 MHz, CDCl$_3$): δ 1.52 (s, 9H), 7.15 (d, 1H), 7.77 (d, 1H).

Preparation 219 tert-Butyl 2,5-dichloro-4-(5-chloro-6-cyclopropylpyridin-3-yloxy)benzoate

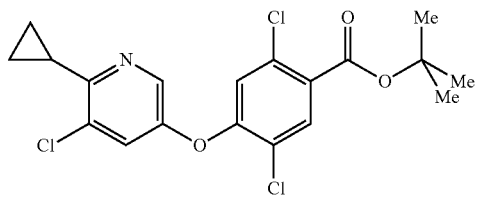 [SMILES: CC(C)(C)OC(=O)c1cc(Cl)c(Oc2cnc(C3CC3)c(Cl)c2)cc1Cl]

tert-Butyl 2,5-dichloro-4-fluorobenzoate (Preparation 218, 251 mg, 0.61 mmol) was added to a solution of 5-chloro-6-cyclopropylpyridin-3-ol (Preparation 69, 161 mg, 0.61 mmol) and potassium carbonate (393 mg, 1.82 mmol) in dimethylsulfoxide (5 mL). The reaction mixture was stirred at room temperature for 18 hours then diluted with sodium hydroxide (1M, 5 mL) and extracted with ethyl acetate (3×15 mL). The combined organic layers were dried (MgSO$_4$), filtered and concentrated in vacuo. The crude compound was purified by silica gel column chromatography eluting with heptane:dichloromethane (from 95:5 to 60:40) to afford the title compound as a colourless oil (116 mg, 30%).

LCMS Rt=4.54 minutes MS m/z 416 [MH]$^+$

¹H NMR (400 MHz, CDCl₃): δ 0.96-1.03 (m, 4H), 1.53 (s, 9H), 2.39-2.46 (m, 1H), 6.85 (s, 1H), 7.21 (d, 1H), 7.84 (s, 1H), 8.08 (d, 1H).

Preparation 220

2,5-Dichloro-4-(5-chloro-6-cyclopropylpyridin-3-yloxy)benzoic acid

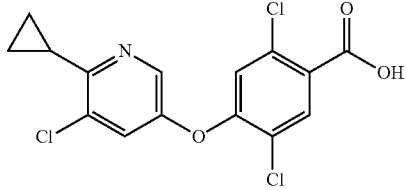 [SMILES: O=C(O)c1cc(Cl)c(Oc2cnc(C3CC3)c(Cl)c2)cc1Cl]

Trifluoroacetic acid (42 μL, 0.56 mmol) was added to a solution of tert-butyl 2,5-dichloro-4-(5-chloro-6-cyclopropylpyridin-3-yloxy)benzoate (Preparation 219, 116 mg, 0.28 mmol) in dichloromethane (3 mL). The reaction mixture was stirred at room temperature for 4 hours then concentrated in vacuo. The residue was dissolved in methanol (10 mL) then concentrated in vacuo to afford the title compound as colourless solid (100 mg, 100%).

LCMS (8 min acidic run) Rt=3.79 minutes MS m/z 360 [MH]⁺

¹H NMR (400 MHz, CDCl₃): δ 0.95-0.98 (m, 2H), 1.00-1.04 (m, 2H), 2.43-2.47 (m, 1H), 7.26 (s, 1H), 7.80 (d, 1H), 8.01 (s, 1H), 8.30 (d, 1H)

Preparation 221

3-chloro-2-cyclopropyl-5-(4,4,5,5-tetramethyl-1-1,3,2-dioxaborolan-2-yl)pyridine

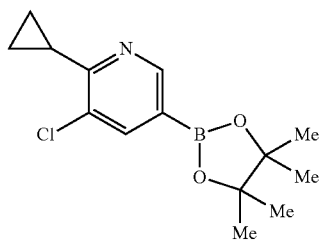 [SMILES: CC1(C)OB(c2cnc(C3CC3)c(Cl)c2)OC1(C)C]

3-chloro-2-cyclopropylpyridine (Preparation 48, 70 mg, 0.46 mmol) and bis(pinacolato)diboron (105 mg, 0.41 mmol) were added to dioxane (100 mL). The solution was degassed by bubbling N₂ through the solution for 30 minutes. The solution was heated to 80° C., and 4,4-di-tert-butyl-2,2-dipyridyl (2.4 mg, 0.009 mmol) plus cyclooctadiene(dimethoxy) Iridium (I) dimer (3.0 mg, 0.005 mmol) were added. The flask was degassed with N₂ (×3), and stirred at 80° C. for 18 hours. The reaction was cooled in an ice bath, and quenched by slow addition of methanol (20 mL) and concentrated to dryness to afford a red-brown oil. The material was purified by silica gel column chromatography eluting with 2:1 heptane:ethyl acetate to afford the title compound as a colourless oil (32 mg, 25%).

LCMS Rt=2.26 minutes, No mass ion seen.

¹HNMR (400 MHz, CDCl₃): δ 0.98-1.28 (m, 4H), 1.30 (s, 12H), 2.47-2.58 (m, 1H), 7.94 (s, 1H), 8.61 (s, 1H).

Preparation 222

5-chloro-6-isopropoxypyridin-3-yl trifluoromethanesulfonate

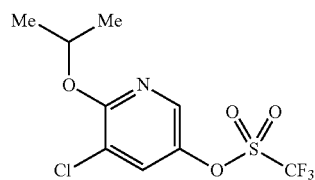 [SMILES: CC(C)Oc1ncc(OS(=O)(=O)C(F)(F)F)cc1Cl]

To a stirred ice-cold solution of 5-chloro-6-isopropoxypyridin-3-ol (Preparation 15, 1050 mg, 3.37 mmol) and triethylamine (356 mg, 0.49 mL, 3.52 mmol) in DCM (10 mL) was added N-phenyltrifluoromethanesulfonimide (633 mg, 2.93 mmol) in portions over 10 minutes. The reaction mixture was allowed to warm to room temperature for 18 hours and then washed with 1M NaOH solution (2×5 mL), water (5 mL), dried over MgSO₄, filtered and evaporated to give the title compound (895 mg, 95%) as a clear oil.

LCMS Rt=2.93 minutes, MS m/z 278 [M−iPrH]⁺

¹HNMR (400 MHz, CDCl₃): δ 1.38 (d, 6H), 5.28-5.40 (m, 1H), 7.60 (s, 1H), 8.03 (s, 1H).

Preparation 223

5-chloro-6-isopropoxy-3-tri-isopropylsilylthiopyridine

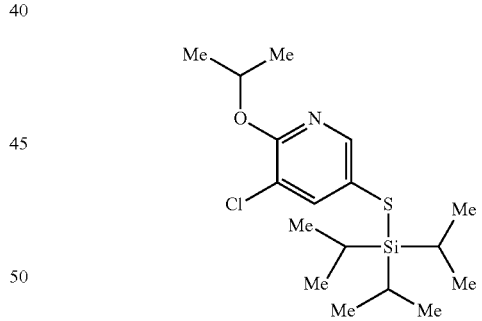

A mixture of 5-chloro-6-isopropoxypyridin-3-yl trifluoromethanesulfonate (Preparation 222, 361 mg, 1.13 mmol) and cesium carbonate (515 mg, 1.58 mmol) in toluene (6 mL) was sparged with nitrogen for 5 minutes before adding tri-isopropylsilylthiol (344 mg, 0.388 mL, 1.81 mmol) as a solution in toluene (2 mL) followed by (1,1'-bis(diphenylphosphino)ferrocene)dichloropalladium(II):complex with dichloromethane (138 mg, 0.169 mmol). The resulting mixture was refluxed under nitrogen for 18 hours. The cooled reaction was diluted with EtOAc (10 mL) and water (10 mL). The organic layer was separated and washed with a saturated aqueous solution of brine (10 mL), dried over MgSO₄, filtered and evaporated. The residue was purified by silica gel column chromatography using EtOAc/pentane as eluent (0:100-5/95) to give the title compound (422 mg, 100%) as a clear oil which was used directly in the next stage.

Preparation 224

4-methylphenyl-5-chloro-4-[(5-chloro-6-isopropoxy-pyridin-3-yl)thio]-2-fluoro-benzoate

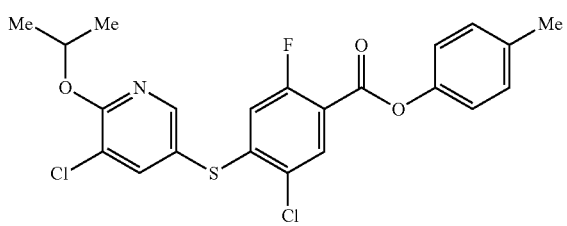 [SMILES: Cc1ccc(OC(=O)c2cc(Cl)c(Sc3cnc(OC(C)C)c(Cl)c3)cc2F)cc1]

To a stirred solution of 4-methylphenyl-5-chloro-2,4-difluorobenzoate (Preparation 12, 275 mg, 0.97 mmol) and 5-chloro-6-isopropoxy-3-tri-isopropylsilylthiopyridine (Preparation 223, (420 mg, 1.17 mmol) in DMSO (3 mL) was added potassium carbonate (269 mg, 1.95 mmol). The resulting mixture was stirred at room temperature for 2 hours and then partitioned between EtOAc (10 mL) and water (5 mL). The organic layer was separated and washed with water (5 mL) and a saturated aqueous brine solution (5 mL), dried over MgSO$_4$, filtered, evaporated and purified using silica gel column chromatography eluting with EtOAc/Pentane 0/100 to 1/9 to yield the title compound (352 mgs, 77%) as a clear oil that was used directly in the next stage.

Preparation 225

2-cyclopropyl-3-(trifluoromethyl)pyridine

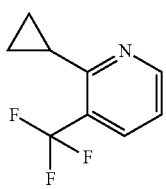 [SMILES: FC(F)(F)c1cccnc1C1CC1]

2-bromo-3-trifluoromethylpyridine (5 g, 22.1 mmol), cyclopropyl boronic acid (2.09 g, 24.3 mmol), and tribasic potassium phosphate (14.1 g, 66.4 mmol) were suspended in a mixture of toluene (150 mL) and water (30 mL), with rapid stirring. The suspension was heated to 80° C., and the solvent de-gassed by direct bubbling of N$_2$ gas through the suspension for 30 minutes. The reaction was then heated to 95° C., and tricyclohexyl phosphine (620 mg, 2.21 mmol) followed by palladium acetate (248 mg, 1.12 mmol) were added. The reaction was left to stir and heat at 95° C. for 6 hours. The reaction was cooled to room temperature, and filtered through a plug of Arbocel™, eluting with ethyl acetate. The solvent was removed to leave a dark yellow oil. TBME was added (300 mL), and the organic phase washed with 2M HCl solution (3×200 mL). The organics were discarded. TBME (300 mL) was added to the combined aqueous layers, and solid sodium bicarbonate was added until the aqueous layer reached pH 7. The organic layer was removed, and the aqueous layer was extracted with TBME (2×100 mL). The combined organic extracts were dried over magnesium sulfate, filtered and concentrated in vacuo. The residue was purified by silica gel column chromatography eluting with 4:1 heptane:ethyl acetate, affording the title compound as a colourless oil (400 mg, 10%).

LCMS Rt=2.77 minutes MS m/z 188 [MH]$^+$
$^1$HNMR (400 MHz, CDCl$_3$): δ 0.96-1.08 (m, 4H), 2.28-2.38 (m, 1H), 7.08 (dd, 1H), 7.83 (d, 1H), 8.58 (d, 1H).

Preparation 226

5-chloro-6-phenylpyridin-3-ol

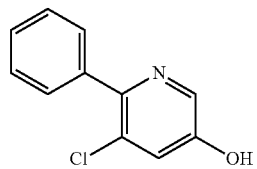 [SMILES: Oc1cnc(-c2ccccc2)c(Cl)c1]

To a solution of 6-bromo-5-chloropyridin-3-ol (Preparation 239, 100 mg, 0.48 mmol), and phenylboronic acid (117 mg, 0.96 mmol) in 1,4-dioxane (5 mL) under nitrogen was added 2M aqueous Na$_2$CO$_3$ solution (1 mL) and palladium tetrakistriphenylphosphine (28 mg, 0.024 mmol). The mixture was stirred at 80° C. for 3.5 hours. The reaction mixture was allowed to cool to room temperature and partitioned between water and EtOAc. The desired product was in the aqueous phase (pH ~11). The organic phase was washed with 10 wt % aqueous NaOH solution (2×15 mL). The combined aqueous phases were neutralised with 1N aqueous citric acid solution and extracted with EtOAc (4×30 mL). The combined organic phases were washed with brine, dried over Na$_2$SO$_4$, filtered, and concentrated in vacuo to give a crude product. The crude product was purified by silica gel chromatography eluting with 0-30% EtOAc in heptane to give the title compound (67 mg, 68%) as a white solid.

$^1$HNMR (400 MHz, CDCl$_3$): δ 6.33 (br s, 1H), 7.31 (d, 1H), 7.43 (m, 3H), 7.66 (m, 2H), 8.22 (d, 1H).
LCMS Rt=2.00 minutes MS m/z 206 [MH]$^+$, 204 [MH]$^-$

Preparation 227 tert-Butyl 3,3-difluorocyclobutanecarboxylate

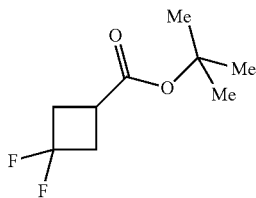 [SMILES: CC(C)(C)OC(=O)C1CC(F)(F)C1]

3,3-difluorocyclobutanecarboxylic acid (1.0 g, 7.3 mmol) was dissolved in DCM (10 mL) and cooled in an ice bath. To the solution was added N,N-dimethylpyridin-4-amine (92 mg, 0.735 mmol) portionwise followed by 2-methylpropan-2-ol (1.1 g, 14.7 mmol) in one portion. A 1M solution of N,N'-dicyclohexylcarbodiimide in DCM (8.1 mL, 8.1 mmol) was added dropwise keeping the temperature below 10° C. The resulting slurry was warmed up to room temperature and stirred for 18 hours. The solid was removed by filtration and the filtrate was washed with 2N aqueous HCl solution (2×15 mL), water (2×15 mL), and then saturated aqueous NaHCO₃ solution (2×15 mL). The organic phase was dried over Na₂SO₄, filtered, and concentrated in vacuo to give 1.49 g of a crude product as a mixture of white solid and yellow oil. To the mixture was added pentane (30 mL) and the mixture as then filtered through a silica gel pad eluting with pentane to give the title compound (896 mg, 63%) as colourless oil.

¹HNMR (400 MHz, CDCl₃): δ 1.47 (s, 9H), 2.81 (m, 5H).

Preparation 228

3-chloro-2-(3,3-difluorocyclobutyl)pyridine

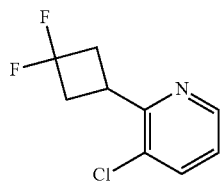 [SMILES: FC1(F)CC(c2ncccc2Cl)C1]

To a solution of tert-butyl 1-(3-chloropyridin-2-yl)-3,3-difluorocyclobutanecarboxylate (Preparation 229, 500 mg, 1.65 mmol) in DCM (6.5 mL) was added TFA (0.50 mL, 6.6 mmol) at room temperature under N₂. The resulting solution was stirred for 18 hours. The solvent was removed in vacuo and toluene (5 mL) was added. The resulting mixture was warmed up to 90° C. and stirred for 18 hours. The reaction mixture was cooled to room temperature and diluted with EtOAc and water. The organic phase was washed with saturated aqueous NaHCO₃ solution, then brine, dried over Na₂SO₄, filtered, and concentrated in vacuo to give the crude product as a dark brown oil. The crude product was purified by silica gel column chromatography eluting with 0-30% EtOAc in heptane to give the title compound (271 mg, 81%) as a colourless oil.

¹HNMR (400 MHz, CDCl₃): δ 3.01 (m, 4H), 3.82 (m, 1H), 7.16 (m, 1H), 7.66 (m, 1H), 8.50 (m, 1H)

LCMS Rt=1.26 minutes MS m/z 204 [MH]⁺

Preparation 229 tert-butyl 1-(3-chloropyridin-2-yl)-3,3-difluorocyclobutanecarboxylate

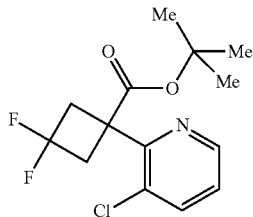 [SMILES: CC(C)(C)OC(=O)C1(c2ncccc2Cl)CC(F)(F)C1]

A solution of 3-chloro-2-fluoropyridine (500 mg, 3.8 mmol) and tert-butyl 3,3-difluorocyclobutanecarboxylate (Preparation 227, 877 mg, 4.6 mmol) in toluene (13 mL) was cooled to 0° C. A solution of sodium 1,1,1,3,3,3-hexamethyldisilazan-2-ide (1M solution in THF, 5.7 mL, 5.7 mmol) was added dropwise. The reaction mixture was stirred for 20 minutes at the same temperature, and then allowed to warm to room temperature and stirred for 4 hours. The reaction was quenched with saturated aqueous NH₄Cl solution and extracted with EtOAc (3×20 mL). The combined organic extracts were washed with 1N aqueous citric acid solution (3×15 mL), then brine (3×15 mL). The organic phase was dried over Na₂SO₄, filtered, and concentrated in vacuo to give a crude product as yellow oil which was purified by silica gel column chromatography eluting with 0-20% EtOAc in heptane to give the title compound (505 mg, 44%) as colourless oil.

¹HNMR (400 MHz, CDCl₃): δ 1.40 (s, 9H), 3.41 (m, 4H), 7.23 (m, 1H), 7.70 (d, 1H), 8.50 (d, 1H).

LCMS Rt=2.85 minutes No mass ion detected.

Preparation 230

4-methylphenyl 5-chloro-4-({5-chloro-6-[(1S)-2,2,2-trifluoro-1-methylethoxy]pyridin-3-yl}oxy)-2-fluorobenzoate

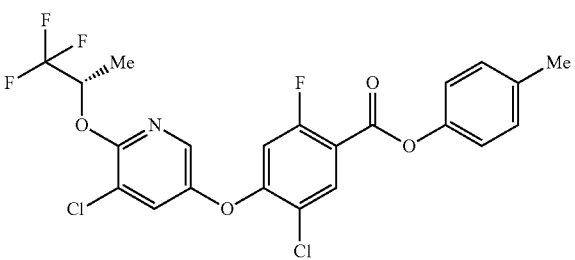 [SMILES: Cc1ccc(OC(=O)c2cc(Cl)c(Oc3cnc(O[C@@H](C)C(F)(F)F)c(Cl)c3)cc2F)cc1]

To a mixture of 5-chloro-6-[(1S)-2,2,2-trifluoro-1-methylethoxy]pyridin-3-ol (Preparation 231, 60 mg, 0.25 mmol) and 4-methylphenyl 5-chloro-2,4-difluorobenzoate (Preparation 26, 70 mg, 0.25 mmol) in DMSO (1 mL) was added K₂CO₃ (69 mg, 0.50 mmol) at room temperature under N₂ and the resulting mixture was stirred for 4 hours. The reaction mixture was warmed up to 50° C. and stirred for 1 hour before cooling to room temperature and stirring for 18 hours. The reaction was quenched with water and partitioned between water and DCM (3×5 mL). The mixture was filtered through a phase separation cartridge, the organic phase was washed with brine (3 mL) and filtered through another phase separation cartridge. The filtrate was dried by N₂ blowing to give a crude product that was purified by silica gel column chromatography eluting with 0-20% EtOAc in heptane to give the title compound (108 mg, 86%) as colourless gum.

¹HNMR (400 MHz, CDCl₃): δ 1.58 (m, 3H), 2.39 (s, 3H), 5.77 (m, 1H), 6.66 (d, 1H), 7.11 (m, 2H), 7.23 (m, 2H), 7.54 (d, 1H), 7.93 (d, 1H), 8.24 (d, 1H).

LCMS Rt=3.64 minutes MS m/z 504 [MH]⁺, 502 [MH]⁻

Preparation 231

5-chloro-6-[(1S)-2,2,2-trifluoro-1-methylethoxy]pyridin-3-ol

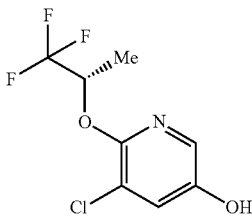 [SMILES: C[C@H](Oc1ncc(O)cc1Cl)C(F)(F)F]

To a solution of 3-chloro-5-(4,4,5,5-tetramethyl-1,3,2-dioxaborolan-2-yl)-2-[(1S)-2,2,2-trifluoro-1-methylethoxy]pyridine (Preparation 232, 130 mg, 0.37 mmol) in acetone (1 mL) was added an aqueous solution of Oxone® (1 mL, 287 mg, 0.44 mmol) dropwise with stirring at 0° C. for 15 minutes. The reaction mixture was diluted with water and extracted with DCM (3×5 mL). The mixture was filtered through a phase separation cartridge, the organic phase was washed with brine (3 mL) and filtered through another phase separation cartridge. The filtrate was dried by $N_2$ blowing to give a crude product that was purified by silica gel column chromatography eluting with 0-30% EtOAc in heptane to give the title compound (62 mg, 69%) as colourless oil.

¹HNMR (400 MHz, CDCl₃): δ 1.51 (d, 3H), 5.63 (m, 1H), 7.30 (d, 1H), 7.66 (d, 1H).

LCMS Rt=2.35 minutes MS m/z 242 [MH]⁺, 240 [MH]⁻

Preparation 232

3-chloro-5-(4,4,5,5-tetramethyl-1,3,2-dioxaborolan-2-yl)-2-[(1S)-2,2,2-trifluoro-1-methylethoxy]pyridine

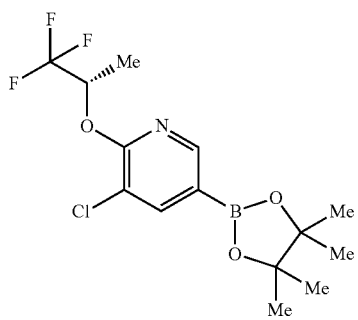

A mixture of 3-chloro-2-[(1S)-2,2,2-trifluoro-1-methylethoxy]pyridine (Preparation 233, 85 mg, 0.38 mmol), 4,4,4',4',5,5,5',5'-octamethyl-2,2'-bi-1,3,2-dioxaborolane (115 mg, 0.45 mmol), di-mu-methanolatodiiridium(Ir—Ir)-cycloocta-1,5-diene (1:2) (7.4 mg, 0.011 mmol) and 4,4'-di-tert-butyl-2,2'-bipyridine (3 mg, 0.011 mmol) in TBME (2 mL) was heated at 80° C. in the microwave for 30 minutes. The solvent was reduced by $N_2$ blowing and the residue was filtered through a silica gel pad eluting with EtOAc (30 mL). The filtrate was concentrated in vacuo to give the title compound. The material was used for the next step without further purification.

LCMS Rt=1.80 minutes MS m/z 352 [MH]⁺

Preparation 233

3-chloro-2-[(1S)-2,2,2-trifluoro-1-methylethoxy]pyridine

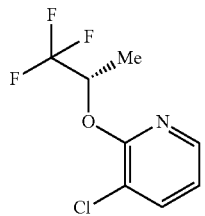 [SMILES: C[C@H](Oc1ncccc1Cl)C(F)(F)F]

To a solution of 3-chloro-2-fluoropyridine (115 mg, 0.88 mmol) and (2S)-1,1,1-trifluoropropan-2-ol (45 wt % solution in TBME, 218 mg, 0.88 mmol) in THF (1 mL) was added potassium 2-methylpropan-2-olate (120 mg, 1.05 mmol) at room temperature under $N_2$. The addition was slightly exothermic (~40° C.). The resulting solution was warmed up to 60° C. for 10 minutes. The reaction mixture was diluted with water and extracted into DCM (3×5 mL) and the mixture was filtered through a phase separation cartridge. The combined organic phases were washed with brine (3 mL) and filtered through another phase separation cartridge. The filtrate was dried by $N_2$ blowing to give a crude product that was purified by silica gel column chromatography eluting with 0-30% EtOAc in heptane to give the title compound (128 mg, 65%) as colourless oil.

¹HNMR (400 MHz, CDCl₃): δ 1.55 (m, 3H), 5.81 (m, 1H), 6.93 (m, 1H), 7.69 (m, 1H), 8.04 (m, 1H).

LCMS Rt=1.38 minutes MS m/z 226 [MH]⁺

Preparation 234

4-methylphenyl 5-chloro-4-({5-chloro-6-[(1R)-2,2,2-trifluoro-1-methylethoxy]pyridin-3-yl}oxy)-2-fluorobenzoate

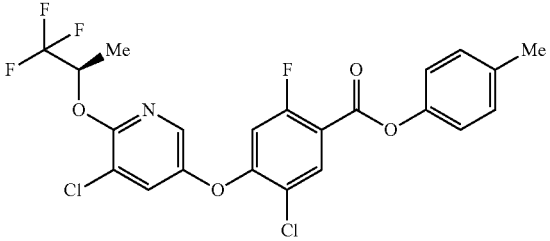 [SMILES: Cc1ccc(OC(=O)c2cc(Cl)c(Oc3cnc(O[C@H](C)C(F)(F)F)c(Cl)c3)cc2F)cc1]

To a mixture of 5-chloro-6-[(1R)-2,2,2-trifluoro-1-methylethoxy]pyridin-3-ol (Preparation 235, 360 mg, 0.86 mmol) and 4-methylphenyl 5-chloro-2,4-difluorobenzoate (Preparation 12, 242 mg, 0.86 mmol) in DMSO (2 mL) was added $K_2CO_3$ (237 mg, 1.7 mmol) at room temperature under $N_2$ and the resulting mixture was stirred for 5 hours. The reaction was quenched with water and extracted with DCM (3×5 mL). The mixture was filtered through a phase separation cartridge. The combined organic phases were washed with brine (3 mL) and filtered through another phase separation cartridge. The filtrate was dried by $N_2$ blowing to give a crude product. The crude product was purified by silica gel column chromatography eluting with 0-40% EtOAc in heptane to give the title compound (429 mg, 99%) as colourless gum.

¹HNMR (400 MHz, CDCl₃): δ 1.58 (m, 3H), 2.38 (s, 3H), 5.77 (m, 1H), 6.65 (d, 1H), 7.09 (m, 2H), 7.23 (m, 2H), 7.55 (d, 1H), 7.93 (d, 1H), 8.24 (d, 1H)

LCMS Rt=3.64 minutes MS m/z 504 [MH]⁺

Preparation 235

5-chloro-6-[(1R)-2,2,2-trifluoro-1-methylethoxy]pyridin-3-ol

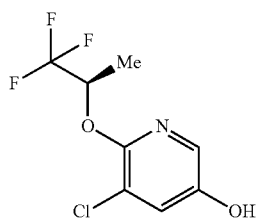

To a solution of 3-chloro-5-(4,4,5,5-tetramethyl-1,3,2-dioxaborolan-2-yl)-2-[(1R)-2,2,2-trifluoro-1-methylethoxy]pyridine (Preparation 236, 560 mg, 1.59 mmol) in acetone (5 mL) was added an aqueous solution of Oxone® (5 mL, 1.24 g, 1.91 mmol) dropwise with stirring at 0° C. for 15 minutes. The reaction mixture was diluted with water and extracted with EtOAc (3×15 mL), the combined organic phases were washed with brine (15 mL), dried over Na₂SO₄, filtered, and concentrated in vacuo to give a crude product as a brown oil. The crude product was purified by silica gel column chromatography eluting with 0-40% EtOAc in heptane to give the title compound (361 mg, 54%) as yellow oil.

¹HNMR (400 MHz, CDCl₃): δ 2.07 (s, 3H), 5.18 (br s, 1H), 5.64 (m, 1H), 7.32 (d, 1H), 7.68 (d, 1H).

LCMS Rt=2.24 minutes MS m/z 242 [MH]⁺, 240 [MH]⁻

Preparation 236

3-chloro-5-(4,4,5,5-tetramethyl-1,3,2-dioxaborolan-2-yl)-2-[(1R)-2,2,2-trifluoro-1-methylethoxy]pyridine

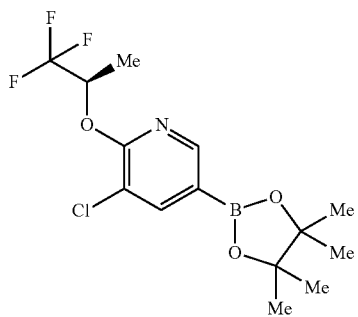 [SMILES: C[C@@H](Oc1ncc(B2OC(C)(C)C(C)(C)O2)cc1Cl)C(F)(F)F]

A mixture of 3-chloro-2-[(1R)-2,2,2-trifluoro-1-methylethoxy]pyridine (Preparation 237, 360 mg, 1.6 mmol), 4,4,4',4',5,5,5',5'-octamethyl-2,2'-bi-1,3,2-dioxaborolane (486 mg, 1.92 mmol), di-mu-methanolatodiiridium(Ir—Ir)-cycloocta-1,5-diene (1:2) (33 mg, 0.05 mmol) and 4,4'-di-tert-butyl-2,2'-bipyridine (13 mg, 0.05 mmol) in TBME (8 ml) was heated at 80° C. in the microwave for 30 minutes. The solvent was reduced by N₂ blowing and the residue was filtered through a silica gel pad eluting with EtOAc (50 mL). The filtrate was concentrated in vacuo to give the title compound. The material was used for the next step without further purification.

LCMS Rt=3.46 minutes MS m/z 352 [MH]⁺

Preparation 237

3-chloro-2-[(1R)-2,2,2-trifluoro-1-methylethoxy]pyridine

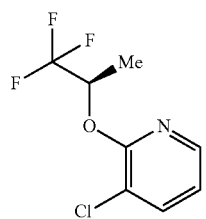

To a solution of 3-chloro-2-fluoropyridine (500 mg, 3.8 mmol) and (2R)-1,1,1-trifluoropropan-2-ol (75 wt % solution in TBME, 752 mg, 4.9 mmol) in DMSO (7 mL) was added Cs₂CO₃ (1.6 g, 4.9 mmol) at room temperature under N₂. The resulting mixture was stirred at 80° C. for 2 hours. To the reaction mixture was added another 500 mg of (2R)-1,1,1-trifluoropropan-2-ol and the mixture stirred at the same temperature for another 2.5 hours. The reaction mixture was cooled to room temperature, and partitioned between water and EtOAc. The organic phase was separated, washed with brine (2×30 mL), dried over Na₂SO₄, filtered, and concentrated in vacuo to give a crude product as colourless oil. The crude product was purified by silica gel column chromatography eluting with 0-30% EtOAc in heptane to give the title compound (365 mg, 43%) as colourless oil.

¹HNMR (400 MHz, CDCl₃): δ 1.55 (m, 3H), 5.81 (m, 1H), 6.93 (m, 1H), 7.69 (m, 1H), 8.04 (m, 1H)

LCMS Rt=2.70 minutes MS m/z 226 [MH]⁺

Preparation 238

2-bromo-3-chloro-5-(4,4,5,5-tetramethyl-1,3,2-dioxaborolan-2-yl)pyridine

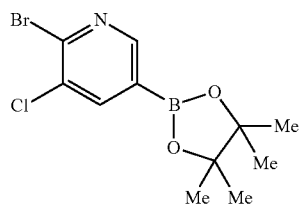 [SMILES: CC1(C)OB(c2cnc(Br)c(Cl)c2)OC1(C)C]

(1,5-Cyclooctadiene)(methoxy)iridium(I) dimer (86 mg, 0.13 mmol) was added to a degassed mixture of 2-bromo-3-chloropyridine (5.0 g, 26.0 mmol), 4,4'-di-tert-butyl-2,2'-dipyridyl (70 mg, 0.26 mmol) and bis(pinacolato)diboron (5.28 g, 20.8 mmol) in heptanes (45 mL) and the reaction heated at 90° C. for 18 hours. The cooled reaction was quenched with methanol (10.0 mL) and evaporated to give the title compound as a red coloured oil which was taken onto the next step without further purification.

¹H-NMR (400 MHz, CDCl₃): δ 1.14 (s, 12H), 7.84 (s, 1H), 8.32 (s, 1H)

LCMS Rt=2.34 minutes, MS m/z 238 [MH]⁺

Preparation 239

6-bromo-5-chloropyridin-3-ol

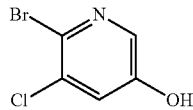

To crude 2-bromo-3-chloro-5-(4,4,5,5-tetramethyl-1,3,2-dioxaborolan-2-yl)pyridine (Preparation 238, 8.27 g, 26.0 mmol) was added methanol (100 mL), and the stirred solution cooled in an ice bath. To the solution was added hydrogen peroxide solution (35% in water, 4.25 mL, 43.8 mmol) over 5 minutes. The solution was allowed to warm slowly to room temperature for 18 hours. The reaction was quenched by addition of 1M aqueous sodium thiosulfate solution (500 mL), with rapid stirring for 15 minutes. The organics were removed in vacuo, and brine (100 mL) was added. The aqueous phase was extracted into ethyl acetate (3×100 mL). The combined organic phases were dried over magnesium sulfate, filtered and the solvent removed to leave an off white solid. The solid was triturated in 4:1 heptene:ethyl acetate and filtered to afford the title compound as a white solid (2.20 g, 41%).

LCMS Rt=2.36 minutes, MS m/z 209 [MH]⁺

¹HNMR (400 MHz, CDCl₃): δ 5.33 (br s, 1H), 7.32 (s, 1H), 7.98 (s, 1H)

Preparation 240

Methyl 5-chloro-2-fluoro-4-methyl benzoate

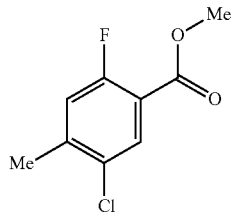 [SMILES: COC(=O)c1cc(Cl)c(C)cc1F]

To a solution of 1-bromo-5-chloro-2-fluoro-4-methylbenzene (10 g, 44.7 mmol) in methanol (200 mL) was added 1,1'-binaphthalene-2,2'-diylbis(diphenylphosphine)-dichloropalladium (1:1) (358 mg, 0.447 mmol) and N,N-diethylethanamine (8.11 mL, 58.2 mmol). The resulting mixture was placed in a bomb and pressurized with carbon monoxide to 80 psi and heated at 80° C. for 18 hours. The cooled reaction mixture was then concentrated in vacuo to yield a semi-solid, which was dissolved in EtOAc (300 mL) and washed with water (200 mL). The organic layer was separated, dried over magnesium sulphate, filtered and concentrated in vacuo to yield an orange oil, which solidified on standing (9.87 g). The solid was purified by silica gel column chromatography eluting with 0 to 20% EtOAc in heptane to afford the title compound as a crystalline white solid (8.47 g, 93%):

¹H NMR (400 MHz, CDCl₃): δ 2.40 (s, 3H), 3.92 (s, 3H), 7.03 (d, 1H), 7.91 (d, 1H)

LCMS Rt=1.64 minutes Molecular ion not observed

Preparation 241

5-Chloro-2-fluoro-4-methylbenzoic acid

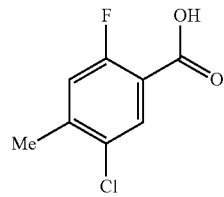 [SMILES: Cc1cc(F)c(C(=O)O)cc1Cl]

To a stirred solution of methyl 5-chloro-2-fluoro-4-methylbenzoate (Preparation 240, 340 mg, 1.68 mmol) in dioxane/water (5:1, 12 mL) was added an aqueous sodium hydroxide solution (5 M, 1.63 mL, 8.39 mmol). The reaction mixture was stirred at room temperature for 18 hours and then evaporated in vacuo. The resulting residue was suspended in water and extracted with diethyl ether (3×20 mL). The aqueous layer was separated, cooled in an ice bath, acidified with aqueous hydrochloric acid (6 M) and then extracted with EtOAc (30 mL). The organic phase was washed with brine (2×20 mL), dried over sodium sulphate, filtered and evaporated in vacuo to yield the title compound as a white solid (266 mg, 84%).

¹H NMR (400 MHz, d₆-DMSO): δ 2.36 (s, 3H), 7.38 (dd, 1H), 7.80 (d, 1H).

LCMS Rt=1.39 minutes MS m/z 187 [M–H]⁻

Preparation 242

5-Chloro-2-fluoro-4-methyl-N-(methylsulfonyl)benzamide

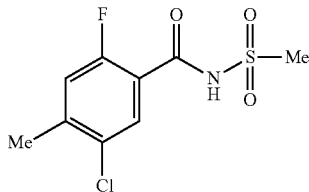 [SMILES: Cc1cc(F)c(C(=O)NS(C)(=O)=O)cc1Cl]

To 5-chloro-2-fluoro-4-methylbenzoic acid (Preparation 241, 200 g, 1.06 mol) in DCM (1.4 L) was added methanesulphonamide (152 g, 1.6 mol), 4-(dimethylamino)pyridine (183 g 1.6 mol) and N-(3-dimethylaminopropyl)-N'-ethylcarbodiimide hydrochloride (306 g, 1.6 mol). The reaction mixture spontaneously heated at 30° C. over 30 minutes, then it was stirred at room temperature for 18 hours under a nitrogen atmosphere. The reaction mixture was washed with aqueous hydrochloric acid (4 M, 0.8 L). The organic layer was separated, washed with water (500 mL), dried over sodium sulphate and concentrated in vacuo to yield a tan solid, which was recrystallised from hot EtOAc (0.9 L) by addition of n-heptane (100 mL) and cooling to yield the title compound (118 g, 45%):

$^1$H NMR (400 MHz, CDCl$_3$): δ 2.42 (s, 3H), 3.42 (s, 3H), 7.10 (d, 1H), 8.05 (d, 1H), 8.78 (br, 1H).

Preparation 243

4-(Bromomethyl)-5-chloro-2-fluoro-N-(methylsulfonyl)benzamide

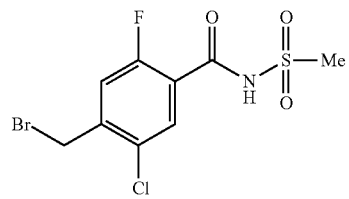 [SMILES: CS(=O)(=O)NC(=O)c1cc(Cl)c(CBr)cc1F]

To a suspension of 5-chloro-2-fluoro-4-methyl-N-(methylsulfonyl)benzamide (Preparation 242, 118 g, 0.45 mol) in 1,2-dichloroethane (1.25 L) was added N-bromosuccinimide (9.1 g, 0.51 mol) and benzoyl peroxide (5 g, 20 mmol) and the mixture heated to reflux for 18 hours. N-bromosuccinimide (30 g, 0.17 mol) was then added and the solution heated 24 hours more. A further portion of N-bromosuccinimide (20 g, 0.11 mol) was added and the solution heated for 3 hours, then cooled and washed with water (1 L) containing aqueous sodium thiosulphate solution (200 mL, 0.5 M). The organic layer was washed with water (500 mL), dried over sodium sulphate and concentrated in vacuo to yield a crude solid. To a solution of this crude solid in EtOAc (1 L) was added diisopropylethylamine (130 mL, 0.75 mol) and diethyl phosphite (27.6 g, 0.2 mol) and the mixture stirred for 5 hours under nitrogen, then washed with aqueous hydrochloric acid (1 L, 2 M), dried over magnesium sulphate and evaporated to yield a dark solid. Trituration with diethyl ether (200 mL) gave the first crop of title compound as a tan solid (68 g). The filtrate was purified by silica gel chromatography eluting with 10% EtOAc in DCM containing acetic acid (1%), followed by crystallization from acetonitrile (130 mL) to yield the second crop of the title compound (30 g):

$^1$H NMR (400 MHz, CDCl$_3$): δ 3.41 (s, 3H), 4.54 (s, 2H), 7.38 (d, 1H), 8.14 (d, 1H), 8.78 (br, 1H).

Preparation 244

2,5-Difluoro-4-methyl-N-(methylsulfonyl)benzamide

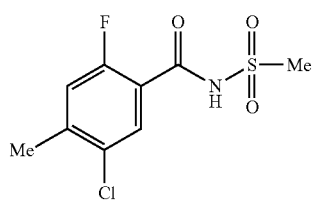 [SMILES: Cc1cc(F)c(C(=O)NS(C)(=O)=O)cc1Cl]

A mixture of 2-5-difluoro-4-methylbenzoic acid (6.0 g, 34.9 mmol), diisopropylethylamine (13.5 g, 105.0 mmol), propanephosphonic acid cyclic anhydride (50 mL, 50% w/w solution in EtOAc, 84.0 mmol) and methanesulphonamide (6.6 g, 69.7 mmol) in THF (200 mL) was heated at reflux under a nitrogen atmosphere for 18 hours. After cooling, the solution was evaporated in vacuo and the resulting residue suspended in water. The mixture was extracted with EtOAc (300 mL) and the organic extract was washed with brine (2×80 mL). The organic layer was dried over sodium sulphate and evaporated in vacuo to yield a solid. Trituration of the solid with hexane afforded the title compound (7.6 g, 87%) as an off white solid.

$^1$H NMR (400 MHz, d$_6$-DMSO): δ 2.26 (s, 3H), 3.34 (s, 3H), 7.33 (m, 1H), 7.44 (m, 1H).

LCMS Rt=1.24 minutes MS m/z 248 [M−H]−

Preparation 245

4-(Bromomethyl)-2,5-difluoro-N-(methylsulfonyl)benzamide

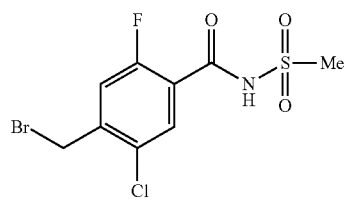 [SMILES: CS(=O)(=O)NC(=O)c1cc(Cl)c(CBr)cc1F]

A stirred mixture of 2,5-difluoro-4-methyl-N-(methylsulfonyl)benzamide (Preparation 244, 5.07 g, 20.3 mmol), N-bromosuccinimide (freshly recrystallised and dried, 4.71 g, 26.4 mmol) and azobisisobutyronitrile (0.05 g, 0.30 mmol) in 1,2-dichloroethane (100 mL) was heated at reflux under nitrogen whilst being irradiated with light from a lamp. After 2 hours, additional azobisisobutyronitrile (0.05 g, 0.30 mmol) was added and the reaction heated under reflux for 2 hours more. The reaction mixture was cooled to room temperature and evaporated in vacuo. The resulting residue was partitioned between brine (200 mL) and EtOAc (2×150 mL). The combine organic extracts were dried over magnesium sulphate and concentrated in vacuo to yield a pale yellow oil which solidified on standing (7.88 g). The solid was purified by silica gel chromatography eluting with 0 to 30% EtOAc in heptane to afford the title compound as a white solid (3.71 g, 56%):

$^1$H NMR (400 MHz, d$_6$-DMSO): δ 3.34 (s, 3H), 4.69 (s, 2H), 7.58 (m, 2H).

LCMS Rt=1.37 minutes MS m/z 326 [M−H]−

Preparation 246

2-bromo-3-(bromo-difluoro-methoxy)-pyridine

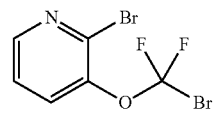 [SMILES: FC(F)(Br)Oc1cccnc1Br]

To a suspension of sodium hydride (1.72 g, 43.1 mmol) in NMP (50 mL) was added a solution of 2-bromo-3-hydroxypyridine (5 g, 28.74 mmol) in NMP (50 mL). This mixture was stirred at room temperature for 30 minutes followed by heating at 50° C. for 45 minutes before cooling to room temperature. Dibromodifluoromethane (3.15 mL, 34.5 mmol) was slowly added and the mixture was stirred at room temperature for 18 hours. The reaction mixture was slowly quenched into saturated aqueous ammonium chloride (100 mL) and extracted with EtOAc (3×100 mL). The combined organic extracts were washed with water (3×100 mL), brine (2×100 mL), dried over MgSO$_4$ and concentrated in vacuo to afford a brown gum. This residue was purified using silica gel column chromatography eluting with 70/30 Heptane/EtOAc to give the title compound as a colourless oil (1.2 g, 14%).

$^1$H NMR (400 MHz, CDCl$_3$): δ 7.35 (m, 1H), 7.65 (m, 1H), 8.40 (m, 1H)

LCMS Rt=2.36 minutes MS m/z 303 [MH]+

Preparation 247

2-Bromo-3-trifluoromethoxypyridine

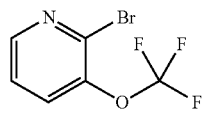

To a cooled solution (−78° C.) of 2-bromo-3-(bromo-difluoro-methoxy)-pyridine (Preparation 246, 1 g, 3.3 mmol) in DCM (20 mL) (in a teflon flask) was added silver tetrafluoroborate (1.41 g, 7.26 mmol). The mixture was slowly warmed to room temperature and allowed to stir for 18 hours. The reaction mixture was partitioned (using phase separation cartridge) between saturated aqueous NaHCO$_3$ (50 mL) and DCM (2×50 mL). The combined organic layers were evaporated to give the title compound as a colourless oil. (635 mg, 80%)

$^1$H NMR (CDCl$_3$, 400 MHz): δ 7.45 (m, 1H), 7.70 (m, 1H), 8.55 (m, 1H)

LCMS Rt=2.03 minutes MS m/z 241 [MH]+

Preparation 248

2-cyclopropyl-3-(trifluoromethoxy)pyridine

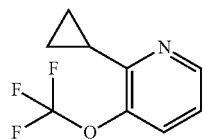

A solution of 2-bromo-3-(trifluoromethoxy)pyridine (Preparation 247, 776 mg, 3.21 mmol), cyclopropyl boronic acid (331 mg, 3.85 mmol) and potassium phosphate tribasic (1.70 g, 8.02 mmol) in toluene (10 mL) and water (3 mL) was degassed with nitrogen for 15 minutes at 80° C. Palladium acetate (36 mg, 0.16 mmol) and tricyclohexyl phosphine (90 mg, 0.32 mmol) were added and the reaction mixture was vigorously stirred for 18 hours at 95° C. under nitrogen. The solution was concentrated in vacuo, diluted with water (25 mL) and extracted with ethyl acetate (3×30 mL). The organic layers were combined, dried over magnesium sulfate, filtered and concentrated in vacuo. The crude material was purified by silica gel column chromatography eluting with 10% diethyl ether in heptane to afford the title compound as a colourless oil (292 mg, 45%).

$^1$H NMR (400 MHz, CDCl3): δ 1.03 (m, 2H), 1.12 (m, 2H), 2.37 (m, 1H), 7.06 (m, 1H), 7.46 (m, 1H), 8.36 (m, 1H)

LCMS Rt=2.51 minutes MS no ionization

Preparation 249 tert-Butyl 1-(3-chloropyridin-2-yl)cyclobutanecarboxylate

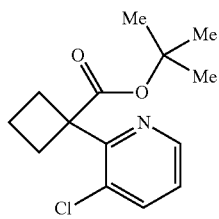 [SMILES: CC(C)(C)OC(=O)C1(c2ncccc2Cl)CCC1]

Prepared according to Preparation 229 using tert-butyl cyclobutylcarboxylate.

LCMS Rt=2.75 minutes MS m/z 268 [MH]$^+$.

$^1$H NMR (400 MHz, CDCl$_3$): δ 1.38 (s, 9H), 1.86 (m, 1H), 2.23 (m, 1H), 2.76 (m, 4H), 7.15 (m, 1H), 7.94 (m, 1H), 8.48 (m, 1H).

Preparation 250

3-Chloro-2-cyclobutylpyridine

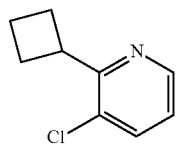 [SMILES: Clc1cccnc1C1CCC1]

Prepared according to Preparation 228 using tert-Butyl 1-(3-chloropyridin-2-yl)cyclobutanecarboxylate (Preparation 249).

LCMS Rt=1.19 minutes MS m/z 168 [MH]$^+$.

$^1$H NMR (400 MHz, CDCl$_3$): δ 1.92 (m, 1H), 2.08 (m, 1H), 2.40 (m, 4H), 4.02 (m, 1H), 7.07 (m, 1H), 7.60 (m, 1H), 8.49 (m, 1H).

Preparation 251 tert-Butyl 2-(3-chloropyridin-2-yl)-2-methylpropanoate

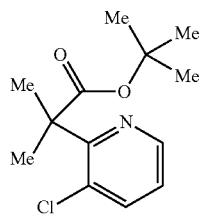 [SMILES: CC(C)(C)OC(=O)C(C)(C)c1ncccc1Cl]

Prepared according to Preparation 229 using tert-butyl isobutyrate.

LCMS Rt=1.39 minutes. MS m/z 256 [MH]$^+$ $^1$H NMR (400 MHz, CDCl$_3$): δ 1.41 (s, 9H), 1.62 (s, 6H), 7.15 (m, 1H), 7.64 (m, 1H), 8.46 (m, 1H).

Preparation 252

3-Chloro-2-isopropylpyridine

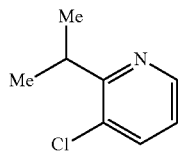

Prepared according to Preparation 228 using tert-Butyl 2-(3-chloropyridin-2-yl)-2-methylpropanoate (Preparation 251).

LCMS Rt=2.24 minutes MS m/z 156 [MH]$^+$ $^1$H NMR (400 MHz, CDCl$_3$): δ 1.30 (d, 6H), 3.58 (m, 1H), 7.07 (m, 1H), 7.62 (m, 1H), 8.47 (m, 1H).

Preparation 253

2,3-dicyclopropylpyridine

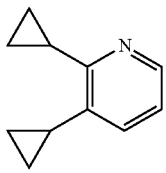 [SMILES: c1cnc(C2CC2)c(C2CC2)c1]

Prepared according to Preparation 48 using cyclopropyl boronic acid and 2-bromo-3-chloropyridine.

LCMS Rt=0.84 minutes MS m/z 160 [MH]+

Preparation 254

5,6-dicyclopropylpyridin-3-ol

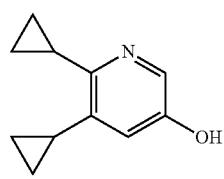 [SMILES: Oc1cnc(C2CC2)c(C2CC2)c1]

Prepared according to Preparation 69 using 2,3-dicyclopropylpyridine (Preparation 253) at reflux with purification using silica gel column chromatography eluting with 50% ethyl acetate in heptane.

LCMS Rt=0.91 minutes MS m/z 176 [MH]+

Preparation 255

3-chloro-2-(1,1,1,3,3,3-hexafluoropropan-2-yloxy)-5-nitropyridine

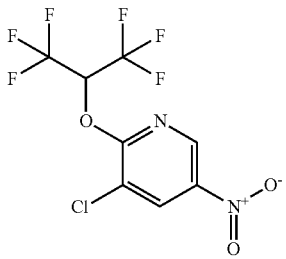 [SMILES: O=[N+]([O-])c1cnc(OC(C(F)(F)F)C(F)(F)F)c(Cl)c1]

A 60% dispersion of sodium hydride in mineral oil (450 mg, 11.25 mmol) was suspended in anhydrous tetrahydrofuran (10 mL). The suspension was cooled to 0° C. and 1,1,1,3,3,3-hexafluoropropan-2-ol (1.74 g, 10.35 mmol) was added over 15 minutes. The suspension was stirred 30 minutes and 2,3-dichloro-5-nitropyridine (1.50 g, 7.77 mmol) was added portionwise. The reaction was stirred at room temperature overnight then concentrated in vacuo. The crude residue was partitioned between ethyl acetate (50 mL) and water (50 mL). The aqueous layer was extracted by ethyl acetate (2×25 mL). Organic layers were combined, dried over magnesium sulfate, and concentrated in vacuo to afford the title compound as an orange oil (2.55 g, 100%).

LCMS rt=3.48 min. MS no ionization $^1$H NMR (400 MHz, CDCl$_3$): δ 6.48 (m, 1H), 8.58 (m, 1H), 9.00 (m, 1H)

Preparation 256

5-chloro-6-(1,1,1,3,3,3-hexafluoropropan-2-yloxy)pyridin-3-amine

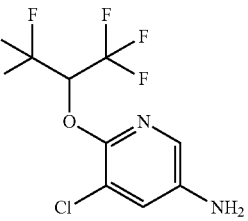

3-Chloro-2-(1,1,1,3,3,3-hexafluoropropan-2-yloxy)-5-nitropyridine (Preparation 255, 2.55 g, 7.9 mmol), ammonium chloride (2.50 g, 46.7 mmol) and iron powder (1.70 g, 30.4 mmol) were suspended in a mixture of ethanol (10 mL) and water (3 mL). The suspension was heated for 3 hours under reflux then allowed to cool to room temperature. The reaction mixture was filtered on a Celite™ pad and the pad was washed with ethanol. The filtrate was concentrated in vacuo and the crude residue was partitioned between water and ethyl acetate. The aqueous layer was separated and extracted by ethyl acetate (2×25 mL). Organic layers were combined, dried over magnesium sulfate and concentrated in vacuo. The crude residue was purified by silica gel chromatography eluting with 50% diethyl ether in heptane to afford the title compound as a light yellow oil (2.0 g, 87%).

LCMS rt=3.24 min, MS m/z 295 [MH]+

$^1$H NMR (400 MHz, CDCl$_3$): δ 3.60 (s, 2H), 6.30 (m, 1H), 7.15 (m, 1H), 7.50 (m, 1H).

Preparation 257 tert-Butyl 4-bromobenzoate

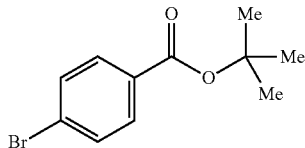

To a solution of tert-butanol (30 mL) was added 4-bromobenzoic acid (4.00 g, 19.9 mmol) and dimethylaminopyridine (0.24 g, 1.99 mmol). After 1 minute was added di-tert-butyl carbonate (8.68 g, 218 mmol), and the reaction heated to 45° C. for 18 hours. The reaction was cooled to room temperature, quenched by addition of an aqueous HCl solution (0.25 M), and extracted into ethyl acetate. The extract was purified through a silica plug (ethyl acetate:heptane, 1:2) followed by silica gel column chromatography eluting with 20% DCM in cyclohexane to afford the title compound as a colourless oil (0.59 g, 10%).

LCMS (4.5 min) Rt=3.87 minutes, no mass ion seen.

$^1$H NMR (400 MHz, CDCl3): δ 1.58 (s, 9H), 7.52 (d, 2H), 7.81 (d, 2H).

Preparation 258 tert-butyl 4-(5-chloro-6-(1,1,1,3,3,3-hexafluoropropan-2-yloxy)pyridin-3-ylamino)benzoate

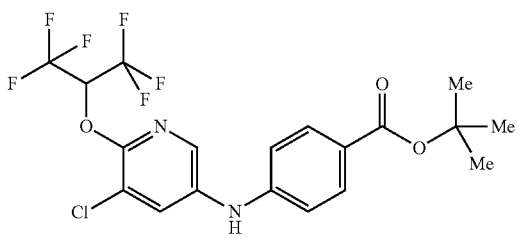 [SMILES: CC(C)(C)OC(=O)c1ccc(Nc2cnc(OC(C(F)(F)F)C(F)(F)F)c(Cl)c2)cc1]

To a degassed suspension of tert-butyl 4-bromobenzoate (Preparation 257, 250 mg, 0.97 mmol), 5-chloro-6-(1,1,1,3,3,3-hexafluoropropan-2-yloxy)pyridin-3-amine (Preparation 256, 430 mg, 1.46 mmol) and potassium carbonate (403 mg, 2.92 mmol) in a mixture of terbutanol (10 ml)/water (0.2 ml) was added Pd(OAc)$_2$ (1 mol %) and BrettPhos (3 mol %). The mixture was heated at 110° C. for 18 hours. After 18 hours, further portions of Pd(OAc)$_2$ (1 mol %) and BrettPhos (3 mol %) were added and the reaction was heated for 24 hours at 110° C. The reaction was cooled to room temperature, ethyl acetate (50 mL) and water (15 mL) were added, the phases were separated and the combined organics evaporated. The crude product was purified by silica gel column chromatography, eluting with DCM in Heptane (10% to 80%), to give the title compound as an oil (0.22 g, 48%).

LCMS (4.5 min) Rt=4.13 minutes, m/z 471 M[H]+

$^1$H NMR (400 MHz, CDCl$_3$): δ 1.50 (s, 9H), 7.05 (m, 3H), 7.80 (m, 2H), 7.90 (s, 1H), 8.05 (s, 1H).

$^{19}$F NMR (400 MHz, CDCl$_3$): δ −72 (s, 6F).

Preparation 259

4-(5-chloro-6-(1,1,1,3,3,3-hexafluoropropan-2-yloxy)pyridin-3-ylamino)benzoic acid

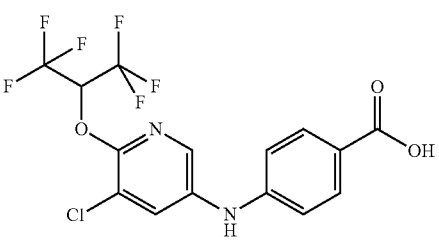

To a dichloromethane (10 mL) solution of tert-butyl 4-(5-chloro-6-(1,1,1,3,3,3-hexafluoropropan-2-yloxy)pyridin-3-ylamino)benzoate (Preparation 258, 220 mg, 0.47 mmol) was added trifluoroacetic acid (2 mL) at room temperature, and the reaction stirred for 18 hours. The reaction mixture was concentrated in vacuo and the residue was purified by reverse phase chromatography eluting with acetonitrile:water (5:95 to 95:5) to yield the title compound as a pale yellow solid (116 mg, 60%).

LCMS (4.5 min) Rt=3.41 minutes, m/z 415 M[H]+

$^1$HNMR (400 MHz, CDCl$_3$): δ 7.00-7.10 (m, 3H), 7.80 (m, 2H), 7.90 (s, 1H), 8.05 (s, 1H), 8.90 (s, 1H).

Preparation 260

2-(2,2,3,3-Tetrafluoropropoxy)-3-(trifluoromethyl)pyridine

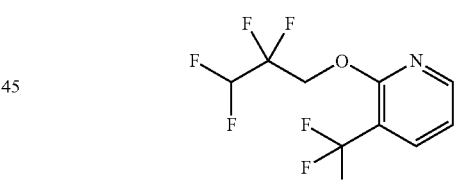

2,2,3,3-Tetrafluoropropan-1-ol (5.54 g, 41.31 mmol) was added to a suspension of sodium hydride (2.20 g, 55.08 mmol, 60% in mineral oil) in tetrahydrofuran (50 mL) and reaction mixture was stirred for 30 minutes at room temperature. Then a solution of 2-chloro-3-(trifluoromethyl)pyridine (5.00 g, 27.54 mmol) in tetrahydrofuran (50 mL) was added and mixture was heated at 40° C. for 18 hours. The reaction mixture was allowed to cool to room temperature and then quenched slowly with water. The layers were separated and the aqueous layer was further extracted with ethyl acetate. The combined organic layers were dried over anhydrous magnesium sulfate, filtered and the filtrate was evaporated. The crude product was purified by flash chromatography on silica gel eluting with 20% ethyl acetate in heptane to give the title compound as a oil (3.10 g, 41%).

LCMS Rt=2.53 minutes, m/z not detected

¹HNMR (400 MHz, CDCl₃): δ 4.82 (t, 2H), 6.17-5.87 (m, 1H), 7.10-7.07 (m, 1H), 7.92 (d, 1H), 8.33 (d, 1H).

Preparation 261

2-(2,2,3,3-Tetrafluoropropoxy)-5-(4,4,5,5-tetramethyl-1,3,2-dioxaborolan-2-yl)-3-(trifluoromethyl)pyridine

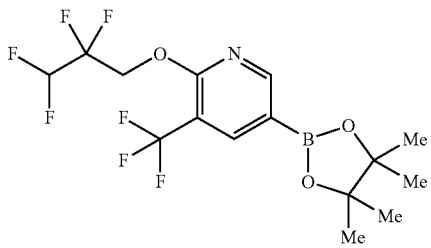 [SMILES: CC1(C)OB(c2cnc(OCC(F)(F)C(F)F)c(C(F)(F)F)c2)OC1(C)C]

2-(2,2,3,3-Tetrafluoropropoxy)-3-(trifluoromethyl)pyridine (Preparation 260, 3.06 g, 11.04 mmol) and bis(pinacolato)diboron (2.52 g, 9.94 mmol) were dissolved in dioxane (30 mL) and the reaction mixture was degassed. The reaction was heated at 90° C. and then bis(1,5-cyclooctadiene)di-μ-methoxydiiridium(I) (72.90 mg, 0.11 mmol) followed by 4,4'-di-tert-butyl-2,2'-dipyridyl (59.00 mg, 0.22 mmol) were added and the reaction mixture was heated for 18 hours. The reaction was cooled to 0° C. (ice-bath), then quenched slowly with methanol and solvent was evaporated. The residue was diluted with ethyl acetate, filtered through pad of silica gel and the filtrate was concentrated in vacuo to give the title compound (4.45 g, 100%).

LCMS Rt=3.94 minutes, m/z 404 [MH]⁺
¹HNMR (400 MHz, CDCl₃): δ 1.35 (s, 12H), 4.85 (t, 2H), 6.15-5.88 (m, 1H), 8.26 (s, 1H), 8.66 (s, 1H).

Preparation 262

6-(2,2,3,3-Tetrafluoropropoxy)-5-(trifluoromethyl)pyridin-3-ol

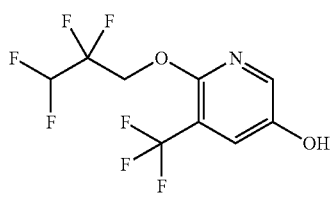 [SMILES: Oc1cnc(OCC(F)(F)C(F)F)c(C(F)(F)F)c1]

Hydrogen peroxide (1.29 mL, 13.33 mmol, 35% solution) was added to a solution of 2-(2,2,3,3-tetrafluoropropoxy)-5-(4,4,5,5-tetramethyl-1,3,2-dioxaborolan-2-yl)-3-(trifluoromethyl)pyridine (Preparation 261, 4.45 g, 11.04 mmol) in methanol (50 mL) at 0° C. (ice-bath) and the reaction mixture was allowed to warm to room temperature. After 3 hours, the reaction was quenched with 1M solution of sodium thiosulfate and then methanol was removed in vacuo. The residue was partitioned between ethyl acetate and water, the organic layer was dried over anhydrous magnesium sulfate, filtered and the filtrate was concentrated in vacuo. The crude product was purified by flash chromatography on silica gel eluting with 30% heptane in ethyl acetate to give the title compound as a oil (2.95 g, 91%).

LCMS Rt=2.30 minutes, m/z 292 [MH]⁻
¹HNMR (400 MHz, CDCl₃): δ 4.73 (t, 2H), 5.35 (br s, 1H), 6.13-5.87 (m, 1H), 7.49 (d, 1H), 7.93 (d, 1H).

Preparation 263

4-methylphenyl-5-chloro-4-(6-(2,2,3,3-tetrafluoropropoxy)-5-(trifluoromethyl)pyridin-3-yloxy)-2-fluorobenzoate

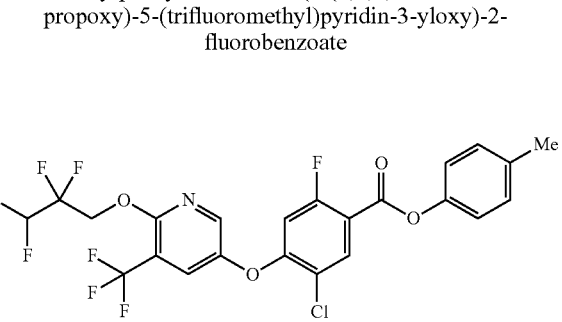

6-(2,2,3,3-Tetrafluoropropoxy)-5-(trifluoromethyl)pyridin-3-ol (300 mg, 1.02 mmol) was dissolved in dimethyl sulfoxide (5 mL) and then potassium carbonate (282 mg, 2.04 mmol) followed by p-tolyl 5-chloro-2,4-difluorobenzoate (290 mg, 1.02 mmol) were added. The reaction mixture was stirred at room temperature for 2 hours. The reaction was then partitioned between ethyl acetate and water, the organic layer was dried over anhydrous magnesium sulfate, filtered and the filtrate was concentrated in vacuo. The crude product was purified by flash chromatography on silica gel eluting with 30% ethyl acetate in heptane to give the title compound as a gum (483 mg, 85%).

LCMS Rt=4.18 minutes, m/z not detected
¹HNMR (400 MHz, CDCl₃): δ 2.38 (s, 3H), 4.84 (t, 2H), 6.17-5.88 (m, 1H), 6.64 (d, 1H), 7.10 (d, 2H), 7.24 (d, 2H), 7.73 (s, 1H), 8.19 (s, 1H), 8.25 (d, 1H).

Preparation 264 tert-butyl 5-chloro-4-[(5-chloro-6-cyclopropylpyridin-3-yl)oxy]-2-fluorobenzoate

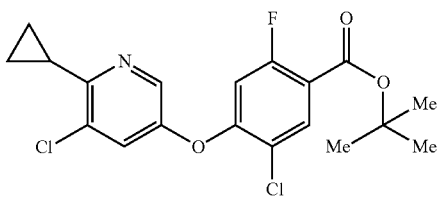 [SMILES: CC(C)(C)OC(=O)c1cc(Cl)c(Oc2cnc(C3CC3)c(Cl)c2)cc1F]

To a solution of tert-butyl 5-chloro-2,4-difluorobenzoate (Preparation 59, 35.7 g, 143.86 mmol) in DMSO (97.6 mL) was added 5-chloro-6-cyclopropylpyridin-3-ol (Preparation 69, 24.4 g, 143.86 mmol) and stirred at room temperature until a solution obtained. Potassium carbonate (49.7 g, 359.65 mmol) was added portion wise maintaining the internal temperature at 15-25° C. with a cold water jacket. The reaction mixture was stirred at room temperature for 12 hours, cold water charged and the resulting slurry stirred for 90 minutes. The mixture was filtered, washed with water and dried to give the title compound as a pale yellow solid (54.0 g, 94%).

HPLC Rt=8.593 minutes

Preparation 265

5-chloro-4-[(5-chloro-6-cyclopropylpyridin-3-yl)oxy]-2-fluorobenzoic acid

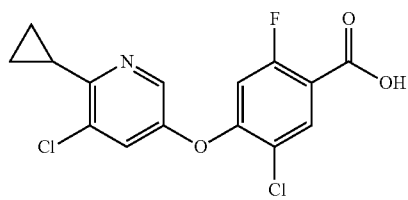 [SMILES: O=C(O)c1cc(Cl)c(Oc2cnc(C3CC3)c(Cl)c2)cc1F]

To a solution of tert-butyl 5-chloro-4-[(5-chloro-6-cyclopropylpyridin-3-yl)oxy]-2-fluorobenzoate (Preparation 264, 54.0 g, 135.59 mmol) in dichloromethane (270 mL) was added trifluoroacetic acid (30.76 mL, 406.77 mmol). The resulting solution was heated at 45° C. for 24 hours and concentrated under reduced pressure at 45° C. tert Butyl methyl ether (100 mL) was added to the residue and the resulting slurry stirred at room temperature for 2.5 hours, filtered, washed with tert butyl methyl ether (20 mL) and dried to give the title compound as an off-white solid (45.0 g, 97%).

$^1$H NMR (400 MHz, CD$_3$OD): δ 1.02-1.09 (m, 4H), 2.48-2.58 (m, 1H), 6.86 (d, 1H), 7.58 (d, 1H), 8.07 (d, 1H), 8.18 (d, 1H)

HPLC Rt=6.485 minutes

Preparation 266

2-bromo-3-(1,1-difluoroethoxy)pyridine

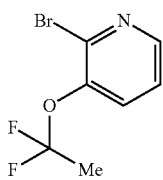 [SMILES: CC(F)(F)Oc1cccnc1Br]

3-Acetyl-2-bromopyridine (1.05 g, 5.25 mmol) in DCM (20 mL) was stirred in a plastic vial with xenon difluoride (1.78 g, 10.5 mmol) and HF/Pyridine (14 mL, 160 mmol) at room temperature for 18 hours. The reaction mixture was diluted with DCM (200 mL) and quenched by slow addition to saturated aqueous NaHCO$_3$ (200 mL) containing excess solid NaHCO$_3$ (10 g). The layers were separated and the aqueous was extracted further with DCM (2×100 mL). The organics were dried over MgSO$_4$, filtered and concentrated in vacuo, azeotroping with toluene to remove pyridine. The crude was dry loaded onto silica and purified by silica gel column chromatography eluting with 95:5 increasing to 70:30 heptane:EtOAc to afford the title compound as a colourless oil (700 mg).

$^1$HNMR (400 MHz, CDCl$_3$): δ 2.03 (t, 3H), 7.26 (dd, 1H), 7.64 (m, 1H), 8.24 (dd, 1H).

LCMS Rt=2.14 minutes, MS m/z 238 [MH]+

Preparation 267

2-cyclopropyl-3-(1,1-difluoroethoxy)pyridine

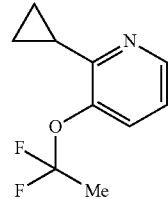 [SMILES: CC(F)(F)Oc1cccnc1C1CC1]

2-Bromo-3-(1,1-difluoroethoxy)pyridine (Preparation 266, 700 mg, 2.948 mmol), cycloproyl boronic acid (252 mg, 2.94 mmol), and potassium phosphate tribasic (1.56 g, 7.35 mmol) were suspended in a mixture of toluene (100 mL) and water (20 mL), with rapid stirring. The suspension was heated to 80° C., and the solvent de-gassed by direct bubbling of N$_2$ gas through the suspension for 30 minutes. The reaction was then heated to 95° C., and tricyclohexyl phosphine (82 mg, 0.29 mmol), rapidly followed by palladium acetate (33 mg, 0.15 mmol), were added. The reaction was left to stir and heat at 95° C. for 18 hours. The reaction was cooled to room temperature, and filtered through a plug of arbocel, eluting with ethyl acetate. The solvent was removed to leave a dark yellow oil. Ethyl acetate was added (100 mL), and the organic phase extracted with 2M HCl solution (3×100 mL). The organic phase was discarded. Ethyl acetate (150 mL) was added to the combined aqueous layers, and solid sodium bicarbonate was added until the aqueous layer reached pH 7. The mixture was transferred to a separating funnel, the organic layer was removed and the aqueous layer was extracted with ethyl acetate (2×100 mL). The combined organic phases were dried over magnesium sulfate, filtered and the solvent removed to leave a yellow oil. The material was purified by silica gel column chromatography eluting with 1:1 heptane:ethyl acetate to afford the title compound as a colourless oil (252 mg, 43%).

LCMS (5.0 min) Rt=3.13 minutes, m/z 200 [MH]+

$^1$HNMR (400 MHz, CDCl$_3$): δ 0.92-0.99 (m, 2H), 1.03-1.10 (m, 2H), 1.97 (t, 3H), 2.30-2.38 (m, 1H), 7.01 (m, 1H), 7.45 (d, 1H), 8.28 (d, 1H).

$^{19}$FNMR (400 MHz, CDCl$_3$): δ −64 (s, 2F).

Preparation 268

2-cyclopropyl-3-(1,1-difluoroethoxy)-5-(4,4,5,5-tetramethyl-1,3,2-dioxaborolan-2-yl)pyridine

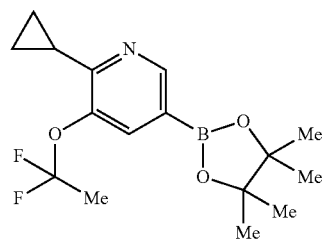 [SMILES: CC(F)(F)Oc1cc(B2OC(C)(C)C(C)(C)O2)cnc1C1CC1]

To dioxane (10 mL) was added 2-cyclopropyl-3-(1,1-difluoroethoxy)pyridine (Preparation 267, 252 mg, 1.27 mmol) and bis(pinacolato)diboron (289 mg, 1.14 mmol). The solution was de-gassed by bubbling $N_2$ through the solution for 30 minutes. The solution was heated to 80° C., and 4,4-di-tert-butyl-2,2-dipyridyl (6.80 mg, 0.03 mmol) plus cyclooctadiene(dimethoxy) Iridium (I) dimer (8.30 mg, 0.01 mmol) were added. The flask was de-gassed with $N_2$, and left at 80° C. for 18 hours. The reaction was cooled in an ice bath, and quenched by slow addition of methanol (20 mL) and concentrated in vacuo to afford the title compound as a red-brown oil which was used crude (412 mg, 1.27 mmol theoretical).

LCMS (5.0 min) Rt=1.92 minutes $^1$HNMR (400 MHz, CDCl$_3$): δ 0.95-1.12 (m, 4H), 1.32 (s, 12H), 1.98 (t, 3H), 2.30-2.40 (m, 1H), 7.79 (s, 1H), 8.60 (s, 1H).

Preparation 269

6-cyclopropyl-5-(1,1-difluoroethoxy)pyridin-3-ol

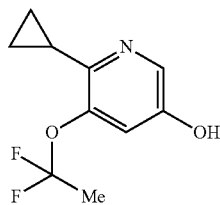 [SMILES: CC(F)(F)Oc1cc(O)cnc1C1CC1]

To the crude 2-cyclopropyl-3-(1,1-difluoroethoxy)-5-(4,4,5,5-tetramethyl-1,3,2-dioxaborolan-2-yl)pyridine (Preparation 268, 412 mg, 1.27 mmol) was added methanol (20 mL), and the stirred solution cooled in an ice bath. To the solution was added hydrogen peroxide solution (35% in water) (0.15 mL, 1.52 mmol) over 2 minutes. The solution was allowed to warm slowly to room temperature over 18 hours. The reaction was quenched by addition of 1M aqueous sodium thiosulfate solution (50 mL), and rapidly stirred for 15 minutes. The organics were removed in vacuo, and brine (50 mL) was added. The aqueous was extracted into ethyl acetate (3×100 mL). The combined organics were dried over magnesium sulfate, filtered and the solvent removed to leave an orange oil. The oil was purified through a plug of silica, eluting with 1:1 ethyl acetate:heptane to provide the title compound a white solid (155 mg, 57%).

LCMS (5.0 min) Rt=2.08 minutes, m/z 216 M[H]+

$^1$HNMR (400 MHz, CDCl$_3$): δ 0.88-0.99 (m, 4H), 1.95 (t, 3H), 2.16-2.25 (m, 1H), 7.14 (s, 1H), 7.87 (s, 1H).

Preparation 270 tert-butyl 5-chloro-4-(6-cyclopropyl-5-(1,1-difluoroethoxy)pyridin-3-yloxy)-2-fluorobenzoate

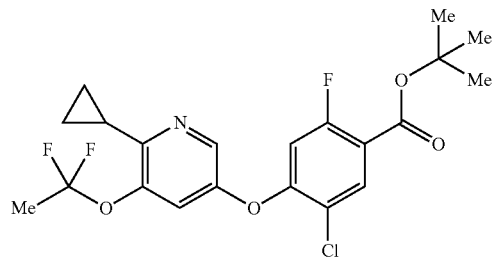 [SMILES: CC(C)(C)OC(=O)c1cc(Cl)c(Oc2cnc(C3CC3)c(OC(C)(F)F)c2)cc1F]

A suspension of 6-cyclopropyl-5-(1,1-difluoroethoxy)pyridin-3-ol (Preparation 269, 155 mg, 0.72 mmol), tert-butyl 5-chloro-2,4-difluorobenzoate (179 mg, 0.72 mmol) and potassium carbonate (299 mg, 2.16 mmol) in dimethyl sulfoxide (3 mL) was stirred for 4 hours at room temperature. The reaction mixture was diluted with water (40 mL) then extracted with ethyl acetate (3×30 mL). The organic layers were combined, dried over magnesium sulfate, filtered and concentrated in vacuo. The crude material was purified by silica gel column chromatography eluting with 5% diethyl ether in heptane to afford the title compound as a white solid (260 mg, 81%).

LCMS Rt=4.23 minutes
MS m/z 444 [MH]+

$^1$H NMR (400 MHz, CD$_3$OD): δ 1.02 (m, 4H), 1.58 (s, 9H), 2.02 (m, 3H), 2.39 (m, 1H), 6.80 (m, 1H), 7.35 (m, 1H), 7.98 (m, 1H), 8.12 (m, 1H).

Preparation 271

5-chloro-4-(6-cyclopropyl-5-(1,1-difluoroethoxy)pyridin-3-yloxy)-2-fluorobenzoic acid

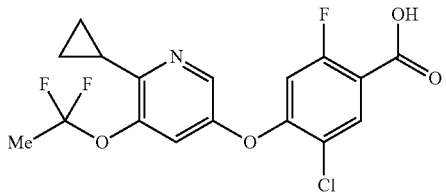 [SMILES: CC(F)(F)Oc1cc(Oc2cc(F)c(C(=O)O)cc2Cl)cnc1C1CC1]

To a solution of tert-butyl 5-chloro-4-(6-cyclopropyl-5-(1,1-difluoroethoxy)pyridin-3-yloxy)-2-fluorobenzoate (Preparation 270, 260 mg, 0.59 mmol) in dichloromethane (5 mL) was added trifluoroacetic acid (440 μL, 5.86 mmol). The reaction mixture was stirred over 48 hours at room temperature then concentrated in vacuo and the crude residue azeotroped with methanol (2×25 mL). The crude material was purified by silica gel column chromatography eluting with 50% ethyl acetate in heptane to afford the title compound as a white solid (200 mg, 96%).

LCMS Rt=2.67 minutes MS m/z 388 [MH]+

$^1$H NMR (400 MHz, CDCl$_3$): δ 1.03 (m, 2H), 1.12 (m, 2H), 2.01 (m, 3H), 2.35 (m, 1H), 6.59 (m, 1H), 7.33 (m, 1H), 8.14 (m, 1H), 8.21 (m, 1H), 10.44 (s, 1H).

The following Preparations were prepared by methods analogous to the Method described for Preparation 22.

| Prep | Name | Data |
|---|---|---|
| 272 | 5-Chloro-4-(6-cyclopropyl-5-(difluoromethoxy)pyridin-3-yloxy)-2-fluorobenzoic acid | LCMS Rt = 1.31 minutes MS m/z 374 [MH]$^+$ |
| 274 | 5-Chloro-4-(6-cyclopropyl-5-(trifluoromethyl)pyridin-3-yloxy)-2-fluorobenzoic acid | LCMS Rt = 3.63 minutes MS m/z 376 [MH]+ |
| 275 | 5-Chloro-4-(6-cyclopropyl-5-(trifluoromethoxy)pyridin-3-yloxy)-2-fluorobenzoic acid | LCMS Rt = 3.65 minutes MS m/z 392 [MH]+ $^1$H NMR (400 MHz, CDCl$_3$): δ 1.01 (m, 2H), 1.06 (m, 2H), 2.31 (m, 1H), 6.58 (m, 1H), 7.21 (m, 1H), 8.06 (m, 1H), 8.15 (m, 1H) |
| 276 | 5-Chloro-4-(5-chloro-6-isopropylpyridin-3-yloxy)-2-fluorobenzoic acid | LCMS Rt = 2.27 minutes, m/z 344 [MH]$^+$ $^1$H NMR (400 MHz, CD$_3$OD): δ 1.27 (d, 6H), 3.57 (sept, 1H), 6.90 (d, 1H), 7.60 (d, 1H), 8.07 (d, 1H), 8.29 (d, 1H). |
| 277 | 5-Chloro-4-(5-chloro-6-cyclobutylpyridin-3-yloxy)-2-fluorobenzoic acid | LCMS Rt = 2.75 minutes MS m/z 356 [MH]+ $^1$HNMR (400 MHz, CDCl$_3$): δ 1.84-1.96 (m, 1H), 2.03-2.14 (m, 1H), 2.32-2.48 (m, 4H), 4.01 (pent, 1H), 6.65 (d, 1H), 7.40 (s, 1H), 8.17 (d, 1H), 8.40 (s, 1H), 10.22 (br s, 1H). |
| 278 | 5-Chloro-4-[(5,6-dicyclopropylpyridin-3-yl)oxy]-2-fluorobenzoic acid | LCMS Rt = 2.30 minutes MS m/z 348 [MH]+ |

The following Preparations were prepared by methods analogous to the Method described for Preparation 23.

| Prep | Name | Data |
|---|---|---|
| 279 | tert-Butyl-5-chloro-4-(6-cyclopropyl-5-(difluoromethoxy)pyridin-3-yloxy)-2-fluorobenzoate | LCMS Rt = 1.31 minutes MS m/z 374 [MH]$^+$ |
| 281 | tert-Butyl 5-chloro-4-(6-cyclopropyl-5-(trifluoromethyl)pyridin-3-yloxy)-2-fluorobenzoate | LCMS Rt = 3.59 minutes MS m/z 432 [MH]+ $^1$HNMR (400 MHz, CDCl$_3$): δ 1.03-1.09 (m, 2H), 1.12-1.19 (m, 2H), 1.53 (s, 9H), 2.24-2.36 (m, 1H), 6.57 (d, 1H), 7.48 (s, 1H), 7.95 (d, 1H), 8.36 (s, 1H). |
| 282 | tert-Butyl 5-chloro-4-(6-cyclopropyl-5-(trifluoromethoxy)pyridin-3-yloxy)-2-fluorobenzoate | LCMS Rt = 4.38 minutes MS m/z 448 [MH]+ $^1$H NMR (400 MHz, CDCl$_3$): δ 1.05 (m, 2H), 1.11 (m, 2H), 1.59 (m, 9H), 2.36 (m, 1H), 6.61 (m, 1H), 7.22 (m, 1H), 8.00 (m, 1H), 8.20 (m, 1H). |
| 283 | tert-Butyl 5-chloro-4-(5-chloro-6-isopropylpyridin-3-yloxy)-2-fluorobenzoate | LCMS Rt = 3.37 minutes MS m/z 400 [MH]$^+$. $^1$H NMR (400 MHz, CDCl$_3$): δ 1.22 (d, 6H), 1.52 (s, 9H), 3.48 (sept, 1H), 6.58 (d, 1H), 7.25 (d, 1H), 7.93 (d, 1H), 8.23 (d, 1H). |
| 284 | tert-Butyl 5-chloro-4-(5-chloro-6-cyclobutylpyridin-3-yloxy)-2-fluorobenzoate | LCMS Rt = 3.84 minutes MS m/z 412 [MH]+ $^1$HNMR (400 MHz, CDCl$_3$): δ 1.58 (s, 9H), 1.82-1.94 (m, 1H), 2.00-2.11 (m, 1H), 2.30-2.49 (m, 4H), 3.96 (pent, 1H), 6.62 (d, 1H), 7.28 (s, 1H), 7.97 (d, 1H), 8.30 (s, 1H). |
| 285 | tert-Butyl 5-chloro-4-[(5,6-dicyclopropylpyridin-3-yl)oxy]-2-fluorobenzoate | LCMS Rt = 3.56 minutes MS m/z 404 [MH]+ |

The following Preparations were prepared by methods analogous to the Method described for Preparation 58 (preceded, in the case of Preparations 290 and 291, by a method analogous to the Method described for Preparation 14).

| Prep | Name | Data |
|---|---|---|
| 286 | 6-Cyclopropyl-5-(difluoromethoxy)pyridin-3-ol | LCMS Rt = 1.68 minutes MS m/z 202 [MH]$^+$ $^1$H NMR (400 MHz; d$_6$-DMSO): δ 0.80 (m, 4H), 2.10-2.20 (m, 1H), 6.95 (m, 1H), 7.00-7.40 (t, 1H), 7.85 (m, 1H), 10.00 (br s, 1H). |
| 287 | 6-Cyclopropyl-5-(trifluoromethyl)pyridin-3-ol | LCMS Rt = 2.56 minutes MS m/z 204 [MH]+ $^1$HNMR (400 MHz, CDCl$_3$): δ 0.88-1.03 (m, 4H), 2.13-2.23 (m, 1H), 7.27 (d, 1H), 8.07 (d, 1H). |
| 288 | 5-Chloro-6-(3,3-difluorocyclobutyl)pyridin-3-ol | LCMS Rt = 2.02 minutes MS m/z 220 [MH]$^+$, 218 [MH]$^-$ $^1$HNMR (400 MHz, CDCl$_3$): δ 2.95 (m, 4H), 3.73 (m, 1H), 5.29 (br s, 1H), 7.22 (d, 1H), 8.15 (d, 1H). |
| 289 | 6-Cyclopropyl-5-(trifluoromethoxy)pyridin-3-ol | LCMS Rt = 2.91 minutes MS m/z 220 [MH]+ $^1$H NMR (400 MHz, CDCl$_3$): δ 1.00 (m, 4H), 2.26 (m, 1H), 5.89 (b s, 1H), 7.07 (m, 1H), 8.03 (m, 1H). |
| 290 | 5-Chloro-6-cyclobutyl-pyridin-3-ol | LCMS Rt = 2.03 minutes MS m/z 184 [MH]$^+$ $^1$H NMR (400 MHz, CDCl$_3$): δ 1.36 (m, 1H), 2.04 (m, 1H), 2.34 (m, 4H), 3.94 (m, 1H), 7.21 (s, 1H), 8.09 (s, 1H). |
| 291 | 5-Chloro-6-isopropyl-pyridin-3-ol | LCMS Rt = 1.90 minutes MS m/z 172 [MH]$^+$ $^1$H NMR (400 MHz, CDCl$_3$): δ 1.26 (d, 6H), 3.52 (m, 1H), 7.24 (m, 1H), 8.06 (m, 1H). |

The following Preparations were prepared by methods analogous to the Method described for Preparation 14.

| Prep | Name | Data |
|---|---|---|
| 292 | 3-Difluoromethoxy-2-cyclopropyl-5-(4,4,5,5-tetramethyl-1,3,2-dioxaborolan-2-yl)pyridine | LCMS Rt = 1.55 minutes MS m/z 230 [MH]$^+$ |
| 293 | 2-Cyclopropyl-5-(4,4,5,5-tetramethyl-1,3,2-dioxaborolan-2-yl)-3-(trifluoromethyl)pyridine | LCMS Rt = 2.74 minutes No mass ion observed. $^1$HNMR (400 MHz, CDCl$_3$): δ 1.02-1.10 (m, 2H), 1.16-1.27 (m, 14H), 2.29-2.38 (m, 1H), 8.18 (s, 1H), 8.83 (s, 1H). |
| 294 | 3-Chloro-2-(3,3-difluorocyclobutyl)-5-(4,4,5,5-tetramethyl-1,3,2-dioxaborolan-2-yl)pyridine | LCMS Rt = 1.88 minutes MS m/z 248 [MH]$^+$, 246 [MH]$^-$. |

-continued

| Prep | Name | Data |
|---|---|---|
| 295 | 2-Cyclopropyl-5-(4,4,5,5-tetramethyl-1,3,2-dioxaborolan-2-yl)-3-(trifluoromethoxy)pyridine | LCMS Rt = 4.13 minutes<br>MS m/z 330 [MH]+ |

The following Preparations were prepared by methods analogous to the method described for Preparation 9.

| Prep | Name | Data |
|---|---|---|
| 296 | 4-Methylphenyl 5-chloro-4-[(5-chloro-6-phenylpyridin-3-yl)oxy]-2-fluorobenzoate | LCMS Rt = 3.58 minutes<br>MS m/z 468 [MH]+<br>$^1$HNMR (400 MHz, CDCl$_3$): δ 2.39 (s, 3H), 6.86 (d, 1H), 7.12 (d, 2H), 7.25 (d, 2H), 7.50 (m, 4H), 7.77 (m, 2H), 8.29 (d, 1H), 8.49 (d, 1H). |
| 297 | 4-Methylphenyl 5-chloro-4-{[5-chloro-6-(3,3-difluorocyclobutyl)pyridin-3-yl]oxy}-2-fluorobenzoate | LCMS Rt = 3.60 minutes<br>MS m/z 482 [MH]+<br>$^1$HNMR (400 MHz, CDCl$_3$): δ 2.39 (s, 3H), 3.00 (m, 4H), 3.83 (m, 1H), 6.76 (d, 1H), 7.10 (d, 2H), 7.24 (d, 2H), 7.42 (d, 1H), 8.26 (d, 1H), 8.36 (d, 1H). |

Preparation 298

(S)-tert-Butyl 5-chloro-4-((5-chloro-6-((1,1,1-trifluoropropan-2-yl)oxy)pyridin-3-yl)oxy)-2-fluorobenzoate

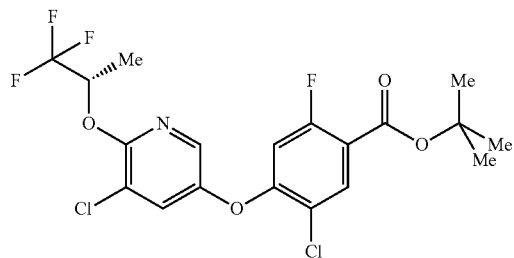 [SMILES: C[C@H](Oc1ncc(Oc2cc(F)c(C(=O)OC(C)(C)C)cc2Cl)cc1Cl)C(F)(F)F]

tert-Butyl 5-chloro-2,4-difluorobenzoate (Preparation 59, 8.3 g, 33.4 mmol) was added to a solution of 5-chloro-6-[(1S)-2,2,2-trifluoro-1-methylethoxy]pyridin-3-ol (Preparation 231, 16.2 g, 66.8 mmol) and potassium carbonate (27.8 g, 200 mmol) in dimethyl sulfoxide (100 mL). The reaction mixture was stirred at room temperature for 18 hours then quenched with an aqueous solution of sodium hydroxide (1 M, 100 mL). A white precipitate formed and was collected by filtration to give the title compound as a white solid (9.2 g).

LCMS Rt=3.43 minutes, m/z 468 [M−H]$^−$ $^1$H NMR (400 MHz, CDCl$_3$): δ 1.55 (d, 3H), 1.59 (s, 9H), 5.73 (m, 1H), 6.58 (d, 1H), 7.47 (d, 1H), 7.86 (d, 1H), 7.99 (d, 1H).

$^{19}$F NMR (400 MHz, CDCl$_3$): δ −79, −108.

Preparation 299

(S)-5-Chloro-4-((5-chloro-6-((1,1,1-trifluoropropan-2-yl)oxy)pyridin-3-yl)oxy)-2-fluorobenzoic acid

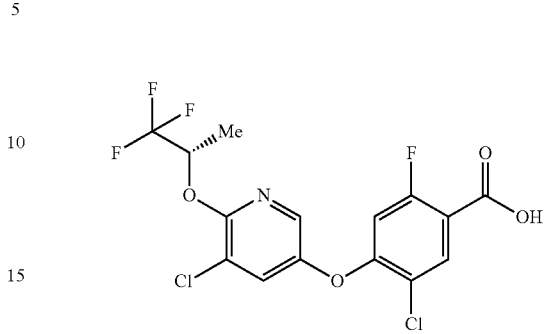

Trifluoroacetic acid (4.4 mL, 58.7 mmol) was added to a solution of (S)-tert-butyl 5-chloro-4-((5-chloro-6-((1,1,1-trifluoropropan-2-yl)oxy)pyridin-3-yl)oxy)-2-fluorobenzoate (Preparation 298, 9.2 g, 19.6 mmol) in dichloromethane (50 mL). The reaction mixture was stirred at room temperature for 20 hours then concentrated in vacuo. The crude was purified by silica gel chromatography, eluting with heptane:ethyl acetate (from 95:5 to 40:60), to provide the title compound as a white solid (6.9 g, 85%).

LCMS Rt=2.88 minutes, m/z 414 [M+H]$^+$ $^1$H NMR (400 MHz, CDCl$_3$): δ 1.56 (d, 3H), 5.75 (m, 1H), 6.60 (d, 1H), 7.52 (d, 1H), 7.90 (d, 1H), 8.15 (d, 1H).

$^{19}$F NMR (400 MHz, CDCl$_3$): δ 79, −105.

The ability of the compounds of formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 μg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 μg/ml G-418 in an incubator at 37° C. with a humidified atmosphere of 10% CO$_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM CaCl$_2$, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" ($EIC_{50}$) values were calculated from single point electrophysiology data by the following equation, (tested concentration, uM) X (100-% inhibition/% inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of $1 \times 10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays were also conducted using the Ionworks Quattro automated electrophysiological platform (Molecular Devices Corp). Intracellular and extracellular solutions were as described above with the following changes, 120 μg/ml amphotericin was added to the intracellular solution to perforate the membrane and allow electrical access to the cells. hSCN9A cells were grown and harvested as for PatchXpress and cells were resuspended in extracellular solution at a concentration of $1 \times 10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assays described above and found to have the Nav1.7 $EIC_{50}$ (μM) values specified in the table below. All data are derived from the PatchXpress assay unless explicitly stated otherwise.

| Ex. | $EIC_{50}$ | Ex. | $EIC_{50}$ | Ex. | $EIC_{50}$ | Ex. | $EIC_{50}$ |
|---|---|---|---|---|---|---|---|
| 1 | 0.16 | 2 | 0.091 | 3 | 0.041 | 4 | 0.30 |
| 5 | 1.0 | 6 | NT | 7 | 0.29 | 8 | 0.24 |
| 9 | >1 | 10 | 0.90 | 11 | 0.21 | 12 | 0.12 |
| 13 | 0.05 | 14 | 0.14 | 15 | 4.6 | 16 | 0.13 |
| 17 | NT | 18 | 0.97 | 19 | NT | 20 | >3 |
| 21 | 0.030 | 22 | 0.019 | 23 | 0.039 | 24 | 0.78 |
| 25 | 9.8 | 26 | >10 | 27 | 0.22 | 28 | 0.033 |
| 29 | 2.3 | 30 | 7.6 | 31 | 1.0 | 32 | 0.34 |
| 33 | 0.70 | 34 | 0.033 | 35 | 0.041 | 36 | 0.31 |
| 37 | 0.14 | 38 | 0.0075 | 39 | 0.025 | 40 | 0.13 |
| 41 | 0.19 | 42 | 0.031 | 43 | 0.011 | 44 | 0.56 |
| 45 | 0.11 | 46 | 0.11 | 47 | 0.68 | 48 | 3.5 |
| 49 | 0.76 | 50 | 0.16 | 51 | 0.27 | 52 | 0.16 |
| 53 | 0.26 | 54 | 0.18 | 55 | 0.048 | 56 | 0.013 |
| 57 | 0.094 | 58 | 0.023 | 59 | NT | 60 | 0.14 |
| 61 | 5.5 | 62 | 0.24 | 63 | 0.16 | 64 | 0.028 |
| 65 | 0.65 | 66 | 0.65 | 67 | 9.9 | 68 | 1.8 |
| 69 | 0.25 | 70 | NT | 71 | 1.7 | 72 | >1 |
| 73 | 0.62 | 74 | 0.050 | 75 | NT | 76 | 0.0094 |
| 77 | 0.015 | 78 | NT | 79 | 0.15 | 80 | 1.5 |
| 81 | NT | 82 | 0.042 | 83 | >10 | 84 | 0.85 |
| 85 | >10 | 86 | 7.2 | 87 | >3 | 88 | >3 |
| 89 | >3 | 90 | >3 | 91 | 0.68 | 92 | 0.050 |
| 93 | 0.47 | 94 | 0.83 | 95 | 0.037 | 96 | 0.073 |
| 97 | 1.0 | 98 | 0.012 | 99 | 0.015 | 100 | 0.072 |
| 101 | 0.034 | 102 | | 103 | 0.40 | 104 | 0.067 |
| 105 | 0.031 | 106 | 1.1 | 107 | 0.049 | 108 | 0.24 |
| 109 | 0.097 | 110 | 0.10 | 111 | 0.29 | 112 | 0.019 |
| 113 | 0.053 | 114 | 0.21 | 115 | 0.054 | 116 | 0.98 |
| 117 | 0.90 | 118 | >1 | 119 | 0.40 | 120 | 0.66 |
| 121 | 0.68 | 122 | 0.25 | 123 | 0.12 | 124 | 0.64 |
| 125 | 0.96 | 126 | 0.47 | 127 | >1 | 128 | 2.4 |
| 129 | 0.54 | 130 | 0.74 | 131 | 0.071 | 132 | 0.16 |
| 133 | 0.17 | 134 | 0.58 | 135 | 0.14 | 136 | 0.89 |
| 137 | 3.2 | 138 | 0.085 | 139 | 2.6 | 140 | 1.6 |
| 141 | 0.27 | 142 | 0.17 | 143 | >1 | 144 | 0.49 |
| 145 | 0.81 | 146 | 0.076 | 147 | NT | 148 | NT |
| 149 | NT | 150 | 0.22 | 151 | NT | 152 | NT |
| 153 | NT | 154 | NT | 155 | NT | 156 | NT |
| 157 | NT | 158 | NT | 159 | NT | 160 | NT |
| 161 | NT | 162 | NT | 163 | NT | 164 | NT |
| 165 | NT | 166 | NT | 167 | NT | 168 | NT |
| 169 | NT | 170 | NT | 171 | NT | 172 | NT |
| 173 | NT | 174 | NT | 175 | NT | 176 | NT |
| 177 | NT | 178 | NT | 179 | NT | 180 | 232 (IW) |
| 181 | NT | 182 | >3 | 183 | >323 (IW) | 184 | 4.4 |
| 185 | >323 (IW) | 186 | >323 (IW) | 187 | >3 | 188 | NT |
| 189 | 232 (IW) | 190 | 29.3 (IW) | 191 | NT | 192 | NT |
| 193 | 2.1 | 194 | 3.1 | 195 | >323 (IW) | 196 | >3 |
| 197 | >323 (IW) | 198 | >323 (IW) | 199 | >323 (IW) | 200 | 173 (IW) |
| 201 | NT | | | | | | |
| L33 | 323 (IW) | L34 | 222 (IW) | L35 | 50.2 (IW) | L36 | >323 (IW) |
| L37 | >323 (IW) | L38 | >323 (IW) | L43 | 41 (IW) | L44 | >323 (IW) |
| L47 | 121 (IW) | L48 | 38.5 (IW) | L51 | 300 (IW) | L55 | 300 (IW) |

-continued

| Ex. | EIC$_{50}$ | Ex. | EIC$_{50}$ | Ex. | EIC$_{50}$ | Ex. | EIC$_{50}$ |
|---|---|---|---|---|---|---|---|
| L58 | 216 (IW) | L61 | 100 (IW) | L62 | 57.4 (IW) | L64 | >323 (IW) |

IW = Ionwork assay
NT = not tested

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated 1C50s are determined at the half inactivation for Nav1.5. These results can be compared to the EIC$_{50}$ value at the Nav1.7 channel to determine the selectivity of a given compound for Nav1.7 vs Nav1.5.

We claim:
1. A compound of formula (I):

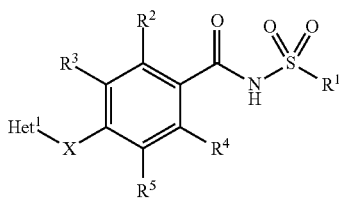

or a pharmaceutically acceptable salt thereof, wherein:
X is O, S, NH, or CH$_2$;
Het$^1$ is (i) a 9- or 10-membered heteroaryl comprising one to three nitrogen atoms; or (ii) a 6-, 9- or 10-membered heteroaryl comprising one to three nitrogen atoms wherein said 6-, 9- or 10-membered heteroaryl is independently substituted by one to three substituents selected from the group consisting of Y$^1$ and Y$^2$;
Y$^1$ and Y$^2$ are independently selected from the group consisting of F; Cl; CN; NO$_2$; (C$_1$-C$_8$)alkyl optionally substituted by (C$_3$-C$_8$)cycloalkyl or one to eight F; (C$_3$-C$_8$)cycloalkyl optionally substituted by one to eight F; NR$^7$R$^8$; (C$_1$-C$_8$)alkyloxy optionally independently substituted by one to three R$^9$ or one to eight F; (C$_3$-C$_8$)cycloalkyloxy optionally substituted by one to eight F wherein said (C$_3$-C$_8$)cycloalkyloxy is optionally fused to a phenyl ring optionally independently substituted with one to three R$^{10}$; phenyl optionally independently substituted by one to three R$^{10}$; phenoxy optionally independently substituted by one to three R$^{10}$; Het$^2$; Het$^2$-oxy; and Het$^3$;
R$^1$ is (C$_1$-C$_6$)alkyl or (C$_3$-C$_8$)cycloalkyl, each of which is optionally substituted by one to eight F;
R$^2$, R$^3$, R$^4$ are independently H, F, Cl or —OCH$_3$;
R$^5$ is H, CN, F, Cl or R$^6$;
R$^6$ is selected from the group consisting of (C$_1$-C$_6$)alkyl and (C$_1$-C$_8$)alkyloxy, wherein each group is optionally substituted by one to eight F;
R$^7$ and R$^8$ are independently H; (C$_1$-C$_8$)alkyl optionally independently substituted by one to three R$^{11}$; (C$_3$-C$_8$)cycloalkyl optionally substituted by one to eight F; 'C-linked' Het$^2$; or 'C-linked' Het$^3$; wherein (C$_3$-C$_8$)cycloalkyl may be optionally fused to a phenyl ring optionally independently substituted by one to eight F or by one to three R$^{10}$; or R$^7$ and R$^8$, taken together with the nitrogen atom to which they are attached, form a saturated, bridged, 7 to 9-membered ring;
R$^9$ is (C$_1$-C$_6$)alkyloxy; (C$_3$-C$_8$)cycloalkyl optionally substituted by one to three F or (C$_1$-C$_6$)alkyl; Het$^2$; or phenyl optionally independently substituted by one to three R$^6$;
R$^{10}$ s Cl, CN or R$^6$;
R$^{11}$ is F; (C$_1$-C$_6$)alkyloxy; (C$_3$-C$_8$)cycloalkyl optionally substituted by one to three F; 'C-linked' Het$^2$; or phenyl optionally independently substituted by one to three R$^6$;
Het$^2$ is a 3- to 8-membered saturated monoheterocycloalkyl comprising one or two ring members selected from the group consisting of —NR$^{12}$— and —O—, said monoheterocycloalkyl is optionally substituted on a ring carbon atom by one to three substituents independently selected from the group consisting of F, (C$_1$-C$_6$)alkyl, (C$_1$-C$_4$)alkyloxy(C$_0$-C$_4$)alkylene and (C$_3$-C$_8$)cycloalkyl;
Het$^3$ is a 5- or 6-membered heteroaryl comprising one to three nitrogen atoms, wherein said heteroaryl is optionally substituted by one to three substituents selected from the group consisting of F, Cl, CN and R$^6$; and
R$^{12}$ is H, (C$_1$-C$_6$)alkyl or (C$_3$-C$_8$)cycloalkyl, wherein (C$_1$-C$_6$)alkyl and (C$_3$-C$_8$)cycloalkyl are optionally substituted by one to three F; provided that when Het$^2$ is 'N-linked', R$^{12}$ is absent from the 'N-linked' nitrogen.

2. The compound according to claim 1 wherein Het$^1$ is a 6-membered heteroaryl comprising one or two nitrogen atoms wherein said heteroaryl is independently substituted by one to three substituents selected from the group consisting of Y$^1$ and Y$^2$.

3. The compound according to claim 1 wherein Het$^1$ is a 6-membered heteroaryl comprising one or two nitrogen atoms wherein said heteroaryl is independently substituted by one or two substituents selected from the group consisting of Y$^1$ and Y$^2$.

4. The compound according to claim 1 wherein Het$^1$ is pyridyl or pyrimidinyl, each independently substituted by one or two substituents selected from the group consisting of Y$^1$ and Y$^2$.

5. The compound according to claim 1 wherein Het$^1$ is pyridyl independently substituted by one or two substituents selected from the group consisting of Y$^1$ and Y$^2$.

6. The compound according to claim 1 wherein Het$^1$ is pyridyl independently substituted by one or two substituents selected from the group consisting of Y$^1$ and Y$^2$; and wherein said pyridyl is orientated as below:

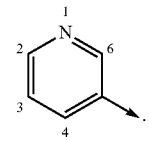

7. The compound according to claim 6 wherein said pyridyl is 2-substituted by Y$^1$, 3-substituted by Y$^2$ or disubstituted wherein said pyridyl is 2-substituted by Y$^1$ and 3-substituted by Y$^2$.

8. The compound according to claim 7 wherein Y$^1$ is (C$_1$-C$_8$)alkyl optionally substituted by (C$_3$-C$_8$)cycloalkyl or by one to eight F; (C$_3$-C$_8$)cycloalkyl optionally substituted by one to eight F; (C$_1$-C$_6$)alkyloxy optionally substituted by one to eight F; (C$_3$-C$_8$)cycloalkyloxy; or Het$^2$.

9. The compound according to claim 8 wherein $Y^2$ is F; Cl; CN; $(C_1-C_8)$alkyl optionally substituted by $(C_3-C_8)$cycloalkyl or by one to eight F; $(C_3-C_8)$cycloalkyl optionally substituted by one to eight F; $(C_1-C_6)$alkyloxy, optionally substituted by one to eight F; $(C_3-C_8)$cycloalkyloxy; or Het².

10. The compound according to claim 9 wherein $R^1$ is $(C_1-C_4)$alkyl or $(C_3-C_6)$cycloalkyl.

11. The compound according to claim 9 wherein $R^1$ is methyl or cyclopropyl.

12. The compound according to claim 11 wherein $R^2$, $R^3$ and $R^4$ are independently H, F or Cl.

13. The compound according to claim 12 wherein $R^5$ is H; CN; F; Cl; $(C_1-C_4)$alkyl optionally substituted by one to eight F; or $(C_1-C_4)$alkyloxy optionally substituted by one to eight F.

14. The compound according to claim 12 wherein $R^5$ is H, CN, F, Cl, $CH_3$, $C_2H_5$, $CF_3$, —$OCH_3$, —$OC_2H_5$ or —$OCF_3$.

15. The compound according to claim 1 wherein X is O.

16. A compound of formula (I)

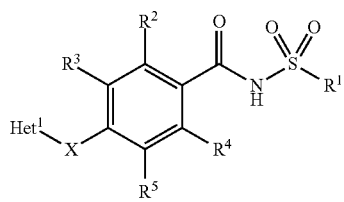

wherein:
X is O;
Het¹ is (i) a 9- or 10-membered heteroaryl comprising one to three nitrogen atoms; or (ii) a 6-, 9- or 10-membered heteroaryl comprising one to three nitrogen atoms wherein said 6-, 9- or 10-membered heteroaryl is independently substituted by one to three substituents selected from the group consisting of $Y^1$ and $Y^2$;
$Y^1$ and $Y^2$ are independently selected from the group consisting of F; Cl; CN; $(C_1-C_8)$alkyl optionally substituted by $(C_3-C_8)$cycloalkyl or one to three F; $(C_3-C_8)$cycloalkyl optionally substituted by one to three F; $NR^7R^8$; $(C_1-C_8)$alkyloxy optionally independently substituted by one to three $R^9$; $(C_3-C_8)$cycloalkyloxy optionally fused to a phenyl ring optionally independently substituted by one to three $R^{10}$; phenyl optionally independently substituted by one to three $R^{10}$; Het² and Het³;
$R^1$ is $(C_1-C_6)$alkyl or $(C_3-C_8)$cycloalkyl, each of which is optionally substituted by one to three F;
$R^2$, $R^3$, $R^4$ are independently H, F, Cl or —$OCH_3$;
$R^5$ is H, CN, F, Cl or $R^6$;
$R^6$ is selected from the group consisting of $(C_1-C_6)$alkyl and $(C_1-C_8)$alkyloxy, wherein each group is optionally substituted by one to five F;
$R^7$ and $R^8$ are independently H; $(C_1-C_8)$alkyl optionally independently substituted by one to three $R^{11}$; $(C_3-C_8)$cycloalkyl; or 'O-linked' Het²; wherein $(C_3-C_8)$cycloalkyl is optionally fused to a phenyl ring optionally independently substituted by one to three $R^{10}$; or
$R^7$ and $R^8$, taken together with the nitrogen atom to which they are attached, form a saturated, bridged, 7 to 9-membered ring;

$R^9$ is F; $(C_1-C_6)$alkyloxy; $(C_3-C_8)$cycloalkyl optionally substituted by one to three F; Het²; or phenyl optionally independently substituted by one to three $R^6$;
$R^{10}$ is F, Cl or $R^6$;
$R^{11}$ is F; $(C_1-C_6)$alkyloxy; $(C_3-C_8)$cycloalkyl optionally substituted by one to three F; 'C-linked' Het²; or phenyl optionally independently substituted by one to three $R^6$;
Het² is a 3- to 8-membered saturated monoheterocycloalkyl comprising one or two ring members selected from the group consisting of —$NR^{12}$— and —O—, wherein said monoheterocycloalkyl is optionally substituted on a ring carbon atom by one to three substituents independently selected from the group consisting of F, $(C_1-C_6)$alkyl, $(C_1-C_4)$alkyloxy$(C_0-C_4)$alkylene and $(C_3-C_8)$cycloalkyl;
Het³ is a 5- or 6-membered heteroaryl comprising one to three nitrogen atoms, wherein said heteroaryl is optionally substituted by one to three substituents selected from the group consisting of F, Cl, CN and $R^6$; and
$R^{12}$ is H, $(C_1-C_6)$alkyl or $(C_3-C_8)$cycloalkyl, wherein $(C_1-C_6)$alkyl and $(C_3-C_8)$cycloalkyl are optionally substituted by one to three F; provided that when Het² is 'N-linked', $R^{12}$ is absent on the 'N-linked' nitrogen.

17. A pharmaceutical composition comprising a compound according to claim 1, or a pharmaceutically acceptable salt thereof, and one or more pharmaceutically acceptable excipients.

18. The pharmaceutical composition according to claim 16 further comprising one or more additional therapeutic agents.

19. 5 chloro-4-[(5-chloro-6-cyclopropylpyridin-3-yl) oxy]-2-fluoro-N-(methanesulfonyl)benzamide or a pharmaceutically acceptable salt thereof.

20. The compound of claim 1 that is 5-chloro-4-({5-chloro-6[(1S)-2,2,2-trifluoro-1-methylethoxy]pyridin-3-yl}oxy)-2-fluoro-N-(methylsulfonyl)benzamide or a pharmaceutically acceptable salt thereof.

21. The compound of claim 1 that is 5-chloro-4-({5-chloro-6[(1R)-2,2,2-trifluoro-1-methylethoxy]pyridin-3-yl}oxy)-2-fluoro-N-(methylsulfonyl)benzamide or a pharmaceutically acceptable salt thereof.

22. The compound of claim 1 that is 5-chloro-4-{[5-chloro-6-(2,2,2-trifluoro-1-methylethoxy)pyridin-3-yl]oxy}-2-fluoro-N-(methylsulfonyl)benzamide or a pharmaceutically acceptable salt thereof.

23. A compound that is

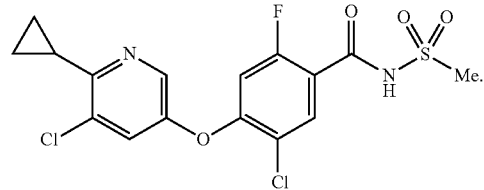 [SMILES: CS(=O)(=O)NC(=O)c1cc(Cl)c(Oc2cnc(C3CC3)c(Cl)c2)cc1F]

24. A method for treating pain comprising administering to a human or animal an effective amount of a compound according to claim 1, or a pharmaceutically acceptable salt thereof.

25. A method according to claim 24 in which said pain is selected from the group consisting of neuropathic pain, nociceptive pain, and inflammatory pain.

* * * * *